(12) United States Patent
Cariou et al.

(10) Patent No.: US 9,701,670 B2
(45) Date of Patent: Jul. 11, 2017

(54) PYRAZOLYL-UREAS AS KINASE INHIBITORS

(71) Applicants: RESPIVERT LIMITED, Buckinghamshire (GB); TOPIVERT PHARMA LIMITED, London (GB)

(72) Inventors: Claire Anne Marie Cariou, Nottingham (GB); Catherine Elisabeth Charron, London (GB); Euan Alexander Fraser Fordyce, Nottingham (GB); Daniel Hamza, Nottingham (GB); Matthew Colin Thor Fyfe, London (GB); Kazuhiro Ito, London (GB); John King-Underwood, Worcestershire (GB); Peter John Murray, London (GB); Stuart Thomas Onions, Nottingham (GB); Stephen Malcolm Thom, Nottingham (GB); Hayley Tegan Angela Watson, Nottingham (GB); Jonathan Gareth Williams, Nottingham (GB)

(73) Assignees: RESPIVERT LIMITED, High Wycombe, Buckinghamshire (GB); TOPIVERT PHARMA LIMITED, London (GB)

( * ) Notice: Subject to any disclaimer, the term of this patent is extended or adjusted under 35 U.S.C. 154(b) by 0 days.

(21) Appl. No.: 14/422,158

(22) PCT Filed: Aug. 16, 2013

(86) PCT No.: PCT/GB2013/052184
§ 371 (c)(1),
(2) Date: Feb. 17, 2015

(87) PCT Pub. No.: WO2014/027209
PCT Pub. Date: Feb. 20, 2014

(65) Prior Publication Data
US 2015/0218137 A1  Aug. 6, 2015

Related U.S. Application Data

(60) Provisional application No. 61/782,793, filed on Mar. 14, 2013.

(51) Int. Cl.
| | | |
|---|---|---|
| *A61K 31/506* | (2006.01) | |
| *A61K 31/5377* | (2006.01) | |
| *C07D 409/14* | (2006.01) | |
| *C07D 403/12* | (2006.01) | |
| *C07D 401/14* | (2006.01) | |

(Continued)

(52) U.S. Cl.
CPC ......... *C07D 409/14* (2013.01); *A61K 31/506* (2013.01); *A61K 31/5377* (2013.01); *A61K 45/06* (2013.01); *C07D 401/12* (2013.01); *C07D 401/14* (2013.01); *C07D 403/12* (2013.01); *C07D 405/14* (2013.01)

(58) Field of Classification Search
None
See application file for complete search history.

(56) References Cited

U.S. PATENT DOCUMENTS 6,319,921 B1  11/2001  Cirillo et al.
6,492,393 B1  12/2002  Breitfelder et al.
(Continued)

FOREIGN PATENT DOCUMENTS

EP    2 578 582 A1    4/2013
WO    WO 99/32110     7/1999
(Continued)

OTHER PUBLICATIONS

Database Registry Chemical Abstracts Service, Columbus, Ohio, Accession No. RN 1384610-90-5, Entered STN: Jul. 27, 2012.*
U.S. Appl. No. 14/349,356, filed Apr. 3, 2014, Ito.
U.S. Appl. No. 14/422,158, filed Feb. 17, 2015, Cariou et al.
U.S. Appl. No. 14/424,240, filed Feb. 26, 2015, Fyfe et al.
U.S. Appl. No. 14/424,627, filed Feb. 27, 2015, Fyfe et al.
U.S. Appl. No. 14/424,361, filed Feb. 26, 2015, Duffy et al.
U.S. Appl. No. 14/424,967, filed Feb. 27, 2015, Fyfe et al.
U.S. Appl. No. 14/561,290, filed Dec. 5, 2014, Murray.
U.S. Appl. No. 14/626,548, filed Feb. 19, 2014, Fyfe et al.
Boehm, et al. 2000 "New inhibitors of p38 kinase" *Expert Opinion on Therapeutic Patents* 10(1): 25-37.
(Continued)

*Primary Examiner* — Samantha Shterengarts
(74) *Attorney, Agent, or Firm* — Knobbe, Martens, Olson & Bear, LLP

(57) ABSTRACT

There are provided compounds of formula I, (I)

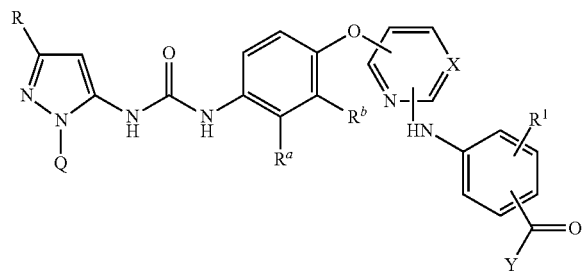

wherein R, $R^1$, $R^a$, $R^b$, Q, X and Y have meanings given in the description, which compounds have antiinflammatory activity (e.g., through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

18 Claims, No Drawings

(51) Int. Cl.
*C07D 401/12* (2006.01)
*A61K 45/06* (2006.01)
*C07D 405/14* (2006.01)

(56) References Cited

U.S. PATENT DOCUMENTS

| | | |
|---|---|---|
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Hao et al. |
| 7,582,638 B2 | 9/2009 | De Dios et al. |
| 7,678,811 B2 | 3/2010 | Dumas et al. |
| 7,838,524 B2 | 11/2010 | Lee et al. |
| 7,838,541 B2 | 11/2010 | Dumas et al. |
| 8,071,616 B2 | 12/2011 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 8,927,563 B2 | 1/2015 | Fyfe et al. |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,249,125 B2 | 2/2016 | Duffy et al. |
| 9,481,648 B2 | 11/2016 | Baker et al. |
| 2004/0152725 A1 | 8/2004 | Moss et al. |
| 2006/0035922 A1 | 2/2006 | Mathias et al. |
| 2008/0300281 A1 | 12/2008 | Dumas et al. |
| 2009/0131437 A1 | 5/2009 | Furet et al. |
| 2010/0160355 A1 | 6/2010 | DeGoey et al. |
| 2010/0168138 A1 | 7/2010 | DeGoey et al. |
| 2011/0118245 A1 | 5/2011 | Abraham et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2013/0150343 A1 | 6/2013 | Van Niel et al. |
| 2013/0156826 A1 | 6/2013 | Murray et al. |
| 2014/0057915 A1 | 2/2014 | Cariou et al. |
| 2014/0114061 A1 | 4/2014 | Kugimoto et al. |
| 2014/0228410 A1 | 8/2014 | Ito et al. |
| 2014/0249169 A1 | 9/2014 | Ito |
| 2014/0296208 A1 | 10/2014 | Baker et al. |
| 2015/0166483 A1 | 6/2015 | Fyfe |
| 2015/0210722 A1 | 7/2015 | Fyfe et al. |
| 2015/0225373 A1 | 8/2015 | Fyfe et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe |
| 2016/0039797 A1 | 2/2016 | Fyfe |
| 2016/0045482 A1 | 2/2016 | Charron |
| 2016/0096805 A1 | 4/2016 | Fyfe |
| 2016/0102059 A1 | 4/2016 | Baker et al. |
| 2016/0115152 A1 | 4/2016 | King-Underwood et al. |
| 2016/0318909 A1 | 11/2016 | Fyfe |
| 2016/0340343 A1 | 11/2016 | Fyfe et al. |
| 2016/0340375 A1 | 11/2016 | Fyfe et al. |
| 2016/0376232 A1 | 12/2016 | Thom |

FOREIGN PATENT DOCUMENTS

| | | |
|---|---|---|
| WO | WO 99/32455 | 7/1999 |
| WO | WO 00/43384 | 7/2000 |
| WO | WO 01/04115 | 1/2001 |
| WO | WO 01/36403 | 5/2001 |
| WO | WO 01/64642 | 9/2001 |
| WO | WO 02/092576 | 11/2002 |
| WO | WO 03/005999 | 1/2003 |
| WO | WO 03/068228 | 8/2003 |
| WO | WO 03/068229 | 8/2003 |
| WO | WO 03/072569 | 9/2003 |
| WO | WO 2005/110994 | 11/2005 |
| WO | WO 2006/072589 | 7/2006 |
| WO | WO 2007/053346 | 5/2007 |
| WO | WO 2009/117080 | 9/2009 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/072155 | 7/2010 |
| WO | WO 2010/075376 | 7/2010 |
| WO | WO 2010/075380 | 7/2010 |
| WO | WO 2010/112936 | 10/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/153553 | 12/2011 |
| WO | WO 2011/158039 | 12/2011 |
| WO | WO 2011/158042 | 12/2011 |
| WO | WO 2011/158044 | 12/2011 |
| WO | WO 2013/050756 | 4/2013 |
| WO | WO 2013/050757 | 4/2013 |
| WO | WO 2013/083604 A1 | 6/2013 |
| WO | WO 2014/033446 A1 | 3/2014 |
| WO | WO 2014/033447 A1 | 3/2014 |
| WO | WO 2014/033448 A1 | 3/2014 |
| WO | WO 2014/033449 A1 | 3/2014 |
| WO | WO 2014/076484 | 5/2014 |
| WO | WO 2014/140582 | 9/2014 |
| WO | WO 2014/162121 | 10/2014 |
| WO | WO 2015/121444 | 8/2015 |

OTHER PUBLICATIONS

Dodeller, et al. 2006 "The p38 mitogen-activated protein kinase signaling cascade in CD4 T cells" *Arthritis Research & Therapy* 8(2): 1-11.

Onions, et al. 2016 "The discovery of narrow spectrum kinase inhibitors: New therapeutic agents for the treatment of COPD and steroid-resistant asthma" *Journal of Medicinal Chemistry*; 1-70.

To, et al. 2015 "Potent anti-inflammatory effects of the narrow spectrum kinase inhibitor RV1088 on rheumatoid arthritis synovial membrane cells" *Britch Journal of Pharmacology* 172: 3805-3816.

CAS Registry No. 1379397-83-7; Jun. 18, 2012; American Chemical Society.

CAS Registry No. 1379547-84-7; Jun. 18, 2012; American Chemical Society.

CAS Registry No. 1379462-42-6; Jun. 18, 2012; American Chemical Society.

Cas Registry No. 1379462-36-8; Jun. 18, 2012; American Chemical Society.

CAS Registry No. 1379401-24-7; Jun. 18, 2012; American Chemical Society.

CAS Registry No. 1384608-34-7; Jul. 27, 2012; American Chemical Society.

CAS Registry No. 1384595-05-4; Jul. 27, 2012; American Chemical Society.

CAS Registry No. 1384611-77-1; Jul. 27, 2012; American Chemical Society.

CAS Registry No. 1384610-90-5; Jul. 27, 2012; American Chemical Society.

CAS Registry No. 1379397-83-7, 2012 American Chemical Society.

CAS Registry No. 1379547-84-7, 2012 American Chemical Society.

CAS Registry No. 1379462-42-6, 2012 American Chemical Society.

(56) References Cited

OTHER PUBLICATIONS

CAS Registry No. 1379462-36-8, 2012 American Chemical Society.
CAS Registry No. 1379401-24-7, 2012 American Chemical Society.
CAS Registry No. 1384608-34-7, 2012 American Chemical Society.
CAS Registry No. 1384595-05-4, 2012 American Chemical Society.
CAS Registry No. 1384611-77-1, 2012 American Chemical Society.
CAS Registry No. 1384610-90-5, 2012 American Chemical Society.
Dumas; et al. 2004 "Recent developments in the discovery of protein kinase inhibitors from the urea class" *Current Opinion in Drug Discovery & Development* 7(5):600-616.
Lee, et al. 2005 "MAP kinase p38 inhibitors: Clinical results and an intimate look at their interactions with p38α protein" *Current Medicinal Chemistry* 12:2979-2994.
Pargellis, et al. 2002 "Inhibition of p38 MAP kinase by utilizing a novel allosteric binding site" *Nature Structural Biology* 9(4):268-272.
Pettus, et al. 2008 "Small molecule p38 MAP kinase inhibitors for the treatment of inflammatory diseases: Novel structures and developments during 2006-2008" *Current Topics in Medicinal Chemistry* 8(16):1452-1467.
Schreiber, et al. 2006 "Oral p38 mitogen-activated protein kinase inhibition with BIRB 796 for active Crohn's Diease: A randomized, double-blind, placebo-controlled trial" *Clinical Gastroenterology and Hepatology* 4:325-334.
Brinkmann, et al. 2010 "Fingolimod (FTY720): discovery and development of an oral drug to treat multiple sclerosis" *Nature Reviews Drug Discovery* 9: 883-897.
Coughlin, et al. 2010 "Approaches and limitations of phosphatidylinositol-3-kinase pathway activation status as a predictive biomarker in the clinical development of targeted therapy" *Breast Cancer Res Treat* 124: 1-11.
Jope, et al. 2007 "Glycogen synthase kinase-3 (GSK3): Inflammation, diseases, and therapeutics" *Neurochem Res* 32: 577-595.
Judge, et al. 2006 "Potassium channel blockers in multiple sclerosis: Neuronal $K_v$ channels and effects of symptomatic treatment" *Pharmacology & Therapeutics* 111: 224-259.

Kim, et al. 2009 "Src family kinases as mediators of endothelial permeability: effects on inflammation and metastasis" *Cell Tissue Res* 335: 249-259.
Kuster "Kinase inhibitors, Methods and Protocols" *Methods in Molecular Biology* 795 Chapters 1 and 2 (in 46 pages).
Lima, et al. 2011 "Anti-inflammatory effects of LASSBio-998, a new drug candidate designed to be a p38 MAPK inhibitor, in an experimental model of acute lung inflammation" *Pharmacological Reports* 63: 1029-1039.
U.S. Appl. No. 15/207,915, filed Jul. 12, 2016, Matthew Colin Thor Fyfe.
U.S. Appl. No. 15/225,377, filed Aug. 1, 2016, Matthew Colin Thor Fyfe, et al.
U.S. Appl. No. 15/228,945, filed Aug. 4, 2016, Matthew Colin Thor Fyfe, et al.
U.S. Appl. No. 15/261,174, filed Sep. 9, 2016, Stephen Malcolm Thom.
Liu, et al. 2011 "Src phosphorylation of endothelial cell surface intercellular adhesion molecule-1 mediates neutrophil adhesion and contributes to the mechanism of lung inflammation" *Arterioscler Thromb Vasc Biol* 31: 1342-1350.
Masuda, et al. 2008 "Syk inhibitors as treatment for allergic rhinitis" *Pulmonary Pharmacology & Therapeutics* 21: 461-467.
McDermott, et al. 2009 "Personalized cancer therapy with selective kinase inhibitors: An emerging paradigm in medical oncology" *Journal of Clinical Oncology* 27(33): 5650-5659.
Sawyers 2008 "The cancer biomarker problem" *Nature* 452: 548-552.
Singh, et al. 2007 "Spleen tyrosine kinase (Syk) biology, inhibitors and therapeutic applications" *Annual Reports in Medicinal Chemistry* 42: 379-391.
Singh, et al. 2010 "A randomized, placebo-controlled study of the effects of the p38 MAPK inhibitor SB-681323 on blood biomarkers of inflammation in COPD patients" *J Clin Pharmacol* 50: 94-100.
Sutherland, et al. 2004 "Management of chronic obstructive pulmonary disease" *The New England Journal of Medicine* 350: 2689-2697.
Weinblatt, et al. 2010 "An oral spleen tyrosine kinase (Syk) inhibitor for rheumatoid arthritis" *The New England Journal of Medicine* 363(14): 1303-1312.
Yamamoto, et al. 2003 "The orally available spleen tyrosine kinase inhibitor 2-[7-(3,4-Dimethoxyphenyl)-imidazo[1,2-c]pyrimidin-5-ylamino]-nicotinamide dihydrochloride (BAY 61-3606) blocks antigen-induced airway inflammation in rodents" *The Journal of Pharmacology and Experimental Therapeutics* 306(3): 1174-1181.

\* cited by examiner

PYRAZOLYL-UREAS AS KINASE INHIBITORS

FIELD OF THE INVENTION

The invention relates to compounds which are inhibitors of the family of p38 mitogen-activated protein kinase enzymes (referred to herein as p38 MAP kinase inhibitors), for example the alpha and gamma sub-types thereof, and of Syk kinase and the Src family of tyrosine kinases, and to their use in therapy, including in pharmaceutical combinations, especially in the treatment of inflammatory diseases, in particular inflammatory diseases of the lung, such as asthma and COPD, as well as those of the gastrointestinal tract, such as ulcerative colitis and Crohn's disease, and of the eye, such as uveitis.

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively), each displaying different patterns of tissue expression, have been identified. The p38 MAPK alpha and beta isoforms are found ubiquitously in the body, being present in many different cell types. The alpha isoform is well characterized in terms of its role in inflammation. Although studies using a chemical genetic approach in mice indicate that the p38 MAPK beta isoform does not play a role in inflammation (O'Keefe, S. J. et al., *J Biol Chem.*, 2007, 282(48):34663-71), it may be involved in pain mechanisms through the regulation of COX2 expression (Fitzsimmons, B. L. et al., *Neuroreport*, 2010, 21(4):313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16):1452-67). As these adverse effects vary with chemotype, and each of these compounds has distinct kinase selectivity patterns, the toxicities observed may be structure—rather than p38 mechanism-based.

Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+ T cells and in endothelial cells (Shmueli, O. et al., *Comptes Rendus Biologies*, 2003, 326(10-11):1067-1072; Smith, S. J. *Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the distribution of p38 MAPK gamma although it is expressed more highly in brain, skeletal muscle and heart, as well as in lymphocytes and macrophages. (Shmueli, O. et al., *Comptes Rendus Biologies*, 2003, 326(10-11):1067-1072, (2003); Hale, K. K., *J. Immunol.*, 1999, 162(7):4246-52: Court, N. W. et al., *J. Mol. Cell. Cardiol.*, 2002, 34(4):413-26; Mertens, S. et al., *FEBS Lett.*, 1996, 383(3):273-6.)

Selective small molecule inhibitors of p38 MAPK gamma and p38 MAPK delta are not currently available, although one previously disclosed compound, BIRB 796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y. *J. Biol. Chem.*, 2005, 280:19472-19479). In addition BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma, COPD (Chung, F., *Chest*, 2011, 139(6):1470-1479) and inflammatory bowel disease (IBD). There is now an abundant literature which demonstrates that p38 MAP kinase is activated by a range of pro-inflammatory cytokines and that its activation results in the recruitment and release of additional pro-inflammatory cytokines. Indeed, data from some clinical studies demonstrate beneficial changes in disease activity in patients during treatment with p38 MAP kinase inhibitors. For instance Smith describes the inhibitory effect of p38 MAP kinase inhibitors on TNFα (but not IL-8) release from human PBMCs.

The use of inhibitors of p38 MAP kinase in the treatment of COPD and IBD has also been proposed. Small molecule inhibitors targeted to p38 MAPK α/β have proved to be effective in reducing various parameters of inflammation in:
- cells and tissues obtained from patients with COPD, who are generally corticosteroid insensitive, (Smith, S. J., *Br. J. Pharmacol.*, 2006, 149:393-404);
- biopsies from IBD patients (Docena, G. et al., *J. of Trans. Immunol.*, 2010, 162:108-115); and
- in vivo animal models (Underwood, D. C. et al., *Am. J. Physiol.*, 2000, 279:L895-902; Nath, P. et al., *Eur. J. Pharmacol.*, 2006, 544:160-167.).

Irusen and colleagues also suggested the possibility of involvement of p38 MAPKα/β on corticosteroid insensitivity via the reduction of binding affinity of the glucocorticoid receptor (GR) in nuclei (Irusen, E. et al., *J. Allergy Clin. Immunol.*, 2002, 109:649-657). Clinical experience with a range of p38 MAP kinase inhibitors, including AMG548, BIRB 796, VX702, SCIO469 and SCIO323 has been described (Lee, M. R. and Dominguez, C., *Current Med. Chem.*, 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., *Mol. Pharmacol.*, 2011, 80(6):1128-1135) demonstrates that silencing p38 MAPK gamma has the potential to restore sensitivity to corticosteroids. Consequently there may be a dual benefit for patients in the use of a p38 MAP kinase inhibitor for the treatment of COPD and severe asthma.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiologic investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G., Papi, A., Psarras, S. and Johnston, S. L., Paediatr. Respir. Rev., 2004, 5(3):255-260). A variety of additional studies support the conclusion that a viral infection can precipitate exacerbations and increase disease severity. For example, experimental clinical infections with rhinovirus have been reported to cause bronchial hyper-responsiveness to histamine in asthmatics which is unresponsive to treatment with corticosteroids (Grunberg, K., Sharon, R. F., et al., Am. J. Respir. Crit. Care Med., 2001, 164(10):1816-1822). Further evidence derives from the association observed between disease exacerbations in patients with cystic fibrosis and HRV infections (Wat, D., Gelder, C., et al., J. Cyst. Fibros., 2008, 7:320-328). Also consistent with this body of data is the finding that respiratory viral infections, including rhinovirus, represent an independent risk factor that correlates negatively with the 12 month survival rate in paediatric, lung transplant recipients (Liu, M., Worley, S., et al., Transpl. Infect. Dis., 2009, 11(4):304-312).

Clinical research indicates that the viral load is proportionate to the observed symptoms and complications and, by implication, to the severity of inflammation. For example, following experimental rhinovirus infection, lower respiratory tract symptoms and bronchial hyper-responsiveness correlated significantly with virus load (Message, S. D., Laza-Stanca, V., et al., PNAS, 2008; 105(36):13562-13567). Similarly, in the absence of other viral agents, rhinovirus infections were commonly associated with lower respiratory tract infections and wheezing, when the viral load was high in immunocompetent paediatric patients (Gerna, G., Piralla, A., et al., J. Med. Virol., 2009, 81(8):1498-1507).

Interestingly, it has been reported recently that prior exposure to rhinovirus reduced the cytokine responses evoked by bacterial products in human alveolar macrophages (Oliver, B. G., Lim, S., et al., Thorax, 2008, 63:519-525). Additionally, infection of nasal epithelial cells with rhinovirus has been documented to promote the adhesion of bacteria, including S. aureus and H. influenzae (Wang, J. H., Kwon, H. J. and Yong, J. J., The Laryngoscope, 2009, 119(7):1406-1411). Such cellular effects may contribute to the increased probability of patients suffering a lower respiratory tract infection following an infection in the upper respiratory tract. Accordingly, it is therapeutically relevant to focus on the ability of novel interventions to decrease viral load in a variety of in vitro systems, as a surrogate predictor of their benefit in a clinical setting.

High risk groups, for whom a rhinovirus infection in the upper respiratory tract can lead to severe secondary complications, are not limited to patients with chronic respiratory disease. They include, for example, the immune compromised who are prone to lower respiratory tract infection, as well as patients undergoing chemotherapy, who face acute, life-threatening fever. It has also been suggested that other chronic diseases, such as diabetes, are associated with a compromised immuno-defence response. This increases both the likelihood of acquiring a respiratory tract infection and of being hospitalised as a result (Peleg, A. Y., Weerarathna, T., et al., Diabetes Metab. Res. Rev., 2007, 23(1): 3-13; Kornum, J. B., Reimar, W., et al., Diabetes Care, 2008, 31(8):1541-1545).

Whilst upper respiratory tract viral infections are a cause of considerable morbidity and mortality in those patients with underlying disease or other risk factors; they also represent a significant healthcare burden in the general population and are a major cause of missed days at school and lost time in the workplace (Rollinger, J. M. and Schmidtke, M., Med. Res. Rev., 2010, Doi 10.1002/med.20176). These considerations make it clear that novel medicines, that possess improved efficacy over current therapies, are urgently required to prevent and treat rhinovirus-mediated upper respiratory tract infections. In general the strategies adopted for the discovery of improved antiviral agents have targeted various proteins produced by the virus, as the point of therapeutic intervention. However, the wide range of rhinovirus serotypes makes this a particularly challenging approach to pursue and may explain why, at the present time, a medicine for the prophylaxis and treatment of rhinovirus infections has yet to be approved by any regulatory agency.

Viral entry into the host cell is associated with the activation of a number of intracellular signalling pathways controlled by the relative activation and inactivation of specific kinases which are believed to play a prominent role in the initiation of inflammatory processes (reviewed by Ludwig, S, 2007; Signal Transduction, 7:81-88) and of viral propagation and subsequent release.

It has been disclosed previously that compounds that inhibit the activity of both c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). For the reasons summarised above, in combination with the inhibition of p38 MAPKs, these are particularly advantageous inherent properties for compounds designed to treat chronic respiratory diseases.

Certain p38 MAPK inhibitors have also been described as inhibitors of the replication of respiratory syncytial virus (Cass, L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. Due to the ubiquitous expression of p38 in inflammatory cells it has become an obvious target for investigation in IBD models. Studies investigating the efficacy of p38 inhibitors in animal models of IBD and human biopsies from IBD patients indicated that p38 could be a target for the treatment of IBD (Hove, T. ten et al., *Gut,* 2002, 50:507-512, Docena, G. et al., *J. of Trans. Immunol.,* 2010, 162:108-115). However, these findings are not completely consistent with other groups reporting no effect with p38 inhibitors (Malamut G. et al., *Dig. Dis. Sci,* 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology,* 2006, 4:325-334). A small clinical study investigating the efficacy of CNI-1493, a p38 and Jnk inhibitor, in patients with severe Crohn's disease showed significant improvement in clinical score over 8 weeks (Hommes, D. et al. *Gastroenterology.* 2002 122:7-14).

T cells are known to play key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol.* 1993 5:1461-71). Furthermore, investigation of mucosal membranes from IBD patients showed an upregulation of CD4+ cells which were either Th1 (IFNγ/IL-2) or Th2 (IL5/TGFβ) biased depending on whether the patient had Crohn's disease or ulcerative colitis (Fuss I J. et al. *J Immunol.* 1996 157:1261-70.). Similarly, T cells are known to play a key role in inflammatory disorders of the eye with several studies reporting increased levels of T cell associated cytokines (IL-17 and IL-23) in sera of Behçets patients (Chi W. et al. *Invest Ophthalmol Vis Sci.* 2008 49:3058-64). In support, Direskeneli and colleagues demonstrated that Behçets patients have increased Th17 cells and decreased Treg cells in their peripheral blood (Direskeneli H. et al. J Allergy Clin Immunol. 2011 128: 665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science.* 1994 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum.* 2008 58:3309-18). Syk kinase is widely expressed in cells of the hematopoietic system, most notably in B cells and mature T cells. Through interaction with immunoreceptor tyrosine-based activation (ITAM) motifs it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine.* 2006 January 33:106-10).

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y. *Nature Reviews Cancer,* 2003, 3:155-168) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.,* 2009, 5(7):e1000446.). Micronucleus formation is implicated in, or associated with, disruption of mitotic processes and is therefore an undesirable manifestation of potential toxicity. Inhibition of glycogen synthase kinase 3α (GSK3α) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology,* 2007, 8:34).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetectable activity against these off-target enzymes and consequently elicit little or no disruption of mitotic processes, as measured in mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. The present invention therefore, inter alia, provides such novel compounds that inhibit the enzyme activity of p38 MAP kinase, for example with certain sub-type specificities, optionally together with Syk kinase and tyrosine kinases within the Src family (particularly c-Src) thereby possessing good anti-inflammatory properties, and suitable for use in therapy.

In one or more embodiments the compounds exhibit a long duration of action and/or persistence of action in comparison to other previously disclosed allosteric p38 MAP kinase inhibitors such as, for example, BIRB796 (Pargellis, C. et al., *Nature Struct. Biol.,* 2002, 9(4):268-272).

SUMMARY OF THE INVENTION

In a first aspect, the invention provides a compound of formula (I),

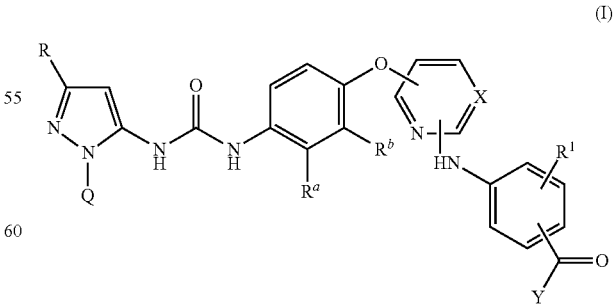

wherein:

Q represents thienyl, phenyl or pyridinyl, either of which may optionally bear 1 to 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $NH_2$, $N(H)$—$C_{1-6}$ alkyl, $N(C_{1-6}$ alkyl$)_2$, $C_{1-6}$ alkylene-5-10 membered heterocycle and $C_{0-3}$ alkylene-O—$C_{0-6}$ alkylene-5-10 membered heterocycle;

X represents CH or N,

Y represents $NR^2R^3$, or a 4-10 heterocycle optionally linked through a heteroatom, wherein said heterocycle bears 0 or 1 substituents selected from halo, OH, $C_{1-6}$ alkyl, $C_{1-4}$ haloalkyl, $C_{0-3}$ alkylene-O—$C_{0-6}$ alkyl, $C_{0-3}$ alkylene-O—$C_{1-3}$ haloalkyl, $C_{0-6}$ alkylene aryl, $C_{0-3}$ alkylene-O—$C_{0-3}$ alkylene aryl, $C_{0-6}$ alkylene heteroaryl, $C_{0-3}$ alkylene-O—$C_{0-3}$ alkylene heteroaryl, $C(O)C_{1-6}$ alkyl, $SO_2NR^4R^5$, $C_{0-3}$ alkylene-$NR^4R^5$, $C_{0-3}$ alkylene-$NR^4SO_2R^5$ and $C_{0-3}$ alkylene-$NR^4C(O)R^5$;

R is
- $C_{1-6}$ alkyl,
- $C_{2-6}$ alkenyl,
- $C_{1-6}$ hydroxyalkyl,
- $C_{1-6}$ haloalkyl,
- $C_{1-6}$ alkyl substituted by $C_{1-3}$ alkoxy or cyano,
- $C_{0-2}$ alkylene-$C_{3-8}$ cycloalkyl optionally substituted with $C_{1-3}$ alkyl, or
- a 4-5 membered heterocycle optionally substituted with $C_{1-3}$ alkyl;

$R^a$ and $R^b$, together with the C-atoms to which they are attached, form a fused phenyl ring that is optionally substituted by one or more substituents selected from $C_{1-3}$ alkyl, $C_{1-3}$ haloalkyl, cyano and halo, or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl;

$R^1$ is selected from hydrogen, OH, halogen, CN, $C_{1-6}$ alkyl, $C_{2-6}$ alkenyl, $C_{2-6}$ alkynyl, $C_{1-6}$ haloalkyl, $C_{0-3}$ alkylene-$C_{3-6}$ cycloalkyl, $C_{0-3}$ alkylene-O—$C_{1-3}$ alkylene-$C_{3-6}$ cycloalkyl, $C_{1-6}$ alkoxy, $C_{1-6}$ haloalkoxy, $C_{1-6}$ hydroxyalkyl, $C_{0-3}$ alkylene-$SO_2C_{1-3}$alkyl, $C_{0-3}$ alkylene-$SO_2NR^4R^5$, and $C_{0-3}$ alkylene-$NR^6R^7$ and $C_{0-3}$ alkylene-$NCOR^6R^7$;

$R^2$ and $R^3$ are each independently selected from H, $C_{1-8}$ alkyl, $C_{0-6}$ alkylene aryl, $C_{0-6}$ alkylene heteroaryl, $C_{0-6}$ alkylene-4-10 membered heterocycle, and $C_{0-3}$ alkylene-O—$C_{0-6}$ alkylene-4-10 membered heterocycle with the proviso that when the said heterocycle is linked through nitrogen there are at least two C-atoms in the alkylene chain that links that nitrogen atom to the essential O atom of the substituent, wherein independently each alkyl or alkylene group optionally bears 1 oxo substituent, and optionally one or two carbon atoms in the alkyl or alkylene chain may each be replaced by a heteroatom selected from O, N or $S(O)_p$, such that when said alkyl or alkylene comprises an amine said amino group is a tertiary amine, wherein each 4-10 membered heterocycle is optionally substituted by 1 or 2 groups independently selected from halo, OH, $C_{1-6}$ alkyl, $C_{1-4}$ haloalkyl, $C_{0-3}$ alkylene-O—$C_{0-6}$ alkyl, $C_{0-3}$ alkylene-O—$C_{1-3}$ haloalkyl, $C_{0-6}$ alkylene aryl, $C_{0-3}$ alkylene-O—$C_{0-3}$ alkylene aryl, $C_{0-6}$ alkylene heteroaryl, $C_{0-3}$ alkylene-O—$C_{0-3}$ alkylene heteroaryl, $C(O)C_{1-6}$ alkyl, $SO_2NR^8R^9$, and $C_{0-3}$ alkylene-$NR^8R^9$, $C_{0-3}$ alkylene-$NR^8SO_2R^9$ and $C_{0-3}$ alkylene-$NR^8C(O)R^9$;

$R^4$ is H or $C_{1-4}$ alkyl;

$R^5$ is H or $C_{1-4}$ alkyl, $R^6$ is H or $C_{1-4}$ alkyl, $C(O)C_{1-3}$alkyl and $SO_2C_{1-3}$alkyl;

$R^7$ is H or $C_{1-4}$ alkyl, $C(O)C_{1-3}$alkyl and $SO_2C_{1-3}$alkyl;

$R^8$ is H or $C_{1-4}$ alkyl, and $R^9$ is H or $C_{1-4}$ alkyl, p is 0, 1 or 2 or a pharmaceutically acceptable salt thereof, including all stereoisomers and tautomers thereof.

Compounds of the invention are inhibitors of p38 MAP kinase especially of the alpha sub-type.

In at least some embodiments compounds of the present invention have low B-Raf binding, for example less than 40% inhibition of the kinase binding at 500 nM, such as 30% inhibition or less in an assay such as the Kinomescan method.

B-Raf is a member of the Raf kinase family of serine/threonine-specific protein kinases. This protein plays a role in regulating the MAP kinase/ERKs signalling pathway, which affects cell division, differentiation, and secretion. A mutation of the gene has been associated with cancer in humans (Davies, H. et al., *Nature*, 2002, 417(6892):949-54).

Cell signalling can bypass selective inhibition of B-Raf with undesirable consequences (Lo, R. S., *Cell Research*, advance online publication 8 May 2012; doi: 10.1038/cr.2012.78). It is therefore preferable that kinase inhibitors intended for use as anti-inflammatory medicines should have minimal potential to interact with B-Raf.

The present compounds also display low affinity for GSK3α kinase in binding assays, which is considered to be beneficial in a therapeutic context, in particular in relation to minimising toxicity in vivo.

In at least some embodiments, compounds of the present invention have p59-HCK inhibitory activity which may also augment their advantageous therapeutic profile.

DETAILED DESCRIPTION OF THE INVENTION

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the or an oxygen atom (e.g. a single oxygen atom) is located within the alkyl chain, for example —$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule, for example —$C_{6-n}$alkyl-O—$C_{6-m}$alkyl in which n=1-5, m=1-5 and n+m=6-10. In one embodiment the alkoxy is linked through oxygen to the remainder of the molecule, for example —$OC_{1-6}$ alkyl. In one embodiment the disclosure relates to straight chain alkoxy. In one embodiment the alkoxy is linked through oxygen to the remainder of the molecule but the alkoxy group contains a further oxygen atom, for example —$OCH_2CH_2OCH_3$.

Halo or halogen includes fluoro, chloro, bromo or iodo, in particular fluoro, chloro or bromo, especially fluoro or chloro.

Alkyl substituted by halo (haloalkyl) as employed herein refers to alkyl groups having 1 to 6 halogen atoms, for example 1 to 5 halogens, such as per haloalkyl, in particular perfluoroalkyl, more specifically —$CF_2CF_3$ or $CF_3$.

Alkyl substituted by hydroxy (hydroxyalkyl) as employed herein refers to alkyl groups having 1 to 3 hydroxy groups, for example 1 or 2 hydroxy substituents thereon, for example —$CH_2CH_2OH$, —$C(CH_3)CH_2OH$, —$C(CH_3)_2CH_2OH$ or similar.

Alkoxy substituted by halo (haloalkoxy) as employed herein refers to alkoxy groups having 1 to 6 halogen atoms, for example 1 to 5 halogens, such as per haloalkoxy, in particular perfluoroalkoxy, more specifically —$OCF_2CF_3$ or —$OCF_3$.

Unless otherwise specified, alkylene as employed herein is a straight chain or branched chain carbon linking group, for example comprising methylenes, between two other moieties. It will be clear to those skilled in the art that groups defined as, for example $C_{2-8}$ alkenyl and $C_{2-8}$ alkynyl may comprise an alkylene portion. For the avoidance of doubt, the term "n-alkylene", when used herein, refers to straight chain alkylene.

It will be clear to persons skilled in the art that the heteroatom may replace a primary, secondary or tertiary carbon, that is a CH$_3$, —CH$_2$— or a —CH—, group, as technically appropriate and hydrogen or branching in the alkyl or alkylene chain will fill the valency of the heteroatom as appropriate to the location, for example where a terminal primary carbon is replaced by an oxygen heteroatom the terminal group will be an alcohol.

C$_{1-6}$ alkyl includes C$_1$, C$_2$, C$_3$, C$_4$, C$_5$ and C$_6$.
C$_{1-6}$ alkoxy includes C$_1$, C$_2$, C$_3$, C$_4$, C$_5$ and C$_6$.

The term 5-10 membered heterocycle, as employed herein refers to a 5 to 10 membered saturated or partially unsaturated non-aromatic ring comprising one or more, for example 1, 2, 3 or 4 heteroatoms independently selected from O, N and S, wherein optionally one or two carbons in the ring may bear an oxo substituent. Any valencies of a heteroatom not employed in forming or retaining the ring structure may be filled by hydrogen or a substituent, as appropriate. Thus the optional substituents on the heterocycles may be attached to a carbon or on a heteroatom, such as nitrogen as appropriate. Examples of 5-10 membered heterocycles include, pyrroline, pyrrolidine, tetrahydrofuran, thiepane, oxepane piperidine, piperazine, morpholine, thiomorpholine, dioxane, tetrahydrothiophene, pyrazoline, imidazoline, pyrazolidine, oxoimidazolidine, dioxolane, thiazolidine, isoxazolidine, dihydropyran, dihydroindene, dihydroisobenzofuran, isoindolin-1-one, chroman, 1,2,3,4-tetrahydroquinoline, 2,3-dihydrobenzo[b][1,4]dioxineazocane, and the like.

The term 5-6 membered heterocycle as employed herein refers to a 5 to 6 membered saturated or partially unsaturated non-aromatic ring comprising one or more, for example 1, 2, 3 or 4 heteroatoms independently selected from O, N and S wherein optionally one or two carbons in the ring may bear an oxo substituent. The definition of C$_{5-6}$ heterocycle as employed herein refers to a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substituent. Clearly any valencies of a heteroatom not employed in forming or retaining the ring structure may be filled by hydrogen or a substituent, as appropriate. Thus substituents on heterocycles may be on carbon or on a heteroatom, such as N as appropriate. Examples of heterocycles and C$_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

When employed herein, the group morpholinyl suitably represents N-morpholinyl.

In one embodiment there is provided a compound of formula (Ia1) or, particularly, formula (Ia2):

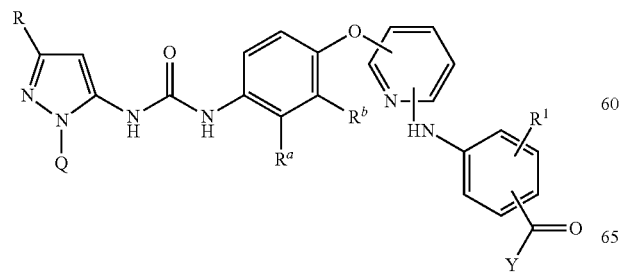

(Ia1)

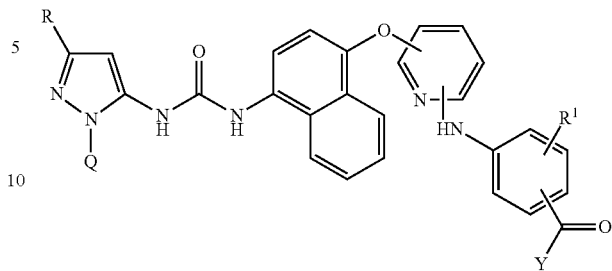

(Ia2)

wherein R, R$^a$, R$^b$, R$^1$, Q and Y are defined as above for compounds of formula (I).

In one embodiment there is provided a compound of formula (Ib1) or, particularly, formula (Ib2):

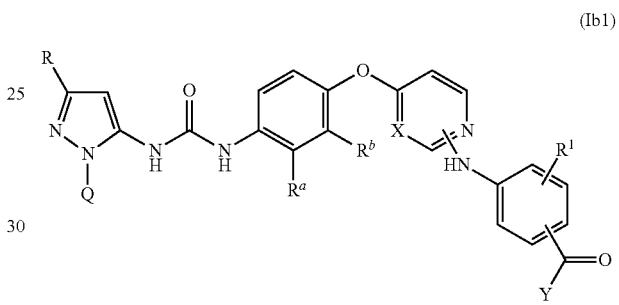

(Ib1)

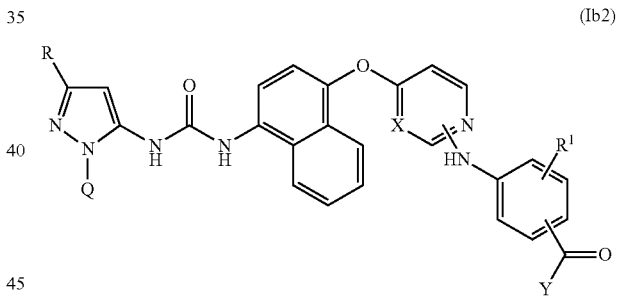

(Ib2)

wherein R, R$^a$, R$^b$, R$^1$, Q, X and Y are defined above for compounds of formula (I)

In one embodiment there is provided a compound of formula (Ic1) or, particularly, formula (Ic2):

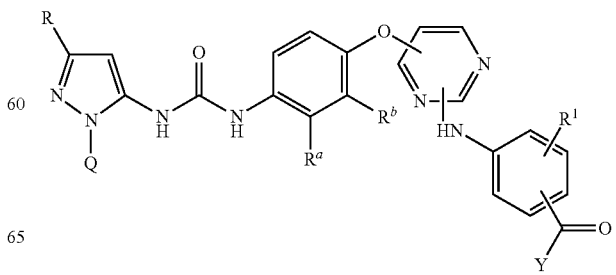

(Ic1)

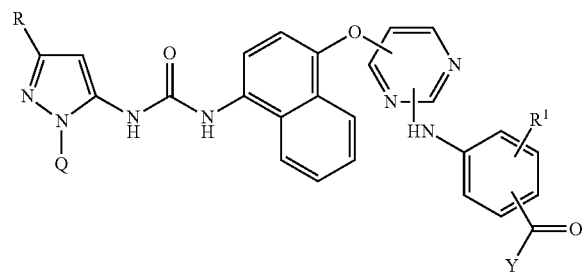
(Ic2)

wherein R, $R^a$, $R^b$, $R^1$, Q and Y are defined above for compounds of formula (I).

In one embodiment there is provided a compound of formula (Id1) or, particularly, formula (Id2):

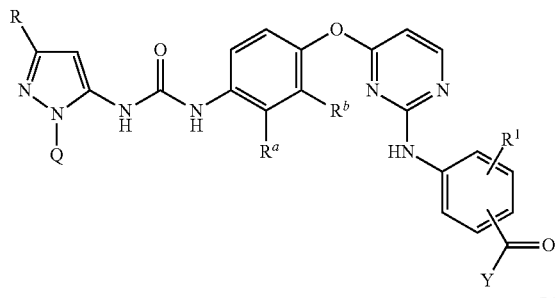
(Id1), (Id2)

wherein R, $R^a$, $R^b$, $R^1$, Q and Y are defined above for compounds of formula (I).

In one embodiment there is provided a compound of formula (Ie1) or, particularly, formula (Ie2):

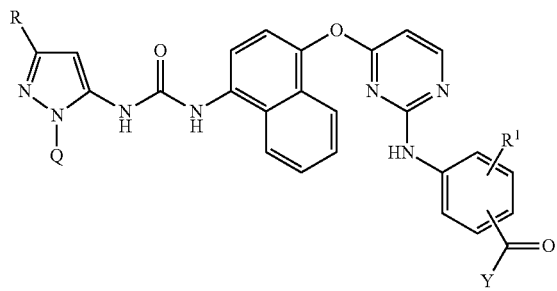
(Ie1)

(Ie2)

wherein R, $R^a$, $R^b$, $R^1$, Q and Y are defined above for compounds of formula (I).

In one embodiment there is provided a compound of formula (If1) or, particularly, formula (If2):

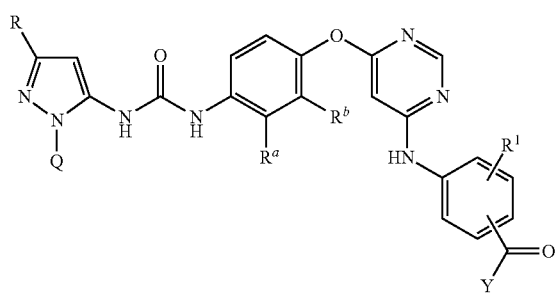
(If1), (If2)

wherein R, $R^a$, $R^b$, $R^1$, Q and Y are defined above for compounds of formula (I).

In one embodiment there is provided a compound of formula (Ig1) or, particularly, formula (Ig2):

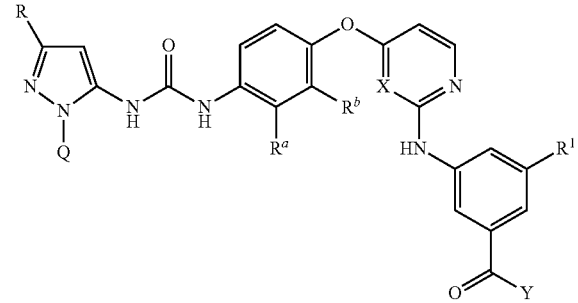
(Ig1)

-continued (Ig2)

wherein R, $R^a$, $R^b$, $R^1$, X, Q and Y are as defined above for compounds of formula (I).

In one embodiment there is provided a compound of formula (Ih1) or, particularly, formula (Ih2):

(Ih1)

(Ih2)

wherein R, $R^a$, $R^b$, $R^1$, X, Q and Y are as defined above for compounds of formula (I).

Generally in substituents such $C_{0-3}$ alkylene-O—$C_{0-6}$ alkylene-5-10 membered heterocycle, for example as defined for $R^2$ or $R^3$, when the said heterocycle is linked through nitrogen the group will then be defined as $C_{0-3}$ alkylene-O—$C_{2-6}$ alkylene-5-10 membered heterocycle.

Generally when Q comprises a phenyl or pyridine substituted with a $C_{1-6}$ alkylene-5-10 membered heterocycle or $C_{0-3}$ alkylene-O—$C_{0-6}$ alkylene-5-10 membered heterocycle then $R^2$ and $R^3$ are independently selected from H, $C_{1-8}$ alkyl, wherein independently each alkyl or alkylene group optionally bears 1 oxo substituent, and optionally up to two carbon atoms in the alkyl or alkylene chain may be replaced by a heteroatom selected from O, N or S(O)$_p$, such that when alkyl or alkylene comprises an amine said amino group is a tertiary amine.

In one embodiment Q represents phenyl bearing one or two substituents independently selected from hydroxyl, halogen, $C_{1-6}$ alkyl, $C_{1-6}$ alkoxy, $C_{1-6}$ haloalkoxy, $C_{1-6}$ hydroxyalkyl, N($C_{1-6}$ alkyl)$_2$, $C_{1-6}$ alkylene-5-10 membered heterocycle and $C_{0-3}$ alkylene-O—$C_{1-6}$ alkylene-5-10 membered heterocycle (e.g. one or two substituents independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle).

In one embodiment Q represents phenyl bearing a methyl, methoxy, —N(CH$_3$)$_2$ or —OCH$_2$CH$_2$OCH$_3$ (e.g. methyl, methoxy, or —OCH$_2$CH$_2$OCH$_3$), for example one of said substituents, in particular in the para position.

In one embodiment Q is dimethyl phenyl, for example where the methyl substituents are in the meta and para position.

In one embodiment Q represents pyridinyl bearing one substituent independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle.

In one embodiment Q is methoxypyridinyl, for example 6-methoxypyridin-3-yl.

In one embodiment Q represents thienyl optionally bearing one substituent independently selected from hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{1-6}$ alkylene-5-10 membered heterocycle.

In one embodiment Y is NR$^2$R$^3$.

In one embodiment Y is a 5-10 membered heterocycle, for example a 6 membered heterocyle bearing a $C_{1-6}$ alkyl substituent.

In one embodiment Y is morpholinyl, piperazinyl or (methyl)piperazinyl, for example 4-methyl piperazin-1-yl.

In one embodiment R is ethyl, isopropyl, tert-butyl, cyclopropyl, 1-methylcyclopropyl, propen-2-yl, CF$_3$, C$_2$F$_5$, oxetanyl, (methyl)oxetanyl or tetrahydrofuranyl (e.g. ethyl, isopropyl, tert-butyl, cyclopropyl, 1-methylcyclopropyl, CF$_3$, C$_2$F$_5$, oxetanyl, (methyl)oxetanyl or tetrahydrofuranyl), such as isopropyl or tert-butyl.

In one embodiment R is C(CH$_3$)$_2$CH$_2$OH or CH(CH$_3$)CH$_2$OH.

In one embodiment R is 1-hydroxy-2-methylpropan-2-yl.

In one embodiment R$^1$ is H, Br, Cl, CH$_3$, CN, N(CH$_3$)$_2$, CF$_3$, ethynyl, OCH$_3$, OCH$_2$CH$_3$ or OCH$_2$(CH$_3$)$_2$.

Generally the atoms of the substituents R$^2$ and R$^3$, in the group NR$^2$R$^3$, which are bonded to the nitrogen are independently selected from hydrogen and carbon.

In one embodiment R$^2$ is H, CH$_3$, —CH$_2$CH$_2$CH$_3$, —(CH$_2$)$_2$OH, —(CH$_2$)$_2$OCH$_3$, —(CH$_2$)$_2$N(CH$_3$)$_2$, —(CH$_2$)$_2$morpholinyl, —(CH$_2$)$_2$piperazinyl or —(CH$_2$)$_2$(4-methyl)piperazinyl.

In one embodiment R$^3$ is H or CH$_3$.
In one embodiment R$^4$ is H or methyl.
In one embodiment R$^5$ is H or methyl.
In one embodiment R$^6$ is H or methyl.
In one embodiment R$^7$ is H or methyl.
In one embodiment R$^8$ is H or methyl.
In one embodiment R$^9$ is H or methyl.

Embodiments of the invention that may be mentioned include compounds of formulae (I), (Ia1), (Ia2), (Ib1), (Ib2), (Ic1), (Ic2), (Id1), (Id2), (Ie1), (Ie2), (If1), (If2), (Ig1), (Ig2), (Ih1) and (Ih2) wherein:

Q represents phenyl bearing one or two substituents independently selected from hydroxyl, halogen, $C_{1-6}$ alkyl, $C_{1-6}$ alkoxy, $C_{1-6}$ haloalkoxy, $C_{1-6}$ hydroxyalkyl, N($C_{1-6}$ alkyl)$_2$, $C_{1-6}$ alkylene-5-10 membered heterocycle and $C_{0-3}$ alkylene-O—$C_{1-6}$ alkylene-5-10 membered heterocycle (e.g. Q represents phenyl mono-substituted (e.g. in the para position) by methyl, methoxy, —N(CH$_3$)$_2$ or —OCH$_2$CH$_2$OCH$_3$ or di-substituted (e.g. in the meta and para positions) by methyl), or Q represents pyridinyl bearing one substituent independently selected from hydroxyl, halogen, C$_{1-6}$ alkyl, C$_{1-6}$ alkoxy, C$_{1-6}$ haloalkoxy, C$_{1-6}$ hydroxyalkyl, C$_{1-6}$ alkylene-5-10 membered heterocycle and C$_{0-3}$ alkylene-O—C$_{1-6}$ alkylene-5-10 membered heterocycle (e.g. Q represents methoxypyridinyl, such as 6-methoxypyridin-3-yl);

R$^a$ and R$^b$, together with the C-atoms to which they are attached, form a fused phenyl ring, or one of R$^a$ and R$^b$ represents halo, C$_{1-3}$ alkyl or C$_{1-3}$ haloalkyl and the other independently represents halo, cyano, C$_{1-3}$ alkyl or C$_{1-3}$ haloalkyl (e.g. R$^a$ and R$^b$ both represent methyl, fluoro or chloro);

R represents
   C$_{1-6}$ alkyl optionally substituted by hydroxy, cyano or methoxy or by one or more fluoro groups,
   C$_{2-6}$ alkenyl or
   C$_{3-4}$ cycloalkyl, which latter group is optionally substituted by C$_{1-3}$ alkyl
(e.g. R represents ethyl, isopropyl, n-propyl, tert-butyl, cyclopropyl, 1-methylcyclopropyl, CF$_3$, C$_2$F$_5$, —C(CH$_3$)$_2$CF$_3$ oxetanyl, (methyl)oxetanyl, tetrahydrofuranyl or propen-2-yl, such as isopropyl, propen-2-yl or tert-butyl); and/or R$^1$ represents H, halogen (e.g. F, Br or Cl), CN, C$_{1-4}$ alkyl (e.g. methyl or ethyl), C$_{2-4}$ alkynyl (e.g. ethynyl), C$_{1-4}$ fluoroalkyl (e.g. CF$_3$), C$_{1-4}$ alkoxy (e.g. OCH$_3$, OCH$_2$CH$_3$ or OCH$_2$(CH$_3$)$_2$), or NR$^6$R$^7$ (e.g. N(CH$_3$)$_2$) (e.g. R$^1$ represents ethynyl or OCH$_3$).

More particular embodiments of the invention that may be mentioned include compounds of formulae (I), (Ia1), (Ia2), (Ib1), (Ib2), (Ic1), (Ic2), (Id1), (Id2), (Ie1), (Ie2), (If1), (If2), (Ig1), (Ig2), (Ih1) and (Ih2) wherein:

Q represents phenyl mono-substituted (e.g. in the para position) by C$_{1-6}$ alkyl (e.g. methyl), C$_{1-6}$ alkoxy (e.g. methoxy), C$_{1-6}$ haloalkoxy or N(C$_{1-6}$ alkyl)$_2$ (e.g. N(CH$_3$)$_2$) (for example, Q represents phenyl substituted in the para position by methyl, methoxy or dimethylamino);

R$^a$ and R$^b$, together with the C-atoms to which they are attached, form a fused phenyl ring;

R represents C$_{1-4}$ alkyl optionally substituted by one or more fluoro groups, C$_{3-4}$ alkenyl or C$_{3-4}$ cycloalkyl, which latter group is optionally substituted by methyl (e.g. R represents ethyl, cyclopropyl, CF$_3$, C$_2$F$_5$, —C(CH$_3$)$_2$CF$_3$ or, particularly, isopropyl, 1-methylcyclopropyl, propen-2-yl or tert-butyl); and/or R$^1$ represents Br, Cl, CN, methyl, ethyl, CF$_3$, OCH$_2$CH$_3$, OCH$_2$(CH$_3$)$_2$, N(CH$_3$)$_2$ or, particularly, ethynyl or OCH$_3$.

Particular embodiments of the invention include the following.

(1) A compound of formula (I), (Ia1), (Ia2), (Ib1), (Ib2), (Ic1), (Ic2), (Id1), (Id2), (Ie1), (Ie2), (If2), (Ig1), (Ig2), (Ih1) or (Ih2) as defined above, or a pharmaceutically acceptable salt thereof.

(2) A compound or salt according to Embodiment (1), wherein Q represents phenyl bearing one or two substituents independently selected from hydroxyl, halogen, C$_{1-6}$ alkyl, C$_{1-6}$ alkoxy, C$_{1-6}$ haloalkoxy, C$_{1-6}$ hydroxyalkyl, N(C$_{1-6}$ alkyl)$_2$, C$_{1-6}$ alkylene-5-10 membered heterocycle and C$_{0-3}$ alkylene-O—C$_{1-6}$ alkylene-5-10 membered heterocycle (e.g. one or two substituents independently selected from hydroxyl, halogen, C$_{1-6}$ alkyl, C$_{1-6}$ alkoxy, C$_{1-6}$ haloalkoxy, C$_{1-6}$ hydroxyalkyl, C$_{1-6}$ alkylene-5-10 membered heterocycle and C$_{0-3}$ alkylene-O—C$_{1-6}$ alkylene-5-10 membered heterocycle).

(3) A compound or salt according to Embodiment (1) or Embodiment (2), wherein Q represents phenyl bearing a methyl, methoxy, —N(CH$_3$)$_2$ or —OCH$_2$CH$_2$OCH$_3$ (e.g. a methyl, methoxy or —OCH$_2$CH$_2$OCH$_3$).

(4) A compound or salt according to any one of Embodiments (1) to (3), wherein Q represents phenyl substituted in the para position by methyl, methoxy, —N(CH$_3$)$_2$ or —OCH$_2$CH$_2$OCH$_3$ (e.g. by methyl, methoxy or —OCH$_2$CH$_2$OCH$_3$).

(5) A compound or salt according to any one of Embodiments (1) to (3), wherein Q is dimethyl phenyl, for example where the methyl substituents are in the meta and para position.

(7) A compound or salt according to Embodiment (1), wherein Q represents pyridinyl bearing one substituent independently selected from hydroxyl, halogen, C$_{1-6}$ alkyl, C$_{1-6}$ alkoxy, C$_{1-6}$ haloalkoxy, C$_{1-6}$ hydroxyalkyl, C$_{1-6}$ alkylene-5-10 membered heterocycle and C$_{0-3}$ alkylene-O—C$_{1-6}$ alkylene-5-10 membered heterocycle.

(8) A compound or salt according to Embodiment (7), wherein Q is methoxypyridinyl, for example 6-methoxypyridin-3-yl.

(9) A compound or salt according to Embodiment (1), wherein Q represents thienyl optionally bearing one substituent independently selected from hydroxyl, halogen, C$_{1-6}$ alkyl, C$_{1-6}$ alkoxy, C$_{1-6}$ haloalkoxy, C$_{1-6}$ hydroxyalkyl, C$_{1-6}$ alkylene-5-10 membered heterocycle and C$_{0-3}$ alkylene-O—C$_{1-6}$ alkylene-5-10 membered heterocycle.

(10) A compound or salt according to any one of Embodiments (1) to (9), wherein Y is NR$^2$R$^3$.

(11) A compound or salt according to any one of Embodiments (1) to (9), wherein Y is a 5-10 membered heterocycle, for example a 6 membered heterocyle bearing a C$_{1-6}$ alkyl substituent.

(12) A compound or salt according to Embodiment (11), wherein Y is morpholinyl, piperazinyl or (methyl)piperazinyl, for example 4-methyl piperazin-1-yl.

(13) A compound or salt according to any one of Embodiments (1) to (12), wherein R is ethyl, isopropyl, tert-butyl, cyclopropyl, 1-methylcyclopropyl, CF$_3$, C$_2$F$_5$, oxetanyl, (methyl)oxetanyl or tetrahydrofuranyl, such as isopropyl or tert-butyl.

(14) A compound or salt according to any one of Embodiments (1) to (12), wherein R is C(CH$_3$)$_2$CH$_2$OH or CH(CH$_3$)CH$_2$OH.

(15) A compound or salt according to any one of Embodiments (1) to (12), wherein R is 1-hydroxy-2-methylpropan-2-yl.

(16) A compound or salt according to any one of Embodiments (1) to (15), wherein R$^1$ is H, Br, Cl, CH$_3$, CN, N(CH$_3$)$_2$, CF$_3$, ethynyl, OCH$_3$, OCH$_2$CH$_3$ or OCH$_2$(CH$_3$)$_2$.

(17) A compound or salt according to any one of Embodiments (1) to (16), wherein R$^2$ is H, CH$_3$, —CH$_2$CH$_2$CH$_3$, —(CH$_2$)$_2$OH, —(CH$_2$)$_2$OCH$_3$, —(CH$_2$)$_2$N(CH$_3$)$_2$, —(CH$_2$)$_2$morpholinyl, —(CH$_2$)$_2$piperazinyl or —(CH$_2$)$_2$(4-methyl)piperazinyl.

(18) A compound or salt according to any one of Embodiments (1) to (17), wherein R$^3$ is H or CH$_3$.

(19) A compound or salt according to any one of Embodiments (1) to (18), wherein R$^4$ is H or methyl.

(20) A compound or salt according to any one of Embodiments (1) to (19), wherein R$^5$ is H or methyl.

(21) A compound or salt according to any one of Embodiments (1) to (20), wherein R$^6$ is H or methyl.

(22) A compound or salt according to any one of Embodiments (1) to (21), wherein $R^7$ is H or methyl.

(23) A compound or salt according to any one of Embodiments (1) to (22), wherein $R^8$ is H or methyl.

(24) A compound or salt according to any one of Embodiments (1) to (23), wherein $R^9$ is H or methyl.

(25) A compound or salt according to any one of Embodiments (1) and (10) to (24), wherein Q represents phenyl mono-substituted (e.g. in the para position) by $C_{1-6}$ alkyl (e.g. methyl), $C_{1-6}$ alkoxy (e.g. methoxy), $C_{1-6}$ haloalkoxy or $N(C_{1-6}$ alkyl$)_2$ (e.g. $N(CH_3)_2$).

(26) A compound or salt according to Embodiment (25), wherein Q represents phenyl substituted in the para position by methyl, methoxy or dimethylamino.

(27) A compound or salt according to any one of Embodiments (1) to (26), wherein $R^a$ and $R^b$, together with the C-atoms to which they are attached, form a fused phenyl ring.

(28) A compound or salt according to any one of Embodiments (1) to (10) and (13) to (27), wherein $R^3$ represents H.

(29) A compound or salt according to any one of Embodiments (1) to (12) and (16) to (28), wherein R represents $C_{1-4}$ alkyl optionally substituted by one or more fluoro groups, $C_{3-4}$ alkenyl or $C_{3-4}$ cycloalkyl, which latter group is optionally substituted by methyl (e.g. R represents ethyl, cyclopropyl, $CF_3$, $C_2F_5$, —$C(CH_3)_2CF_3$ or, particularly, isopropyl, 1-methylcyclopropyl, propen-2-yl or tert-butyl).

(30) A compound or salt according to any one of Embodiments (1) to (15) and (17) to (29), wherein $R^1$ represents Br, Cl, CN, methyl, ethyl, $CF_3$, $OCH_2CH_3$, $OCH_2(CH_3)_2$, $N(CH_3)_2$, ethynyl or $OCH_3$.

(31) A compound or salt according to Embodiment (30), wherein $R^1$ represents ethynyl or $OCH_3$.

(32) A compound or salt according to any one of Embodiments (1) to (31) above, wherein the compound has the structural formula

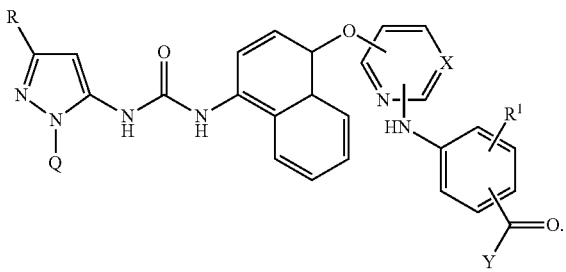

wherein:
Q represents thienyl, phenyl or pyridinyl, either of which may optionally bear 1 to 3 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $C_{1-6}$ alkylene-5-10 membered heterocycle and $C_{0-3}$ alkylene-O—$C_{0-6}$ alkylene-5-10 membered heterocycle;
R is $C_{1-6}$ alkyl, $C_{1-6}$ hydroxyalkyl, $C_{1-6}$ haloalkyl, $C_{0-2}$ alkylene-$C_{3-8}$ cycloalkyl optionally substituted with $C_{1-3}$ alkyl, $C_{1-6}$ haloalkyl or a 4-5 membered heterocycle optionally substituted with $C_{1-3}$ alkyl;
$R^2$ and $R^3$ are each independently selected from H, $C_{1-8}$ alkyl, $C_{0-6}$ alkylene aryl, $C_{0-6}$ alkylene heteroaryl, $C_{0-6}$ alkylene-4-10 membered heterocycle, and $C_{0-3}$ alkylene-O—$C_{0-6}$ alkylene-4-10 membered heterocycle with the proviso that when the said heterocycle is linked through nitrogen there are at least two C-atoms in the alkylene chain that links that nitrogen atom to the essential O atom of the substituent, wherein independently each alkyl or alkylene group optionally bears 1 oxo substituent, and optionally one or two carbon atoms in the alkyl or alkylene chain may each be replaced by a heteroatom selected from O, N or $S(O)_p$, such that when said alkyl or alkylene comprises an amine said amino group is a tertiary amine,
wherein each 4-10 membered heterocycle is optionally substituted by 1 or 2 groups independently selected from halo, OH, $C_{1-6}$ alkyl, $C_{1-4}$ haloalkyl, $C_{0-3}$ alkylene-O—$C_{0-6}$ alkyl, $C_{0-3}$ alkylene-O—$C_{1-3}$ haloalkyl, $C_{0-6}$ alkylene aryl, $C_{0-3}$ alkylene-O—$C_{0-3}$ alkylene aryl, $C_{0-6}$ alkylene heteroaryl, $C_{0-3}$ alkylene-O—$C_{0-3}$ alkylene heteroaryl, $C(O)C_{1-6}$ alkyl, $SO_2NR^8R^9$, and $C_{0-3}$ alkylene-$NR^8R^9$, $C_{0-3}$ alkylene-$NR^8SO_2R^9$ and $C_{0-3}$ alkylene-$NR^8C(O)R^9$.

(33) A compound or salt according to any one of Embodiments (1) to (31) above, wherein:
Q represents thienyl, phenyl or pyridinyl, either of which is substituted by $NH_2$, $N(H)$—$C_{1-6}$ alkyl or $N(C_{1-6}$ alkyl$)_2$ and is optionally further substituted by 1 or 2 substituents independently selected from, hydroxyl, halogen, $C_{1-6}$ alkyl, $C_{1-6}$ alkoxy, $C_{1-6}$ haloalkoxy, $C_{1-6}$ hydroxyalkyl, $NH_2$, $N(H)$—$C_{1-6}$ alkyl, $N(C_{1-6}$ alkyl$)_2$, $C_{1-6}$ alkylene-5-10 membered heterocycle and $C_{0-3}$ alkylene-O—$C_{0-6}$ alkylene-5-10 membered heterocycle;
R represents $C_{2-6}$ alkenyl (e.g. $C_{3-4}$ alkenyl, such as propen-2-yl) or $C_{1-6}$ alkyl substituted by $C_{1-3}$ alkoxy or cyano (e.g. secondary $C_{3-6}$ alkyl substituted by methoxy or cyano, such as —$C(CH_3)_2OCH_3$ or —$C(CH_3)_2CN$); and/or
$R^a$ and $R^b$, together with the C-atoms to which they are attached, form a fused phenyl ring that is substituted by one or more substituents selected from $C_{1-3}$ alkyl, $C_{1-3}$ haloalkyl, cyano and halo,
or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl.

(34) A compound or salt according to any one of Embodiments (1) to (33) above, wherein R represents:
$C_{1-6}$ n-alkyl,
$C_{4-6}$ branched alkyl,
$C_{2-6}$ alkenyl,
$C_{1-6}$ hydroxyalkyl,
$C_{1-6}$ haloalkyl,
$C_{1-6}$ alkyl substituted by $C_{1-3}$ alkoxy or cyano,
$C_{0-2}$ alkylene-$C_{3-8}$ cycloalkyl optionally substituted with $C_{1-3}$ alkyl, or
a 4-5 membered heterocycle optionally substituted with $C_{1-3}$ alkyl
(e.g. R represents ethyl, cyclopropyl, $CF_3$, $C_2F_5$, —$C(CH_3)_2CF_3$ or, particularly, 1-methylcyclopropyl, propen-2-yl or tert-butyl).

In one embodiment there is provided a compound of formula (I), (Ib2), (Ic2), (Id2) or (Ig2) as defined above, or a pharmaceutically acceptable salt thereof, wherein the compound is not 3-((4-((4-(3-(3-Isopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide or a pharmaceutically acceptable salt thereof.

In one embodiment there is provided a compound of formula (I), (Ib2), (Ic2), (Id2) or (Ig2) as defined above, or a pharmaceutically acceptable salt thereof, wherein the compound is not 3-((4-((4-(3-(3-Isopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide.

Exemplary compounds of formula (I) are selected from the group consisting of:

3-((4-((4-(3-(3-tert-butyl)-1-(p-tolyl)-1H-pyrazol-5-yl)ureido)naphthalen-1-yl)oxy)pyridin-2-yl)amino)-5-methoxy-N-(2-morpholinoethyl)benzamide;

3-((4-((4-(3-(3-tert-butyl)-1-(p-tolyl)-1H-pyrazol-5-yl)ureido)naphthalen-1-yl)oxy)pyrimidin-2-yl)amino)benzamide;

3-((4-((4-(3-(3-tert-butyl)-1-(p-tolyl)-1H-pyrazol-5-yl)ureido)naphthalen-1-yl)oxy)pyrimidin-2-yl)amino)-N-(2-morpholinoethyl)benzamide;

4-((4-((4-(3-(3-tert-butyl)-1-(p-tolyl)-1H-pyrazol-5-yl)ureido)naphthalen-1-yl)oxy)pyrimidin-2-yl)amino)-N-(2-hydroxyethyl)-3-methoxybenzamide;

N-(2-(dimethylamino)ethyl)-3-((4-((4-(3-(3-isopropyl-1-(p-tolyl)-1H-pyrazol-5-yl)ureido) naphthalen-1-yl)oxy)pyrimidin-2-yl)amino)-5-methoxybenzamide;

N-(2-(dimethylamino)ethyl)-3-((4-((4-(3-(3-isopropyl-1-(4-methoxyphenyl)-1H-pyrazol-5-yl) ureido)naphthalen-1-yl)oxy)pyrimidin-2-yl)amino)-5-methoxybenzamide;

3-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)-5-(trifluoromethyl)benzamide;

3-((4-((4-(3-(3-isopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide;

3-methoxy-N-(2-morpholinoethyl)-5-((4-((4-(3-(3-(perfluoroethyl)-1-(p-tolyl)-1H-pyrazol-5-yl) ureido)naphthalen-1-yl)oxy)pyrimidin-2-yl)amino)benzamide;

3-((4-((4-(3-(3-isopropyl-1-(6-methoxypyridin-3-yl)-1H-pyrazol-5-yl)ureido)naphthalen-1-yl)oxy)pyrimidin-2-yl)amino)-5-methoxy-N-(2-morpholinoethyl)benzamide;

3-((4-((4-(3-(3-isopropyl-1-(4-methoxyphenyl)-1H-pyrazol-5-yl)ureido)naphthalen-1-yl)oxy) pyrimidin-2-yl)amino)-5-methoxy-N-(2-methoxyethyl)benzamide;

1-isopropyl-1-(p-tolyl)-1H-pyrazol-5-yl)-3-(4-((2-((3-methoxy-5-(morpholine-4-carbonyl)phenyl)amino)pyrimidin-4-yl)oxy)naphthalen-1-yl)urea;

5-((4-((4-(3-(3-tert-butyl)-1-(p-tolyl)-1H-pyrazol-5-yl)ureido)naphthalen-1-yl)oxy)pyrimidin-2-yl)amino)-2-methoxy-N-(2-morpholinoethyl)benzamide;

3-((6-((4-(3-(3-isopropyl-1-(4-methoxyphenyl)-1H-pyrazol-5-yl)ureido)naphthalen-1-yl)oxy) pyrimidin-4-yl)amino)-5-methoxy-N-(2-morpholinoethyl)benzamide;

3-((4-((4-(3-(3-isopropyl-1-(4-methoxyphenyl)-1H-pyrazol-5-yl)ureido)naphthalen-1-yl)oxy)pyridin-2-yl)amino)-5-methoxy-N-(2-morpholinoethyl)benzamide;

3-((4-((4-(3-(3-tert-butyl)-1-(p-tolyl)-1H-pyrazol-5-yl)ureido)naphthalen-1-yl)oxy)pyrimidin-2-yl)amino)-N-methylbenzamide;

3-(4-(4-(3-(3-tert-butyl)-1-(4-methoxyphenyl)-1H-pyrazol-5-yl)ureido)naphthalen-1-yloxy) pyrimidin-2-ylamino)-N-propylbenzamide;

3-((4-((4-(3-(3-tert-butyl)-1-(p-tolyl)-1H-pyrazol-5-yl)ureido)naphthalen-1-yl)oxy)pyrimidin-2-yl)amino)-N-(2-(dimethylamino)ethyl)benzamide;

3-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide;

3-((4-((4-(3-(3-isopropyl-1-(4-methoxyphenyl)-1H-pyrazol-5-yl)ureido)naphthalen-1-yl)oxy) pyrimidin-2-yl)amino)-N-(2-morpholinoethyl)benzamide;

3-((4-((4-(3-(3-tert-butyl)-1-(4-methoxyphenyl)-1H-pyrazol-5-yl)ureido)naphthalen-1-yl)oxy) pyrimidin-2-yl)amino)-N-(2-morpholinoethyl)benzamide;

3-((4-((4-(3-(3-(3-methyloxetan-3-yl)-1-(p-tolyl)-1H-pyrazol-5-yl)ureido)naphthalen-1-yl)oxy) pyrimidin-2-yl)amino)-N-(2-morpholinoethyl)benzamide;

3-((4-((4-(3-(1-(4-methoxyphenyl)-3-(3-methyloxetan-3-yl)-1H-pyrazol-5-yl)ureido)naphthalen-1-yl)oxy)pyrimidin-2-yl)amino)-N-(2-morpholinoethyl)benzamide;

3-((4-((4-(3-(3-tert-butyl)-1-(4-methylthiophen-2-yl)-1H-pyrazol-5-yl)ureido)naphthalen-1-yl)oxy)pyrimidin-2-yl)amino)-N-(2-morpholinoethyl)benzamide;

3-((4-((4-(3-(3-tert-butyl)-1-(p-tolyl)-1H-pyrazol-5-yl)ureido)naphthalen-1-yl)oxy)pyrimidin-2-yl)amino)-N-(2-(4-methylpiperazin-1-yl)ethyl)benzamide;

3-((4-((4-(3-(3-tert-butyl)-1-(p-tolyl)-1H-pyrazol-5-yl)ureido)naphthalen-1-yl)oxy)pyrimidin-2-yl)amino)-N,N-dimethylbenzamide;

1-(3-(tert-butyl)-1-(p-tolyl)-1H-pyrazol-5-yl)-3-(4-((2-((3-(morpholine-4-carbonyl)phenyl)amino) pyrimidin-4-yl)oxy)naphthalen-1-yl)urea;

N-(2-(dimethylamino)ethyl)-3-((4-((4-(3-(3-isopropyl-1-(p-tolyl)-1H-pyrazol-5-yl)ureido) naphthalen-1-yl)oxy)pyrimidin-2-yl)amino)-4-methoxybenzamide;

3-((4-((4-(3-(3-tert-butyl)-1-(p-tolyl)-1H-pyrazol-5-yl)ureido)naphthalen-1-yl)oxy)pyrimidin-2-yl)amino)-N-(2-(dimethylamino)ethyl)-4-methoxybenzamide;

3-((4-((4-(3-(3-isopropyl-1-(p-tolyl)-1H-pyrazol-5-yl)ureido)naphthalen-1-yl)oxy)pyrimidin-2-yl)amino)-4-methoxy-N-(2-morpholinoethyl)benzamide;

3-((4-((4-(3-(3-tert-butyl)-1-(p-tolyl)-1H-pyrazol-5-yl)ureido)naphthalen-1-yl)oxy)pyrimidin-2-yl)amino)-4-methoxy-N-(2-morpholinoethyl)benzamide;

N-(2-hydroxyethyl)-3-((4-((4-(3-(3-isopropyl-1-(p-tolyl)-1H-pyrazol-5-yl)ureido)naphthalen-1-yl)oxy)pyrimidin-2-yl)amino)-4-methoxybenzamide;

3-((4-((4-(3-(3-tert-butyl)-1-(p-tolyl)-1H-pyrazol-5-yl)ureido)naphthalen-1-yl)oxy)pyrimidin-2-yl)amino)-N-(2-hydroxyethyl)-4-methoxybenzamide;

N-(2-hydroxyethyl)-3-((4-((4-(3-(3-isopropyl-1-(4-methoxyphenyl)-1H-pyrazol-5-yl)ureido) naphthalen-1-yl)oxy)pyrimidin-2-yl)amino)-4-methoxybenzamide;

N-(2-(dimethylamino)ethyl)-4-((4-((4-(3-(3-isopropyl-1-(p-tolyl)-1H-pyrazol-5-yl)ureido) naphthalen-1-yl)oxy)pyrimidin-2-yl)amino)-3-methoxybenzamide;

4-((4-((4-(3-(3-isopropyl-1-(p-tolyl)-1H-pyrazol-5-yl)ureido)naphthalen-1-yl)oxy)pyrimidin-2-yl)amino)-3-methoxy-N-(2-morpholinoethyl)benzamide;

4-((4-((4-(3-(3-tert-butyl)-1-(p-tolyl)-1H-pyrazol-5-yl)ureido)naphthalen-1-yl)oxy)pyrimidin-2-yl)amino)-3-methoxy-N-(2-morpholinoethyl)benzamide;

4-((4-((4-(3-(3-isopropyl-1-(4-methoxyphenyl)-1H-pyrazol-5-yl)ureido)naphthalen-1-yl)oxy) pyrimidin-2-yl)amino)-3-methoxy-N-(2-morpholinoethyl)benzamide;

N-(2-hydroxyethyl)-4-((4-((4-(3-(3-isopropyl-1-(p-tolyl)-1H-pyrazol-5-yl)ureido)naphthalen-1-yl)oxy)pyrimidin-2-yl)amino)-3-methoxybenzamide;

3-((4-((4-(3-(3-tert-butyl)-1-(p-tolyl)-1H-pyrazol-5-yl)ureido)naphthalen-1-yl)oxy)pyrimidin-2-yl)amino)-5-methylbenzamide;

3-((4-((4-(3-(3-tert-butyl)-1-(4-methoxyphenyl)-1H-pyrazol-5-yl)ureido)naphthalen-1-yl)oxy) pyrimidin-2-yl)amino)-5-methoxybenzamide;

3-bromo-5-((4-((4-(3-(3-(tert-butyl)-1-(4-methoxyphenyl)-1H-pyrazol-5-yl)ureido)naphthalen-1-yl)oxy)pyrimidin-2-yl)amino)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)-5-methoxybenzamide;

3-((4-((4-(3-(3-isopropyl-1-(p-tolyl)-1H-pyrazol-5-yl)ureido)naphthalen-1-yl)oxy)pyrimidin-2-yl)amino)-5-methyl-N-(2-morpholinoethyl)benzamide;

3-((4-((4-(3-(3-isopropyl-1-(4-methoxyphenyl)-1H-pyrazol-5-yl)ureido)naphthalen-1-yl)oxy) pyrimidin-2-yl)amino)-5-methyl-N-(2-morpholinoethyl)benzamide;

3-((4-((4-(3-(3-isopropyl-1-(4-methoxyphenyl)-1H-pyrazol-5-yl)ureido)naphthalen-1-yl)oxy) pyrimidin-2-yl)amino)-N-(2-morpholinoethyl)-5-(trifluoromethyl)benzamide;

3-methoxy-N-(2-morpholinoethyl)-5-((4-((4-(3-(1-(p-tolyl)-3-(trifluoromethyl)-1H-pyrazol-5-yl)ureido)naphthalen-1-yl)oxy)pyrimidin-2-yl)amino)benzamide;

3-((4-((4-(3-(3-ethyl-1-(p-tolyl)-1H-pyrazol-5-yl)ureido)naphthalen-1-yl)oxy)pyrimidin-2-yl)amino)-5-methoxy-N-(2-morpholinoethyl)benzamide;

3-((4-((4-(3-(3-cyclopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide;

3-methoxy-5-((4-((4-(3-(3-(1-methylcyclopropyl)-1-(p-tolyl)-1H-pyrazol-5-yl)ureido)naphthalen-1-yl)oxy)pyrimidin-2-yl)amino)-N-(2-morpholinoethyl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-methoxy-N-(2-morpholinoethyl)benzamide;

3-((4-((4-(3-(3-isopropyl-1-(4-methoxyphenyl)-1H-pyrazol-5-yl)ureido)naphthalen-1-yl)oxy) pyrimidin-2-yl)amino)-5-methoxy-N-(2-morpholinoethyl)benzamide;

3-((4-((4-(3-(3-(tert-butyl)-1-(4-methoxyphenyl)-1H-pyrazol-5-yl)ureido)naphthalen-1-yl)oxy) pyrimidin-2-yl)amino)-5-methoxy-N-(2-morpholinoethyl)benzamide;

3-((4-((4-(3-(3-(tert-butyl)-1-(3-(2-methoxyethoxy)phenyl)-1H-pyrazol-5-yl)ureido)naphthalen-1-yl)oxy)pyrimidin-2-yl)amino)-5-methoxy-N-(2-morpholinoethyl)benzamide;

3-((4-((4-(3-(1-(3,4-dimethylphenyl)-3-isopropyl-1H-pyrazol-5-yl)ureido)naphthalen-1-yl)oxy) pyrimidin-2-yl)amino)-5-methoxy-N-(2-morpholinoethyl)benzamide;

3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)-5-methoxy-N-(2-morpholinoethyl)benzamide;

3-methoxy-5-((4-((4-(3-(1-(4-methoxyphenyl)-3-(tetrahydrofuran-2-yl)-1H-pyrazol-5-yl)ureido) naphthalen-1-yl)oxy)pyrimidin-2-yl)amino)-N-(2-morpholinoethyl)benzamide;

3-methoxy-5-((4-((4-(3-(1-(4-methoxyphenyl)-3-(tetrahydrofuran-3-yl)-1H-pyrazol-5-yl)ureido) naphthalen-1-yl)oxy)pyrimidin-2-yl)amino)-N-(2-morpholinoethyl)benzamide;

3-chloro-5-((4-((4-(3-(3-isopropyl-1-(p-tolyl)-1H-pyrazol-5-yl)ureido)naphthalen-1-yl)oxy) pyrimidin-2-yl)amino)-N-(2-morpholinoethyl)benzamide;

3-chloro-5-((4-((4-(3-(3-isopropyl-1-(4-methoxyphenyl)-1H-pyrazol-5-yl)ureido)naphthalen-1-yl)oxy)pyrimidin-2-yl)amino)-N-(2-morpholinoethyl)benzamide;

3-bromo-5-((4-((4-(3-(3-(tert-butyl)-1-(p-tolyl)-1H-pyrazol-5-yl)ureido)naphthalen-1-yl)oxy) pyrimidin-2-yl)amino)-N-(2-morpholinoethyl)benzamide;

N-(2-hydroxyethyl)-3-((4-((4-(3-(3-isopropyl-1-(p-tolyl)-1H-pyrazol-5-yl)ureido)naphthalen-1-yl)oxy)pyrimidin-2-yl)amino)-5-methoxybenzamide;

3-((4-((4-(3-(3-(tert-butyl)-1-(p-tolyl)-1H-pyrazol-5-yl)ureido)naphthalen-1-yl)oxy)pyrimidin-2-yl)amino)-N-(2-hydroxyethyl)-5-methoxybenzamide;

N-(2-hydroxyethyl)-3-((4-((4-(3-(3-isopropyl-1-(4-methoxyphenyl)-1H-pyrazol-5-yl)ureido) naphthalen-1-yl)oxy)pyrimidin-2-yl)amino)-5-methoxybenzamide;

3-((4-((4-(3-(3-isopropyl-1-(p-tolyl)-1H-pyrazol-5-yl)ureido)naphthalen-1-yl)oxy)pyrimidin-2-yl)amino)-5-methoxy-N-(2-methoxyethyl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-methoxy-N-(2-methoxyethyl)benzamide;

3-((4-((4-(3-(3-isopropyl-1-(p-tolyl)-1H-pyrazol-5-yl)ureido)naphthalen-1-yl)oxy)pyrimidin-2-yl)amino)-5-methoxy-N-methyl-N-(2-morpholinoethyl)benzamide;

1-(3-isopropyl-1-(p-tolyl)-1H-pyrazol-5-yl)-3-(4-((2-((3-methoxy-5-(4-methylpiperazine-1-carbonyl)phenyl) amino)pyrimidin-4-yl)oxy)naphthalen-1-yl)urea, 5-((4-((4-(3-(3-isopropyl-1-(p-tolyl)-1H-pyrazol-5-yl)ureido)naphthalen-1-yl)oxy)pyrimidin-2-yl)amino)-2-methoxy-N-(2-morpholinoethyl)benzamide;

3-((6-((4-(3-(3-isopropyl-1-(p-tolyl)-1H-pyrazol-5-yl)ureido)naphthalen-1-yl)oxy)pyrimidin-4-yl)amino)-5-methoxy-N-(2-morpholinoethyl)benzamide;

3-((6-((4-(3-(3-(tert-butyl)-1-(p-tolyl)-1H-pyrazol-5-yl)ureido)naphthalen-1-yl)oxy)pyrimidin-4-yl)amino)-5-methoxy-N-(2-morpholinoethyl)benzamide;

3-ethynyl-5-((4-((4-(3-(3-isopropyl-1-(p-tolyl)-1H-pyrazol-5-yl)ureido)naphthalen-1-yl)oxy) pyrimidin-2-yl)amino)-N-(2-morpholinoethyl)benzamide;

3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)-5-ethynyl-N-(2-morpholinoethyl)benzamide;

3-ethynyl-N-(2-morpholinoethyl)-5-((4-((4-(3-(3-(perfluoroethyl)-1-(p-tolyl)-1H-pyrazol-5-yl)ureido)naphthalen-1-yl)oxy)pyrimidin-2-yl)amino)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-morpholinoethyl)benzamide;

3-ethynyl-N-(2-morpholinoethyl)-5-((4-((4-(3-(1-(p-tolyl)-3-(1,1,1-trifluoro-2-methylpropan-2-yl)-1H-pyrazol-5-yl)ureido)naphthalen-1-yl)oxy)pyrimidin-2-yl)amino)benzamide;

3-((4-((4-(3-(3-(tert-butyl)-1-(4-methoxyphenyl)-1H-pyrazol-5-yl)ureido)naphthalen-1-yl)oxy)pyrimidin-2-yl)amino)-5-ethynyl-N-(2-morpholinoethyl)benzamide;

3-((4-((4-(3-(3-(2-cyanopropan-2-yl)-1-(p-tolyl)-1H-pyrazol-5-yl)ureido)naphthalen-1-yl)oxy)pyrimidin-2-yl)amino)-5-ethynyl-N-(2-morpholinoethyl)benzamide;

3-ethynyl-5-((4-((4-(3-(3-(2-methoxypropan-2-yl)-1-(p-tolyl)-1H-pyrazol-5-yl)ureido)-naphthalen-1-yl)oxy)pyrimidin-2-yl)amino)-N-(2-morpholinoethyl)benzamide;

3-((4-((4-(3-(3-(tert-butyl)-1-(4-(dimethylamino)phenyl)-1H-pyrazol-5-yl)ureido)naphthalen-1-yl)oxy)pyrimidin-2-yl)amino)-5-ethynyl-N-(2-morpholinoethyl)benzamide;

(S)-3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(1-morpholinopropan-2-yl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-methyl-1-morpholinopropan-2-yl)benzamide;

(R)-3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(1-morpholinopropan-2-yl)benzamide;

3-((4-((4-(3-(3-(tert-butyl)-1-(4-methoxyphenyl)-1H-pyrazol-5-yl)ureido)-naphthalen-1-yl)oxy)pyrimidin-2-yl)amino)-5-ethynyl-N-(2-methoxyethyl)benzamide;

(S)-3-((4-((4-(3-(3-(tert-butyl)-1-(4-methoxyphenyl)-1H-pyrazol-5-yl)ureido)-naphthalen-1-yl)oxy)pyrimidin-2-yl)amino)-5-ethynyl-N-(1-methoxypropan-2-yl)benzamide;

3-methoxy-5-((4-((4-(3-(1-(4-methoxyphenyl)-3-(prop-1-en-2-yl)-1H-pyrazol-5-yl)ureido)-naphthalen-1-yl)oxy)pyrimidin-2-yl)amino)-N-(2-morpholinoethyl)benzamide;

3-((4-(2,3-Dichloro-4-(3-(3-isopropyl-1-(p-tolyl)-1H-pyrazol-5-yl)ureido)phenoxy)pyrimidin-2-yl)amino)-5-ethynyl-N-(2-morpholinoethyl)benzamide;

3-((4-(2,3-Difluoro-4-(3-(3-isopropyl-1-(p-tolyl)-1H-pyrazol-5-yl)ureido)phenoxy)pyrimidin-2-yl)amino)-5-ethynyl-N-(2-morpholinoethyl)benzamide;

3-((4-(2,3-Dichloro-4-(3-(3-isopropyl-1-(p-tolyl)-1H-pyrazol-5-yl)ureido)phenoxy)pyrimidin-2-yl)amino)-5-ethynylbenzamide;

3-((4-(2,3-Dichloro-4-(3-(3-isopropyl-1-(p-tolyl)-1H-pyrazol-5-yl)ureido)phenoxy)pyrimidin-2-yl)amino)-N-(2-(dimethylamino)ethyl)-5-ethynylbenzamide;

3-((6-(4-(3-(3-(tert-butyl)-1-(4-methoxyphenyl)-1H-pyrazol-5-yl)ureido)-2,3-dimethylphenoxy)-pyrimidin-4-yl)amino)-5-methoxy-N-(2-morpholinoethyl)benzamide, and pharmaceutically acceptable salts thereof.

Thus in one embodiment the compound of the invention is 3-((4-((4-(3-(3-Isopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide or a pharmaceutically acceptable salt thereof.

The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

Stereoisomers as employed herein refers to isomeric molecules that have the same molecular formula and sequence of bonded atoms (constitution), but that differ only in the three-dimensional orientations of their atoms in space. This contrasts with structural isomers, which share the same molecular formula, but the bond connections and/or their order differ(s) between different atoms/groups. In stereoisomers, the order and bond connections of the constituent atoms remain the same, but their orientation in space differs.

As employed herein below the definition of compounds of formula (I) is intended to include all tautomers of said compounds, and solvates of said compounds (including solvates of salts of said compounds) unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from O-dealkylation.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

Generic routes by which compound examples of the invention may be conveniently prepared are summarised below. Those routes are specifically exemplified for compounds of formula (I) in which $R^a$ and $R^b$, together with the C-atoms to which they are attached, form a fused phenyl ring. However, compounds of formula (I) having other definitions of $R^a$ and $R^b$ may be prepared by analogous routes.

Thus, for example, compounds of formula (I) may be obtained by a general process (Scheme 1, Route A) whereby a naphthylamine precursor represented by Intermediate B is coupled with an activated, electrophilic derivative Intermediate A* prepared from the corresponding amine precursor, Intermediate A (G=H). The amine radical $NR^aR^b$ in compounds of Intermediate B either comprise the group Y, as defined for compounds of formula (I) above or a protected derivative of the same. The fragment $LG_1$ in Intermediate A* is a suitable leaving group such as an imidazolyl ($C_3H_3N_2$) or an aryloxy radical such as a phenoxy ($C_6H_5O$) group. It will be understood by persons skilled in the art that, in some instances, the compound represented by Intermediate A* may be isolated or in other cases may be a transient intermediate, that is not isolated, but generated in situ and used directly.

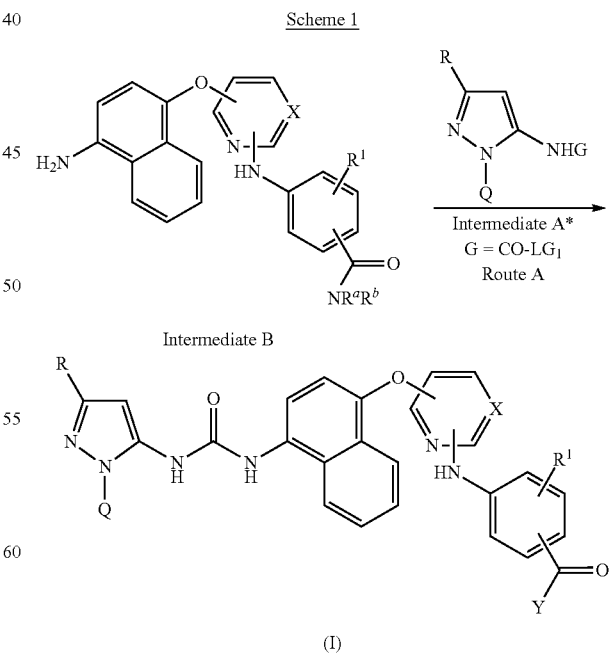

Scheme 1

In the case wherein $LG_1$ is imidazolyl, compounds represented by Intermediate A* are obtained by reaction of the corresponding amine with an activating agent such as CDI in a non-polar aprotic solvent, such as DCM and are conveniently generated in situ at RT and then reacted without isolation with compounds represented by Intermediate B.

In the case wherein $LG_1$ is aryloxy the required activated amine may be generated by treatment of the amine precursor with a suitable chloroformate, such as, for example, phenyl chloroformate, in the presence of a base. In some instances it is advantageous to conduct the activation process under Schotten-Baumann type conditions, that is using an aqueous base, such as aq sodium carbonate under biphasic conditions. The activated amine derivatives represented by Intermediate A* wherein $LG_1$ is aryloxy, for example phenoxy, may thereby be generated optionally in situ and then reacted without isolation with compounds represented by Intermediate B to provide compound examples of formula (I).

Compounds of formula (I) may include those in which the substituent Y incorporates one or more functional groups that have been protected during the coupling process and therefore require(s) subsequent deprotection. An example of such a procedure is the removal of a tert-butoxycarbonyl (Boc) group from a secondary amine, by treatment with an appropriate acid.

Alternatively, compound examples of formula (I) may be generated by an $S_NAr$ displacement reaction between an electrophilic heteroaryloxy fragment represented by Intermediate C, wherein $LG_2$ is a suitable leaving group, typically a halogen atom, for example chlorine, with an aniline component represented by Intermediate D (Scheme 2, Route B). The reaction proceeds under acidic conditions, for example in the presence of p-TSA and in a polar aprotic solvent such as THF and typically at elevated temperatures, for example at 70° C.

Scheme 2

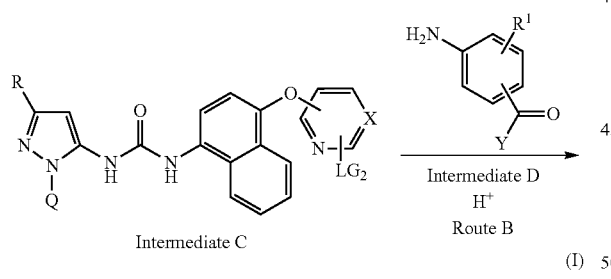

Optionally, compound examples of the invention may be prepared by a general synthetic process comprising of an amide bond forming reaction between a carboxylic acid derivative with an amine $R^aR^bNH$ (Scheme 3, Routes $C_1$ and $C_2$) whereby $NR^aR^b$ comprises Y or a protected derivative thereof, in which latter case the compounds of formula (I) are revealed following an appropriate deprotection step(s). The amide coupling may be conducted on an alkyl ester represented by Intermediate E ($R^c$=alkyl), for example a methyl ester, with the amine, in the presence of a trialkylaluminium, for example trimethylaluminium (Scheme 3, Route $C_1$). The reaction is conveniently carried out in an aprotic solvent such as THF and at ambient or slightly elevated temperatures, typically RT to 40° C.

Scheme 3

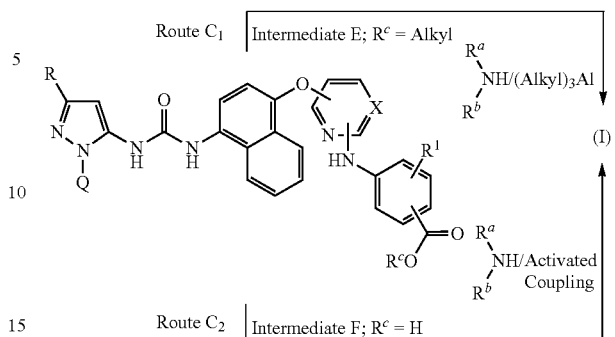

Alternatively the amide products of formula (I) may be derived from the parent carboxylic acids represented by Intermediate F ($R^c$=H) by reaction with the amine $R^aR^bNH$ under the influence of an amide (peptide) coupling reagent, and in the presence a non-nucleophilic base (Scheme 3, Route $C_2$). An example of a reagent that is frequently employed for these transformations is HATU and suitable bases include DIPEA and N-methylmorpholine and the like. The amidation reaction is typically conducted in polar aprotic solvents such as THF and at ambient temperature.

Compounds represented by Intermediate A are either commercially available, or may be prepared by synthetic approaches that are well established in the art. For example compounds of this general structure may be prepared by condensation of the appropriate hydrazine, optionally in the form of a protected derivative thereof or a suitable salt, with the relevant ketonitrile (Scheme 4). An example of an appropriate salt is a hydrochloride salt, and a suitable protective group for this transformation is an acid labile carbamate, for example a Boc group ($R^d$=tert-Bu) that is readily removed under the cyclisation conditions Scheme 4

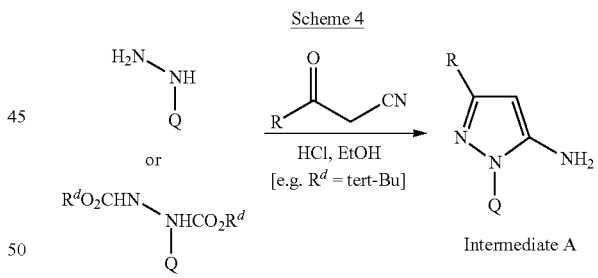

to generate the parent hydrazine in situ. The condensation/cyclisation reaction is suitably conducted in a polar protic solvent such as ethanol and in the presence of a strong acid for example concentrated hydrochloric acid and at elevated temperatures, typically at reflux.

In some instances it may be advantageous to prepare such intermediates by one or other alternative methodologies, as best suits the availability of starting materials and/or the functionality represented in the compounds and/or the need to protect one or more of them, during the synthetic processes in question or in subsequent transformations. For example compounds represented by Intermediate A may also be accessed via a copper (I) mediated coupling reaction between a 1H-pyrazol-5-amine and a suitable arene Q-$LG_3$ in which Q is an optionally substituted aromatic nucleus as defined for compounds of formula (I) and LG₃ is a halide such as an iodine atom (Scheme 5). The reaction is conveniently conducted in an Scheme 5

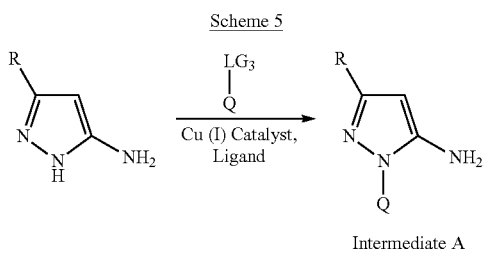

Intermediate A aprotic non-polar solvent such as toleune, employing a copper (I) salt as the catalyst, for example copper (I) iodide and in the presence of a copper co-ordinating ligand such as $N^1,N^2$-dimethylcyclohexane-1,2-diamine and in the presence of a base, for example potassium carbonate and typically at elevated temperature for example at reflux.

It will be evident to those skilled in the art that it may be advantageous to convert one intermediate described herein into another example of the same by one or more transformations that are well known and precedented and thereby gain access to additional compounds of the invention. As an example of such a process those compounds represented by Intermediate A wherein Q is a phenyl ring substituted with an alkoxy group (OR$^e$ wherein R$^e$ is alkyl), such as a methoxy group, may be converted into the corresponding phenol by an O-dealkylation reaction (Scheme 6). This type of transformation may be effected with a boron trihalide, for example boron tribromide, in a non-polar, aprotic solvent such as DCM, at reduced temperatures for example at −5 to 0° C.

Scheme 6

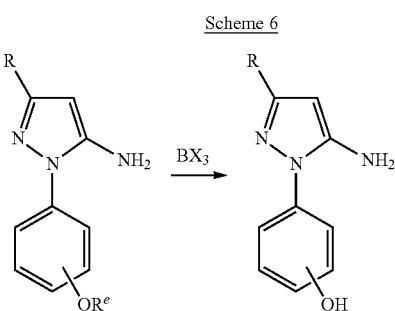

A further demonstration of the conversion of one intermediate, into another compound of the same generic type is provided by the functionalisation of the phenol examples of Intermediate A described hereinabove. For example intermediates of this composition can be conveniently alkylated on the phenolic oxygen by reaction with an alkyl halide, for example with a simple alkyl bromide. Alternatively, the phenol products may be reacted with a functionalised alkyl halide, for example with a nitrogen mustard, that is, with a salt of a 2-haloethylamine of formula R$^f$(CH₂)₂LG₄, wherein LG₄ is a halogen such as a chlorine and R¹ is selected such that O(CH₂)₂R$^f$ is allowable by the definition of Q in compounds of formula (I)

Scheme 7

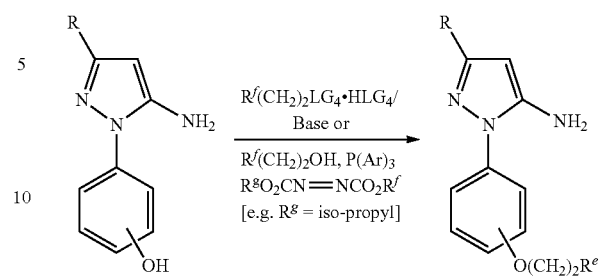

or is a suitably protected derivative thereof (Scheme 7). An example of a salt of a 2-haloethylamine that could be used in O-alkylations of this kind is 4-(2-chloroethyl)morpholine hydrochloride. Reaction of this kind are usefully undertaken in polar non protic solvents such as acetonitrile or DMF and in the presence of a base such as potassium carbonate and with heating if necessary.

In some instances it may be advantageous to effect the O-alkylation under Mitsunobu conditions, by interaction of the phenol with the corresponding alcohol R$^f$(CH₂)₂OH in the presence of a triaryl phosphine such as triphenyphosphine, together with a suitable diazodicarboxylate coupling reagent, for example diisopropyl diazene-1,2-dicarboxylate. Such reactions are typically carried out in non-polar, aprotic solvents such as THF at reduced to ambient temperatures, for example at −50° C. to RT.

Compounds represented by Intermediate B may be obtained from S$_N$Ar displacement reactions between electrophilic aryloxy naphthylamines represented by Intermediate G, wherein LG₂ is a suitable leaving group such as a halogen atom, for example chlorine, with an aniline component represented by Intermediate D (Scheme 8). The coupling reaction may be undertaken on the free naphthylamine (G₁=H) or optionally, in order to control Scheme 8

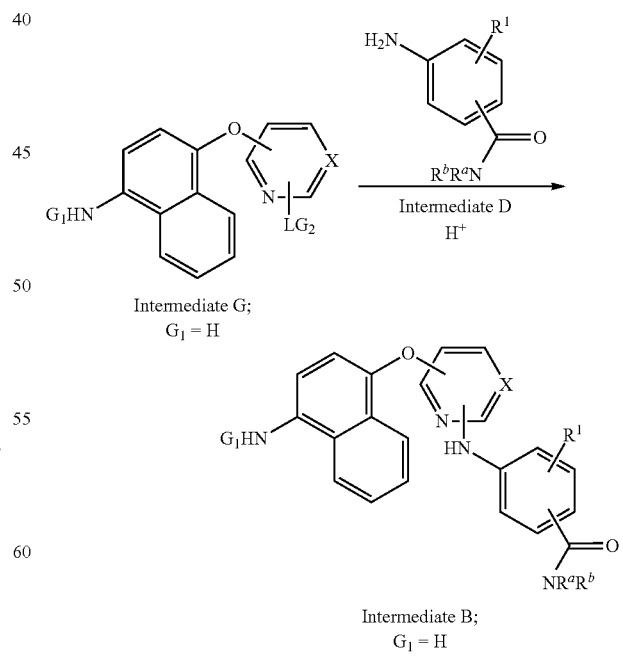

chemoselectivity and thereby enhance efficiency, upon a protected derivative thereof. Intermediate G(P) (G₁=protective group). The reaction proceeds under acidic conditions, for example in the presence of p-TSA and in a polar aprotic solvent such as THF and typically at elevated temperatures, for example at 70° C. In those instances in which a protective group has been employed the products represented by Intermediate B are subsequently revealed by a suitable deprotection step(s). For example a carbamate, such as a Boc group, may be used to protect the naphthylamine nitrogen ($G_1$=tert-BuO$_2$C) during the S$_N$Ar coupling reaction and afterwards removed by treatment with a strong acid, for example with TFA.

The synthetic processes cited hereinabove (Routes $C_1$ and $C_2$, Scheme 3) may likewise be exploited to access compounds represented by Intermediate B (Scheme 9). Thus examples of Intermediate B may be prepared by reaction of an activated derivative of a carboxylic acid represented by Intermediate J ($R^c$=$G_1$=H) or a protected derivative thereof. Intermediate J(P) ($G_1$=protective group) with an amine $R^aR^bNH$, whereby NR$^a$R$^b$ comprises Y or a protected derivative thereof. Alternatively the interconversion may be undertaken on an ester Intermediate H ($R^c$=alkyl, $G_1$=H) or a protected derivative thereof. Intermediate H(P) ($R^c$=alkyl, $G_1$=protective group) with an amine $R^aR^bNH$ in the presence of a trialkyl aluminium, as already described. A suitable protective group for these transformations is a urethane

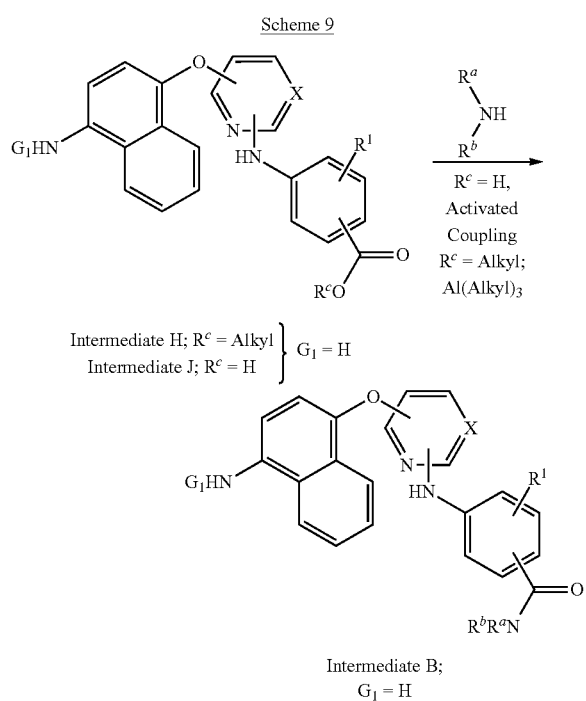

derivative ($G_1$=$R^hO_2C$) in which case the desired anilines ($G_1$=H) represented by Intermediate B are obtained following an appropriate deprotection procedure. An example of a urethane protective group which is suitable for this purpose is a Boc group ($G_1$=tert-BuO$_2$C), which can be removed following the amidation reaction by treatment with acid.

The ester and acid precursors represented by Intermediates E and F are obtainable by use of the same or analogous procedures, to those disclosed hereinabove (Scheme 1), that provide compound examples of the present invention. In this manner Intermediates E and F are conveniently obtained by the reaction of Intermediates H and J respectively with the activated aminopyrazole derivatives Intermediates A* (Scheme 10). It will be evident to those skilled in the art that the esters: Intermediates H and E may be readily transformed into the corresponding carboxylic acids: Intermediates J and F by hydrolysis under suitable acidic or basic conditions. For example this conversion can be effected by saponification, using a base such as lithium hydroxide, in a protic solvent or mixture of solvents, for example THF and water and at modestly elevated temperatures, typically RT to 40° C.

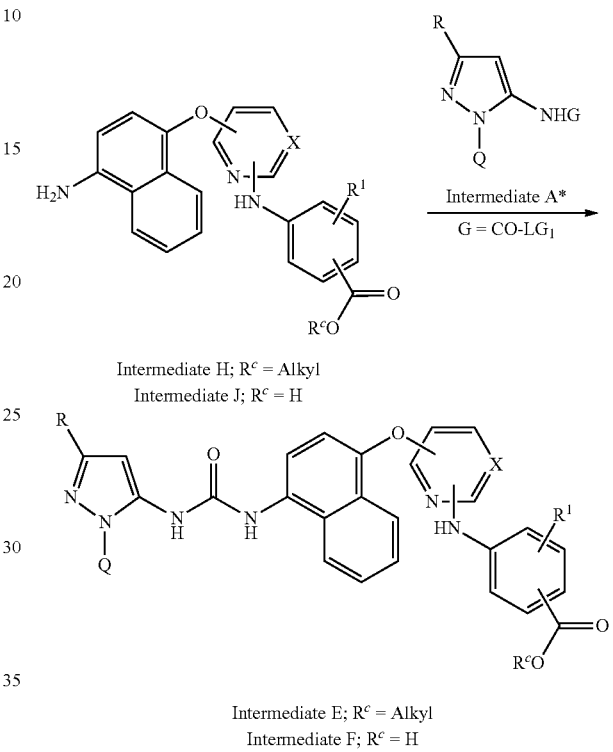

The precursors represented by Intermediate G are conveniently prepared by an S$_N$Ar displacement reaction between 4-aminonaphthalen-1-ol, either in the form of a salt or a suitable, protected derivative and an electrophilic heteroaromatic (Scheme 11), for example a dihalo heteroaromatic wherein the leaving groups LG$_2$ and LG$_5$ are both halogen atoms,

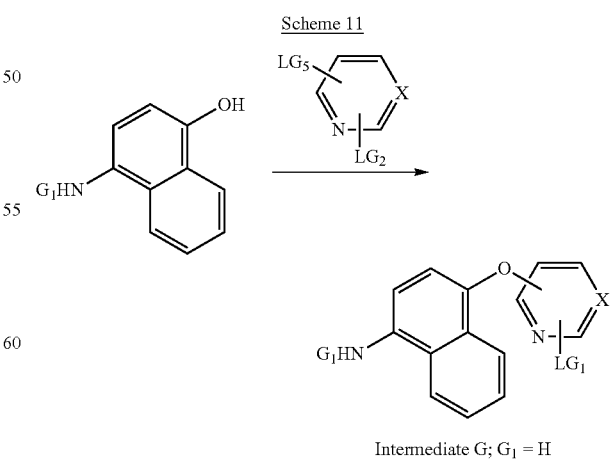

such as chlorine. A suitable protective group for this transformation is a Boc group ($G_1$=tert-BuO$_2$C) which may be retained, in order to control chemoselectivity, during one or more subsequent transformations, such as those described hereinabove (Schemes 8 and 9). The displacement step is conveniently carried out in a polar, aprotic solvent such as acetonitrile and in the presence of a hindered base, typified by DBU and at reduced temperature, for example at 0° C.

Those compounds represented by Intermediates H and J were assembled by analogous synthetic procedures to those already described above (Scheme 8) for the preparation of Intermediates B by substituting anilino acids or anilino esters represented by Intermediate K in place of Intermediate D (Scheme 12). In a similar manner the acid mediated $S_NAr$ coupling may be conducted on the free naphthylamine Intermediate G ($G_1$=H) or optionally, using a protected derivative of the same, Intermediate G(P) ($G_1$=protective group), to maintain the desired chemoselectivity in this and/or subsequent transformations. The $S_NAr$ coupling is suitably carried out in a polar non protic solvent, for example THF or IPA or DMF and in the presence of an acid catalyst such as p-TSA or TFA and most usually at elevated temperatures, typically at 60-70° C.

Scheme 12

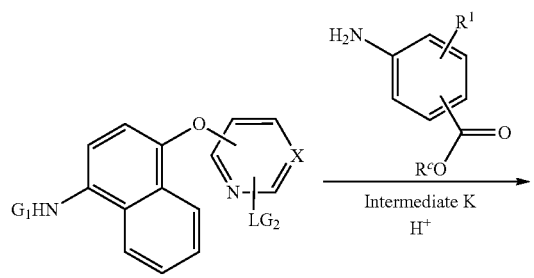

Intermediate G; $G_1$ = H;
Intermediate G(P); $G_1$ = PG

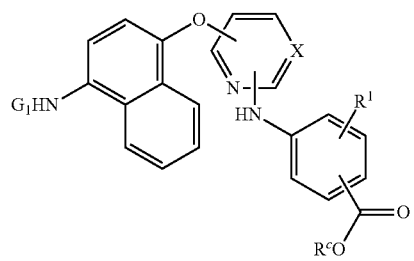

$G_1 = H$ { Intermediate H; $R^c$ = Alkyl
Intermediate J; $R^c$ = H

The known aniline components represented by Intermediate D and Intermediate K were either procured from commercial sources or prepared according to published procedures. Novel examples disclosed herein were synthesised from commercially available starting materials using functional group interconversions that are well established in the art (Scheme 13). For example, the (leaving) group $LG_6$ may be displaced with a desired $R^1$ group via an $S_NAr$ reaction or transition metal-catalysed coupling. In some instances the desired anilines are readily obtainable from appropriately substituted, amino benzoic acids ($R^c$=$G_2$=H) and/or amino benzoic acid esters ($R^c$=alkyl $G_2$=H) that may be optionally N-protected ($G_2$=PG) to ensure that subsequent reactions can be conducted effectively. Transposition of the substituent $R^h$ into a group $R^1$ as defined for compounds of formula (I), Scheme 13

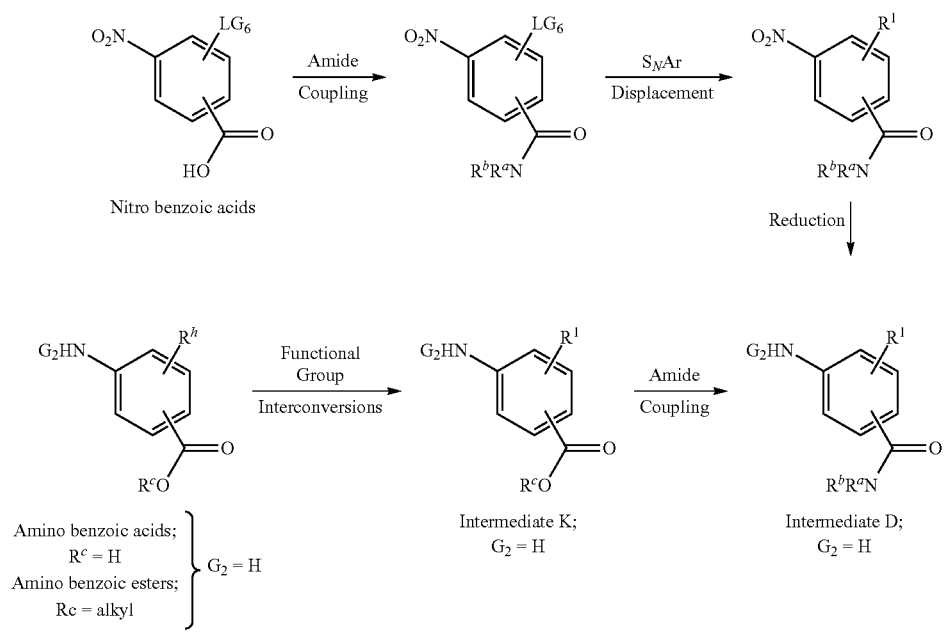

provides compounds represented by Intermediate K which may be hydrolysed and subjected to an amide coupling reaction to furnish examples of Intermediate D, after removal, where employed, of the nitrogen protective group.

Additional examples of Intermediate D are readily made from commercially available nitro benzoic acids that are substituted with a suitable leaving group $LG_6$, such as a halogen, for example fluorine. Compounds of this composition may be converted into the examples of the desired anilines by a series of reactions comprising of an amide coupling, followed by an $S_NAr$ displacement reaction and reduction of the nitro group into an amine.

Compounds of formula (I) may alternatively be obtained by coupling of Intermediate B to an pyrazole-5-isocyanate compound, Intermediate L. In this route, Intermediate L may, for example, be conveniently prepared via a copper (II)-mediated Chan-Lam reaction (see, for example: *Tetrahedron Lett.* 1998, 39, 2941-2944), wherein an ester of a suitable pyrazole-5-carboxylic acid is coupled to an aryl- or heteroaryl-boronic acids. The resulting N-aryl pyrazole acid ester is saponified to yield the corresponding carboxylic acid (Intermediate M), which acid is converted to an acyl azide (e.g. using source of a leaving group and activated azide ion, such as diphenyl phosphorazidate (DPPA); see, for example, *Tetrahedron* 1974, 30, 2151-2157)) before undergoing a Curtis rearrangement to yield Intermediate L.

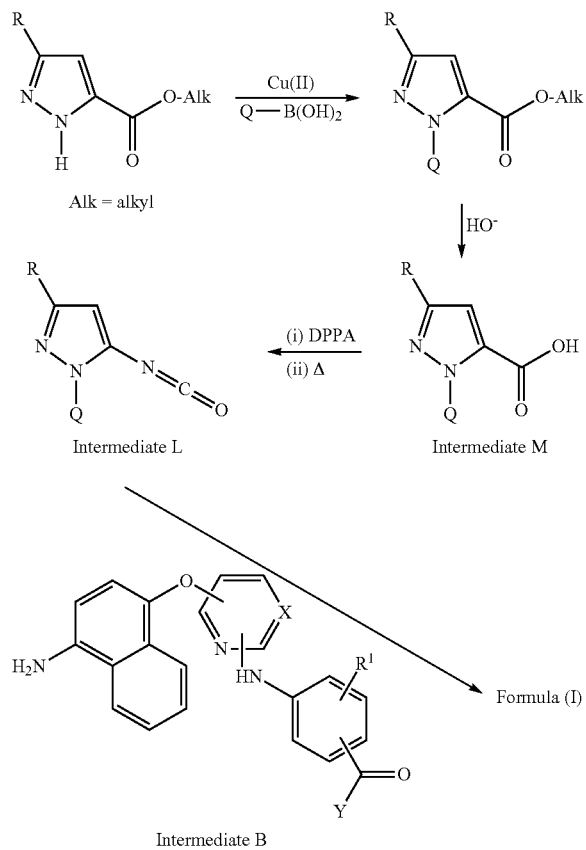

It will be evident to those skilled in the art that in some cases it is technically advantageous to use alternative protective groups and/or to conduct the transformations described above in a similar manner but in a different order, so as to improve the overall efficiency of the synthetic processes.

Protective groups and the means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates as described herein form an aspect of the invention. In this respect, further aspects of the invention relate to:

(i) a compound of formula (II),

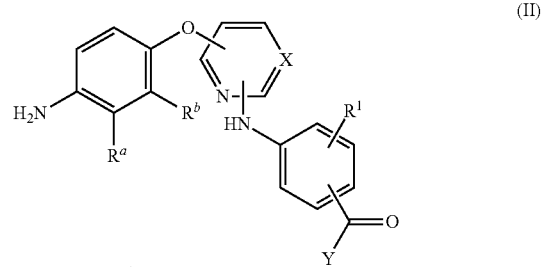

wherein $R^a$, $R^b$, X, Y and $R^1$ are as hereinbefore defined, or a salt or protected derivative thereof; and (ii) a compound of formula (III),

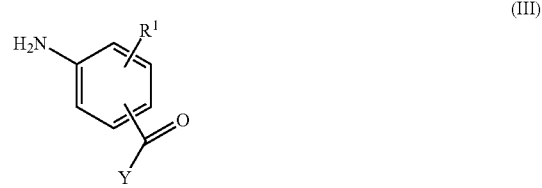

wherein Y and $R^1$ are as hereinbefore defined, or a salt or protected derivative thereof.

Compounds of formulae (II) and (III) that may be mentioned include those in which:
$R^a$ and $R^b$, together with the C-atoms to which they are attached, form a fused phenyl ring that is optionally substituted by one or more substituents selected from $C_{1-3}$ alkyl, $C_{1-3}$ haloalkyl, cyano and halo;
X represents N;
Y represents $NR^2R^3$; and/or
$R^1$ represents $C_{2-6}$ alkynyl.

Particular compounds of formulae (II) and (III) that may be mentioned include those of formula (IIa) and (IIIa), respectively:

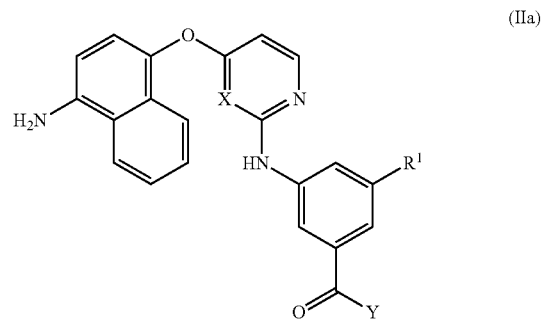

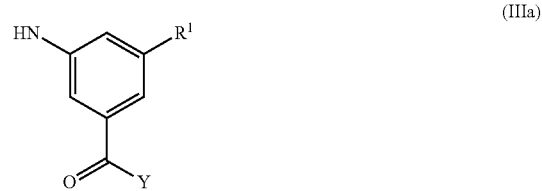

wherein X, $R^1$ and Y are as hereinbefore defined.

Compounds of formulae (IIa) and (IIIa) that may be mentioned include those in which:
X represents N;
Y represents $N(H)$—$CH_2CH_2$-(morpholin-1-yl); and/or
$R^1$ represents $C_{2-3}$ alkynyl (e.g. —C≡C—H).

Protected derivatives of the compounds of formulae (II) and (III) include those in which the essential NH$_2$ group is protected. In this respect, such protected derivatives include amides or, particularly, carbamates of those compounds. For example, those protected derivatives include compounds in which a H-atom of the NH$_2$ group is replaced by:

R'—C(O)—, wherein R' is H, C$_{1-8}$ alkyl, phenyl or benzyl, which latter two groups are optionally substituted by one or more groups selected from halo, hydroxy, methyl and methoxy; or R"—O—C(O)—, wherein R" is tert-butyl, phenyl, benzyl or fluorenyl, which latter three groups are optionally substituted by one or more groups selected from halo, hydroxy, methyl and methoxy.

The compounds of formula (I) are p38 MAP kinase inhibitors (especially of the alpha subtype) and in one aspect the compounds are useful in the treatment of inflammatory diseases, for example COPD and/or asthma.

Surprisingly, in at least some embodiments, the compounds of formula (I) exhibit a long duration of action and/or persistence of action in comparison to other previously disclosed allosteric p38 MAP kinase inhibitors such as, for example, BIRB796 (Pargellis, C et al., *Nature Struct. Biol.*, 2002, 9(4):268-272).

In one embodiment the compounds of formula (I) do not strongly inhibit, or bind to GSK 3α, for example they have an IC$_{50}$ value against GSK 3α of 1500 nM or greater; such as 2,000, 3,000, 4,000, 5,000, 6,000, 7,000, 8,000, 9,000 or 10,000 nM or greater.

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compounds of formula (I) are expected to be potent in vivo.

Typically, the prior art compounds developed to date have been intended for oral administration. This strategy involves optimizing the pharmacokinetic profile of drug substances in order to achieve an adequate duration of action. In this manner a sufficiently high drug concentration is established and maintained between doses to provide sustained clinical benefit. The inevitable consequence of this approach is that all bodily tissues, and especially the liver and the gut, are likely to be exposed to supra-therapeutically active concentrations of the drug, whether or not they are adversely affected by the disease being treated.

An alternative strategy is to design treatment paradigms in which the drug is dosed directly to the inflamed organ, that is, to exploit topical administration. Whilst this approach is not suitable for treating all chronic inflammatory diseases, it has been exploited in lung disorders, such as asthma and COPD; in skin diseases, for example against atopic dermatitis and psoriasis; for nasal conditions, typified by allergic rhinitis; and in gastrointestinal diseases, such as ulcerative colitis and Crohn's disease and inflammatory diseases of the eye, such as uveitis.

In topical therapy, one way in which efficacy can be achieved is by the use of a drug that has a sustained duration of action and is retained in the relevant organ, thereby minimizing the risk of systemic toxicity. Alternatively, in some cases, a formulation can be developed that generates a "reservoir" of the active drug which is available to sustain its desired effects. The first approach is exemplified by the anticholinergic drug tiotropium (Spiriva). This compound is administered topically to the lung as a treatment for COPD, and has an exceptionally high affinity for its target receptor resulting in a very slow off rate and consequently displays a sustained duration of action.

In one aspect of the disclosure the compounds of formula (I) is particularly suitable for topical delivery, such as topical delivery to the lungs, in particular for the treatment of respiratory disease, for example chronic respiratory diseases such as COPD and/or asthma.

In one embodiment the compounds of formula (I) is suitable for sensitizing patients to treatment with a corticosteroid who have become refractory to such treatment regimens.

The compounds of formula (I) may have antiviral properties, for example the ability to prevent the infection of cells (such as respiratory epithelial cells) with a picornavirus, in particular a rhinovirus, influenza or respiratory syncytial virus.

Thus the compound is thought to be an antiviral agent, in particular suitable for the prevention, treatment or amelioration of picornavirus infections, such as rhinovirus infection, influenza or respiratory syncytial virus.

In one embodiment the compounds of formula (I) are able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay as described in the Examples herein.

In one embodiment the compounds of formula (I) are able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compounds of formula (I) particularly suitable for use in the treatment (including prophylaxis) of exacerbations of inflammatory diseases, in particular viral exacerbations, or in the treatment of viral infections, in patients with one or more chronic conditions such as congestive heart failure, COPD, asthma, diabetes, cancer and/or in immunosuppressed patients, for example post-organ transplant. Such use may be in combination with anti-viral agents such as zanamivir, oseltamivir (for example oseltamivir phosphate) peramivir or laninamivir.

In general, the compounds of formula (I) may be useful in the treatment of one or more conditions having an inflammatory component which, suitably, may be treated by topical or local therapy.

In particular, the compounds of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema).

The compounds of formula (I) may be useful in the treatment of eye diseases or disorders including keratoconjunctivitis sicca (dry eye), allergic conjunctivitis, conjunctivitis, diabetic retinopathy, macular oedema (including wet macular oedema and dry macular oedema), post-operative cataract inflammation or, particularly, uveitis (including posterior, anterior and pan uveitis) (e.g. eye diseases or disorders including allergic conjunctivitis, conjunctivitis, diabetic retinopathy, macular oedema (including wet macular oedema and dry macular oedema), post-operative cataract inflammation or, particularly, uveitis (including posterior, anterior and pan uveitis)).

The compounds of formula (I) may be useful in the treatment of skin diseases or disorders including allergic dermatitis, contact dermatitis, atopic dermatitis or psoriasis.

The compounds of formula (I) may be useful in the treatment of gastrointestinal diseases or disorders including ulcerative colitis or Crohn's disease.

The compounds of formula (I) may be useful in the treatment of joint diseases or disorders including rheumatoid arthritis or osteoarthritis and particularly inflamed joints secondary to such conditions.

The compounds of formula (I) may be useful in the treatment of cancers including cancer of the stomach and in the inhibition of the growth and metastasis of tumours including non-small cell lung carcinoma, gastric carcinoma, colorectal carcinomas and malignant melanoma.

It is also expected that the compounds of formula (I) may be useful in the treatment of certain other conditions including periodontitis, gingivitis and pharyngitis.

Compounds of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

The present invention also provides a process for preparing such a pharmaceutical composition (for example a pharmaceutical composition for parenteral, oral, topical, mucosal or rectal administration), said process comprising mixing the ingredients.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably a compound of formula (I) is administered topically to the lung, eye or bowel. Hence we provide according to the invention a pharmaceutical composition comprising a compound of the disclosure optionally in combination with one or more topically acceptable diluents or carriers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean aerodynamic diameter (MMAD) of 1-10 μm. The formulation will typically contain a topically acceptable diluent such as lactose, usually of large particle size e.g. an MMAD of 100 μm or more. Examples of dry powder delivery systems include SPINHALER, DISKHALER, TURBOHALER, DISKUS and CLICKHALER.

The compounds of the present invention (i.e. compounds of formula (I), (Ia1), (Ia2), (Ib1), (Ib2), (Ic1), (Ic2), (Id1), (Id2), (Ie1), (Ie2), (If1), (If2), (Ig1), (Ig2), (Ih1) or (Ih2), as defined above, or pharmaceutically acceptable salts thereof) may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of the present invention. In addition, the compound of the present invention may also be introduced by means of ocular implants or inserts.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkoniurn chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

A compound of formula (I) has therapeutic activity. In a further aspect, the present invention provides a compound of the disclosure for use as a medicament. Thus, in a further aspect, the present invention provides a compound as described herein for use in the treatment of one or more of the above mentioned conditions.

In one embodiment a dry powder formulation according the present disclosure comprises magnesium or calcium stearate. Such formulations may have superior chemical and/or physical stability especially when such formulations also contain lactose.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the disclosure or a pharmaceutical composition comprising the compound.

The word "treatment" is intended to embrace prophylaxis as well as therapeutic treatment. Treatment of conditions or disorders also embraces treatment of exacerbations thereof.

A compound of the disclosure may also be administered in combination with one or more other active ingredients e.g. active ingredients suitable for treating the above mentioned conditions.

For example, possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol), xanthines (e.g. theophylline), anticholinergics (e.g. ipratropium or tiotropium, for example as the bromide) and anti-viral agents (e.g. zanamivir, oseltamivir, for example as the phosphate, peramivir and laninamivir).

Further, for the treatment of gastrointestinal disorders (such as Crohn's disease or ulcerative colitis), possible combinations include combinations with, for example, one or more agents selected from the list comprising:
  5-aminosalicylic acid, or a prodrug thereof (such as sulfasalazine, olsalazine or bisalazide);
  corticosteroids (e.g. prednisolone, methylprednisolone, or budesonide);
  immunosuppressants (e.g. cyclosporin, tacrolimus, methotrexate, azathioprine or 6-mercaptopurine);
  anti-TNFα antibodies (e.g., infliximab, adalimumab, certolizumab pegol or golimumab);
  anti-IL12/IL23 antibodies (e.g., ustekinumab) or small molecule IL12/IL23 inhibitors (e.g., apilimod);
  Anti-α4β7 antibodies (e.g., vedolizumab);
  MAdCAM-1 blockers (e.g., PF-00547659);
  antibodies against the cell adhesion molecule α4-integrin (e.g., natalizumab);
  antibodies against the IL2 receptor a subunit (e.g., daclizumab or basiliximab);
  JAK3 inhibitors (e.g., tofacitinib or R348);
  Syk inhibitors and prodrugs thereof (e.g., fostamatinib and R-406);
  Phosphodiesterase-4 inhibitors (e.g., tetomilast);
  HMPL-004;
  probiotics;
  Dersalazine;
  semapimod/CPSI-2364; and
  protein kinase C inhibitors (e.g. AEB-071).

For the treatment of eye disorders (such as keratoconjunctivitis sicca or uveitis), possible combinations include combinations with, for example, one or more agents selected from the list comprising:
  corticosteroids (e.g. dexamethasone, prednisolone, triamcinolone acetonide, difluprednate or fluocinolone acetonide);
  immunosuppressants (e.g. cyclosporin, voclosporin, azathioprine, methotrexate, mycophenolate mofetil or tacrolimus);
  anti-TNFα antibodies (e.g., infliximab, adalimumab, certolizumab pegol, ESBA-105 or golimumab);
  anti-IL-17A antibodies (e.g., secukinumab);
  mTOR inhibitors (e.g., sirolimus);
  VGX-1027;
  JAK3 inhibitors (e.g., tofacitinib or R348); and
  protein kinase C inhibitors (e.g. AEB-071).

Hence another aspect of the invention provides a compound of formula (I) in combination with one or more further active ingredients, for example one or more active ingredients described above.

Similarly, another aspect of the invention provides a combination product comprising:
(A) a compound of the present invention (i.e. a compound of formula (I), (Ia1), (Ia2), (Ib1), (Ib2), (Ic1), (Ic2), (Id1), (Id2), (Ie1), (Ie2), (If1), (If2), (Ig1), (Ig2), (Ih1) or (Ih2), as defined above, or a pharmaceutically acceptable salt thereof); and
(B) another therapeutic agent,
wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of the present invention and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of the present invention in admixture with a pharmaceutically acceptable adjuvant, diluent or carrier; and
(ii) a pharmaceutical formulation including another therapeutic agent, in admixture with a pharmaceutically-acceptable adjuvant, diluent or carrier,
which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

The other therapeutic agent (i.e. component (B) above) may be, for example, any of the agents mentioned above in connection with the treatment of respiratory, gastrointestinal and eye disorders.

The combination product (either a combined preparation or kit-of-parts) of this aspect of the invention may be used in the treatment or prevention of an inflammatory disease (e.g. the inflammatory diseases mentioned above, such as:
  respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema);
  eye diseases or disorders including allergic conjunctivitis, conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation or, particularly, uveitis (including posterior, anterior and pan uveitis), corneal graft and limbal cell transplant rejection;
  skin diseases or disorders including allergic dermatitis, contact dermatitis, atopic dermatitis or psoriasis; and
  gastrointestinal diseases or disorders including gluten sensitive enteropathy (coeliac disease), eosinophilic esophagitis, intestinal graft versus host disease or, particularly, ulcerative colitis or Crohn's disease.

The aspects of the invention described herein (e.g. the above-mentioned compound, combinations, methods and uses) may have the advantage that, in the treatment of the conditions described herein, they may be more convenient for the physician and/or patient than, be more efficacious than, be less toxic than, be longer acting than, have better selectivity over, have a broader range of activity than, be more potent than, produce fewer side effects than, have a better pharmacokinetic and/or pharmacodynamic profile than, have more suitable solid state morphology than, have better stability than, or may have other useful pharmacological properties over, similar compounds, combinations, methods (treatments) or uses known in the prior art for use in the treatment of those conditions or otherwise.

Relative to compounds of the prior art, the compounds of formula (I) may additionally (or alternatively):
- exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma);
- have a reduced risk of extravascular exposure following intravenous administration (e.g. due to a low volume of distribution for the compounds of formula (I)); exhibit superior potency with respect to selected kinases (e.g. Syk and/or a panel of kinases, such as Syk, Src and p38 MAPKα);
- exhibit reduced β-catenin induction and/or inhibition of mitosis in cells;
- exhibit no or less time-dependent inhibition of members of the cytochrome P450 superfamily; and/or
- produce less problematic (e.g. less toxic) metabolites, e.g. following administration to a patient.

Experimental Section

Abbreviations used herein are defined below (Table 1). Any abbreviations not defined are intended to convey their generally accepted meaning.

TABLE 1

| Abbreviations | |
|---|---|
| AcOH | glacial acetic acid |
| aq | aqueous |
| ATP | adenosine-5'-triphosphate |
| BALF | bronchoalveolar lavage fluid |
| br | broad |
| BSA | bovine serum albumin |
| CatCart ® | catalytic cartridge |
| CDI | 1,1-carbonyl-diimidazole |
| COPD | chronic obstructive pulmonary disease |
| c-Src | cellular sarc(oma) kinase |
| d | doublet |
| DCM | dichloromethane |
| DMEM | Dulbecco's Modified Eagle Medium |
| DMSO | dimethyl sulfoxide |
| DSS | dextran sodium sulphate |
| d-U937 cells | PMA differentiated U-937 cells |
| (ES+) | electrospray ionization, positive mode |
| Et | ethyl |
| EtOAc | ethyl acetate |
| FCS | foetal calf serum |
| FRET | fluorescence resonance energy transfer |
| GR | glucocorticoid receptor |
| GSK3α | glycogen synthase kinase 3α |
| HBEC | primary human bronchial epithelial cells |
| hr | hour(s) |
| HRP | horseradish peroxidise |
| HRV | human rhinovirus |

TABLE 1-continued

| Abbreviations | |
|---|---|
| IBD | inflammatory bowel disease |
| ICAM-1 | inter-cellular adhesion molecule 1 |
| IL-8 | interleukin 8 |
| JNK | c-Jun N-terminal kinase |
| LPS | lipopolysaccharide |
| (M + H)+ | protonated molecular ion |
| MAPK | mitogen-activated protein kinase |
| MAPKAP-K2 | mitogen-activated protein kinase-activated protein kinase-2 |
| Me | methyl |
| MeCN | acetonitrile |
| MeOH | methanol |
| MHz | megahertz |
| MMAD | mass median aerodynamic diameter |
| MOI | multiplicity of infection |
| min | minute(s) |
| MPO | myeloperoxidase |
| MTT | 3-(4,5-dimethylthiazol-2-yl)-2,5-diphenyltetrazolium bromide |
| m/z: | mass-to-charge ratio |
| NMR | nuclear magnetic resonance (spectroscopy) |
| NT | Not tested |
| PBMC | peripheral blood mononuclear cell |
| PBS | phosphate buffered saline |
| PG | protective group |
| Ph | phenyl |
| PHA | phytohaemagglutinin |
| PMA | phorbol myristate acetate |
| p-TSA | 4-methylbenzenesulfonic acid |
| q | quartet |
| RT | room temperature |
| RP HPLC | reverse phase high performance liquid chromatography |
| RSV | respiratory syncytial virus |
| s | singlet |
| sat | saturated |
| SCX | solid supported cation exchange (resin) |
| SDS | sodium dodecyl sulphate |
| $S_NAr$ | nucleophilic aromatic substitution |
| Syk | spleen tyrosine kinase |
| t | triplet |
| T3P | 1-propanephosphonic acid cyclic anhydride |
| TBDMS | tert-butyldimethylsilyl |
| $TCID_{50}$ | 50% tissue culture infectious dose |
| THF | tetrahydrofuran |
| TMB | 3,3',5,5'-tetramethylbenzidine |
| TNBS | 2,4,6-trinitrobenzenesulfonic acid |
| TNFα | tumor necrosis factor alpha |
| WB | washing buffer |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH The desired material was then eluted by washing with 0.7 M $NH_3$ in MeOH.

Preparative Reverse Phase High Performance Liquid Chromatography

Agilent Scalar column C18, 5 μm (21.2×50 mm), flow rate 28 mL min$^{-1}$ eluting with a $H_2$O-MeCN gradient containing 0.1% v/v formic acid over 10 min using UV detection at 215 and 254 nm. Gradient information: 0.0-0.5 min; 95% $H_2$O-5% MeCN; 0.5-7.0 min; ramped from 95%

H₂O-5% MeCN to 5% H₂O-95% MeCN; 7.0-7.9 min; held at 5% H₂O-95% MeCN; 7.9-8.0 min; returned to 95% H₂O-5% MeCN; 8.0-10.0 min; held at 95% H₂O-5% MeCN.

Analytical Methods

Reverse Phase High Performance Liquid Chromatography

Method 1:

Agilent Scalar column C18, 5 μm (4.6×50 mm) or Waters XBridge C18, 5 μm (4.6×50 mm) flow rate 2.5 mL min$^{-1}$ eluted with a H₂O-MeCN gradient containing either 0.1% v/v formic acid (Method 1 acidic) or NH₃ (Method 1 basic) over 7 min employing UV detection at 215 and 254 nm. Gradient information: 0.0-0.1 min, 95% H₂O-5% MeCN; 0.1-5.0 min, ramped from 95% H₂O-5% MeCN to 5% H₂O-95% MeCN; 5.0-5.5 min, held at 5% H₂O-95% MeCN; 5.5-5.6 min, held at 5% H₂O-95% MeCN, flow rate increased to 3.5 mL min$^{-1}$; 5.6-6.6 min, held at 5% H₂O-95% MeCN, flow rate 3.5 mL min$^{-1}$; 6.6-6.75 min, returned to 95% H₂O-5% MeCN, flow rate 3.5 mL min$^{-1}$; 6.75-6.9 min, held at 95% H₂O-5% MeCN, flow rate 3.5 mL·min$^{-1}$; 6.9-7.0 min, held at 95% H₂O-5% MeCN, flow rate reduced to 2.5 mL min$^{-1}$.

Method 2:

Agilent Extend C18 column, 1.8 μm (4.6×30 mm) at 40° C.; flow rate 2.5-4.5 mL min$^{-1}$ eluted with a H₂O-MeCN gradient containing either 0.1% v/v formic acid (Method 2 acidic) or NH₃ (Method 2 basic) over 4 min employing UV detection at 254 nm. Gradient information: 0-3.00 min, ramped from 95% H₂O-5% MeCN to 5% H₂O-95% MeCN; 3.00-3.01 min, held at 5% H₂O-95% MeCN, flow rate increased to 4.5 mL min$^{-1}$; 3.01-3.50 min, held at 5% H₂O-95% MeCN; 3.50-3.60 min, returned to 95% H₂O-5% MeCN, flow rate reduced to 3.50 mL min$^{-1}$; 3.60-3.90 min, held at 95% H₂O-5% MeCN; 3.90-4.00 min, held at 95% H₂O-5% MeCN, flow rate reduced to 2.5 mL min$^{-1}$.

Method 3:

Waters Xselect CSH C18 3.5 μm (4.6×50 mm) flow rate 2.5 mL min$^{-1}$ eluted with a H₂O-MeCN gradient containing 0.1% v/v formic acid over 7 min employing UV detection at 215 and 254 nm. Gradient information: 0.0-0.1 min, 95% H₂O-5% MeCN; 0.1-5.0 min, ramped from 95% H₂O-5% MeCN to 5% H₂O-95% MeCN; 5.0-5.5 min, held at 5% H₂O-95% MeCN; 5.5-5.6 min, held at 5% H₂O-95% MeCN, flow rate increased to 3.5 mL min$^{-1}$; 5.6-6.6 min, held at 5% H₂O-95% MeCN, flow rate 3.5 mL min$^{-1}$; 6.6-6.75 min, returned to 95% H₂O-5% MeCN, flow rate 3.5 mL min$^{-1}$; 6.75-6.9 min, held at 95% H₂O-5% MeCN, flow rate 3.5 mL·min$^{-1}$; 6.9-7.0 min, held at 95% H₂O-5% MeCN, flow rate reduced to 2.5 mL min$^{-1}$.

Method 4:

Waters Xselect CSH C18 3.5 μm (4.6×50 mm); flow rate 2.5-4.5 mL min$^{-1}$ eluted with a H₂O-MeCN gradient containing 0.1% v/v formic acid over 4 min employing UV detection at 254 nm. Gradient information: 0-3.00 min, ramped from 95% H₂O-5% MeCN to 5% H₂O-95% MeCN; 3.00-3.01 min, held at 5% H₂O-95% MeCN, flow rate increased to 4.5 mL min$^{-1}$; 3.01-3.50 min, held at 5% H₂O-95% MeCN; 3.50-3.60 min, returned to 95% H₂O-5% MeCN, flow rate reduced to 3.50 mL min$^{-1}$; 3.60-3.90 min, held at 95% H₂O-5% MeCN; 3.90-4.00 min, held at 95% H₂O-5% MeCN, flow rate reduced to 2.5 mL min$^{-1}$.

$^1$H NMR Spectroscopy $^1$H NMR spectra were acquired on a Bruker Avance III spectrometer at 400 MHz using residual undeuterated solvent as reference and unless specified otherwise were run in DMSO-d$_6$.

Those intermediates, used to prepare compound examples of the invention, that have been previously disclosed were obtained using the procedures contained in the references cited below (Table 2). Additional intermediates were prepared by the representative synthetic processes described herein.

TABLE 2

Compound Intermediates

| No. | Structure | Name, LCMS Data and Reference |
|---|---|---|
| A1 | (F₃C-pyrazole with N-p-tolyl and NH₂ substituents) | 1-(p-tolyl)-3-(trifluoromethyl)-1H-pyrazol-5-amine. R$^t$ 2.10 min (Method 2, acidic); m/z 228 (M + H)$^+$, (ES$^+$). Abraham, S. et al., WO 2009/117080, 24 Sep. 2009. |
| A2 | (Et-pyrazole with N-p-tolyl and NH₂ substituents) | 3-ethyl-1-(p-tolyl)-1H-pyrazol-5-amine. R$^t$ 3.30 min (Method 1, acidic); m/z 202 (M + H)$^+$, (ES$^+$). Ito, K. et al., WO 2010/067130, 17 Jun. 2010. |

TABLE 2-continued

| | Compound Intermediates | |
|---|---|---|
| No. | Structure | Name, LCMS Data and Reference |
| A3 | [Structure: 3-(perfluoroethyl)-1-(p-tolyl)-1H-pyrazol-5-amine with C$_2$F$_5$ group, pyrazole with NH$_2$, N-linked p-tolyl (Me)] | 3-(perfluoroethyl)-1-(p-tolyl)-1H-pyrazol-5-amine.<br>Rt 2.39 min (Method 2, acidic); m/z 292 (M + H)$^+$, (ES$^+$).<br>De Dios, A. et al., WO 2007/ 053346, 10 May 2007. |
| A4 | [Structure: 3-isopropyl-1-(p-tolyl)-1H-pyrazol-5-amine with $^i$Pr group, pyrazole with NH$_2$, N-linked p-tolyl (Me)] | 3-isopropyl-1-(p-tolyl)-1H-pyrazol-5-amine.<br>R$^t$ 3.14 min (Method 1, acidic, X-Select); m/z 216 (M + H)$^+$, (ES$^+$).<br>Ito, K. et al., WO 2010/067130, 17 Jun. 2010 |
| A5 | [Structure: 3-isopropyl-1-(4-methoxyphenyl)-1H-pyrazol-5-amine with $^i$Pr group, pyrazole with NH$_2$, N-linked p-methoxyphenyl (OMe)] | 3-isopropyl-1-(4-methoxyphenyl)-1H-pyrazol-5-amine.<br>R$^t$ 1.04 min (Method 2 acidic); m/z 232 (M + H)$^+$, (ES$^+$).<br>Abraham, S. et al., WO 2009/117080, 24 Sep. 2009. |
| A6 | [Structure: 3-cyclopropyl-1-(p-tolyl)-1H-pyrazol-5-amine with cyclopropyl group, pyrazole with NH$_2$, N-linked p-tolyl (Me)] | 3-cyclopropyl-1-(p-tolyl)-1H-pyrazol-5-amine.<br>R$^t$ 3.35 min (Method 1, acidic); m/z 214 (M + H)$^+$, (ES$^+$).<br>King-Underwood, J. et al., WO 2011/124930, 13 Oct. 2011. |

TABLE 2-continued

Compound Intermediates

| No. | Structure | Name, LCMS Data and Reference |
|---|---|---|
| A7 | 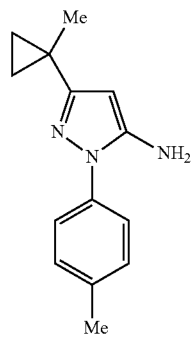 [SMILES: Cc1ccc(-n2nc(C3(C)CC3)cc2N)cc1] | 3-(1-methylcyclopropyl)-1-(p-tolyl)-1H-pyrazol-5-amine. R$^t$ 3.72 min (Method 1, acidic); m/z 228 (M + H)$^+$, (ES$^+$). De Dios, A. et al., WO 2007/ 053346, 10 May 2007. |
| A8 | | 3-tert-butyl-1-p-tolyl-1H-pyrazol-5-amine. R$^t$ 2.46 min (Method 1 basic); m/z 230 (M + H)$^+$, (ES$^+$). Cirillo, P. F. et al., WO 2000/43384, 27 Jul. 2000. |
| A8* | | phenyl (3-(tert-butyl)-1-(p-tolyl)-1H-pyrazol-5-yl)carbamate LCMS m/z 350 (M + H)$^+$ (ES$^+$); 348 (M − H)$^-$ (ES$^-$) Kapadia, S. R. et al., U.S. Pat. No. 6,492,529, 10 Dec. 2002. |
| A9 | | 3-tert-butyl-1-(4-methoxyphenyl)-1H-pyrazol-5-amine. R$^t$ 1.32 min (Method 2, acidic); m/z 246 (M + H)$^+$, (ES$^+$). Mathias, J. P. et al., U.S. Pat. No. 2006/0035922, 10 Aug. 2005. |
| A9* | | phenyl (3-(tert-butyl)-1-(4-methoxyphenyl)-1H-pyrazol-5-yl)carbamate LCMS m/z 366 (M + H)$^+$ (ES$^+$); 364 (M − H)$^-$ (ES$^-$) Abraham, S. et al., WO 2009/117080, 24 Sep. 2009. |

TABLE 2-continued

| No. | Structure | Name, LCMS Data and Reference |
|---|---|---|
| A10 | 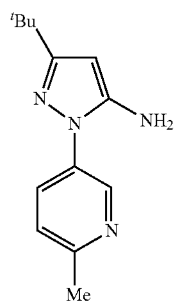 [SMILES: Cc1ccc(-n2nc(C(C)(C)C)cc2N)cn1] | 3-(tert-butyl)-1-(6-methylpyridin-3-yl)-1H-pyrazol-5-amine. R$^t$ 1.25 min (Method 2, acidic); m/z 231 (M + H)$^+$, (ES$^+$). Baron, James A. et al., WO 2001/032627, 10 May 2001. |
| A11 | 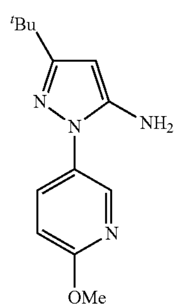 [SMILES: COc1ccc(-n2nc(C(C)(C)C)cc2N)cn1] | 3-tert-butyl-1-(6-methoxypyridin-3-yl)-1H-pyrazol-5-amine. R$^t$ 1.38 min (Method 2 acidic); m/z 247 (M + H)$^+$, (ES$^+$). Abraham, S. et al., WO 2009/117080, 24 Sep. 2009. |
| G1 | 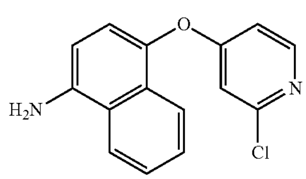 | 4-((2-chloropyridin-4-yl)oxy)naphthalen-1-amine. R$^t$ 3.13 min (Method 3); m/z 271/273 (M + H)$^+$, (ES$^+$). Ito, K. et al., WO 2010/112936, 07 Oct. 2010 |
| G2 | 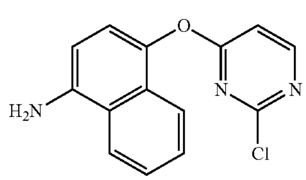 [SMILES: Nc1ccc(Oc2ccnc(Cl)c2)c2ccccc12] | 4-((2-chloropyrimidin-4-yl)oxy)naphthalen-1-amine. R$^t$ 1.80 min (Method 2, acidic); m/z 272/274 (M + H)$^+$, (ES$^+$). Cirillo, P. F. et al., WO 2002/92576, 21 Nov. 2000. |
| G2(P) | 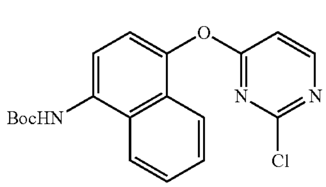 [SMILES: CC(C)(C)OC(=O)Nc1ccc(Oc2ccnc(Cl)n2)c2ccccc12] | tert-butyl (4-((2-chloropyrimidin-4-yl)oxy) naphthalen-1-yl)carbamate. R$^t$ 2.43 min (Method 2, acidic); m/z 372/374 (M + H)$^+$, (ES$^+$). Ito, K. et al., WO 2010/067130, 17 Jun. 2010 |

Intermediate A3*: Phenyl (3-(perfluoroethyl)-1-(p-tolyl)-1H-pyrazol-5-yl)carbamate

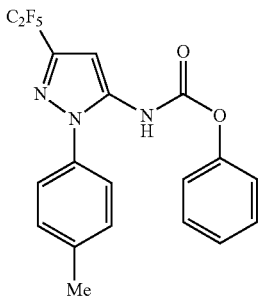

To a stirred solution of Intermediate A3 (3.00 g, 10.30 mmol) and NaHCO$_3$ (1.70 g, 20.24 mmol) in DCM (25 mL) and THF (10 mL) was added phenyl chloroformate (1.40 ml, 11.14 mmol) and the resulting mixture stirred overnight. An additional 0.2 eq. of phenyl chloroformate was added and stirring continued for a further 60 h. The reaction was diluted with water and DCM and the mixture passed through a phase separation cartridge. The resulting yellow filtrate was concentrated in vacuo giving an orange oil which solidified to a pale orange solid upon addition of a small volume of hexane and vigorous scratching. The solid was triturated in isohexane and collected by filtration. The product was washed with further isohexane providing Intermediate A3* (3.86 g) as a white solid.

$^1$H NMR (400 MHz; CDCl$_3$) δ 7.38-7.43 (m, 6H), 7.25-7.29 (m, 1H), 6.89-7.14 (m, 4H), 2.46 (s, 3H)

LCMS m/z 412 (M+H)$^+$ (ES$^+$); 410 (M–H)$^-$ (ES$^-$)

Intermediate A4*: Phenyl (3-isopropyl-1-(p-tolyl)-1H-pyrazol-5-yl)carbamate

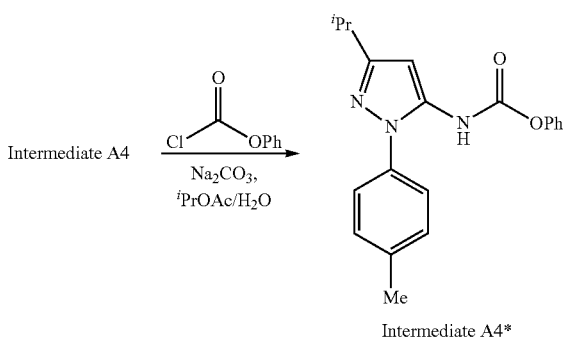 [SMILES: O=C(Cl)Oc1ccccc1 ; Cc1ccc(-n2nc(C(C)C)cc2NC(=O)Oc2ccccc2)cc1]

Intermediate A4*

To a biphasic mixture of isopropyl acetate (300 mL) and a solution of Na$_2$CO$_3$ (15.0 g, 142 mmol) in water (100 mL) was added Intermediate A4 (25.0 g, 116 mmol). The resulting suspension was stirred at RT until all solids had dissolved (ca. 10 mins) and was then treated with phenyl chloroformate (16.0 mL, 128 mmol) and the mixture stirred at RT for 2 hr. Water (200 mL) was added and the layers were separated. The organic phase was washed with water (2×100 mL) and with brine (100 mL) and then dried and concentrated in vacuo. The resultant thick yellow oil was triturated with 5% diethylether in iso-hexanes (ca. 250 mL) and the solid so produced was collected by filtration and washed with isohexane (50 mL) to afford the title compound Intermediate A4* as a white powder (28.4 g, 72%); R$^t$ 3.48 min (Method 1 acidic); m/z 336 (M+H)$^+$ (ES$^+$); $^1$H NMR δ: 1.23 (6H, d), 2.37 (3H, s), 2.91 (1H, sept), 6.29 (1H, s), 7.05-7.45 (9H, overlapping m), 9.95 (1H, s).

Intermediate A11*: Phenyl (3-(tert-butyl)-1-(6-methoxypyridin-3-yl)-1H-pyrazol-5-yl)-carbamate

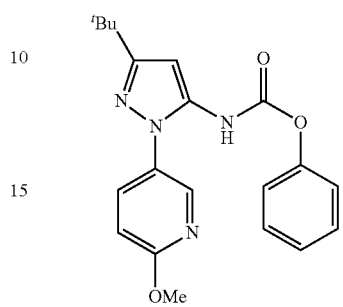

To a stirred suspension of Intermediate A11 (780 mg, 3.17 mmol) and NaHCO$_3$ (532 mg, 6.33 mmol) in DCM (8 mL) and THF (2 mL) was added phenyl chloroformate (481 µL, 3.80 mmol). The resulting mixture was stirred at rt overnight. The reaction mixture was partitioned between DCM (100 mL) and water (100 mL). The aqueous phase was back extracted with DCM (100 mL) and the combined organic extracts were dried (MgSO$_4$), filtered and concentrated in vacuo to afford an oil, which was triturated with a mixture of diethyl ether and isohexane to afford Intermediate A11* (736 mg) as a white solid.

$^1$H NMR (DMSO-d6) 400 MHz, δ: 10.12 (s, 1H), 8.32-8.31 (m, 1H), 7.85-7.82 (m, 1H), 7.41-7.37 (m, 2H), 7.24 (t, 1H), 7.10 (br s, 2H), 7.00 (d, 1H), 6.37 (s, 1H), 3.92 (s, 3H), 1.28 (s, 9H).

LCMS m/z 367 (M+H)$^+$ (ES$^+$)

Intermediate A12: 1-(4-Methoxyphenyl)-3-(tetrahydrofuran-3-yl)-1H-pyrazol-5-amine

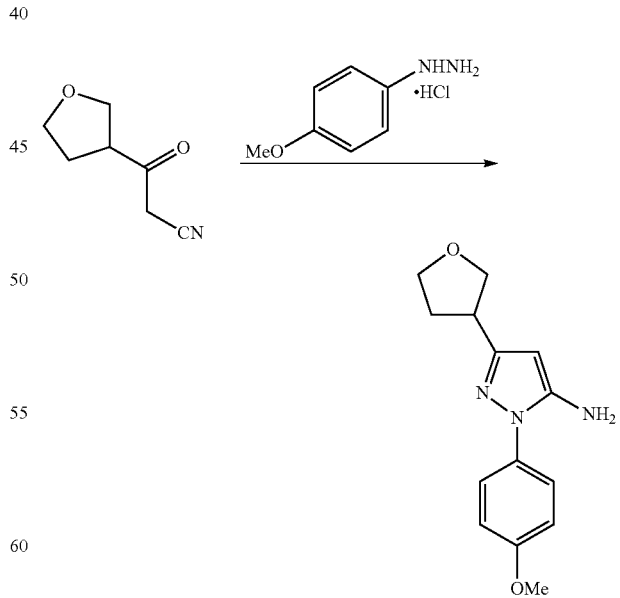

Intermediate A12

To a solution of 3-oxo-3-(tetrahydrofuran-3-yl)propanenitrile (718 mg, 4.64 mmol) in EtOH (20 mL) was added conc. hydrochloric acid (0.387 mL, 4.64 mmol) and (4-methoxyphenyl)hydrazine hydrochloride (737 mg, 4.22 mmol). The reaction mixture was heated to 80° C. for 4 hr and was then cooled to RT and adjusted to pH8 by the addition of aq NaOH (2M, <5 mL). The resulting mixture was partitioned between water (20 mL) and Et$_2$O (25 mL) and the aq layer was separated and extracted with ether (25 mL). The combined organic extracts were dried and evaporated in vacuo and the residue was purified by flash column chromatography (SiO$_2$, 40 g, 0-5% MeOH in DCM, gradient elution) to afford the title compound, Intermediate A12, as a pale orange solid (503 mg, 45%); R$^t$ 1.04 min (Method 2); m/z 260 (M+H)$^+$, (ES$^+$).

Intermediate A13: 3-(3-Methyloxetan-3-yl)-1-(p-tolyl)-1H-pyrazol-5-amine

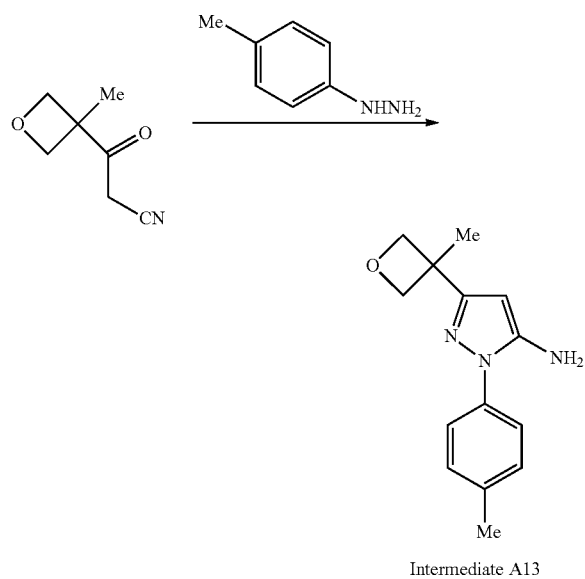

Intermediate A13

A solution of p-tolylhydrazine (79 mg, 0.65 mmol) and 3-(3-methyloxetan-3-yl)-3-oxo propanenitrile, (Abraham, S. et al., WO 2011/022473, 24 Feb. 2011) (100 mg, 0.65 mmol) in anhydrous toluene (3.0 mL) was heated to 110° C. for 6 hr and was then cooled to RT for 18 hr. The reaction mixture was evaporated in vacuo and the residue was purified by flash column chromatography (SiO$_2$, 12 g, eluted 10-40% EtOAc in isohexane, gradient elution) to afford the title compound, Intermediate A13 (117 mg, 87% purity by HPLC, 65%); R$^t$ 1.50 min (Method 2 acidic); m/z 244 (M+H)$^+$, (ES$^+$). The material so obtained was used in subsequent reactions without additional purification.

Intermediate A14: 1-(4-Methoxyphenyl)-3-(3-methyloxetan-3-yl)-1H-pyrazol-5-amine

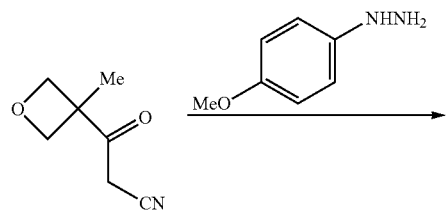

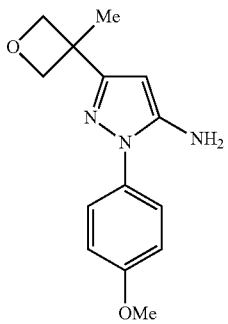

Intermediate A14

A solution of 3-(3-methyloxetan-3-yl)-3-oxopropanenitrile, (750 mg, 5.40 mmol) and (4-methoxyphenyl)hydrazine (750 mg, 5.40 mmol) in anhydrous toluene (7.0 mL) was heated to 110° C. for 4 hr in an apparatus equipped with a Dean-Stark distillation trap. The reaction mixture was cooled to RT for 18 hr and was then evaporated in vacuo. The residue was purified by flash column chromatography (SiO$_2$, 40 g, 10-75%, EtOAc in isohexane, gradient elution) to afford the title compound, Intermediate A14 as a blue solid (980 mg, 66%); R$^t$ 1.24 min (Method 2 acidic); m/z 260 (M+H)$^+$, (ES$^+$).

Intermediate A15: 3-(tert-Butyl)-1-(3-(2-methoxyethoxyl)phenyl)-1H-pyrazol-5-amine

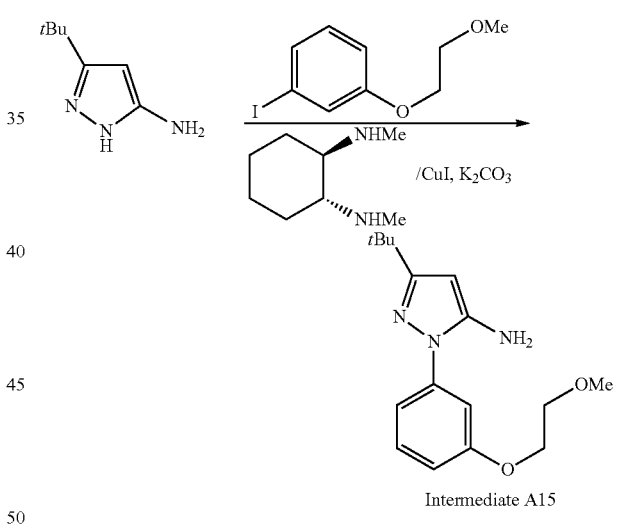

Intermediate A15

To a solution of 1-iodo-3-(2-methoxyethoxyl)benzene (1.18 g, 4.05 mmol) in anhydrous toluene (7.0 mL) was added 3-(tert-butyl)-1H-pyrazol-5-amine (619 mg, 4.45 mmol) followed by (1R,2R)—N$^1$,N$^2$-dimethylcyclohexane-1,2-diamine (255 μL, 1.62 mmol) and potassium carbonate (1.96 g, 14.2 mmol). The mixture was purged with nitrogen, after which copper(I) iodide (77 mg, 0.41 mmol) was added and the reaction mixture heated at reflux under nitrogen for 18 hr. The resulting mixture was cooled to RT and was partitioned between EtOAc (250 mL) and water (250 mL). The organic layer was separated and was washed with water (2×250 mL) and brine (250 mL) and was then dried and evaporated in vacuo. The residue was purified by flash column chromatography (SiO$_2$, 120 g, 0-5% [0.7 M NH$_3$ in MeOH] in DCM, gradient elution) to afford the title compound, Intermediate A15, as a brown gum (1.04 g, 84%); R$^t$ 2.20 min (Method 1, acidic); m/z 290 (M+H)$^+$ (ES$^+$).

Intermediate A16: 3-Isopropyl-1-(6-methoxypyridin-3-yl)-1H-pyrazol-5-amine

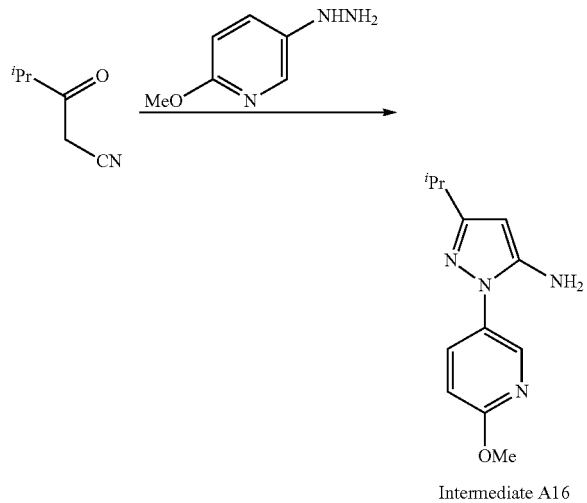

Intermediate A16

A solution of 4-methyl-3-oxopentanenitrile, (599 mg, 5.39 mmol) and 5-hydrazinyl-2-methoxy pyridine (750 mg, 5.40 mmol) in anhydrous toluene (7.0 mL) was heated to 110° C. for 4 hr in an apparatus equipped with a Dean-Stark distillation trap. The reaction mixture was cooled to RT for 18 hr and was then evaporated in vacuo. The residue was purified by flash column chromatography (SiO$_2$, 40 g, 10-80%, EtOAc in isohexane, gradient elution) to afford the title compound, Intermediate A16 as a pale yellow solid (825 mg, 63%); R$^r$ 1.15 min (Method 2 acidic); m/z 233 (M+H)$^+$, (ES$^+$).

Intermediate A17: 1-(4-Methoxyphenyl)-3-(tetrahydrofuran-2-yl)-1H-pyrazol-5-amine

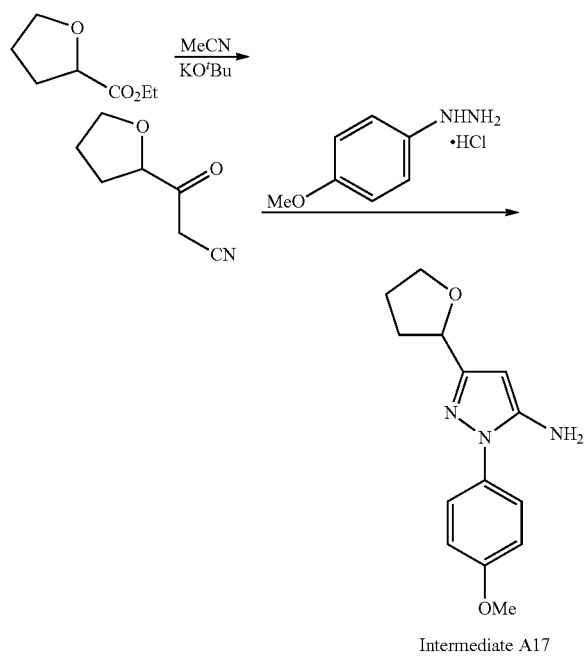

Intermediate A17

To a solution of potassium 2-methylpropan-2-olate (5.74 g, 51.2 mmol) in THF (30 mL) was added, over 25 min, a solution of methyl tetrahydrofuran-2-carboxylate (4.0 mL, 34 mmol) and MeCN (2.7 mL, 51 mmol) in THF (13.0 mL). The resulting mixture was kept at RT for 18 hr and was then quenched by the addition of 1M hydrochloric acid (30 mL), providing a biphasic mixture. The phases were separated, the organic phase was retained and the aq phase was extracted with Et$_2$O (2×30 mL) and with DCM (2×30 mL). The original organic phase and both organic extracts were combined and resulting solution was dried and then carefully concentrated in vacuo to afford a mixture that comprised of 3-oxo-3-(tetrahydrofuran-2-yl)propanenitrile, THF and $^t$BuOH (in an approximate ratio of 1:1:1 w/w/w) (9.07 g, ~30% w/w by $^1$H-NMR, ~60%); $^1$H NMR δ: 1.90-2.10 (3H, overlapping m), 2.26 (1H, m), 3.70 (1H, d), 3.76 (1H, d), 3.90-3.99 (2H, overlapping m), 4.39 (1H, m). This material was used in the subsequent reactions without additional purification.

To a solution of the crude ketonitrile described above, (1.0 g, ~30% purity, ~2.0 mmol) and (4-methoxyphenyl)hydrazine hydrochloride (148 mg, 0.849 mmol) in EtOH (11.0 mL) was added concentrated hydrochloric acid (80 μL, 12 M, 1 mmol). The reaction mixture was heated to reflux for 4 hr and then cooled to RT and evaporated in vacuo. The residue was partitioned between DCM (5.0 mL) and saturated aq. NaHCO$_3$ (5.0 mL). The aq layer was separated and extracted with DCM (3×5 mL) and the combined organic extracts were evaporated in vacuo. The residue was purified by flash column chromatography (SiO$_2$, 40 g, 0-10% [0.7 M NH$_3$ in MeOH] in DCM, gradient elution then SiO$_2$, 40 g, 0-100%, EtOAc in isohexane, gradient elution) to afford the title compound, Intermediate A17 as an orange oil (51 mg, 21%); R$^r$ 1.14 min (Method 2 acidic); m/z 260 (M+H)$^+$, (ES$^+$).

Intermediate A18: 1-(3,4-Dimethylphenyl)-3-isopropyl-1H-pyrazol-5-amine

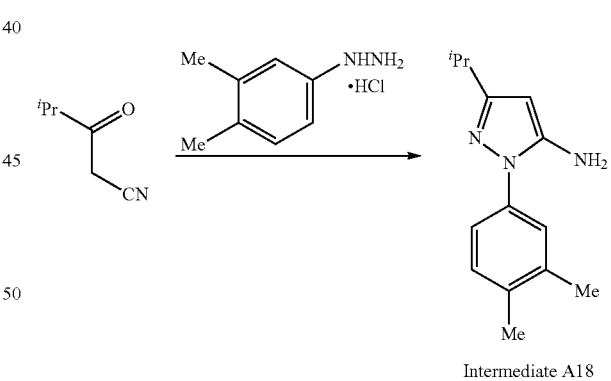

Intermediate A18

To a solution of (3,4-dimethylphenyl)hydrazine hydrochloride (3.0 g, 17 mmol) and 4-methyl-3-oxopentanenitrile (2.3 mL, 19 mmol) in EtOH (20 mL) was added concentrated hydrochloric acid (1.7 mL, 12 M, 20 mmol). The reaction mixture was heated to reflux for 18 hr and was then cooled to RT and evaporated in vacuo. The residue was partitioned between DCM (50 mL) and water (20 mL). The aq phase was separated and was extracted with DCM (2×50 mL). The combined organic extracts were dried and evaporated in vacuo and the residue was purified by flash column chromatography (SiO$_2$, 80 g, 0-100% Et$_2$O in isohexane, gradient elution) to afford the title compound, Intermediate A18 as an orange oil (2.69 g, 67%); R$^r$ 1.49 min (Method 2 acidic); m/z 230 (M+H)$^+$, (ES$^+$).

Intermediate A19*: Phenyl (1-(p-tolyl)-3-(1,1,1-trifluoro-2-methylpropan-2-yl)-1H-pyrazol-5-yl)carbamate

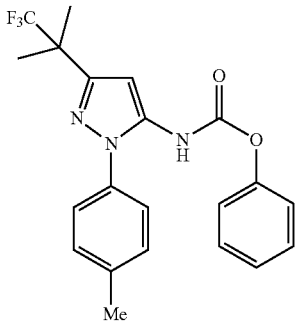 [SMILES: Cc1ccc(-n2nc(C(C)(C)C(F)(F)F)cc2NC(=O)Oc2ccccc2)cc1]

p-Tolylhydrazine, HCl (3.2 g, 19.97 mmol) and 5,5,5-trifluoro-4,4-dimethyl-3-oxopentanenitrile (4.3 g, 20.40 mmol) were heated to reflux in ethanol (15 mL) for 8 h. The mixture was concentrated under reduced pressure to yield a brown oil. Saturated NaHCO$_3$ (50 mL) and water (50 mL) were added and the mixture was extracted with diethyl ether (3×50 mL). The combined organic phases were concentrated and the residue was purified by chromatography on the Companion (40 g column, 0-50% diethyl ether/iso-hexane) to afford an orange oil which crystallised on standing. Recrystallisation in cyclohexane (30 mL) followed by washing with iso-hexane (2×30 mL) yielded 1-(p-tolyl)-3-(1,1,1-trifluoro-2-methylpropan-2-yl)-1H-pyrazol-5-amine (Intermediate A19, 1.75 g) as a colourless crystalline solid.

$^1$H NMR (400 MHz; CDCl$_3$) δ 7.42 (d, 2H), 7.26 (d, 2H), 5.67-5.64 (m, 1H), 3.72 (s, 2H), 2.39 (s, 3H), 1.52 (s, 6H).

LCMS m/z 284 (M+H)$^+$ (ES$^+$)

Phenyl chloroformate (0.85 ml, 6.79 mmol) was added to a stirred mixture of Intermediate A19 (1.75 g, 6.18 mmol) and NaHCO$_3$ (1.05 g, 12.50 mmol) in DCM (20 mL) and THF (15 mL) at rt. The mixture was stirred for 2 h then partitioned between DCM (50 mL) and water (50 mL). The organic layer was separated, dried (MgSO$_4$) and evaporated under reduced pressure to yield a colourless oil. The oil was crystallised from cyclohexane to yield Intermediate A19* (2.14 g) as a white solid.

$^1$H NMR (CDCl$_3$) 400 MHz, δ: 7.43-7.31 (m, 6H), 7.30-7.22 (m, 1H), 7.20-7.07 (m, 2H), 7.05-6.88 (m, 1H), 6.68-6.55 (m, 1H), 2.44 (s, 3H), 1.56 (s, 6H).

Intermediate A20*: Phenyl (3-(2-cyanopropan-2-yl)-1-(p-tolyl)-1H-pyrazol-5-yl)-carbamate

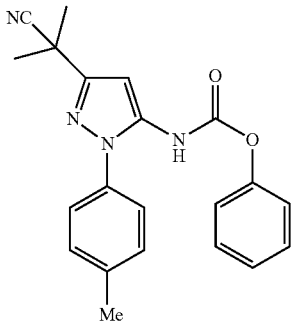 [SMILES: Cc1ccc(-n2nc(C(C)(C)C#N)cc2NC(=O)Oc2ccccc2)cc1]

A mixture of p-tolylhydrazine hydrochloride (6.5 g, 41.0 mmol) and 2,2-dimethyl-3-oxopentanedinitrile (5.58 g, 20.49 mmol) in EtOH (80 mL) was heated under reflux for 2 h. The mixture was cooled and the solvent evaporated under reduced pressure. The residue was partitioned between EtOAc (200 mL) and aq NaHCO$_3$ soln (100 mL), the organic layer separated, washed with water (100 mL), dried (MgSO$_4$), filtered and evaporated under reduced pressure. The crude product was purified by chromatography on silica gel (120 g column, 0-40% EtOAc/isohexane) to afford 2-(5-amino-1-(p-tolyl)-1H-pyrazol-3-yl)-2-methylpropanenitrile (Intermediate A20, 2.834 g) as a white solid.

$^1$H NMR (400 MHz; CDCl$_3$) δ 7.40 (d, 2H), 7.27 (d, 2H), 5.67 (s, 1H), 3.80 (s, 2H), 2.39 (s, 3H), 1.73 (s, 6H).

LCMS m/z 241 (M+H)$^+$ (ES$^+$)

Phenyl chloroformate (1.6 ml, 12.77 mmol) was added to a stirred mixture of Intermediate A20 (2.83 g, 11.78 mmol) and NaHCO$_3$ (2 g, 23.81 mmol) in DCM (40 mL) and THF (10 mL) at rt. The mixture was stirred for 18 h then partitioned between DCM (100 mL) and water (100 mL). The organic layer was separated, washed with brine (100 mL), dried (MgSO$_4$), filtered and evaporated under reduced pressure. The residue was triturated with ether/isohexane, the solid filtered and dried to afford Intermediate A20* (3.86 g) LCMS m/z 361 (M+H)$^+$ (ES$^+$); 359 (M−H)$^-$ (ES$^-$)

Intermediate A21: 3-(Prop-1-en-2-yl)-1-(p-tolyl)-1H-pyrazol-5-amine

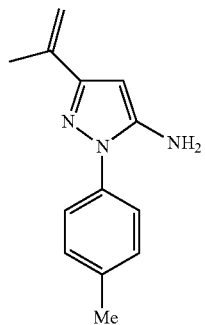 [SMILES: C=C(C)c1cc(N)n(-c2ccc(C)cc2)n1]

A mixture of 4-fluoro-4-methyl-3-oxopentanenitrile (5.5 g, 36.2 mmol) and p-tolylhydrazine hydrochloride (8.61 g, 54.3 mmol) in EtOH (80 mL) was heated at 80° C. for 3 h. The mixture was cooled, the solvent evaporated and the residue partitioned between ether (200 mL) and sat aq NaHCO$_3$ soln (200 mL). The organic layer was separated, washed with water (100 mL), dried (MgSO$_4$), filtered and evaporated under reduced pressure. The crude product was purified by chromatography on silica gel (120 g column, 0-40% EtOAc/isohexane) to afford Intermediate A21 (3.51 g).

$^1$H NMR (400 MHz; CDCl$_3$) δ 7.44 (d, 2H), 7.26 (d, 2H), 5.77 (s, 1H), 5.46 (s, 1H), 5.06 (s, 1H), 3.73 (s, 2H), 2.39 (s, 3H), 2.13 (s, 3H).

LCMS m/z 214 (M+H)$^+$ (ES$^+$)

Intermediate A22*: Phenyl (3-(2-methoxypropan-2-yl)-1-(p-tolyl)-1H-pyrazol-5-yl)-carbamate

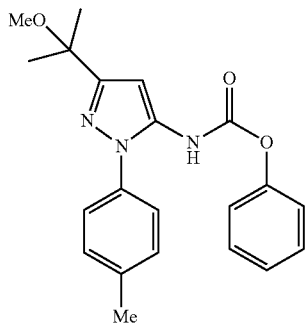 [SMILES: COC(C)(C)c1cc(NC(=O)Oc2ccccc2)n(-c2ccc(C)cc2)n1]

A mixture of Intermediate A21 (2 g, 9.38 mmol) and 4M HCl in dioxane (5 mL, 20 mmol) in MeOH (20 mL) was heated at 60° C. in a sealed tube for 72 h. The solvent was evaporated and the residue partitioned between EtOAc (150 mL) and aq NaHCO₃ soln (100 mL). The organic layer was separated, washed with brine (100 mL), dried (MgSO₄), filtered and evaporated under reduced pressure. The crude product was purified by chromatography on silica gel (80 g column, 0-50% EtOAc/isohexane) to afford 3-(2-methoxypropan-2-yl)-1-(p-tolyl)-1H-pyrazol-5-amine (Intermediate A22, 1.202 g) as a white solid.

$^1$H NMR (400 MHz; CDCl$_3$) δ 7.42 (d, 2H), 7.26 (d, 2H), 5.63 (s, 1H), 3.74 (s, 2H), 3.17 (s, 3H), 2.39 (s, 3H), 1.55 (s, 6H).

LCMS m/z 246 (M+H)$^+$ (ES$^+$)

Phenyl chloroformate (1.1 ml, 8.78 mmol) was added to a stirred mixture of Intermediate A22 (1.95 g, 7.95 mmol) and NaHCO₃ (1.4 g, 16.67 mmol) in DCM (25 mL) and THF (7 mL) at rt. The mixture was stirred for 3 h then partitioned between DCM (150 mL) and water (200 mL). The organic layer was separated, washed with brine (100 mL), dried (MgSO₄), filtered and evaporated under reduced pressure. The residue was recrystallised form cyclohexane, the solid filtered and dried to afford the sub-title compound (1.568 g)

$^1$H NMR (400 MHz; CDCl$_3$) δ 7.41-7.23 (m, 7H), 7.17 (brs, 2H), 6.97 (brs, 1H), 6.59 (brs, 1H), 3.18 (s, 3H), 2.44 (s, 3H), 1.58 (s, 6H).

LCMS m/z 366 (M+H)$^+$ (ES$^+$); 364 (M–H)$^-$ (ES$^-$)

Intermediate B1: 3-((4-((4-Aminonaphthalen-1-yl)oxy)pyridin-2-yl)amino)-5-methoxy-N-(2-morpholinoethyl)benzamide

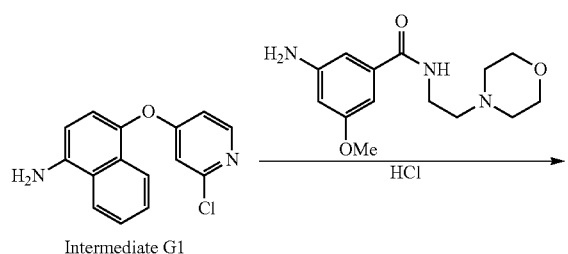

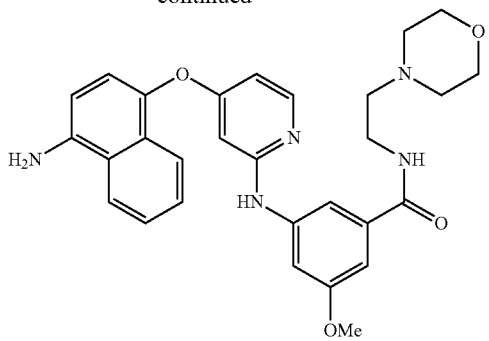

Intermediate B1

To a solution of Intermediate G1 (485 mg, 1.79 mmol) in NMP (5.0 mL) was added 3-amino-5-methoxy-N-(2-morpholinoethyl)benzamide (500 mg, 1.79 mmol) and a solution of HCl in dioxane (4.0 M, 900 µL, 3.6 mmol) and the resulting mixture was heated at 120° C. in a sealed tube for 24 hr. The reaction mixture was cooled to RT, an additional aliquot of HCl in dioxane (450 µL, 1.8 mmol) was added and the mixture heated at 120° C. for a further 24 hr and then re-cooled to RT. The resulting mixture was subjected to SCX capture and release and the crude product so obtained was purified by flash column chromatography (SiO₂, 120 g, 30-100% EtOAc in isohexane, gradient elution and then 0-20% MeOH in DCM, gradient elution) to afford the title compound, Intermediate B1, as a purple solid (459 mg, 80% pure by HPLC, 40%); R$^t$ 1.73 min (Method 3, 80% pure); m/z 514 (M+H)$^+$, (ES$^+$). This material was used in subsequent steps without additional purification.

Intermediate B2: 3-((4-((4-Aminonaphthalen-1-yl)oxy)pyrimidin-2-yl)amino)-N-propyl benzamide

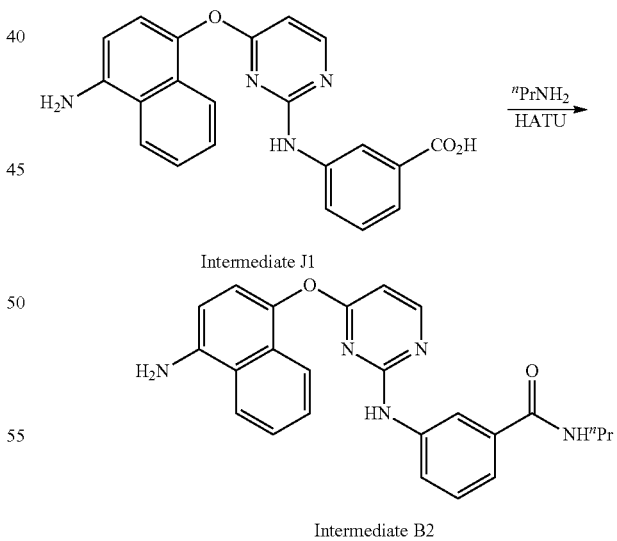

To a solution of Intermediate J1 (50 mg, 0.13 mmol), propan-1-amine (13 µL, 0.16 mmol) and DIPEA (47 µL, 0.27 mmol) in DMF (2.0 mL) was added HATU (61 mg, 0.16 mmol) and the resulting mixture maintained at RT. Additional portions of HATU (61 mg, 0.16 mmol) were added after 17 hr and after 24 hr and after a further 18 hr at RT the mixture was partitioned between EtOAc (5.0 mL) and saturated aq. NaHCO₃ (5.0 mL). The organic phase was separated and was washed with brine (2×5.0 mL) and then dried and evaporated in vacuo to afford the title compound, Intermediate B2, as a purple solid (37 mg, 63%); $R^t$ 1.78 min (Method 2 acidic); m/z 414 (M+H)$^+$, (ES$^+$).

Intermediate B3: 3-((4-((4-Aminonaphthalen-1-yl)oxy)pyrimidin-2-yl)amino)-N-(2-morpholinoethyl)benzamide

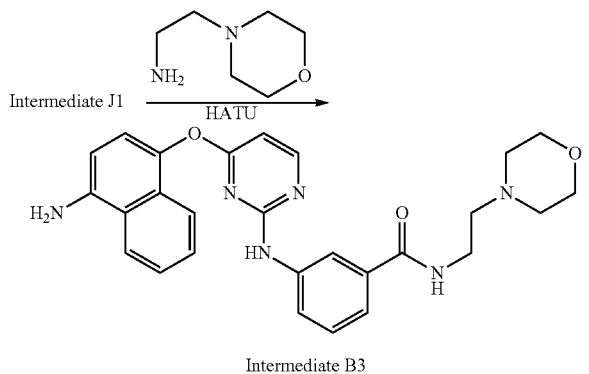

Intermediate B3

To a solution of Intermediate J1 (247 mg, 0.617 mmol), 2-morpholinoethanamine (100 μL, 0.760 mmol) and DIPEA (550 μL, 3.2 mmol) in DMF (2.0 mL) was added HATU (285 mg, 0.750 mmol) and the resulting mixture maintained at RT for 3 hr and then partitioned between EtOAc (20 mL) and saturated aq. NaHCO$_3$ (20 mL). The organic phase was separated and was extracted with hydrochloric acid (1.0 M, 20 mL). The acidic extract was neutralised by the addition of aq NaOH (2.0 M, 10 mL) and the resulting aq phase extracted with EtOAc (2×30 mL). The extracts from the neutralised aq phase were combined, and washed with water (2×30 mL) and with brine (2×30 mL), and then dried and evaporated in vacuo to afford the title compound, Intermediate B3, as a pale red solid (226 mg, 68%); $R^t$ 1.38 min (Method 2 acidic); m/z 485 (M+H)$^+$, (ES$^+$).

Intermediate B4: 3-((4-((4-Aminonaphthalen-1-yl)oxy)pyrimidin-2-yl)amino)-N-(2-(dimethylamino)ethyl)-4-methoxybenzamide

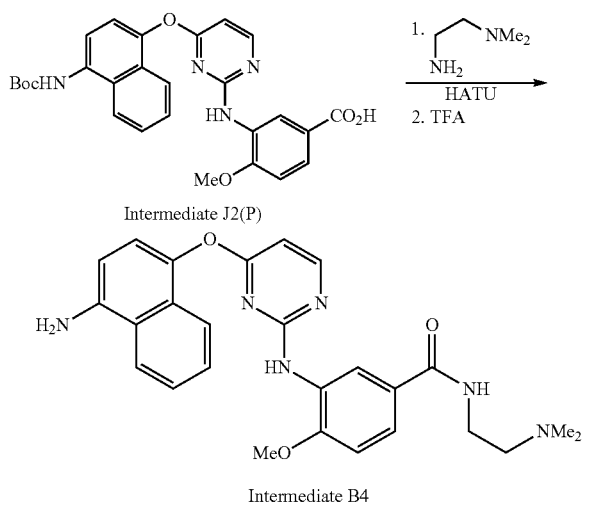

Intermediate B4

To a solution of Intermediate J2(P) (243 mg, 0.451 mmol), N$^1$,N$^1$-dimethylethane-1,2-diamine (74 μL, 0.68 mmol) and DIPEA (160 μL, 0.9 mmol) in DMF (25 mL) at 0° C. was added HATU (257 mg, 0.676 mmol). The resulting mixture was warmed to RT and after 3 days was partitioned between DCM (10.0 mL) and aq NaOH (1.0 M, 10.0 mL). The organic phase was separated and was washed with water (2×15 mL) and with brine (2×15 mL) and then dried and evaporated in vacuo. The residue was purified by flash column chromatography (SiO$_2$, 12 g, 0-10% [0.7 M NH$_3$ in MeOH] in DCM, gradient elution) to afford tert-butyl (4-((2-((5-((2-(dimethylamino)ethyl)carbamoyl)-2-methoxyphenyl)amino) pyrimidin-4-yl)oxy)naphthalen-1-yl)carbamate as an orange solid (137 mg, 80% pure, 43%); $R^t$ 2.66 min (Method 3); m/z 573 (M+H)$^+$, (ES$^+$). This material was used in the subsequent deprotection step without additional purification.

To a solution of the Boc-protected amine described above (137 mg, 80% pure, 0.239 mmol) in DCM (3.0 mL) was added TFA (0.50 mL, 6.7 mmol) and the reaction mixture kept at RT for 3 hr and then evaporated in vacuo. The residue was purified by SCX capture and release to afford the title compound, Intermediate B4, as a pale pink solid (108 mg, 92%); $R^t$ 1.96 min (Method 3); m/z 473 (M+H)$^+$, (ES$^+$).

Intermediate B5: 3-((4-((4-Aminonaphthalen-1-yl)oxy)pyrimidin-2-yl)amino)-4-methoxy-N-(2-morpholinoethyl)benzamide

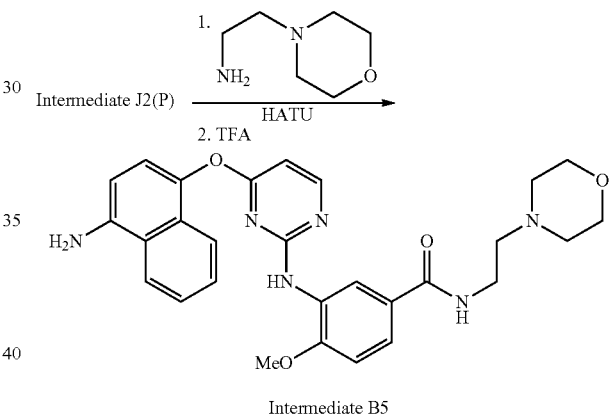

Intermediate B5

To a solution of Intermediate J2(P) (500 mg, 0.930 mmol), 2-morpholinoethanamine (183 μL, 1.39 mmol) and DIPEA (320 μL, 0.900 mmol) in DMF (3.0 mL) at 0° C. was added HATU (529 mg, 1.39 mmol) and the resulting mixture allowed to warmed to RT. A precipitate formed after 10 min and after 30 min the solid material was collected by filtration and was washed with water and then dried in vacuo to afford tert-butyl (4-((2-((2-methoxy-5-((2-morpholinoethyl)carbamoyl)phenyl)amino)pyrimidin-4-yl)oxy)naphthalen-1-yl) carbamate as an off-white solid (511 mg, 84%); $R^t$ 2.69 min (Method 3); m/z 615 (M+H)$^+$, (ES$^+$).

To a solution of the Boc-protected amine described above (508 mg, 0.826 mmol) in DCM (10.0 mL) was added TFA (2.0 mL, 27 mmol) and the reaction mixture kept at RT for 18 hr and then evaporated in vacuo. The residue was partitioned between CH$_2$Cl$_2$ (10.0 mL) and sat. aq NaHCO$_3$ (10.0 mL). The organic phase was separated and was washed with water (2×20 mL) and with brine (2×20 mL) and then dried and evaporated in vacuo. The residue was purified by SCX capture and release to afford the title compound, Intermediate B5, as a pale pink solid (162 mg, 85% pure by HPLC, 32%); $R^t$ 1.24 min (Method 3); m/z 515 (M+H)$^+$, (ES$^+$). This material was used in subsequent steps without additional purification.

Intermediate B6: 3-((4-((4-Aminonaphthalen-1-yl)oxy)pyrimidin-2-yl)amino)-N-(2-hydroxyethyl)-4-methoxybenzamide

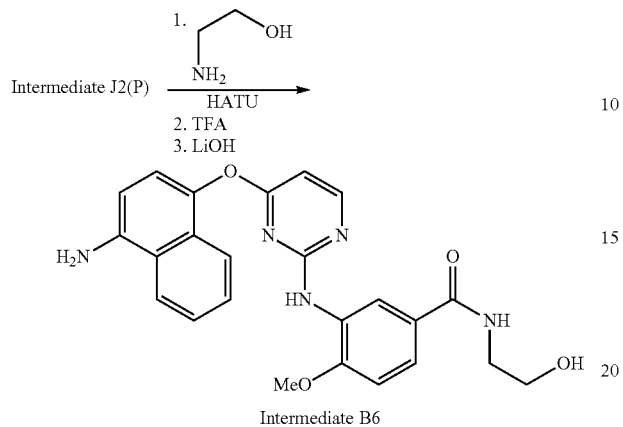

Intermediate B6

To a solution of Intermediate J2(P) (411 mg, 0.763 mmol), 2-aminoethanol (69 μL, 1.1 mmol) and DIPEA (270 μL, 1.50 mmol) in DMF (25 mL) at 0° C. was added HATU (435 mg, 1.14 mmol). The resulting mixture was warmed to RT for 18 hr and was then partitioned between aq NaOH (1.0 M, 10.0 mL) and DCM (10.0 mL). The organic phase was separated and was washed with brine (2×15 mL) and with water (2×15 mL) and then dried and evaporated in vacuo. The residue so obtained was combined with the crude product from an earlier, smaller scale reaction (100 mg of Intermediate J2(P)) which was performed in an identical manner and the combined materials were purified by flash column chromatography (SiO$_2$, 40 g, 0-5% [0.7 M NH$_3$ in MeOH] in DCM, gradient elution) to afford tert-butyl (4-((2-((3-((2-hydroxyethyl)carbamoyl)-2-methoxyphenyl)amino)pyrimidin-4-yl)oxy)naphthalen-1-yl) carbamate as a pale pink solid (230 mg, 43%); R$^t$ 3.23 min (Method 3); m/z 546 (M+H)$^+$, (ES$^+$).

To a solution of the Boc-protected amine described above (228 mg, 0.418 mmol) in DCM (5.0 mL) was added TFA (1.0 mL, 13 mmol) and the reaction mixture kept at RT for 18 hr and then evaporated in vacuo. The residue was taken up in THF (4.0 mL) and a solution of LiOH (15 mg, 0.62 mmol) in aq MeOH (1:1 v/v, 2.0 mL) was added and reaction mixture was maintained at RT for 3 days, [in order to saponify the trifluoroacetate that results from the proceeding deprotection step] and was then evaporated in vacuo. The residue was purified by SCX capture and release to afford the title compound, Intermediate B6, as an orange solid (169 mg, 48%); R$^t$ 2.31 min (Method 3); m/z 446 (M+H)$^+$, (ES$^+$).

Intermediate B7: 4-((4-((4-Aminonaphthalen-1-yl)oxy)pyrimidin-2-yl)amino)-N-(2-(dimethylamino)ethyl)-3-methoxybenzamide

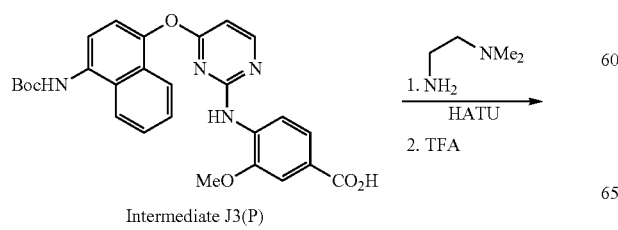

Intermediate J3(P)

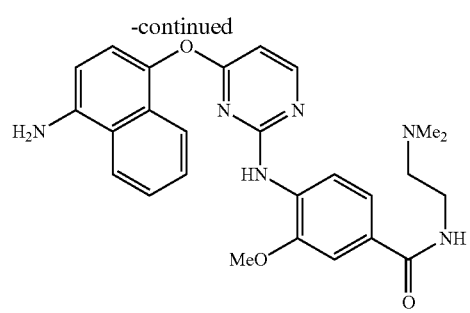

Intermediate B7

To a solution of Intermediate J3(P) (355 mg, 0.706 mmol), N$^1$,N$^1$-dimethylethane-1,2-diamine (116 μL, 1.06 mmol) and DIPEA (250 μL, 1.40 mmol) in DMF (1.5 mL) was added HATU (403 mg, 0.676 mmol) and the resulting mixture kept at RT for 3 hr and then partitioned between DCM (15 mL) and aq NaOH (1.0 M, 15 mL). The organic phase was separated and was washed with brine (2×15 mL) and with water (2×15 mL) and then dried and evaporated in vacuo. The residue was purified by flash column chromatography (SiO$_2$, 40 g, 0-10% [0.7 M NH$_3$ in MeOH] in DCM, gradient elution) to afford tert-butyl (4-((2-((4-((2-(dimethylamino)ethyl)carbamoyl)-2-methoxyphenyl)amino)pyrimidin-4-yl)oxy)naphthalen-1-yl)carbamate as an orange solid (284 mg, 67%); R$^t$ 2.74 min (Method 3); m/z 573 (M+H)$^+$, (ES$^+$).

To a solution of the Boc-protected amine described above (137 mg, 80% pure, 0.239 mmol) in DCM (3.0 mL) was added TFA (1.0 mL, 13 mmol) and the reaction mixture maintained at RT for 18 hr and then evaporated in vacuo. The residue was purified by SCX capture and release to afford the title compound, Intermediate B7, as a pale orange solid (208 mg, 88%); R$^t$ 2.20 min (Method 3); m/z 473 (M+H)$^+$, (ES$^+$).

Intermediate B8: 4-((4-((4-Aminonaphthalen-1-yl)oxy)pyrimidin-2-yl)amino)-3-methoxy-N-(2-morpholinoethyl)benzamide

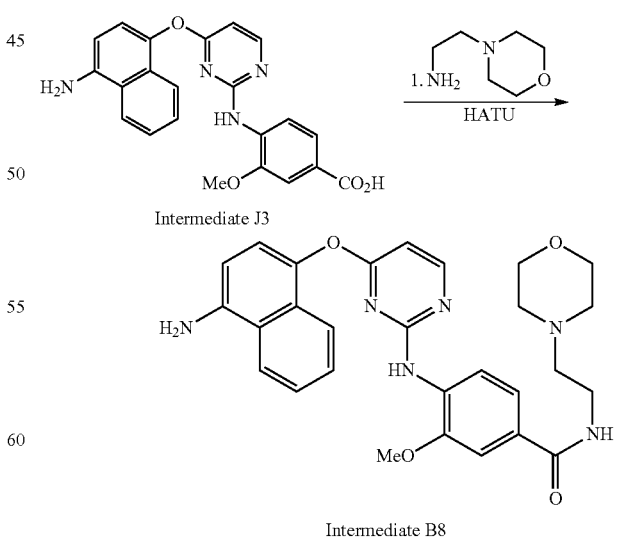

Intermediate B8

To a solution of Intermediate J3 (320 mg, 0.810 mmol), 2-morpholinoethanamine (159 μL, 1.21 mmol) and DIPEA (280 μL, 1.60 mmol) in DMF (2.0 mL) at 0° C. was added HATU (459 mg, 1.21 mmol). The resulting mixture was allowed to warmed to RT and after 3 hr was partitioned between DCM (10.0 mL) and aq NaOH (1.0 M, 10.0 mL). The organic phase was separated and was washed with water (2×20 mL) and then dried and evaporated in vacuo. The residue was purified by flash column chromatography (SiO₂, 12 g, 0-60% [0.7 M NH₃ in MeOH] in DCM, gradient elution) to afford the title compound, Intermediate B8, as a pale pink solid (338 mg, 78%); R$^t$ 1.53 min (Method 2 acidic); m/z 515 (M+H)$^+$, (ES$^+$).

Intermediate B9: 4-((4-((4-Aminonaphthalen-1-yl)oxy)pyrimidin-2-yl)amino)-N-(2-hydroxyethyl)-3-methoxybenzamide

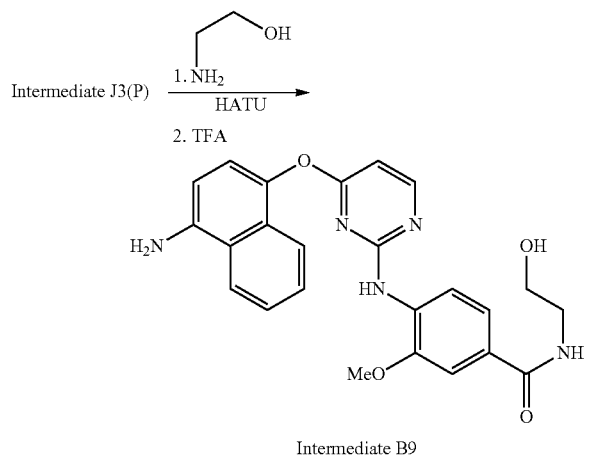

Intermediate B9

To a solution of Intermediate J3(P) (370 mg, 0.736 mmol), 2-aminoethanol (67 μL, 1.1 mmol) and DIPEA (260 μL, 1.50 mmol) in DMF (1.5 mL) was added HATU (529 mg, 1.39 mmol). The resulting mixture was maintained at RT for 3 hr and was then partitioned between DCM (15 mL) and aq NaOH (1.0 M, 15 mL). The organic phase was separated and was washed with water (2×15 mL) and with brine (2×15 mL) and was then dried and evaporated in vacuo. The residue was purified by flash column chromatography (SiO₂, 40 g, 0-7%, [0.7 M NH₃ in MeOH] in DCM, gradient elution) to afford tert-butyl (4-((2-((4-((2-hydroxyethyl)carbamoyl)-2-methoxyphenyl)amino)pyrimidin-4-yl)oxy)naphthalen-1-yl) carbamate as pale pink solid (318 mg, 77%); R$^t$ 3.45 min (Method 3); m/z 546 (M+H)$^+$, (ES$^+$).

To a solution of the Boc-protected amine described above (316 mg, 0.579 mmol) in DCM (6.0 mL) was added TFA (0.80 mL, 11 mmol) and the reaction mixture kept at RT for 1.5 hr and then evaporated in vacuo. The residue was taken up into THF (5.0 mL) and treated with a solution of LiOH (10 mg, 0.44 mmol) in aq MeOH (1:1 v/v, 2.0 mL) and the mixture maintained at RT for 18 hr and then evaporated in vacuo. The residue was purified by SCX capture and release to afford the title compound, Intermediate B9, as a pale purple solid (253 mg, 81%); R$^t$ 2.66 min (Method 3); m/z 446 (M+H)$^+$, (ES$^+$).

Intermediate B10: 3-((4-((4-Aminonaphthalen-1-yl)oxy)pyrimidin-2-yl)amino)-5-chloro-N-(2-morpholinoethyl)benzamide

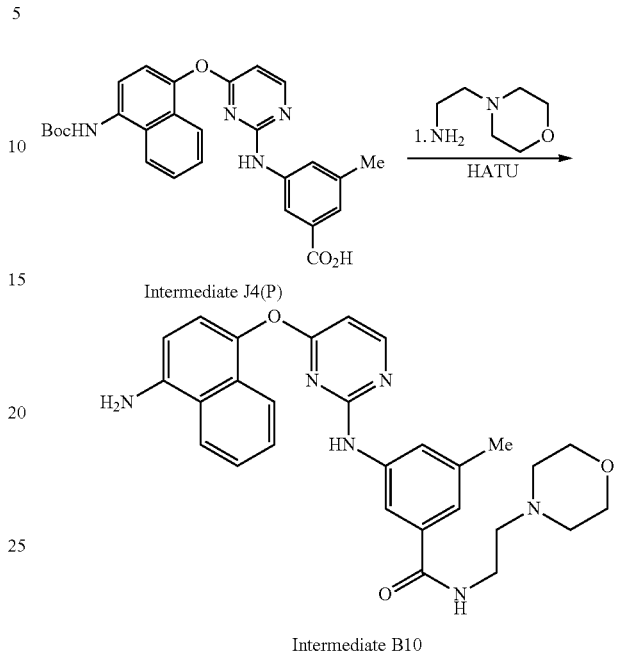

Intermediate B10

To a solution of Intermediate J4(P) (500 mg, 1.00 mmol), 2-morpholinoethanamine (229 μL, 1.75 mmol) and DIPEA (360 μL, 1.50 mmol) in DMF (2.0 mL) at 0° C. was added HATU (586 mg, 1.10 mmol). The resulting mixture was allowed to warm to RT and after 4 hr was diluted with water (20 mL). The resulting suspension was sonicated for 10 min and the precipitate was then collected by filtration to afford tert-butyl (4-((2-((3-methyl-5-((2-morpholinoethyl) carbamoyl)phenyl)amino)pyrimidin-4-yl)oxy)naphthalen-1-yl)carbamate as a pale brown solid (589 mg, 89%); R$^t$ 2.77 min (Method 3); m/z 599 (M+H)$^+$, (ES$^+$).

To a solution of the Boc-protected amine described above (580 mg, 0.900 mmol) in DCM (10.0 mL) was added TFA (2.0 mL, 27 mmol) and the reaction mixture kept at RT for 3.5 hr and then evaporated in vacuo. The residue was purified by SCX capture and release to afford the title compound, Intermediate B10, as a brown solid (475 mg, 100%); R$^t$ 2.14 min (Method 3); m/z 499 (M+H)$^+$, (ES$^+$).

Intermediate B11: 3-((4-((4-Aminonaphthalen-1-yl)oxy)pyrimidin-2-yl)amino)-N-(2-morpholinoethyl)-5-(trifluoromethyl)benzamide

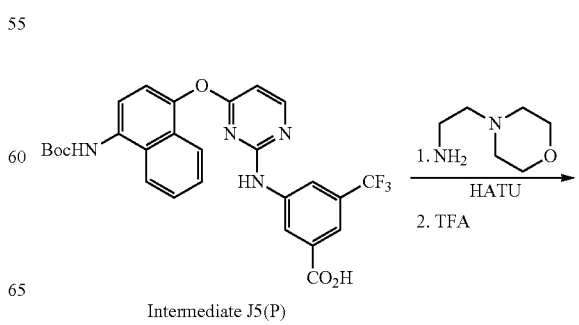

Intermediate J5(P)

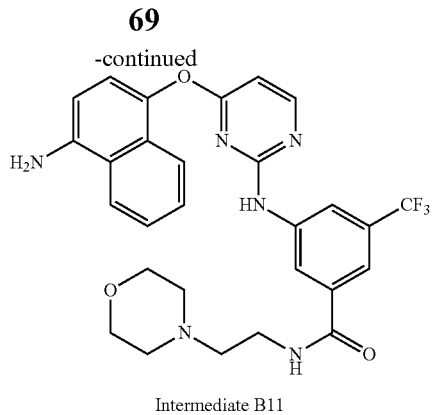

Intermediate B11

To a solution of Intermediate J5(P) (577 mg, 1.07 mmol), 2-morpholinoethanamine (210 µL, 1.6 mmol) and DIPEA (370 µL, 2.1 mmol) in DMF (2.0 mL) at 0° C. was added HATU (609 mg, 1.60 mmol). The reaction mixture was warmed to RT for 3 hr, then diluted with water (40 mL) and the resulting suspension sonicated for 5 min. The precipitate was collected by filtration to afford tert-butyl (4-((2-((3-((2-morpholinoethyl)carbamoyl)-5-(trifluoromethyl)phenyl)amino)pyrimidin-4-yl)oxy)naphthalen-1-yl)carbamate as a pale brown solid (640 mg, 87%); $R^r$ 2.97 min (Method 3); m/z 653 (M+H)$^+$, (ES$^+$).

To a solution of the Boc-protected amine described above (637 mg, 0.976 mmol) in DCM (12.0 mL) was added TFA (2.0 mL, 27 mmol). After 3 hr at RT the reaction mixture was evaporated in vacuo and the residue purified by SCX capture and release to afford the title compound, Intermediate B11, as a brown solid (515 mg, 91%); $R^r$ 2.41 min (Method 3); m/z 553 (M+H)$^+$, (ES$^+$).

Intermediate B12: 3-((4-((4-Aminonaphthalen-1-yl)oxy)pyrimidin-2-yl)amino)-N-(2-(dimethylamino)ethyl)-5-methoxybenzamide

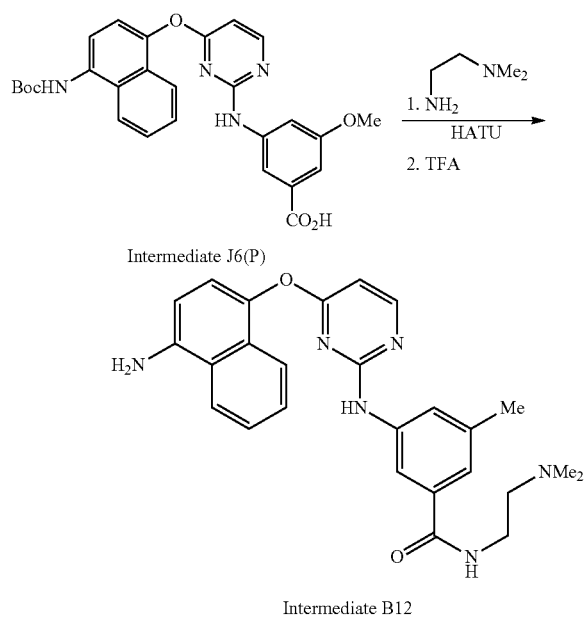

Intermediate J6(P)

Intermediate B12

To a solution of Intermediate J6(P) (647 mg, 1.19 mmol), N$^1$,N$^1$-dimethylethane-1,2-diamine (142 µL, 1.30 mmol) and DIPEA (330 µL, 1.90 mmol) in DCM (25 mL) at 0° C. was added HATU (540 mg, 1.42 mmol) and after 10 min the resulting mixture was allowed to warm to RT. After 18 hr the reaction mixture was washed with aq NaOH (1.0 M, 25 mL) and then dried and evaporated in vacuo. The residue was purified by flash column chromatography (SiO$_2$, 120 g, 0-10% [0.7 M NH$_3$ in MeOH] in DCM, gradient elution) to afford tert-butyl (4-((2-((3-((2-(dimethylamino)ethyl)carbamoyl)-5-methoxyphenyl)amino)pyrimidin-4-yl)oxy)naphthalen-1-yl)carbamate as an orange oil (425 mg, 60%); $R^r$ 1.67 min (Method 2 acidic); m/z 573 (M+H)$^+$, (ES$^+$).

To a solution of the Boc-protected amine described above (425 mg, 0.742 mmol) in DCM (5.0 mL) was added TFA (0.60 mL, 8.0 mmol) and the reaction mixture kept at RT for 5 hr. A second aliquot of TFA (0.60 mL, 8.0 mmol) was added and the reaction mixture was maintained at RT for 3 days and then evaporated in vacuo. The residue was partitioned between EtOAc (20 mL) and sat. aq NaHCO$_3$ (20 mL) and the organic phase was separated and dried and then evaporated in vacuo to afford the title compound, Intermediate B12, as an orange oil (277 mg, 75%); Fe 1.28 min (Method 2 acidic); m/z 473 (M+H)$^+$, (ES$^+$).

Intermediate B13: 3-((4-((4-Aminonaphthalen-1-yl)oxy)pyrimidin-2-yl)amino)-5-methoxy-N-(2-morpholinoethyl)benzamide

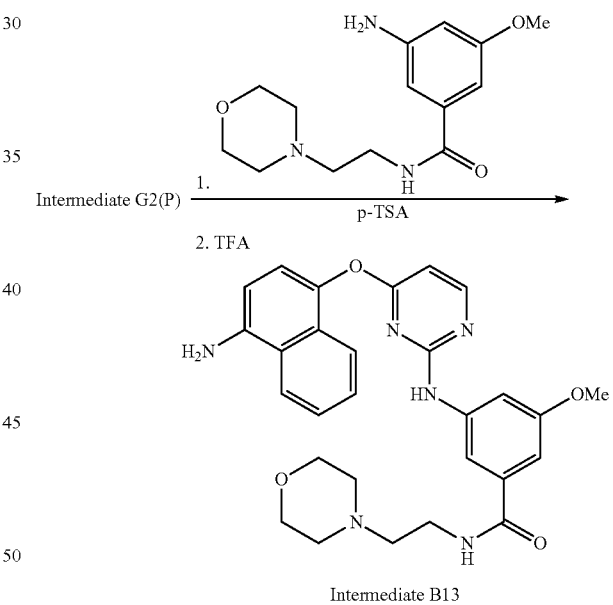

Intermediate B13

A suspension of Intermediate G2(P) (15.0 g, 40.0 mmol), p-TSA (12.2 g, 64.0 mmol), and 3-amino-5-methoxy-N-(2-morpholinoethyl)benzamide (15.0 g, 52.0 mmol) in THF (150 mL) was heated to 60° C. for 20 h. The reaction mixture was concentrated in vacuo and the residue was triturated with saturated aq. NaHCO$_3$ (250 mL). The solid that was formed was collected by filtration, taken up in DCM (500 mL) and was washed with sat. aq. NaHCO$_3$ (2×200 mL) and with water (2×250 mL). The organic phase was concentrated in vacuo to provide a brown solid. The sat. aq. NaHCO$_3$ washings were filtered to afford additional material. The brown solids were combined and dried under reduced pressure to afford a mixture (ca. 30:70) of the title compound, Intermediate B13, and the corresponding N-Boc derivative:

tert-butyl (4-((2-((3-methoxy-5-((2-morpholinoethyl)carbamoyl)phenyl)amino)pyrimidin-4-yl)oxy) naphthalen-1-yl)carbamate. This material was used directly in the next step without further manipulation.

The crude mixture described above was suspended in DCM (300 mL), cooled to 0° C. and treated with TFA (60 mL, 0.80 mol) dropwise, over 10 min. The resulting dark solution was stirred for 2 h at RT and was then concentrated in vacuo. The residue was taken up into DCM (500 mL) and was washed with saturated aq. NaHCO₃ (2×250 mL). The combined aq phase was extracted with DCM (200 mL) and the combined organic extracts were washed with brine (2×200 mL) and then dried and concentrated in vacuo to afford the title compound Intermediate B13, as a brown solid (13.4 g, 55% yield over 2 steps); $R^t$ 1.78 min (Method 1 basic); m/z 515 (M+H)⁺ (ES⁺).

Intermediate B14: 3-((4-((4-Aminonaphthalen-1-yl)oxy)pyrimidin-2-yl)amino)-5-chloro-N-(2-morpholinoethyl)benzamide

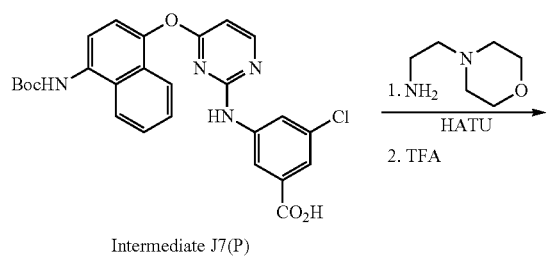

To a solution of Intermediate J7(P) (372 mg, 0.734 mmol), 2-morpholinoethanamine (144 μL, 1.10 mmol) and DIPEA (260 μL, 1.5 mmol) in DMF (1.5 mL) at 0° C. was added HATU (419 mg, 1.10 mmol) and the reaction mixture allowed to warmed to RT. After 18 hr the mixture was diluted with water (30 mL) and the resulting suspension was sonicated for 5 min. The precipitate was collected by filtration and dried to afford tert-butyl (4-((2-((3-chloro-5-((2-morpholinoethyl)carbamoyl)phenyl)amino)pyrimidin-4-yl)oxy)naphthalen-1-yl)carbamate as a pale brown solid (300 mg, 63%); $R^t$ 2.86 min (Method 3); m/z 619 (M+H)⁺, (ES⁺).

To a solution of the Boc-protected amine described above (300 mg, 0.485 mmol) in DCM (5.0 mL) was added TFA (0.80 mL, 11 mmol) and the reaction mixture kept at RT for 3.5 hr and then evaporated in vacuo. The residue was purified by SCX capture and release to afford the title compound, Intermediate B14, as a brown solid (248 mg, 94%); $R^t$ 2.25 min (Method 3); m/z 519 (M+H)⁺, (ES⁺).

Intermediate B15: 3-((4-((4-Aminonaphthalen-1-yl)oxy)pyrimidin-2-yl)amino)-5-bromo-N-(2-morpholinoethyl)benzamide To a solution of Intermediate J8(P) (1.28 g, 2.32 mmol), 2-morpholinoethanamine (0.52 mL, 4.0 mmol) and DIPEA (0.81 mL, 4.6 mmol) in DMF (4.5 mL) at 0° C. was added HATU (1.32 g, 3.48 mmol) and the reaction mixture then allowed to warm to RT for 18 hr. The mixture was diluted with water (50 mL) and suspension thus obtained was sonicated for 20 min. The precipitate so formed was collected by filtration to afford tert-butyl (4-((2-((3-bromo-5-((2-morpholinoethyl)carbamoyl)phenyl)amino)pyrimidin-4-yl)oxy)naphthalen-1-yl) carbamate as a pale grey solid (1.55 g, 96%); $R^t$ 2.89 min (Method 3); m/z 663/665 (M+H)⁺, (ES⁺).

To a solution of the Boc-protected amine described above (633 mg, 0.954 mmol) in DCM (11.0 mL) was added TFA (2.5 mL, 34 mmol) and the reaction mixture maintained at RT for 18 hr. The mixture was evaporated in vacuo and the residue was partitioned between DCM (50 mL) and saturated aq. NaHCO₃ (50 mL). The organic phase was separated and washed sequentially with saturated aq. NaHCO₃ (40 mL), water (2×30 mL) and with brine (2×30 mL) and then dried and evaporated in vacuo to afford the title compound, Intermediate B15, as a brown solid (515 mg, 91%); $R^t$ 1.41 min (Method 4); m/z 563/565 (M+H)⁺, (ES⁺).

Intermediate B16: 3-((4-((4-Aminonaphthalen-1-yl)oxy)pyrimidin-2-yl)amino)-5-methoxy-N-methyl-N-(2-morpholinoethyl)benzamide

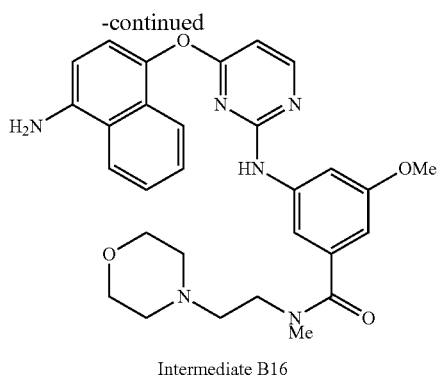

Intermediate B16

To a solution of Intermediate J6(P) (926 mg, 1.71 mmol) in THF (10 mL) under $N_2$ was added EDC.HCl (657 mg, 3.43 mmol) and N-methyl-2-morpholinoethanamine (531 mg, 3.69 mmol). The resulting mixture was kept at RT for 18 hr, heated to 40° C. for 24 hr and then cooled to RT for a further 3 days. An additional portion of N-methyl-2-morpholinoethanamine (266 mg, 1.84 mmol) was added and the reaction mixture was maintained at RT for a further 5 hr and was then partitioned between water (50 mL) and EtOAc (50 mL). The organic phase was separated, dried and evaporated in vacuo and the residue was purified by flash column chromatography ($SiO_2$, 80 g, 0-10% [0.7 M $NH_3$ in MeOH] in DCM, gradient elution) to give tert-butyl (4-((2-((3-methoxy-5-(methyl(2-morpholinoethyl)carbamoyl)phenyl)amino)pyrimidin-4-yl)oxy)naphthalen-1-yl)carbamate as a pale brown solid (612 mg, 91% pure by HPLC, 52%); $R^t$ 1.74 min (Method 2 acidic); m/z 629 (M+H)$^+$, (ES$^+$).

To a solution of the Boc-protected amine described above (612 mg, 91% pure, 0.886 mmol) in DCM (5.0 mL) was added TFA (1.5 mL, 20 mmol) and the reaction mixture maintained at RT for 18 hr and then evaporated in vacuo. The residue was partitioned between EtOAc (20 mL) and sat. aq $NaHCO_3$ (20 mL). The organic phase was separated, dried and evaporated in vacuo to provide the title compound, Intermediate B16, as an orange oil (355 mg, 94% pure by HPLC, 71%); $R^t$ 1.27 min (Method 2 acidic); m/z 529 (M+H)$^+$, (ES$^+$). This material was used in subsequent steps without additional purification.

Intermediate B17: 3-((4-((4-Aminonaphthalen-1-yl)oxy)pyrimidin-2-yl)amino)-N-(2-hydroxyethyl)-5-methoxybenzamide

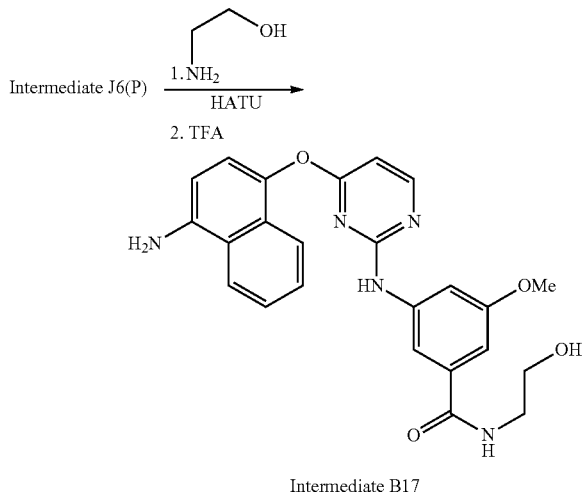

Intermediate B17

To a solution of Intermediate J6(P) (795 mg, 1.46 mmol), 2-aminoethanol (97 μL, 1.6 mmol) and DIPEA (0.41 mL, 2.3 mmol) in DCM (25 mL) at 0° C. was added HATU (664 mg, 1.75 mmol) and the resulting mixture kept at 0° C. for 10 min and then warmed to RT. After 18 hr the reaction mixture was diluted with DMF (5.0 mL) and maintained at RT for a further 24 hr. A second aliquot of DMF (5.0 mL) was added and the resulting mixture was heated to 40° C. for 4 days and then cooled and partitioned between aq NaOH (1.0 M, 100 mL) and EtOAc (150 mL). The organic phase was separated and was washed with brine (2×100 mL) and then dried and evaporated in vacuo. The residue was purified by flash column chromatography ($SiO_2$, 80 g, 0-10% [0.7 M $NH_3$ in MeOH] in DCM, gradient elution) to afford tert-butyl (4-((2-((3-((2-hydroxyethyl)carbamoyl)-5-methoxyphenyl)amino)pyrimidin-4-yl)oxy) naphthalen-1-yl)carbamate as a pale brown solid (399 mg, 49%); $R^t$ 2.09 min (Method 2 acidic); m/z 546 (M+H)$^+$, (ES$^+$).

To a solution of the Boc-protected amine described above (399 mg, 0.731 mmol) in DCM (5.0 mL) was added TFA (0.60 mL, 8.0 mmol). After 5 hr at RT an additional aliquot of TFA (0.60 mL, 8.0 mmol) was added and the reaction mixture kept at RT for a further 3 days and then evaporated in vacuo. The residue was partitioned between EtOAc (20 mL) and sat. aq $NaHCO_3$ (20 mL) and the organic phase was separated and dried and then evaporated in vacuo. The residue was taken up into a mixture of THF (2.0 mL), water (1.0 mL) and MeOH (0.5 mL) and treated with a solution of LiOH (18 mg, 0.73 mmol) in water (1.0 mL) at RT for 16 hr. The resulting mixture was neutralized by the addition of aq hydrochloric acid (1.0 M, 0.5 mL) and was partitioned between water (20 mL) and EtOAc (20 mL). The organic phase was separated and dried and then evaporated in vacuo to furnish the title compound, Intermediate B17, as a brown solid (160 mg, 48%); $R^t$ 1.51 min (Method 2 acidic); m/z 446 (M+H)$^+$, (ES$^+$).

Intermediate B18: 3-((4-((4-Aminonaphthalen-1-yl)oxy)pyrimidin-2-yl)amino)-5-methoxy-N-(2-methoxyethyl)benzamide

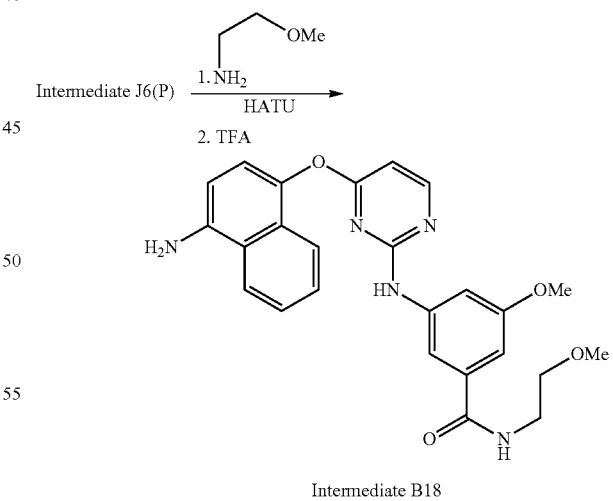

Intermediate B18

To a solution of Intermediate J5(P) (841 mg, 1.67 mmol), 2-methoxyethanamine (190 μL, 2.2 mmol) and DIPEA (470 μL, 2.7 mmol) in DCM (10.0 mL) was added HATU (115 mg, 0.301 mmol). The reaction mixture was maintained at RT for 18 hr and was then washed with aq NaOH (1.0 M, 50 mL). The aq layer was separated and was extracted with DCM (50 mL) and the combined organic phases were washed with water (2×50 mL) and then dried and evaporated in vacuo. The residue was purified by flash column chromatography (SiO$_2$, 120 g, 0-10% [0.7 M NH$_3$ in MeOH] in DCM, gradient elution) to afford tert-butyl (4-((2-((3-methoxy-5-((2-methoxyethyl)carbamoyl)phenyl)amino)pyrimidin-4-yl)oxy)naphthalen-1-yl)carbamate as a yellow solid (900 mg, 86%); R$^t$ 2.36 min (Method 2 acidic); m/z 560 (M+H)$^+$, (ES$^+$).

To a solution of the Boc-protected amine described above (900 mg, 1.61 mmol) in DCM (10.0 mL) was added TFA (1.2 mL, 16 mmol) and the reaction mixture maintained at RT for 5 hr and then evaporated in vacuo. The residue was partitioned between EtOAc (40 mL) and sat. aq NaHCO$_3$ (40 mL) and the organic phase was separated and dried and then evaporated in vacuo to give the title compound, Intermediate B18, (549 mg, 72%); R$^t$ 1.70 min (Method 3); m/z 460 (M+H)$^+$, (ES$^+$).

Intermediate B19: 5-((4-((4-Aminonaphthalen-1-yl)oxy)pyrimidin-2-yl)amino)-2-methoxy-N-(2-morpholinoethyl)benzamide

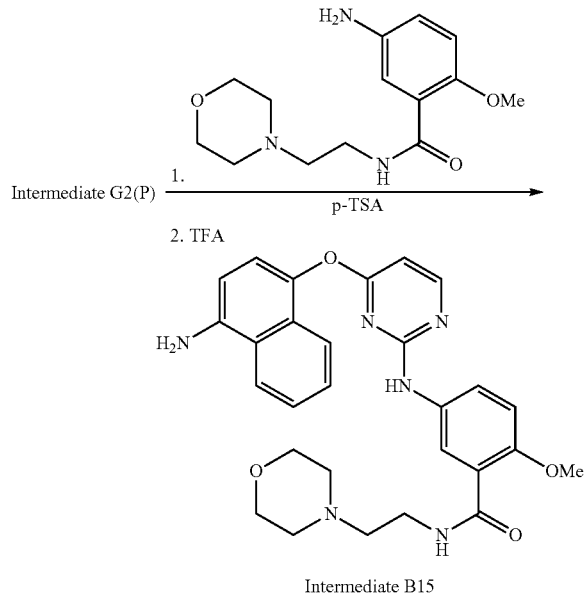

To a mixture of Intermediate G2(P) (950 mg, 2.56 mmol) and 5-amino-2-methoxy-N-(2-morpholinoethyl)benzamide (1.07 g, 3.32 mmol) in THF (10.0 mL) was added p-TSA.H$_2$O (778 mg, 4.09 mmol). The resulting suspension was heated at 60° C. for 18 hr and was then cooled to RT and partitioned between dichloromethane (50 mL) and saturated aq NaHCO$_3$ (50 mL). The organic phase was separated and washed with water (2×50 mL) and with brine (2×50 mL) and then dried and evaporated in vacuo. The residue was purified by flash column chromatography (SiO$_2$, 12 g, 0-80% [0.7 M NH$_3$ in MeOH] in DCM, gradient elution) to afford tert-butyl (4-((2-((4-methoxy-3-((2-morpholinoethyl)carbamoyl)phenyl)amino) pyrimidin-4-yl)oxy)naphthalen-1-yl)carbamate as a peach coloured solid (566 mg, 34%); R$^t$ 2.72 min (Method 3); m/z 615 (M+H)$^+$, (ES$^+$).

To a suspension of the Boc-protected aminonaphthalene described above (566 mg, 0.875 mmol) in DCM (10.0 mL) was added TFA (2.0 mL, 27 mmol) dropwise and the resulting solution kept at RT for 18 hr and then evaporated in vacuo. The residue was purified by SCX capture and release to provide the title compound, Intermediate B19, as a pale pink solid (479 mg, 90% purity by HPLC, 98%); R$^t$ 2.05 min (Method 3); m/z 515 (M+H)$^+$, (ES$^+$).

Intermediate B20: 3-((6-((4-Aminonaphthalen-1-yl)oxy)pyrimidin-4-yl)amino)-5-methoxy-N-(2-morpholinoethyl)benzamide

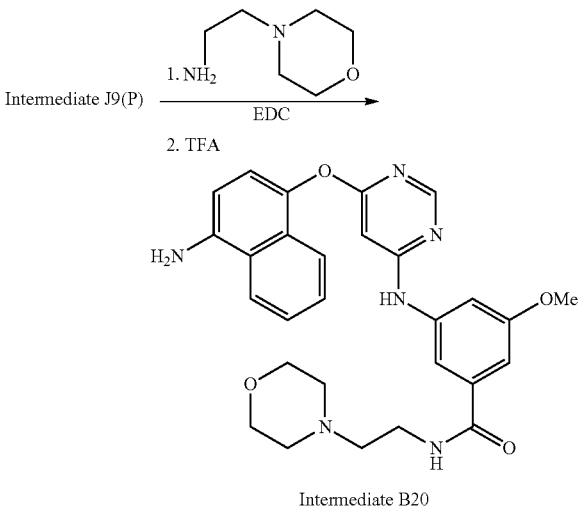

To a solution of Intermediate J9(P) (0.50 g, 1.0 mmol) and EDC (381 mg, 1.99 mmol) in THF (6.0 mL) was added 2-morpholinoethanamine (261 μL, 1.99 mmol) and the reaction mixture kept at RT for 18 hr and then diluted with water (15 mL). The resulting precipitate was collected by filtration and was washed with water (3×5.0 mL) and with ether (3×5.0 mL). and then re-suspended in THF (5.0 mL) at RT for 3 days. The solid was collected by filtration and was washed with THF (2×5.0 mL) and with ether (2×5.0 mL) and dried in vacuo to afford tert-butyl (4-((6-((3-methoxy-5-((2-morpholinoethyl)carbamoyl)phenyl)amino) pyrimidin-4-yl)oxy)naphthalen-1-yl)carbamate as a white solid (227 mg, 36%); R$^t$ 2.68 min (Method 4); m/z 615 (M+H)$^+$, (ES$^+$).

To a suspension of the Boc-protected amine described above (227 mg, 0.370 mmol) in MeOH (3.5 mL) was added conc. hydrochloric acid (0.90 mL, 10 mmol) and the reaction mixture kept at RT for 18 hr. The resulting mixture was purified directly by SCX capture and release to afford the title compound, Intermediate B20, as a brown solid (181 mg, 89%); R$^t$ 2.14 min (Method 4); m/z 515 (M+H)$^+$, (ES$^+$).

Intermediate B21: 3-((4-((4-Aminonaphthalen-1-yl)oxy)pyrimidin-2-yl)amino)-5-ethynyl-N-(2-morpholinoethyl)benzamide

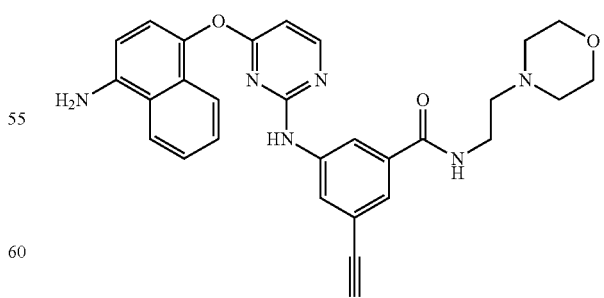

Intermediate G2(P) (6.46 g, 17.37 mmol), Intermediate D1 (7.12 g, 26.0 mmol) and p-TSA monohydrate (5.62 g, 29.5 mmol) in DMF (60 mL) was heated at 60° C. (block temperature, 55° C. internal temperature) for 7 h. The mixture was cooled and added dropwise to sat. aq NaHCO$_3$ (1 L). The solid was filtered, washed with water (50 mL) then isohexane (100 mL). The amorphous solid was stirred in MeOH (200 mL) and product crystallised. Slurried overnight, then filtered and solid washed with MeOH (20 ml) and dried to afford tert-butyl (4-((2-((3-ethynyl-5-((2-morpholinoethyl)carbamoyl)-phenyl)amino)pyrimidin-4-yl)oxy)naphthalen-1-yl)carbamate (Intermediate B21(P), 8 g).

$^1$H NMR (400 MHz, DMSO-d6) b 9.76 (s, 1H), 9.32 (s, 1H), 8.45 (d, 1H), 8.41-8.33 (m, 1H), 8.16-8.03 (m, 2H), 7.90 (t, 1H), 7.85-7.78 (m, 1H), 7.67-7.51 (m, 3H), 7.48-7.37 (m, 2H), 6.58 (d, 1H), 4.16 (s, 1H), 3.56 (t, 4H), 3.46-3.27 (m, 2H), 2.49-2.30 (m, 6H), 1.52 (s, 9H). 10% w/w de-BOC compound.

LCMS m/z 609 (M+H)$^+$ (ES$^+$)

TFA (22 ml, 286 mmol) was added dropwise to a stirred solution of Intermediate B21(P) (9 g, 14.05 mmol) in DCM (50 mL). The reaction was stirred at rt for 2 h, then added dropwise to stirred water (100 mL) and 1M potassium carbonate solution (280 mL, 280 mmol) and stirring continued until effervescence ceased. The mixture was extracted with dichloromethane (2×250 mL) then the combined organic phases were dried (MgSO$_4$) and concentrated under reduced pressure. The crude product was purified by chromatography on the Companion (120 g column, 2% MeOH:DCM to 6%) to afford Intermediate B21 (6.7 g) as a pale brown foam.

$^1$H NMR (400 MHz, DMSO-d6) δ 9.77 (s, 1H), 8.39 (t, 1H), 8.36 (d, 1H), 8.17-8.10 (m, 1H), 8.06 (s, 1H), 7.94 (dd, 1H), 7.67-7.59 (m, 1H), 7.49-7.38 (m, 3H), 7.15 (d, 1H), 6.70 (d, 1H), 6.37 (d, 1H), 5.79 (s, 2H), 4.20 (s, 1H), 3.56 (t, 4H), 3.41-3.30 (m, 2H), 2.48-2.34 (m, 6H).

LCMS m/z 509 (M+H)$^+$ (ES$^+$)

Intermediate B22: (S)-3-((4-((4-Aminonaphthalen-1-yl)oxy)pyrimidin-2-yl)amino)-5-ethynyl-N-(1-morpholinopropan-2-yl)benzamide

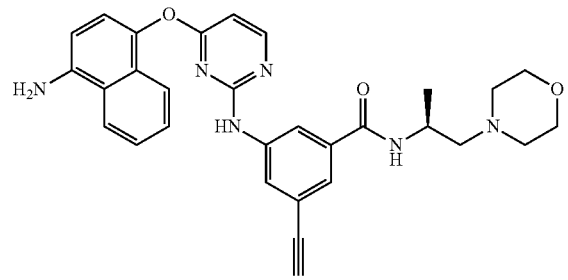 [SMILES: C#Cc1cc(Nc2nccc(Oc3ccc(N)c4ccccc34)n2)cc(C(=O)N[C@@H](C)CN2CCOCC2)c1]

To a stirred solution of (S)-1-morpholinopropan-2-amine, HCl (72.6 mg, 0.402 mmol), Intermediate J10(P) (200 mg, 0.402 mmol) and HATU (200 mg, 0.526 mmol) in DMF (4 mL) was added Hunig's base (280 μL, 1.608 mmol) and the reaction was stirred overnight. The reaction was diluted with water, resulting in the precipitation of a beige solid. The suspension was stirred for an additional 20 minutes then the solid collected by filtration, washing with water. The crude product was purified by chromatography on the Companion (40 g column, 0-5% MeOH in DCM) to afford (S)-tert-butyl (4-((2-((3-ethynyl-5-((1-morpholinopropan-2-yl)carbamoyl)phenyl)amino)pyrimidin-4-yl)oxy)naphthalen-1-yl)-carbamate (133 mg) as a pale orange solid.

$^1$H NMR (DMSO-d6) 400 MHz, δ: 9.73 (s, 1H), 9.30 (s, 1H), 8.44 (d, 1H), 8.08-8.15 (m, 3H), 7.91 (s, 1H), 7.82 (d, 1H), 7.54-7.63 (m, 3H), 7.46 (s, 1H), 7.42 (d, 1H), 6.57 (d, 1H), 4.13-4.20 (m, 1H), 4.15 (s, 1H), 3.54 (t, 4H), 2.23-2.44 (m, 6H), 1.52 (s, 9H), 1.13 (d, 3H).

LCMS m/z 312 (M+2H)$^{2+}$ (ES$^+$)

To a stirred solution of the product from the step immediately above (133 mg, 0.214 mmol) in DCM (10 ml) was added TFA (2000 μL, 26.0 mmol) and the reaction stirred at rt for 2 h. The mixture was concentrated in vacuo and the residue loaded onto a pre-conditioned cartridge of SCX resin. The resin was washed with MeOH then the product released in 1% NH$_3$ in MeOH and concentrated in vacuo to afford Intermediate B22 (100 mg) as a pale brown solid.

$^1$H NMR (DMSO-d6) 400 MHz, δ: 9.73 (s, 1H), 8.36 (d, 1H), 8.12-8.15 (m, 2H), 8.05 (s, 1H), 7.95 (s, 1H), 7.62-7.65 (m, 1H), 7.41-7.46 (m, 3H), 7.14 (d, 1H), 6.71 (d, 1H), 6.36 (d, 1H), 5.77 (s, 2H), 4.12-4.20 (m, 1H), 4.18 (s, 1H), 3.54 (t, 4H), 2.24-2.45 (m, 6H), 1.13 (d, 3H).

LCMS m/z 523 (M+H)$^+$ (ES$^+$)

Intermediate B23: 3-((4-((4-Aminonaphthalen-1-yl)oxy)pyrimidin-2-yl)amino)-5-ethynyl-N-(2-methyl-1-morpholinopropan-2-yl)benzamide

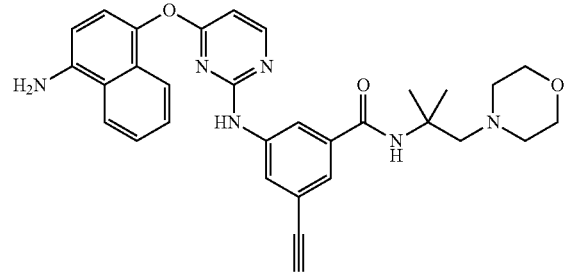 [SMILES: C#Cc1cc(Nc2nccc(Oc3ccc(N)c4ccccc34)n2)cc(C(=O)NC(C)(C)CN2CCOCC2)c1]

To a stirred solution of 2-methyl-1-morpholinopropan-2-amine (64.0 mg, 0.404 mmol), Intermediate J10(P) (200 mg, 0.402 mmol) and HATU (200 mg, 0.526 mmol) in DMF (4 mL) was added Hunig's base (280 μL, 1.608 mmol) and the reaction was stirred overnight. The reaction was diluted with water resulting in the precipitation of an off-white solid and the suspension was left stirring for 20 mins. The suspension was filtered in vacuo and the solid washed with water, affording tert-butyl (4-((2-((3-ethynyl-5-((2-methyl-1-morpholinopropan-2-yl)carbamoyl)phenyl)amino)pyrimidin-4-yl)oxy)naphthalen-1-yl)carbamate (Intermediate B23(P), 245 mg) as a cream-coloured solid which was dried at 40° C. under vacuum for 2 h.

$^1$H NMR (DMSO-d6) 400 MHz, δ: 9.70 (s, 1H), 9.30 (s, 1H), 8.43 (d, 1H), 8.10 (d, 1H), 8.00 (s, 1H), 7.89 (s, 1H), 7.81 (d, 1H), 7.53-7.62 (m, 4H), 7.41 (d, 1H), 7.37 (s, 1H), 7.57 (d, 1H), 4.13 (s, 1H), 3.51-3.54 (m, 4H), 2.61 (s, 2H), 2.45-2.47 (m, 4H), 1.51 (s, 9H), 1.30 (s, 6H).

LCMS m/z 637 (M+H)$^+$ (ES$^+$)

To a stirred solution of Intermediate B23(P) (245 mg, 0.385 mmol) in DCM (10 mL) was added TFA (2000 μL, 26.0 mmol) and the reaction stirred at rt for 4 h. The mixture was concentrated in vacuo and the residue loaded onto a pre-conditioned cartridge of SCX resin. The resin was washed with MeOH then the product released in 1% NH$_3$ in MeOH and concentrated in vacuo affording Intermediate B23 (200 mg) as a pale brown solid.

$^1$H NMR (DMSO-d6) 400 MHz, δ: 9.71 (s, 1H), 8.36 (d, 1H), 8.12-8.15 (m, 1H), 7.95 (d, 2H), 7.62-7.63 (m, 2H), 7.41-7.46 (m, 2H), 7.36 (s, 1H), 7.14 (d, 1H), 6.70 (d, 1H), 6.36 (d, 1H), 5.77 (s, 2H), 4.17 (s, 1H), 3.52-3.55 (m, 4H), 2.61 (s, 2H), 2.46-2.48 (m, 4H), 1.31 (s, 6H).

LCMS m/z 537 (M+H)$^+$ (ES$^+$)

Intermediate B24: (R)-3-((4-((4-Aminonaphthalen-1-yl)oxy)pyrimidin-2-yl)amino)-5-ethynyl-N-(1-morpholinopropan-2-yl)benzamide

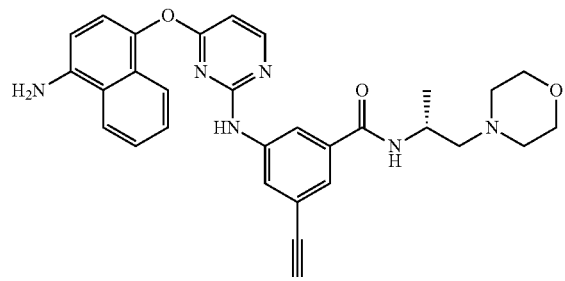 [SMILES: C#Cc1cc(Nc2nccc(Oc3ccc(N)c4ccccc34)n2)cc(C(=O)N[C@H](C)CN2CCOCC2)c1]

To a stirred solution of (R)-1-morpholinopropan-2-amine, HCl (73 mg, 0.404 mmol), Intermediate J10(P) (200 mg, 0.402 mmol) and HATU (200 mg, 0.526 mmol) in DMF (4 mL) was added Hunig's base (280 μL, 1.608 mmol) and the reaction was stirred overnight. The reaction was diluted with water resulting in the precipitation of a beige solid. The suspension was stirred for an additional 20 minutes then the solid collected by filtration, washing with water. The crude product was purified by chromatography on the Companion (40 g column, 0-5% MeOH in DCM) to afford (R)-tert-butyl (4-((2-((3-ethynyl-5-((1-morpholinopropan-2-yl)carbamoyl)phenyl)amino)pyrimidin-4-yl)oxy)naphthalen-1-yl)carbamate (Intermediate B24(P), 153 mg) as a pale orange solid.

$^1$H NMR (DMSO-d6) 400 MHz, δ: 9.73 (s, 1H), 9.30 (s, 1H), 8.44 (d, 1H), 8.09-8.15 (m, 3H), 7.91 (s, 1H), 7.82 (d, 1H), 7.54-7.63 (m, 3H), 7.46 (s, 1H), 7.42 (d, 1H), 6.57 (d, 1H), 4.13-4.20 (m, 1H), 4.15 (s, 1H), 3.54 (t, 4H), 2.23-2.44 (m, 6H), 1.52 (s, 9H), 1.13 (d, 3H).

LCMS m/z 312 (M+2H)$^{2+}$ (ES$^+$)

To a stirred solution of Intermediate B24(P) (153 mg, 0.246 mmol) in DCM (10 mL) was added TFA (2000 μL, 26.0 mmol) and the reaction stirred at rt for 2 h. The mixture was concentrated in vacuo and the residue loaded onto a pre-conditioned cartridge of SCX resin. The resin was washed with MeOH then the product released in 1% NH$_3$ in MeOH and concentrated in vacuo affording Intermediate B24 (120 mg) as a pale brown, glassy solid.

$^1$H NMR (DMSO-d6) 400 MHz, δ: 9.73 (s, 1H), 8.36 (d, 1H), 8.12-8.15 (m, 2H), 8.04 (s, 1H), 7.95 (s, 1H), 7.62-7.65 (m, 1H), 7.41-7.46 (m, 3H), 7.14 (d, 1H), 6.71 (d, 1H), 6.36 (d, 1H), 5.77 (s, 2H), 4.13-4.20 (m, 1H), 4.18 (s, 1H), 3.54 (t, 4H), 2.24-2.45 (m, 6H), 1.13 (d, 3H).

LCMS m/z 262 (M+2H)$^{2+}$ (ES$^+$)

Intermediate C1: 1-(4-(2-Chloropyrimidin-4-yloxy)naphthalen-1-yl)-3-(3-isopropyl-1-p-tolyl-1H-pyrazol-5-yl)urea

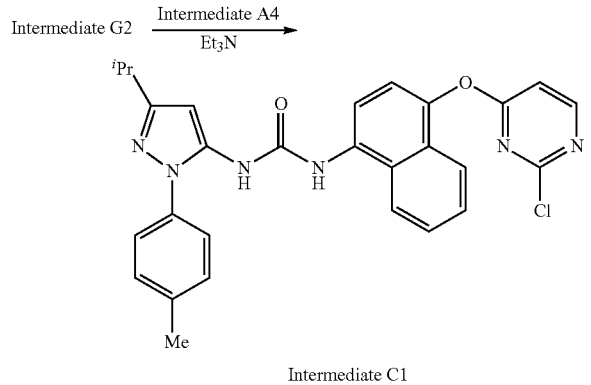

Intermediate C1

To a solution of Intermediate G2 (5.00 g, 18.4 mmol) in a mixture of isopropyl acetate (50 mL) and anhydrous THF (50 mL) was added portion-wise phenyl (3-isopropyl-1-(p-tolyl)-1H-pyrazol-5-yl)carbamate Intermediate A4* (7.72 g, 23.0 mmol) followed by triethylamine (0.64 mL, 4.6 mmol) and the reaction mixture maintained at RT for 18 hr. During this interval a thick purple precipitate formed which was collected by filtration and then washed with a mixture of isopropyl acetate and THF (1:1 v/v, 3×40 mL). The solid was purified by flash column chromatography (SiO$_2$, 330 g, 0-5% MeOH in DCM, gradient elution) to afford the title compound, Intermediate C1 as a pale purple solid (5.72 g, 47%); R$^t$ 2.48 min (Method 4); m/z 513 (M+H)$^+$ (ES$^+$).

Intermediate C2: 1-(3-(tert-Butyl)-1-(p-tolyl)-1H-pyrazol-5-yl)-3-(4-((2-chloropyrimidin-4-yl)oxy)naphthalen-1-yl)urea

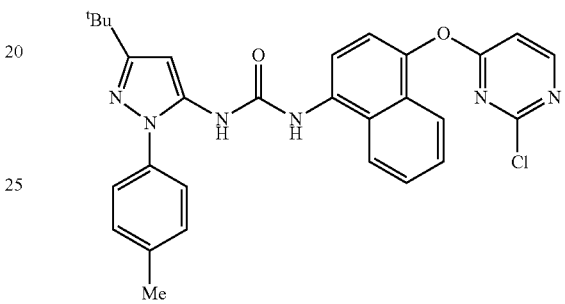

A stirred suspension of Intermediate A8* (3 g, 8.59 mmol) and Intermediate G2 (2.333 g, 8.59 mmol) in isopropyl acetate (100 mL) was treated with triethylamine (0.3 mL, 2.152 mmol) and stirred at 60° C. (bath) for 1 h. The solution was diluted with ethyl acetate (300 mL), washed with water (2×100 mL) followed by brine (100 mL), was dried (Na$_2$SO$_4$) and evaporated. The residue was purified on a 220 g redisep silica cartridge using 5%, for 17 column volumes, and then 40% of acetone in toluene as eluent and then on another 220 g redisep silica cartridge using 0 to 3% MeOH/DCM as eluent to give Intermediate C2 (3.703 g) as a buff foam.

$^1$H NMR (400 MHz, DMSO-d6) δ 9.14 (s, 1H), 8.79 (s, 1H), 8.65 (d, 1H), 8.09 (d, 1H), 7.96 (d, 1H), 7.79 (d, 1H), 7.67-7.64 (m, 1H), 7.60-7.56 (m, 1H), 7.47-7.37 (m, 5H), 7.26 (d, 1H), 6.41 (s, 1H), 2.40 (s, 3H), 1.28 (s, 9H).

LCMS m/z 527/529 (M+H)$^+$ (ES$^+$)

Intermediate C3: 1-(3-(tert-Butyl)-1-(4-methoxyphenyl)-1H-pyrazol-5-yl)-3-(4-((2-chloropyrimidin-4-yl)oxy)naphthalen-1-yl)urea

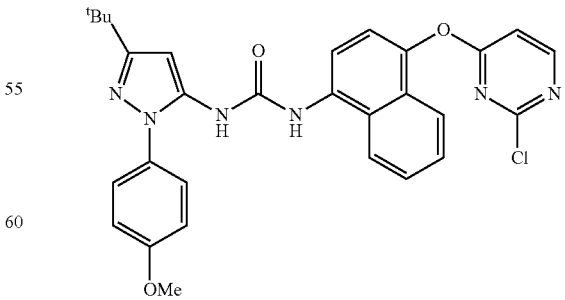

In a 100 mL flask, a solution of Intermediate A9* (1917 mg, 5.24 mmol) and Intermediate G2 (1500 mg, 5.24 mmol) in isopropyl acetate (58 mL) was treated with triethylamine (113 μL, 0.813 mmol). The resultant brown solution was heated at 70° C. for 2 h then the solvent removed in vacuo to afford a thick brown oil. The crude product was purified by chromatography on silica gel (120 g column, EtOAc 0-15% in DCM) to afford Intermediate C3 (2.169 g) as a white crystalline solid.

¹H NMR (400 MHz, DMSO-d6) δ 9.14 (s, 1H), 8.75 (s, 1H), 8.66 (d, 1H), 8.09 (d, 1H), 7.97 (d, 1H), 7.82-7.77 (m, 1H), 7.69-7.62 (m, 1H), 7.58 (ddd, 1H), 7.51-7.46 (m, 2H), 7.43 (d, 1H), 7.27 (d, 1H), 7.15-7.10 (m, 2H), 6.40 (s, 1H), 3.84 (s, 3H), 1.29 (s, 9H).

LCMS m/z 544 (M+H)⁺ (ES⁺)

Intermediate C4: 1-(2,3-Dichloro-4-((2-chloropyrimidin-4-yl)oxy)phenyl)-3-(3-isopropyl-1-(p-tolyl)-1H-pyrazol-5-yl)urea

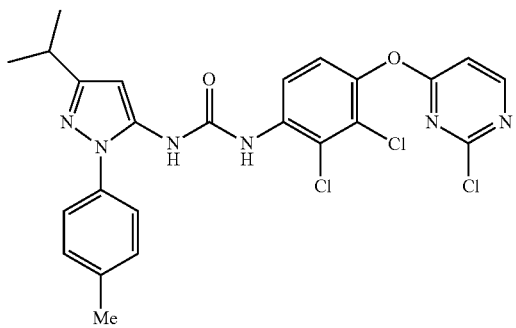 [SMILES: Cc1ccc(-n2nc(C(C)C)cc2NC(=O)Nc2ccc(Oc3ccnc(Cl)n3)c(Cl)c2Cl)cc1]

Et₃N (0.1 ml, 0.717 mmol) was added to a mixture of Intermediate A4* (1556 mg, 4.64 mmol) and Intermediate G4 (1348 mg, 4.64 mmol) in iPrOAc (30 mL) and heated at 60° C. for 7 h. The mixture was partitioned between EtOAc (200 mL) and brine (100 mL), the organic layer separated washed with water, dried (MgSO₄) and evaporated under reduced pressure. The residue was triturated with ether, filtered, washed with iPrOAc, ether and dried to afford Intermediate C4 (986 mg) as a white solid.

¹H NMR (400 MHz; DMSO-d6) δ 9.23 (s, 1H), 8.88 (s, 1H), 8.71 (d, 1H), 8.15 (d, 1H), 7.47 (d, 1H), 7.42 (d, 2H), 7.37-7.35 (m, 3H), 6.35 (s, 1H), 2.89 (septet, 1H), 2.39 (s, 3H), 1.23 (d, 6H).

LCMS m/z 531/3 (M+H)+ (ES+)

Intermediate C5: 1-(4-((2-Chloropyrimidin-4-yl)oxy)-2,3-difluorophenyl)-3-(3-isopropyl-1-(p-tolyl)-1H-pyrazol-5-yl)urea

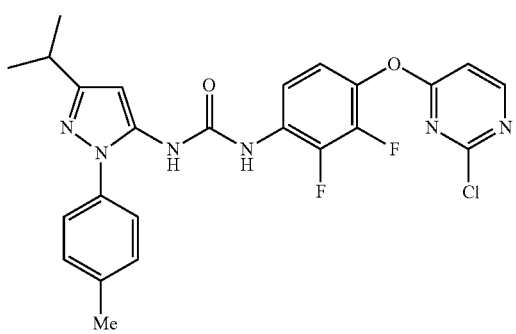 [SMILES: Cc1ccc(-n2nc(C(C)C)cc2NC(=O)Nc2ccc(Oc3ccnc(Cl)n3)c(F)c2F)cc1]

Et₃N (0.1 ml, 0.717 mmol) was added to a mixture of Intermediate A4* (1.556 g, 4.64 mmol) and Intermediate G5 (1.195 g, 4.64 mmol) in iPrOAc (30 mL) and heated at 60° C. for 7 h. The mixture was partitioned between EtOAc (200 mL) and brine (100 mL), the organic layer separated washed with water, dried (MgSO₄) and evaporated under reduced pressure. The residue was triturated with ether/isohexane, filtered and dried to afford Intermediate C5 (1.708 g) as a light tan solid.

¹H NMR (400 MHz; CDCl₃) δ 8.48 (d, 1H), 7.94-7.89 (m, 1H), 7.54 (s, 1H), 7.26 (d, 2H), 7.19 (d, 2H), 6.97-6.92 (m, 3H), 6.34 (s, 1H), 2.97 (septet, 1H), 2.34 (s, 3H), 1.29 (d, 6H).

LCMS m/z 499/501 (M+H)+ (ES+)

Intermediate D1:
3-Amino-5-ethynyl-N-(2-morpholinoethyl)benzamide

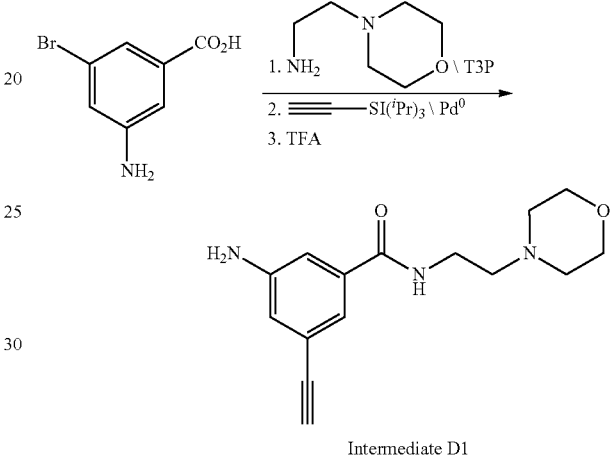

Intermediate D1

To a suspension of T3P (2.76 mL, 4.63 mmol), 3-amino-5-bromobenzoic acid (1.00 g, 4.63 mmol) and Et₃N (1.9 mL, 14 mmol) in DCM (20 mL) at 0° C. was added 2-morpholino ethanamine (0.91 mL, 6.9 mmol) and the mixture allowed to warm to RT for 18 hr. Additional aliquots of T3P (2.76 mL, 4.63 mmol) and 2-morpholinoethanamine (0.91 mL, 6.9 mmol) were added and after 1 hr the resulting mixture was partitioned with sat. aq NaHCO₃ (20 mL). The aq layer was separated and was extracted with DCM (20 mL) and the combined organics layers were washed with brine and then dried and evaporated in vacuo. The residue was purified by flash column chromatography (SiO₂, 40 g, MeOH in DCM, 2-5%, gradient elution) to afford 3-amino-5-bromo-N-(2-morpholinoethyl)benzamide as a yellow crystalline solid (1.4 g, 92%); R$^t$ 0.16 min (Method 2 acidic); m/z 328/330 (M+H)⁺ (ES⁺).

To a degassed suspension of the benzamide obtained above (500 mg, 1.52 mmol), copper(I) iodide (29.0 mg, 0.152 mmol), and ethynyltriisopropylsilane (0.51 mL, 2.3 mmol) in a mixture of Et₃N (3.0 mL) and DMF (3.0 mL), was added Pd(PPh₃)₄ (176 mg, 0.152 mmol) and the mixture heated to 80° C. for 1 hr, and then cooled to RT. The solids were removed by filtration through celite and the volatiles evaporated in vacuo to provide a crude product which was purified by flash column chromatography (SiO₂, 12 g, MeOH in DCM, 5-10%, gradient elution) to afford 3-amino-N-(2-morpholinoethyl)-5-((triisopropylsilyl)ethynyl)benzamide as a pale yellow gum (600 mg, 92%); R$^t$ 1.84 min (Method 2 acidic); m/z 430 (M+H)⁺ (ES⁺)

To a solution of the alkynylsilane obtained above (500 mg, 1.164 mmol) in THF (5.0 mL) was added TBAF (116 mL, 1.16 mmol) and the mixture maintained at RT for 1 h. An additional aliquot of TBAF (114 μL, 1.16 mmol) was added and after 30 min the reaction mixture was partitioned between water (10 mL) and ethyl acetate (10 mL). The organic layer was separated and was washed with brine and then dried and evaporated in vacuo. The residue was purified by flash column chromatography (SiO$_2$, 12 g, MeOH in DCM, 2-5%, gradient elution) to afford the title compound Intermediate D1, as a colourless gum (260 mg, 82%); R$^t$ 1.17 min (Method 2 basic); LCMS m/z 274 (M+H)$^+$ (ES$^+$).

Intermediate D2:
3-Amino-5-methoxy-N-(2-morpholinoethyl)benzamide

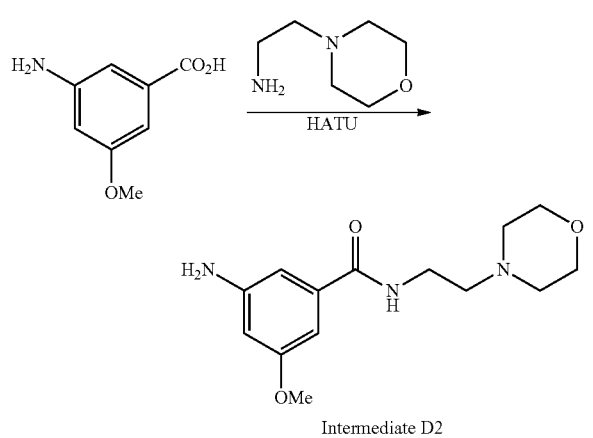

Intermediate D2

To a solution of 3-amino-5-methoxybenzoic acid (2.00 g, 12.0 mmol) in DCM (20 mL) at 0° C. was added 2-morpholinoethanamine (1.90 mL, 14.5 mmol) and DIPEA (4.20 mL, 24.1 mmol) and then HATU (5.46 g, 14.4 mmol) was added portion-wise over 2 hr. During this time a thick beige precipitate formed and additional DCM (13 mL) was added to facilitate stirring and the reaction mixture was warmed to RT for 18 hr. The resulting solution was diluted with DCM (50 mL) and was washed with sat. aq NaHCO$_3$ (40 mL), with sat aq NH$_4$Cl (40 mL) and with brine (40 mL) and then dried and evaporated in vacuo. The residue was purified by flash column chromatography (SiO$_2$, 80 g, [0.7 M NH$_3$ in MeOH] in DCM, 0-10%, gradient elution) to afford the title compound, Intermediate D2, as a colourless oil (1.95 g, 58%); R$^t$ 0.75 min (Method 4); m/z 280 (M+H)$^+$ (ES$^+$).

Intermediate D3:
3-Amino-5-bromo-N-(2-methoxyethyl)benzamide

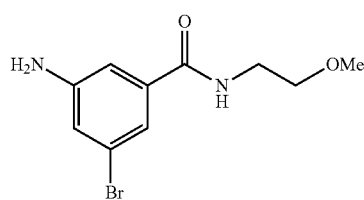 [SMILES: COCCNC(=O)c1cc(N)cc(Br)c1]

To a stirred solution of 3-amino-5-bromobenzoic acid (1.90 g, 8.53 mmol), 2-methoxyethanamine (1.50 ml, 17.08 mmol) and triethylamine (3.60 mL, 25.8 mmol) in DCM (30 mL) at 0° C. was added 50 wt % T3P in EtOAc (7.65 ml, 12.85 mmol). The reaction was stirred at rt overnight then refluxed for 90 min. The reaction was cooled to rt, whereupon a further quantity of triethylamine (3.60 ml, 25.8 mmol) was added. The reaction vessel was then cooled in an ice bath and 50 wt % T3P in EtOAc (7.65 ml, 12.85 mmol) from a fresh bottle was added. The ice bath was removed, the reaction allowed to warm to rt, and stirred at this temperature for 1 h. The reaction was partitioned between sat. NaHCO$_3$ (50 mL) and DCM (50 mL). The aqueous phase was back extracted with fresh DCM (50 mL). The combined organic extracts were dried (MgSO$_4$), filtered and concentrated in vacuo to afford an orange oil (3.12 g). The crude product was purified by chromatography on silica gel (80 g column, 0-10% MeOH in DCM) to afford Intermediate D3 (1.96 g) as an orange oil.

$^1$H NMR (DMSO-d6) 400 MHz, δ: 8.37 (t, 1H), 7.08 (t, 1H), 7.00-6.99 (m, 1H), 6.84 (t, 1H), 5.57 (s, 2H), 3.44-3.41 (m, 2H), 3.39-3.33 (m, 2H), 3.25 (s, 3H).

LCMS m/z 273/275 (M+H)$^+$ (ES$^+$)

Intermediate D4:
3-Amino-5-ethynyl-N-(2-methoxyethyl)benzamide

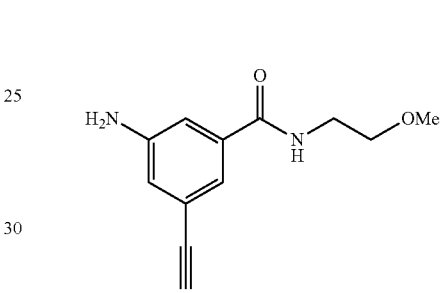

To a degassed suspension of Intermediate D3 (1.91 g, 6.85 mmol), copper(I) iodide (0.065 g, 0.343 mmol) and ethynyltriisopropylsilane (2.30 mL, 10.25 mmol) in TEA (4.1 mL, 29.4 mmol) and DMF (20 mL) was added Pd(PPh$_3$)$_4$ (0.396 g, 0.343 mmol). The reaction was heated at 85° C. (external temperature) for 4 h. The reaction was cooled to rt then partitioned between EtOAc (50 mL) and brine (50 mL). The aqueous phase was back extracted with EtOAc (50 mL). The combined organic extracts were washed with brine (100 mL), dried (MgSO$_4$), filtered and concentrated in vacuo to afford a brown oil (3.41 g). The crude product was purified by chromatography on silica gel (120 g column, 0-100% EtOAc in isohexane) to afford 3-amino-N-(2-methoxyethyl)-5-((triisopropylsilyl)ethynyl)benzamide (1.34 g) as a yellow solid.

$^1$H NMR (DMSO-d6) 400 MHz, δ: 8.43 (t, 1H), 7.06-7.03 (m, 2H), 6.78-6.77 (m, 1H), 5.45 (s, 2H), 3.43-3.40 (m, 2H), 3.38-3.34 (m, 2H), 3.25 (s, 3H), 1.10 (s, 21H).

LCMS m/z 375 (M+H)$^+$ (ES$^+$)

To a stirred solution of the (triisopropylsilyl)ethynyl-substituted benzamide obtained immediately above (1.32 g, 3.52 mmol) in EtOAc (21 mL) was added 1M TBAF in THF (3.52 mL, 3.52 mmol). The reaction was stirred at rt for 1 h. The reaction mixture was partitioned between water (50 mL) and EtOAc (50 mL). The organic layer was washed with brine (50 mL), dried (MgSO$_4$), filtered and concentrated to afford an orange oil. The crude product was dissolved in the minimum quantity of MeOH and loaded onto SCX. The column was eluted with MeOH followed by 1% NH$_3$ in MeOH. The filtrate was concentrated in vacuo to afford the Intermediate D4 (534 mg) as a brown oil.

$^1$H NMR (DMSO-d6) 400 MHz, δ: 8.37 (t, 1H), 7.07-7.04 (m, 2H), 6.75-6.74 (m, 1H), 5.45 (s, 2H), 4.07 (s, 1H), 3.44-3.40 (m, 2H), 3.38-3.34 (m, 2H), 3.25 (s, 3H).

LCMS m/z 219 (M+H)$^+$ (ES$^+$)

Intermediate D5: (S)-3-Amino-5-bromo-N-(1-methoxypropan-2-yl)benzamide

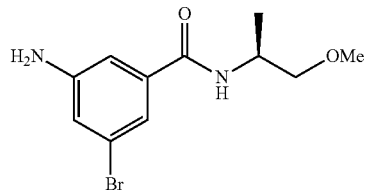 [SMILES: COC[C@H](C)NC(=O)c1cc(N)cc(Br)c1]

A stirred mixture of 3-amino-5-bromobenzoic acid (900 mg, 4.04 mmol), (S)-1-methoxypropan-2-amine (860 μL, 8.14 mmol) and triethylamine (1.7 mL, 12.20 mmol) in DCM (15 mL) was cooled in an ice bath. 50 wt % T3P in EtOAc (3.6 mL, 6.05 mmol) was added dropwise, the ice bath was removed and the reaction mixture allowed to warm to rt. DMF (2 mL) was added to aid solubility and the reaction stirred at rt overnight. The reaction mixture was partitioned between sat. aq. NaHCO$_3$ (50 mL) and DCM (50 mL). The aqueous phase was back extracted with fresh DCM (50 mL). The combined organic extracts were washed with water (100 mL), brine (100 mL), dried (MgSO$_4$), filtered and concentrated in vacuo to afford an orange oil. The crude product was purified by chromatography on silica gel (40 g column, 0-5% MeOH in DCM) to afford Intermediate D5 (1.07 g) as an orange oil.

$^1$H NMR (DMSO-d6) 400 MHz, δ: 8.11 (d, 1H), 7.08 (t, 1H), 6.99-6.98 (m, 1H), 6.84 (t, 1H), 5.56 (s, 2H), 4.18-4.08 (m, 1H), 3.39-3.35 (m, 1H), 3.26-3.22 (m, 1H), 3.25 (s, 3H), 1.09 (d, 3H)

LCMS m/z 287/289 (M+H)$^+$ (ES$^+$)

Intermediate D6: (S)-3-Amino-5-ethynyl-N-(1-methoxypropan-2-yl)benzamide

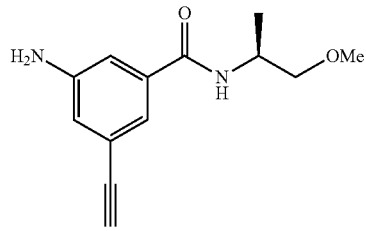 [SMILES: C#Cc1cc(N)cc(C(=O)N[C@@H](C)COC)c1]

To a degassed solution of Intermediate D5 (970 mg, 3.31 mmol), ethynyltriisopropylsilane (1.12 mL, 4.99 mmol), copper(I) iodide (32 mg, 0.168 mmol) and TEA (2 mL, 14.35 mmol) in DMF (10 mL) was added Pd(PPh$_3$)$_4$ (193 mg, 0.167 mmol). The reaction was heated at 85° C. for 3 h. The reaction was cooled to rt then partitioned between EtOAc (50 mL) and brine (50 mL). The aqueous phase was back extracted with EtOAc (50 mL). The combined organic extracts were washed with brine (100 mL), dried (MgSO$_4$), filtered and concentrated in vacuo to afford an orange oil (1.5 g). The crude product was purified by chromatography on silica gel (80 g column, 0-3% MeOH in DCM) to afford (S)-3-amino-N-(1-methoxypropan-2-yl)-5-((triisopropylsilyl)ethynyl)benzamide (894 mg) as an orange oil.

$^1$H NMR (DMSO-d6) 400 MHz, δ: 8.13 (d, 1H), 7.04-7.03 (m, 1H), 7.01 (t, 1H), 6.79-6.78 (m, 1H), 5.42 (s, 2H), 4.18-4.11 (m, 1H), 3.40-3.36 (m, 1H), 3.26-3.22 (m, 4H), 1.11-1.09 (m, 24H).

LCMS m/z 389 (M+H)$^+$ (ES$^+$)

To a stirred solution of the (triisopropylsilyl)ethynyl-substituted benzamide obtained immediately above (875 mg, 2.026 mmol) in EtOAc (12 mL) was added 1M TBAF in THF (2026 μL, 2.026 mmol). The reaction was stirred at rt for 1 h. The reaction mixture was partitioned between water (30 mL) and EtOAc (20 mL). The organic layer was washed with brine (20 mL), dried (MgSO$_4$), filtered and concentrated to afford an orange oil (876 mg). The crude product was dissolved in the minimum quantity of MeOH and loaded onto SCX. The column was eluted with MeOH followed by 1% NH$_3$ in MeOH. The filtrate was concentrated in vacuo to afford a brown oil which was purified by chromatography on silica gel (40 g column, 0-5% MeOH in DCM) to afford Intermediate D6 (307 mg) as an orange oil.

$^1$H NMR (DMSO-d6) 400 MHz, δ: 8.11 (d, 1H), 7.07-7.03 (m, 2H), 6.75-6.74 (m, 1H), 5.44 (s, 2H), 4.17-4.12 (m, 1H), 3.39-3.34 (m, 1H), 3.25-3.21 (m, 4H), 1.09 (d, 3H).

LCMS m/z 233 (M+H)$^+$ (ES$^+$)

Intermediate D7: 3-Amino-5-ethynyl benzamide

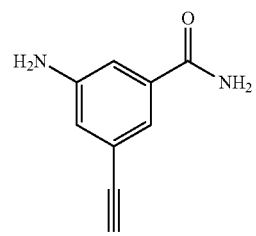

Pd(PPh$_3$)$_4$ (0.269 g, 0.233 mmol) was added to a degassed suspension of 3-amino-5-bromobenzamide (0.5 g, 2.325 mmol), CuI (0.044 g, 0.233 mmol), and ethynyltriisopropylsilane (0.782 mL, 3.49 mmol) in TEA (2 mL) and DMF (2 mL). Heated at 80° C. (block temp.) for 1 h, then cooled and filtered (Whatman glass fibre pad GF/A). Solvents evaporated and the residue partitioned between EtOAc (20 mL) and 20% w/w NaCl solution (25 mL) Organic layer was separated, dried (MgSO$_4$), filtered and solvent evaporated to a thick brown oil. The crude product was purified by chromatography on the Companion (40 g column, 2% MeOH:DCM to 8%) to afford 3-amino-5-((triisopropylsilyl)-ethynyl)benzamide (475 mg) as a pale tan solid.

$^1$H NMR (400 MHz, DMSO-d6) δ 7.87 (s, 1H), 7.21 (s, 1H), 7.13-7.02 (m, 2H), 6.79 (dd, 1H), 5.40 (s, 2H), 1.11 (s, 21H).

LCMS m/z 317 (M+H)+ (ES+)

The (triisopropylsilyl)ethynyl-substituted benzamide obtained immediately above (475 mg, 1.501 mmol) was dissolved in THF (5 mL) and 1M TBAF in THF (1501 μL, 1.501 mmol) added. Stirred for 1 h then partitioned between water (20 mL) and ethyl acetate (20 mL), organic layer separated, dried (MgSO$_4$), filtered and solvent evaporated. The crude product was purified by chromatography on the Companion (12 g column, 5% MeOH:DCM to 10%) to afford Intermediate D7 (145 mg) as a colourless crystalline solid.

$^1$H NMR (400 MHz, DMSO-d6) b 7.82 (s, 1H), 7.22 (s, 1H), 7.09 (dt, 2H), 6.76 (dd, 1H), 5.41 (s, 2H), 4.06 (s, 1H).

LCMS m/z 161 (M+H)+ (ES+)

Intermediate D8: 3-Amino-N-(2-(dimethylamino)ethyl)-5-ethynylbenzamide

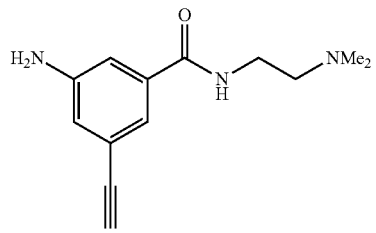 [SMILES: C#Cc1cc(N)cc(C(=O)NCCN(C)C)c1]

Pd(PPh$_3$)$_4$ (0.218 g, 0.189 mmol) was added to a degassed suspension of 3-amino-5-bromo-N-(2-(dimethylamino)ethyl)benzamide (0.54 g, 1.887 mmol), CuI (0.036 g, 0.189 mmol), and ethynyltriisopropylsilane (0.635 mL, 2.83 mmol) in TEA (2 mL) and DMF (2 mL). Heated at 80° C. (block temp.) for 1 h then cooled and filtered (Whatman glass fibre pad GF/A). Solvents were evaporated and the residue partitioned between EtOAc (20 mL) and 20% w/w NaCl soln. (25 mL). The organic layer was separated, dried (MgSO$_4$) filtered and solvent evaporated to a thick brown oil. The crude product was purified by chromatography on the Companion 40 g column, 10% MeOH:DCM to) to afford 3-amino-N-(2-(dimethylamino)ethyl)-5-((triisopropylsilyl)ethynyl)benzamide (600 mg) as a colourless gum which solidified on standing.

$^1$H NMR (400 MHz, DMSO-d6) δ 8.27 (t, 1H), 7.04 (dd, 1H), 7.02 (t, 1H), 6.79 (dd, 1H), 5.43 (s, 2H), 3.33-3.26 (m, 2H), 2.37 (t, 2H), 2.17 (s, 6H), 1.11 (s, 21H).

LCMS m/z 388 (M+H)+ (ES+)

The (triisopropylsilyl)ethynyl-substituted benzamide obtained immediately above (600 mg, 1.548 mmol) was dissolved in THF (50 mL) and 1M TBAF in THF (1548 μL, 1.548 mmol) added. Stirred for 1 h then partitioned between water (100 mL) and ethyl acetate (100 mL), organic layer was separated, washed with 20% w/w NaCl soln. (100 mL), dried (MgSO$_4$), filtered and evaporated. The crude product was purified by chromatography on the Companion (12 g column, 10% MeOH:DCM) to afford Intermediate D8 (240 mg) as a pale yellow gum.

$^1$H NMR (400 MHz, DMSO-d6) δ 8.22 (t, 1H), 7.10-6.99 (m, 2H), 6.76 (dd, 1H), 5.44 (s, 2H), 4.07 (s, 1H), 3.32-3.24 (m, 2H), 2.37 (t, 2H), 2.17 (s, 6H).

Intermediate E1: Methyl 3-((4-((4-(3-(3-(tert-butyl)-1-(p-tolyl)-1H-pyrazol-5-yl)ureido) naphthalen-1-yl)oxy)pyrimidin-2-yl)amino)benzoate

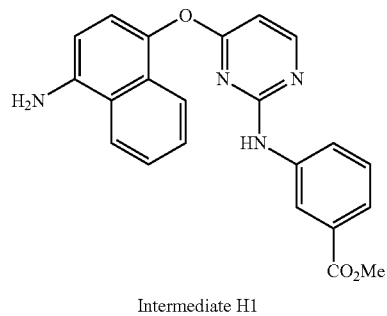

Intermediate H1

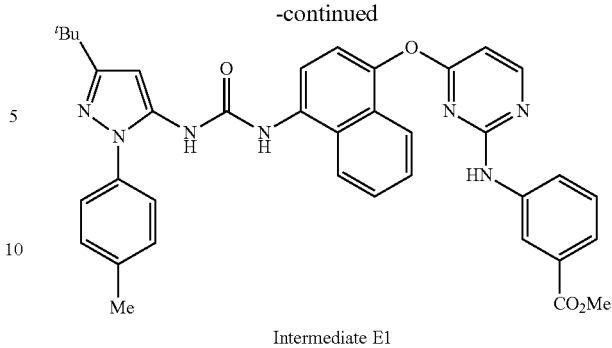

Intermediate E1

To a solution of CDI (1.47 g, 9.08 mmol) in DCM (35 mL) was added Intermediate A8 (2.08 g, 9.08 mmol) and the activation reaction mixture kept at RT for 18 hr, following which it was added dropwise to a solution of Intermediate H1 (1.3 g, 60% pure, 2.0 mmol) in DCM (20 mL). After 2 hr at RT the reaction mixture was washed with a mixture of saturated aq. NaHCO$_3$ (100 mL), water (100 mL) and brine (100 mL) and the organic layer was separated and evaporated in vacuo. The residue was triturated with MeOH (100 mL) and the resulting solid was collected by filtration, washed with MeOH (50 mL) and dried in vacuo. A second crop was isolated in a similar manner from the filtrate and the two solids were combined to afford the title compound, Intermediate E1, as a purple solid (755 mg, 85% purity, 50%); R$^t$ 2.64 min (Method 2 acidic); m/z 642 (M+H)$^+$ (ES$^+$). This material was used in the subsequent step described below without further purification.

Intermediate E2: Methyl 3-((4-((4-(3-(3-(tert-butyl)-1-(p-tolyl)-1H-pyrazol-5-yl)ureido) naphthalen-1-yl)oxy)pyrimidin-2-yl)amino)-5-methylbenzoate

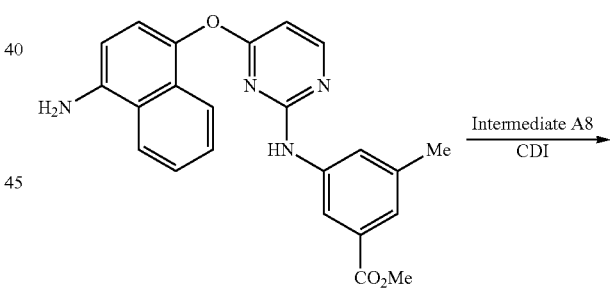

Intermediate H4

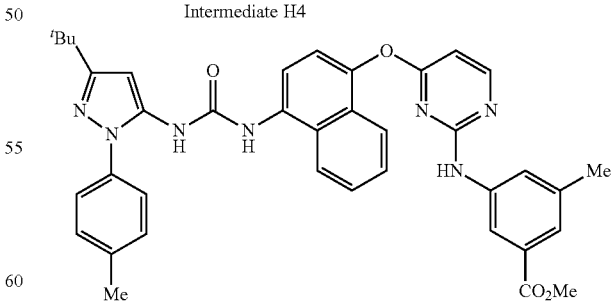

Intermediate E2

To a solution of CDI (364 mg, 2.25 mmol) in DCM (10.0 mL) was added Intermediate A8 (515 mg, 2.25 mmol) and the mixture maintained at RT for 1 hr. An aliquot of the resulting solution (5.0 mL, 1.1 mmol) was then added to a solution of Intermediate H4 (200 mg, 0.499 mmol) in DCM (3.0 mL) after which the combined reaction mixture was diluted with THF to aid stirring (5.0 mL) and kept at RT for 2 hr. The reaction was quenched by addition of MeOH (10 mL) and the resulting precipitate was collected by filtration, washed with MeOH (20 mL) and dried in vacuo to afford methyl the title compound, Intermediate E2, as a pale pink solid (178 mg, 54%); $R^t$ 2.69 min (Method 2 acidic); m/z 656 (M+H)$^+$ (ES$^+$).

Intermediate E3: Methyl 3-((4-((4-(3-(3-(tert-Butyl)-1-(4-methoxyphenyl)-1H-pyrazol-5-yl) ureido) naphthalen-1-yl)oxy)pyrimidin-2-yl)amino)-5-methoxybenzoate

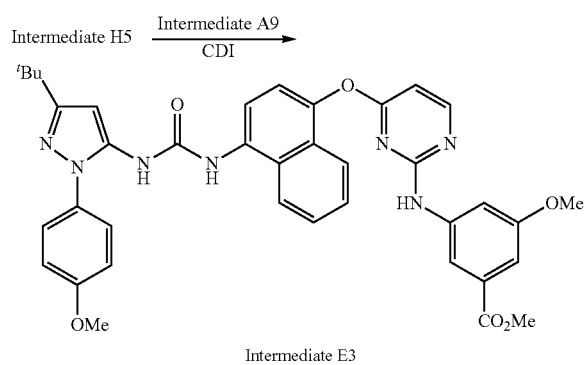

Intermediate E3

To a solution of CDI (82 mg, 0.50 mmol) in DCM (2.0 mL) was added Intermediate A9 (124 mg, 0.50 mmol) and the mixture kept at RT for 18 hr. An aliquot of this solution (1.0 mL, 0.25 mmol) was added to a solution Intermediate H5 (70 mg, 0.17 mmol) in DCM (2.0 mL) and the reaction mixture was maintained at RT for 2 h and then quenched by the addition of MeOH (3.0 mL). The resulting mixture was evaporated in vacuo and the residue was partitioned between DCM (6.0 mL) and sat aq NaHCO$_3$ (6.0 mL). The organic phase was separated and was washed with water (10 mL) and with brine (10 mL) and then dried and evaporated in vacuo. The residue was triturated with MeOH (10 mL) and the product collected by filtration and dried in vacuo to provide the title compound, Intermediate E3, as a pale pink solid (116 mg, 100%); $R^t$ 2.65 min (Method 2 acidic); m/z 688 (M+H)$^+$ (ES$^+$).

Intermediate E4: Methyl 3-bromo-5-((4-((4-(3-(3-(tert-butyl)-1-(4-methoxyphenyl)-1H-pyrazol-5-yl) ureido)naphthalen-1-yl)oxy)pyrimidin-2-yl)amino) benzoate

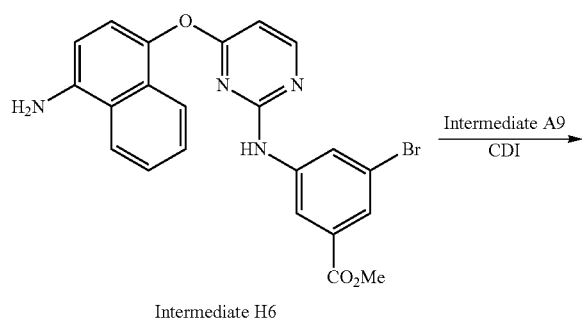

Intermediate H6

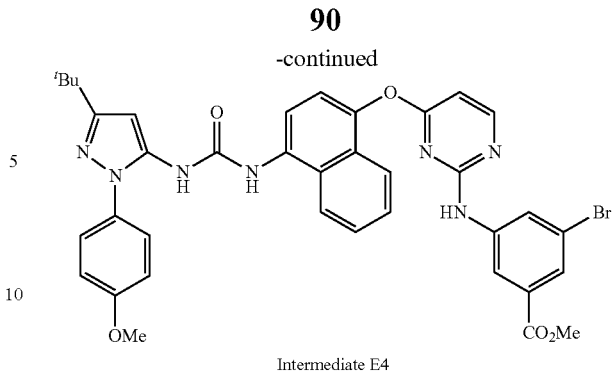

Intermediate E4

To a solution of CDI (73 mg, 0.45 mmol) in DCM (2.0 mL) was added Intermediate A9 (111 mg, 0.45 mmol) and the mixture maintained at RT for 18 hr. An aliquot of the resulting solution (1.0 mL, 0.23 mmol) was added to a solution Intermediate H6 (60 mg, 0.13 mmol) in DCM (2.0 mL) and the reaction mixture maintained at RT for 2 hr and then quenched by addition of MeOH (3.0 mL). The volatiles were evaporated in vacuo and the residue was partitioned between DCM (6.0 mL) and saturated aq. NaHCO$_3$ (6.0 mL). The organic phase was separated and was washed with water (10 mL) and with brine (10 mL) and then dried and evaporated in vacuo. The residue was triturated with MeOH (10 mL) and the solid so obtained was collected by filtration and dried in vacuo to furnish the title compound, Intermediate E4, as an off white solid (58 mg, 61%); $R^t$ 2.90 min (Method 2 acidic); m/z 736/738 (M+H)$^+$ (ES$^+$).

Intermediate E5: Methyl 3-((4-((4-(3-(3-isopropyl-1-(p-tolyl)-1H-pyrazol-5-yl)ureido) naphthalen-1-yl) oxy)pyrimidin-2-yl)amino)-5-methoxybenzoate

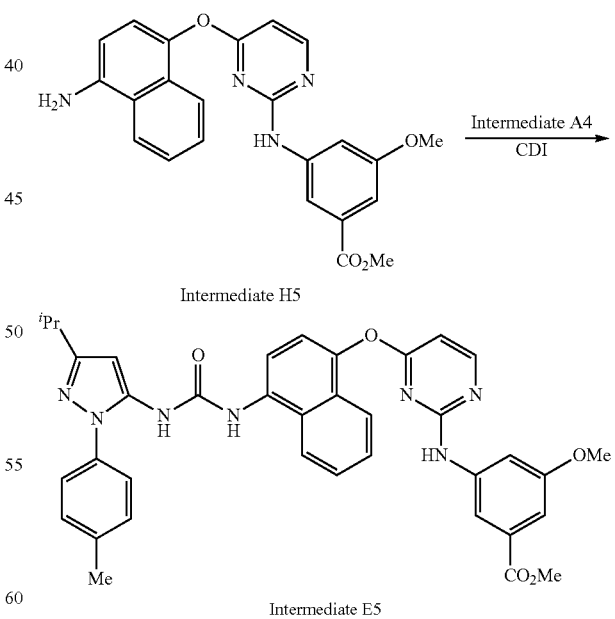

Intermediate E5

To a solution of CDI (320 mg, 1.98 mmol) in DCM (2.0 mL) was added Intermediate A4 (425 mg, 1.98 mmol) and the reaction mixture kept at RT for 18 hr. The resulting solution was added to a solution of Intermediate H5 (329 mg, 0.790 mmol) in THF (2.0 mL) at RT and the reaction mixture maintained at RT for 2 hr, at which time a precipitate had formed. The solids were collected by filtration, washed with THF (10 mL) and then dried in vacuo to give the title compound Intermediate E5, as a white solid (407 mg, 76%); R$^t$ 2.65 min (Method 2 acidic); m/z 658 (M+H)$^+$ (ES$^+$);

Intermediate F1: 3-((4-((4-(3-(3-(tert-Butyl)-1-(p-tolyl)-1H-pyrazol-5-yl)ureido)naphthalen-1-yl)oxy)pyrimidin-2-yl)amino)benzoic acid

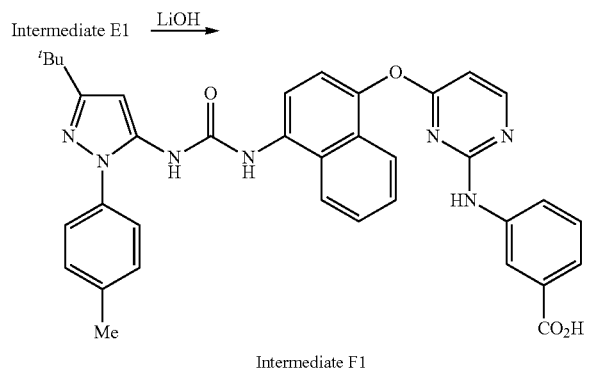

Intermediate F1

To a suspension of the Intermediate E1 obtained as described above (750 mg, 0.993 mmol) in THF (6.0 mL) was added LiOH (36 mg, 1.5 mmol) in a mixture of water (1.0 mL) and MeOH (1.0 mL) and the resulting heterogeneous mixture heated at 40° C. for 3 hr and then cooled to RT for 18 hr. The mixture was concentrated in vacuo to half of its original volume and then poured into hydrochloric acid (1.0 M, 40 mL). The mixture was diluted with EtOAc (10 mL) and was sonicated for 10 min, providing a white precipitate in the aq phase which was collected by filtration and dried in vacuo to give the title compound, Intermediate F1, as an off white solid (300 mg, 47%); R$^t$ 2.51 min (Method 2 acidic); m/z 628 (M+H)$^+$ (ES$^+$).

Intermediate F2: 3-((4-((4-(3-(3-(tert-Butyl)-1-(p-tolyl)-1H-pyrazol-5-yl)ureido)naphthalen-1-yl)oxy)pyrimidin-2-yl)amino)-5-methylbenzoic acid

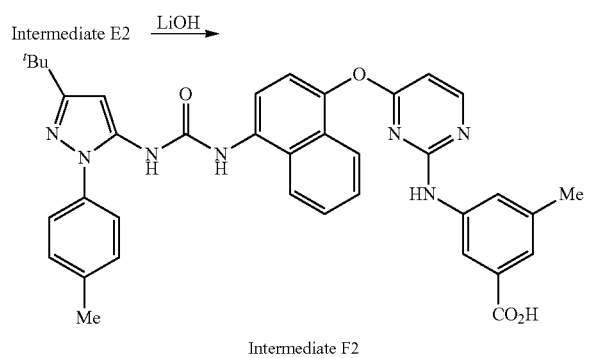

Intermediate F2

To a suspension of Intermediate E2 obtained above (175 mg, 0.267 mmol) in THF (6.0 mL) was added LiOH (9.6 mg, 0.40 mmol) in a mixture of water (1.0 mL) and MeOH (1.0 mL) and the resulting heterogeneous mixture was heated at 50° C. for 5 hr and the cooled to RT. After 18 hr the reaction was re-heated to 50° C. for 3 hr and was then cooled to RT and acidified by the addition of hydrochloric acid (1.0 M, 4.0 mL). The mixture was diluted with water (6.0 mL) and the precipitate which formed was collected by filtration, washed with water (3.0 mL) and dried in vacuo to afford the title compound, Intermediate F2, as a white solid (161 mg, 92%); R$^t$ 2.59 min (Method 2 acidic); m/z 642 (M+H)$^+$ (ES$^+$).

Intermediate F3: 3-((4-((4-(3-(3-(tert-Butyl)-1-(4-methoxyphenyl)-1H-pyrazol-5-yl)ureido) naphthalen-1-yl)oxy)pyrimidin-2-yl)amino)-5-methoxybenzoic acid

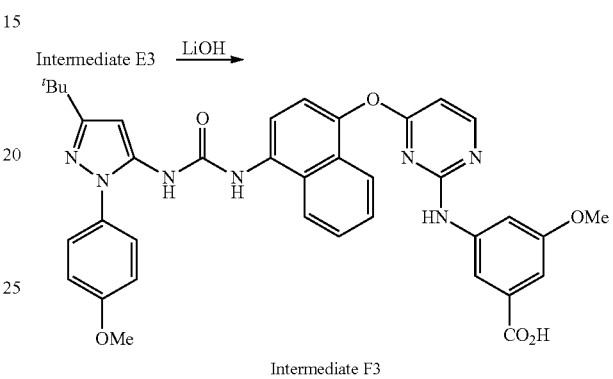

Intermediate F3

To a suspension of Intermediate E3 (116 mg, 0.174 mmol) in THF (6.0 mL) was added LiOH (6.3 mg, 0.26 mmol) in a mixture of water (1.0 mL) and MeOH (1.0 mL) and the resulting heterogeneous mixture heated at 40° C. for 2 hr and then cooled to RT. After 18 hr the mixture was diluted with THF (2.0 mL) and was re-heated to 50° C. for 1 hr during which time a solution was obtained. After cooling to RT the mixture was acidified with hydrochloric acid (1.0 M, 3.0 mL) and then diluted with water (5.0 mL). The precipitate so formed was collected by filtration, washed with water (3.0 mL) and then dried in vacuo to afford the title compound, Intermediate F3 as a pale brown solid (67 mg, 52%); R$^t$ 2.38 min (Method 2 acidic); m/z 674 (M+H)$^+$ (ES$^+$).

Intermediate F4: 3-Bromo-5-((4-((4-(3-(3-(tert-butyl)-1-(4-methoxyphenyl)-1H-pyrazol-5-yl)ureido) naphthalen-1-yl)oxy)pyrimidin-2-yl)amino)benzoic acid

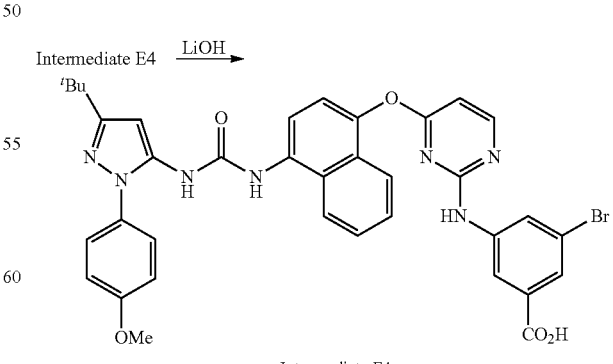

Intermediate F4

To a suspension of Intermediate E4 (58 mg, 0.079 mmol) in THF (6.0 mL) was added LiOH (2.8 mg, 0.12 mmol) in a mixture of water (1.0 mL) and MeOH (1.0 mL) and the resulting heterogeneous mixture heated at 40° C. for 2 hr and then cooled to RT. After 18 hr the mixture was diluted with THF (2.0 mL) and was heated to 50° C. for 3 hr and then cooled to RT. After an additional 24 hr the reaction mixture was acidified with hydrochloric acid (1.0 M, 3.0 mL) and was diluted with water (5.0 mL). The precipitate thus formed was collected by filtration and was washed with water (3.0 mL) and dried in vacuo to afford the title compound, Intermediate F4, as a pale pink solid (42 mg, 74%); R$^t$ 2.70 min (Method 2 acidic); m/z 722/724 (M+H)$^+$ (ES$^+$).

Intermediate G1(P): tert-Butyl (4-((2-chloropyridin-4-yl)oxy)naphthalen-1-yl)carbamate

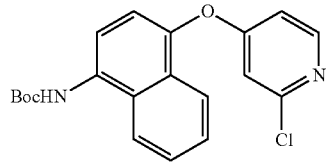 [SMILES: CC(C)(C)OC(=O)Nc1ccc(Oc2ccnc(Cl)c2)c2ccccc12]

A mixture of Intermediate G1 (1000 mg, 3.69 mmol) di-tert-butyl dicarbonate (750 mg, 3.44 mmol) in t-BuOH (10 mL) was stirred at reflux for 18 h. The mixture was diluted with water (15 mL) and collected by filtration. The solid was triturated in diethyl ether to yield Intermediate G1(P) (1002 mg) as a pale grey solid.

$^1$H NMR (DMSO-d6) 400 MHz, δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H). LCMS m/z 371 (M+H)$^+$ (ES$^+$); 369 (M−H)$^−$ (ES$^−$)

Intermediate G3:
4-((6-Chloropyrimidin-4-yl)oxy)naphthalen-1-amine

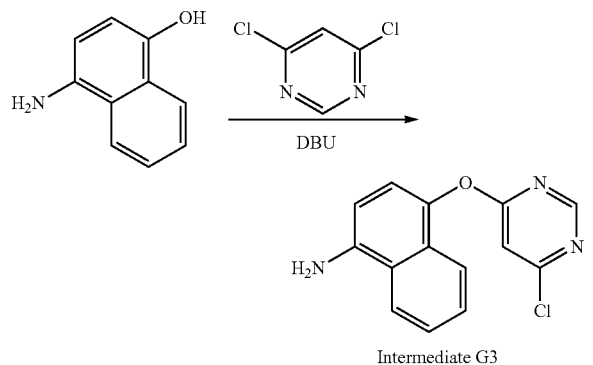

To a solution of 4-aminonaphthalen-1-ol hydrochloride (6.82 g, 31.4 mmol) in acetonitrile (80 mL) at 0° C. was added drop-wise DBU (11.0 mL, 75.0 mmol). After 10 min 4,6-dichloropyrimidine (5.00 g, 34.0 mmol) was added portion-wise over 5 min and the reaction mixture warmed to RT for 3 hr and then evaporated in vacuo. The residue was diluted with water (250 mL) and sonicated for 15 min and then stirred at RT for 16 hr. The resulting precipitate was isolated by filtration, washed with water (3×100 mL) and dried in vacuo to afford the title compound, Intermediate G3, as a grey solid (8.27 g, 97%); R$^t$ 1.85 min (Method 2, acidic); m/z 272 (M+H)$^+$, (ES$^+$).

Intermediate G3(P): tert-Butyl (4-((6-chloropyrimidin-4-yl)oxy)naphthalen-1-yl) carbamate

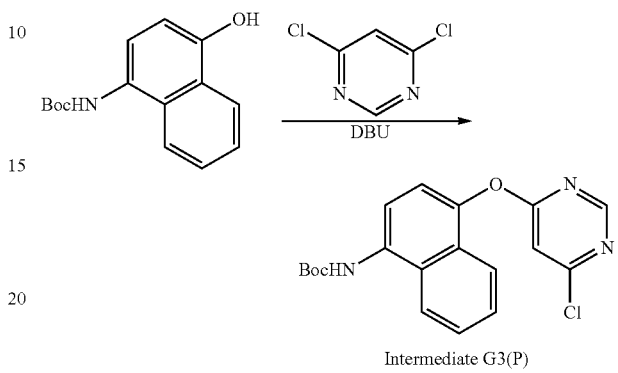

Intermediate G3(P)

To a solution of tert-butyl (4-hydroxynaphthalen-1-yl) carbamate (10.0 g, 29.3 mmol) and 4,6-dichloropyrimidine (4.37 g, 29.3 mmol) in MeCN (75 mL) under N$_2$ was added DBU (5.3 mL, 35 mmol) at such a rate that the internal temperature was maintained in the range 18-21° C. After 1 hr water (75 mL) was added and the resulting heterogeneous mixture was maintained at RT for 18 hr. The resulting precipitate was collected by filtration and was washed with water (2×75 mL) and then dried in vacuo to afford the title compound, Intermediate G3(P), as a brown solid (10.4 g, 95%); R$^t$ 2.57 min (Method 2 acidic); m/z 372 (M+H)$^+$, (ES$^+$).

Intermediate G4: 2,3-Dichloro-4-((2-chloropyrimidin-4-yl)oxy)aniline

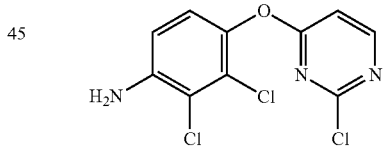

DBU (11.85 mL, 79 mmol) was added over 5 min to a stirred mixture of 4-amino-2,3-dichlorophenol (10 g, 56.2 mmol) in MeCN (150 mL) at 0-5° C. After stirring for 5 min, 2,4-dichloropyrimidine (8.95 g, 60.1 mmol) was added portionwise over 5 min then the mixture warmed to it and stirred for 2 h. The solvent was evaporated under reduced pressure and the residue partitioned between ether (200 mL) and water (200 mL). The aqueous layer was extracted with ether (200 mL) then the combined organic layers washed with brine (200 mL), dried (MgSO$_4$), filtered through a pad of silica and evaporated under reduced pressure. The residue was triturated with ether-isohexane, filtered and dried to afford Intermediate G4 (14.403 g) as a light brown solid.

$^1$H NMR (CDCl$_3$) 400 MHz, δ: 8.45 (d, 1H), 6.96 (d, 1H), 6.84 (d, 1H), 6.73 (d, 1H), 4.22 (s, 2H) LCMS m/z 290/2/4 (M+H)+ (ES+)

Intermediate G5: 4-((2-Chloropyrimidin-4-yl)oxy)-2,3-difluoroaniline

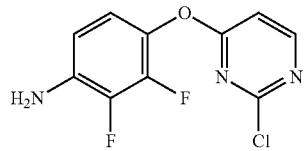 [SMILES: Nc1ccc(Oc2ccnc(Cl)n2)c(F)c1F]

DBU (7.27 ml, 48.2 mmol) was added over 5 min to a stirred mixture of 4-amino-2,3-difluorophenol (5 g, 34.5 mmol) in MeCN (100 mL) at 0-5° C. After stirring for 5 min, 2,4-dichloropyrimidine (5.49 g, 36.9 mmol) was added portionwise over 5 min then the mixture warmed to rt and stirred for 2 h. The solvent was evaporated under reduced pressure and the residue partitioned between ether (200 mL) and water (200 mL). The aqueous layer was extracted with ether (200 mL) then the combined organic layers washed with brine (200 mL), dried (MgSO$_4$) and evaporated under reduced pressure. The crude product was purified by chromatography on silica gel (120 g column, 0-40% EtOAc/isohexane) to afford Intermediate G5 (4.827 g) as a solid.

$^1$H NMR (400 MHz; CDCl$_3$) δ 8.46 (d, 1H), 6.89 (d, 1H), 6.81-6.77 (m, 1H), 6.58-6.53 (m, 1H), 3.85 (s, 2H).

LCMS m/z 258/260 (M+H)+ (ES+)

Intermediate H1: Methyl 3-((4-((4-aminonaphthalen-1-yl)oxy)pyrimidin-2-yl)amino)benzoate

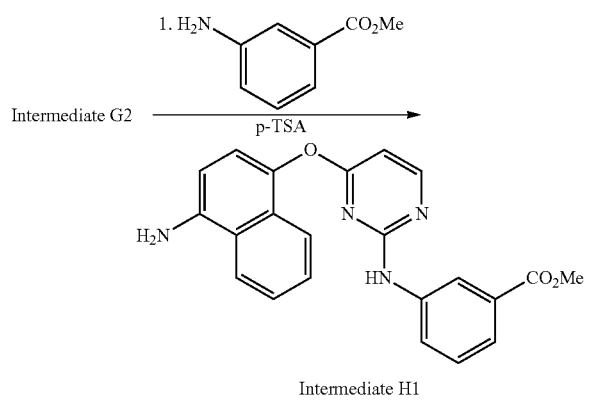

To a solution of Intermediate G2 (5.20 g, 17.0 mmol) and methyl 3-aminobenzoate (5.90 g, 39.0 mmol) in THF (60 mL) was added p-TSA (592 mg, 3.11 mmol) and the resulting suspension heated at reflux for 16 hr. The reaction mixture was cooled to RT and the suspended solids were collected by filtration, washed with THF (2×50 mL) and with Et$_2$O (2×50 mL) and then dried in vacuo to afford the title compound, Intermediate H1, as a purple solid (1.91 g, 29%); R$^t$ 2.06 min (Method 2 acidic); m/z 387 (M+H)$^+$, (ES$^+$).

Intermediate H2(P): Methyl 3-((4-((4-((tert-butoxycarbonyl)amino)naphthalen-1-yl)oxy) pyrimidin-2-yl)amino)-4-methoxybenzoate

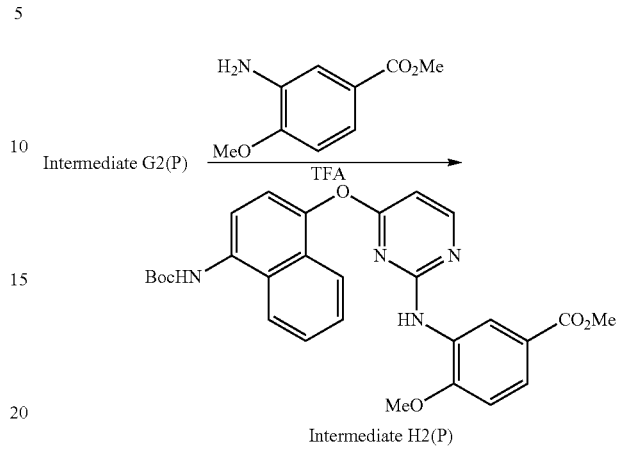

To a degassed suspension of Intermediate G2(P) (2.0 g, 5.4 mmol) in isopropyl acetate (15 mL) was added methyl 3-amino-4-methoxybenzoate (1.95 g, 10.8 mmol) and TFA (0.42 mL, 5.6 mmol). The reaction mixture was diluted with isopropyl acetate to facilitate mixing (15 mL) and was heated to 65° C. for 3 days and then cooled to RT. A precipitate formed which was removed by filtration. Analysis of the solid by LCMS indicated that it did not contain the required product and the material was discarded. The filtrate was partitioned between EtOAc (100 mL) and saturated aq NaHCO$_3$ [100 mL] and the organic phase was separated and was washed with brine (2×50 mL) and then dried and evaporated in vacuo. The residue was purified by flash column chromatography (SiO$_2$, 80 g, 0-50%, EtOAc in isohexane, gradient elution) to afford the title compound, Intermediate H2(P), as a pale pink solid (1.79 g, 64%); R$^t$ 2.70 min (Method 2 acidic); m/z 517 (M+H)$^+$, (ES$^+$).

Intermediate H3: Methyl 4-((4-((4-aminonaphthalen-1-yl)oxy)pyrimidin-2-yl)amino)-3-methoxybenzoate

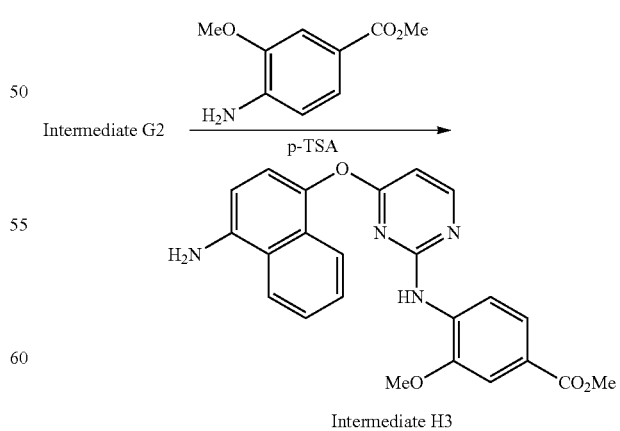

To a solution of Intermediate G2 (1.5 g, 5.5 mmol) in DMF (6.5 mL) was added methyl 4-amino-3-methoxybenzoate (1.20 g, 6.62 mmol) and p-TSA monohydrate (1.57 g, 8.28 mmol). The reaction mixture was heated to 60° C. for 6 hr and then cooled to RT and partitioned between EtOAc (50 mL) and saturated aq NaHCO₃ (50 mL). The organic phase was separated and was washed with brine (2×50 mL). A precipitate formed which was collected by filtration. Analysis of the solid by LCMS indicated that it did not contain the required product and the material was discarded. The filtrate was evaporated in vacuo to furnish a red oil which was purified by flash column chromatography (SiO₂, 80 g, 0-70% EtOAc in isohexane, gradient elution) to provide, Intermediate H3, as a dark purple solid (459 mg, 20%); $R^t$ 2.26 min (Method 2 acidic); m/z 417 (M+H)⁺, (ES⁺).

Intermediate H3(P): Methyl 4-((4-((4-((tert-butoxycarbonyl)amino)naphthalen-1-yl)oxy) pyrimidin-2-yl)amino)-3-methoxybenzoate

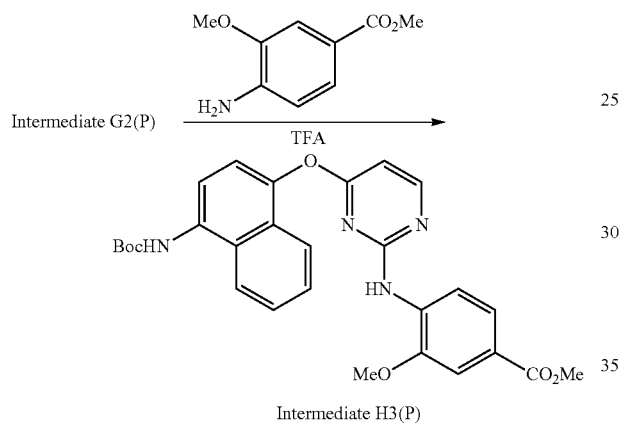

Intermediate H3(P)

To a degassed suspension of Intermediate G2(P) (4.08 g, 11.0 mmol) in isopropyl acetate (30.0 mL) was added methyl 4-amino-3-methoxybenzoate (2.98 g, 16.5 mmol) and TFA (0.85 mL, 11 mmol). The reaction mixture was diluted with isopropyl acetate (30 mL) to facilitate stirring and the resulting suspension was heated to 65° C. for 3 days and then cooled to RT. The suspended solids were collected by filtration, washed with isopropyl acetate and the crude product so obtained was purified by flash column chromatography (SiO₂, 80 g, 0-100%, EtOAc in isohexane, gradient elution) to afford, the title compound, Intermediate H3(P), as a pale purple solid (1.65 g, 28%); $R^t$ 2.80 min (Method 2 acidic); m/z 517 (M+H)⁺, (ES⁺).

Intermediate H4: Methyl 3-((4-((4-aminonaphthalen-1-yl)oxy)pyrimidin-2-yl)amino)-5-methylbenzoate

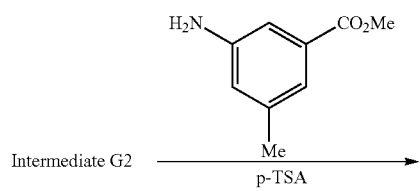

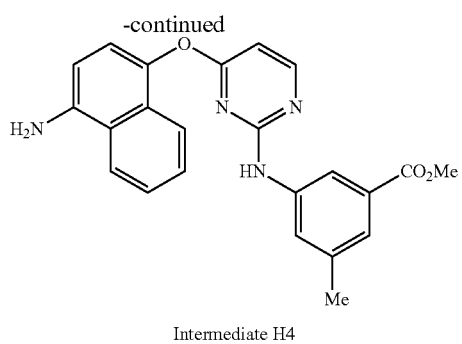

Intermediate H4

To a solution of Intermediate G2 (806 mg, 2.97 mmol) and methyl 3-amino-5-methyl benzoate (490 mg, 2.97 mmol) in DMF (20 mL) was added p-TSA (1.13 g, 5.93 mmol) and the reaction mixture heated to 60° C. for 16 hr. After cooling to RT, the mixture was partitioned between EtOAc (30 mL) and saturated aq NaHCO₃ (30 mL). The organic phase was separated and was washed with water (30 mL) and brine (40 mL) and then dried and evaporated in vacuo. The residue was purified by flash column chromatography (SiO₂, 12.0 g, 0-100% EtOAc in isohexane, gradient elution) to afford the title compound, Intermediate 4, as a red oil (680 mg, 25%); $R^t$ 2.13 min (Method 2 acidic); m/z 401 (M+H)⁺, (ES⁺).

Intermediate H5: Methyl 3-((4-((4-aminonaphthalen-1-yl)oxy)pyrimidin-2-yl)amino)-5-methoxybenzoate

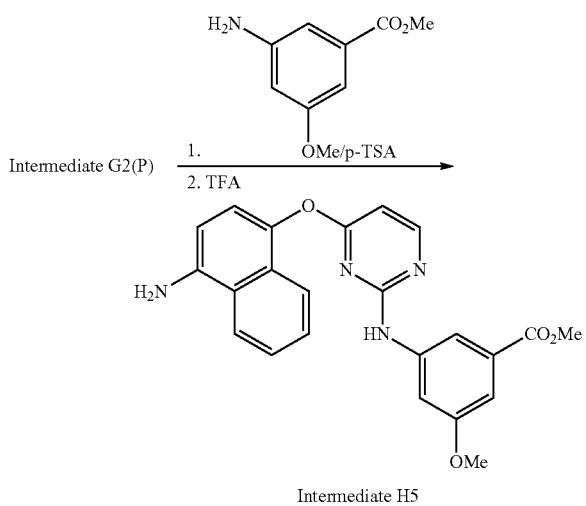

Intermediate H5

To a mixture of Intermediate G2(P) (41.0 g, 110 mmol) and methyl 3-amino-5-methoxy benzoate (20.3 g, 111 mmol) in THF (200 mL) was added p-TSA (592 mg, 3.11 mmol) and the resulting suspension was heated at 60° C. for 18 hr. The reaction mixture was cooled to RT and the suspended solids were collected by filtration, washed with THF (2×100 mL) and then re-suspended in a solution of NH₃ in MeOH (0.7 M) and stirred vigorously. After 30 min the solid was collected by filtration, washed with NH₃ in MeOH (0.7 M) and then dried in vacuo to afford methyl 3-((4-((4-((tert-butoxycarbonyl)amino)naphthalen-1-yl)oxy)pyrimidin-2-yl)amino)-5-methoxybenzoate, Intermediate H5(P), as a beige solid (34.0 g, 92% purity by HPLC, 56%).

To a suspension of Intermediate H5(P) (10.2 g, 92% pure, 18.2 mmol) in DCM (50 mL) was added TFA (10 mL, 130 mmol) dropwise and the resulting black solution kept at RT for 21 hr. An additional aliquot of TFA (5.0 mL, 67 mmol) was added and after a further 3 hr the reaction mixture was evaporated in vacuo. The residue was co-evaporated with toluene (100 mL) then with a solution of NH$_3$ in MeOH (0.7 M, 2×100 mL), triturated with MeOH (100 mL) then the resulting solid was collected by filtration, washed with MeOH (50 mL) and dried in vacuo to afford the title compound, Intermediate H5, as a beige solid (7.9 g, 99%); R$^t$ 2.15 min (Method 2 acidic, 92% pure); m/z 417 (M+H)$^+$, (ES$^+$).

Intermediate H6: Methyl 3-((4-((4-aminonaphthalen-1-yl)oxy)pyrimidin-2-yl)amino)-5-bromobenzoate

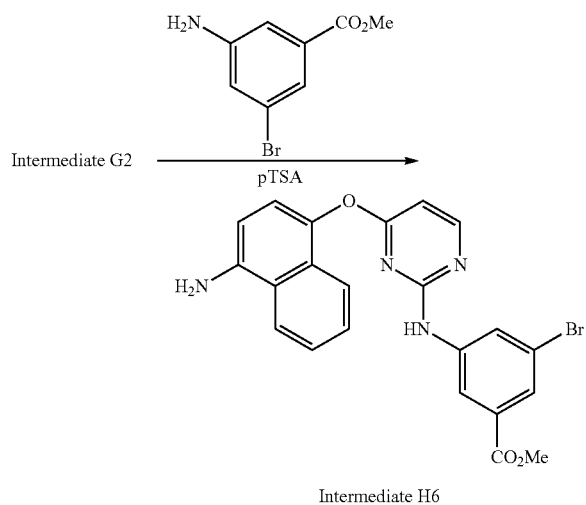

Intermediate H6

To a solution of Intermediate G2 (236 mg, 0.869 mmol) and methyl 3-amino-5-bromo benzoate (200 mg, 0.869 mmol) in DMF (6.0 mL) was added p-TSA (331 mg, 1.74 mmol) and the resulting mixture was heated at 60° C. for 8 hr. After cooling to RT the reaction mixture was partitioned between EtOAc (10 mL) and saturated aq NaHCO$_3$ (10 mL). The organic phase was separated and was washed with brine (10 mL) and then dried and evaporated in vacuo. The residue was purified by flash column chromatography (SiO$_2$, 12 g, 0-100% EtOAc in isohexane, gradient elution) to afford the title compound, Intermediate H6, as a brown solid (124 mg, 82% purity by HPLC, 25%); R$^t$ 2.15 min (Method 2 acidic, 82% pure); m/z 465/467 (M+H)$^+$, (ES$^+$). This material was used in subsequent steps without additional purification.

Intermediate J1: 3-((4-((4-Aminonaphthalen-1-yl)oxy)pyrimidin-2-yl)amino)benzoic acid

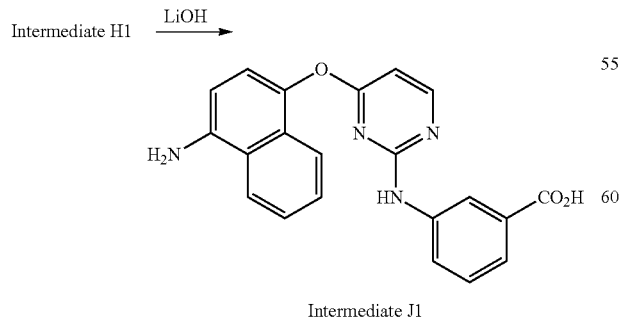

Intermediate J1

To a solution of Intermediate H1, (905 mg, 2.34 mmol) in a mixture of THF (5.0 mL) and water (2.0 mL) was added aq. NaOH (2.0 M, 1.4 mL, 2.8 mmol) and the reaction mixture maintained at RT for 3 hr. The resulting mixture was acidified to pH 6 by the addition of 2 M hydrochloric acid which generated a purple precipitate. The solid was collected by filtration and was washed with water and dried in vacuo to provide the title compound, Intermediate J1, as a pale purple solid (643 mg, 73%); R$^t$ 1.62 min (Method 2 basic); m/z 373 (M+H)$^+$, (ES$^+$).

Intermediate J2(P): 3-((4-((4-((tert-Butoxycarbonyl)amino)naphthalen-1-yl)oxy) pyrimidin-2-yl)amino)-4-methoxybenzoic acid

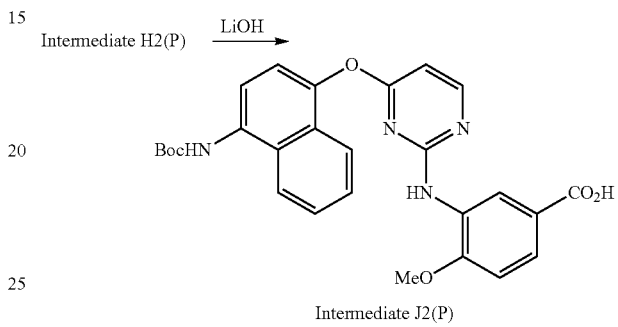

Intermediate J2(P)

To a suspension of the methyl ester Intermediate H2(P), (1.75 g, 3.39 mmol) in THF (12 mL) was added a solution of LiOH (122 mg, 5.08 mmol) in aq MeOH (1:1 v/v, 6.0 mL). The reaction mixture was heated to 40° C. for 40 min, cooled to RT for 18 hr and then re-heated to 40° C. for 2 hr. A second batch of LiOH (41 mg, 1.7 mmol) was added and the reaction mixture was maintained at RT for 24 hr and then evaporated in vacuo to half of its original volume. The concentrate was poured onto hydrochloric acid (1.0 M, 20 mL), which provided an off white precipitate. The solid was collected by filtration and was washed with water and then dried in vacuo to afford the title compound, Intermediate J2(P) as a white solid (1.25 g, 64%); R$^t$ 2.46 min (Method 2 acidic); m/z 503 (M+H)$^+$, (ES$^+$).

Intermediate J3: 4-((4-((4-Aminonaphthalen-1-yl)oxy)pyrimidin-2-yl)amino)-3-methoxy benzoic acid

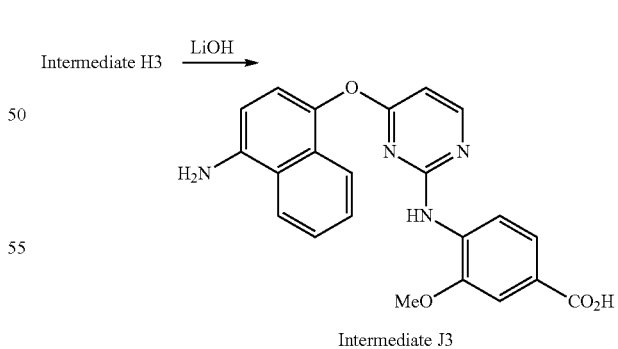

Intermediate J3

To a suspension of Intermediate H3, (450 mg, 1.08 mmol) in THF (4.0 mL) was added a solution of LiOH (39 mg, 1.6 mmol) in a mixture of water and MeOH (1:1 v/v, 2.0 mL) and the reaction mixture heated to 40° C. for 4 hr and then maintained at RT for 3 days. The resulting mixture was concentrated to half of its original volume in vacuo and the concentrate was poured into aq hydrochloric acid (1.0 M, 10.0 mL). The mixture was neutralized with aq NaOH (2.0 M) and extracted with DCM. The organic extract was washed with brine (2×30 mL) and then dried and evaporated in vacuo to afford the title compound, Intermediate J3, as a brown solid (328 mg, 72%); $R^t$ 1.92 min (Method 2 acidic); m/z 403 (M+H)$^+$, (ES$^+$).

Intermediate J3(P): 4-((4-((4-(((tert-Butoxycarbonyl)amino)naphthalen-1-yl)oxy) pyrimidin-2-yl)amino)-3-methoxybenzoic acid

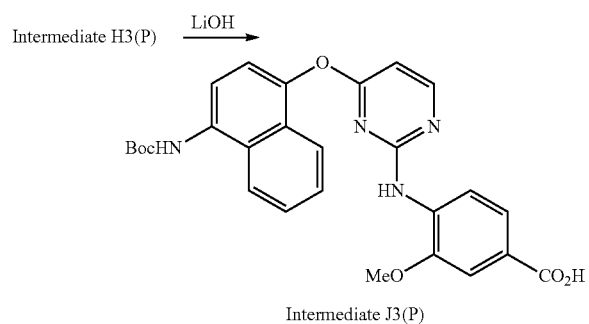

Intermediate J3(P)

To a suspension of the methyl ester Intermediate H3(P) (1.65 g, 3.19 mmol) in THF (12 mL) was added a solution of LiOH (115 mg, 4.79 mmol) in aq MeOH (1:1 v/v, 6.0 mL) and the mixture heated to 40° C. for 18 hr. After cooling to RT the mixture was evaporated in vacuo to half of its original volume and the resulting concentrate then poured into hydrochloric acid (1.0 M, 20 mL). A precipitate formed which was collected by filtration, washed with water and dried in vacuo to afford the title compound, Intermediate J3(P), as a pale pink solid (1.12 g, 68%); $R^t$ 3.86 min (Method 3); m/z 503 (M+H)$^+$, (ES$^+$).

Intermediate J4(P): 3-((4-((4-(((tert-Butoxycarbonyl)amino)naphthalen-1-yl)oxy) pyrimidin-2-yl)amino)-5-methylbenzoic acid

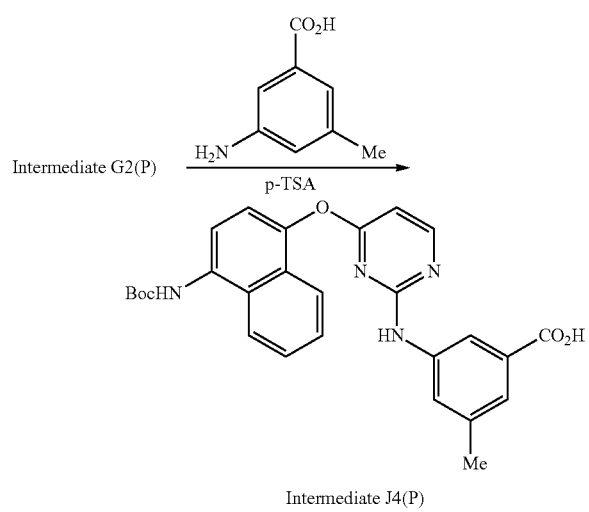

Intermediate J4(P)

To a solution of Intermediate G2(P) (950 mg, 2.56 mmol) in anhydrous THF (15 mL) was added 3-amino-5-methyl-benzoic acid (772 mg, 5.11 mmol) and p-TSA monohydrate (97 mg, 0.51 mmol) and the reaction mixture heated to 65° C. for 24 hr and then cooled to RT. The resulting mixture was diluted with NH$_3$ in MeOH, (0.7 M, 50 mL) and re-evaporated in vacuo. The residue was triturated with MeOH (30 mL) to provide the title compound, Intermediate J4(P), as a brown solid (727 mg, 56%); $R^t$ 3.81 min (Method 3); m/z 487 (M+H)$^+$, (ES$^+$).

Intermediate J5(P): 3((4-((4-(((tert-Butoxycarbonyl)amino)naphthalen-1-yl)oxy) pyrimidin-2-yl)amino)-5-(trifluoromethyl)benzoic acid

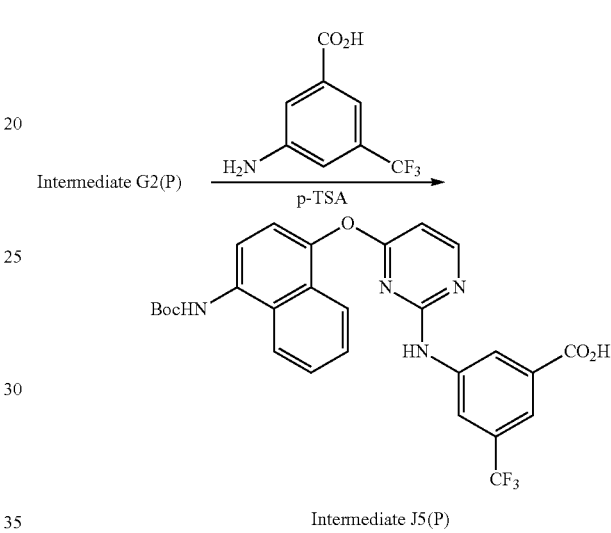

Intermediate J5(P)

To a degassed solution of Intermediate G2(P) (1.00 g, 2.71 mmol) in anhydrous THF (15 mL) was added 3-amino-5-(trifluoromethyl)benzoic acid (1.11 g, 5.42 mmol) and p-TSA monohydrate (103 mg, 0.542 mmol) and the mixture heated to 65° C. for 24 hr and then cooled to RT. The resulting mixture was diluted with NH$_3$ in MeOH (0.7 M, 30 mL) and re-evaporated in vacuo and the residue was re-suspended in NH$_3$ in MeOH (0.7 M, 60 mL) and evaporated in vacuo. The co-evaporation was repeated once more and the residue so obtained was triturated with MeOH (20 mL). The solid product was collected by filtration and dried in vacuo to furnish the title compound, Intermediate J5(P), as a pale brown solid (577 mg, 37%); $R^t$ 4.02 min (Method 3); m/z 541 (M+H)$^+$, (ES$^+$).

Intermediate J6(P): 3-((4-((4-(((tert-Butoxycarbonyl)amino)naphthalen-1-yl)oxy) pyrimidin-2-yl)amino)-5-methoxybenzoic acid

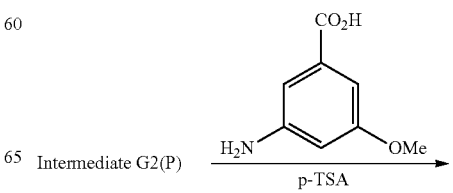

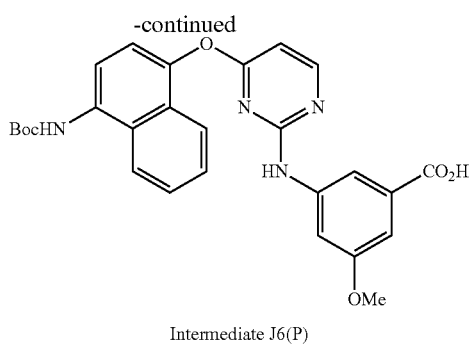

Intermediate J6(P)

To a degassed solution of Intermediate G2(P) (10.0 g, 27.0 mmol) in anhydrous THF (150 mL) was added 3-amino-5-methoxybenzoic acid (8.99 g, 53.8 mmol) and p-TSA monohydrate (1.02 g, 5.38 mmol) and the reaction mixture heated to 65° C. for 24 hr and then cooled to RT and evaporated in vacuo. The residue was suspended in $NH_3$ in MeOH (0.7 M, 100 mL) and evaporated in vacuo. This procedure was repeated (0.7 M in MeOH, 250 mL) and the material so obtained was combined with the crude product from an identical reaction performed on the same scale. The combined material was slurried with MeOH (4×125 mL) and the resulting solid was collected by filtration and dried in vacuo to afford the title compound as pale brown solid, Intermediate J6(P), (11.3 g, 30%); $R^t$ 1.60 min (Method 2 basic); m/z 503 (M+H)$^+$, (ES$^+$).

Intermediate J7(P): 3-((4-((4-(((tert-Butoxycarbonyl) amino)naphthalen-1-yl)oxy) pyrimidin-2-yl)amino)-5-chlorobenzoic acid

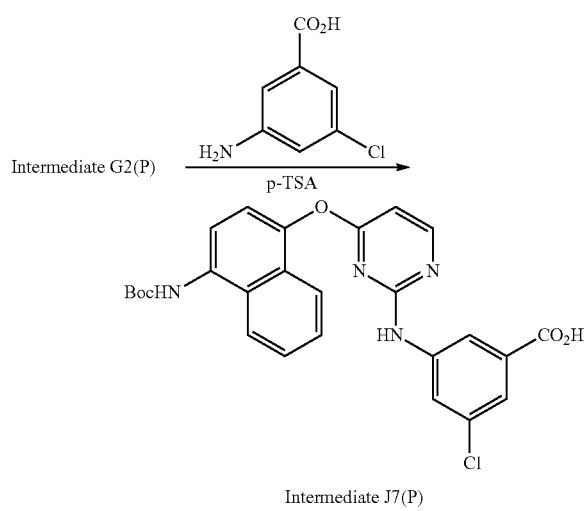

Intermediate J7(P)

To a solution of Intermediate G2(P) (1.01 g, 2.72 mmol) in anhydrous THF (15 mL) was added 3-amino-5-chlorobenzoic acid (1.11 g, 5.42 mmol) and p-TSA monohydrate (103 mg, 0.542 mmol) and the reaction mixture heated to 65° C. for 24 hr. The resulting mixture was cooled to RT, diluted with $NH_3$ in MeOH (0.7 M, 60 mL) and evaporated in vacuo. The same process was then repeated twice more and the residue was triturated with MeOH (30 mL). The resulting solid was collected by filtration to afford the title compound, Intermediate J7(P), as a brown solid (374 mg, 27%); $R^t$ 4.06 min (Method 3); m/z 507 (M+H)$^+$, (ES$^+$).

Intermediate J8(P): 3-Bromo-5((4-((4-(((tert-butoxycarbonyl)amino)naphthalen-1-yl)oxy) pyrimidin-2-yl)amino)benzoic acid

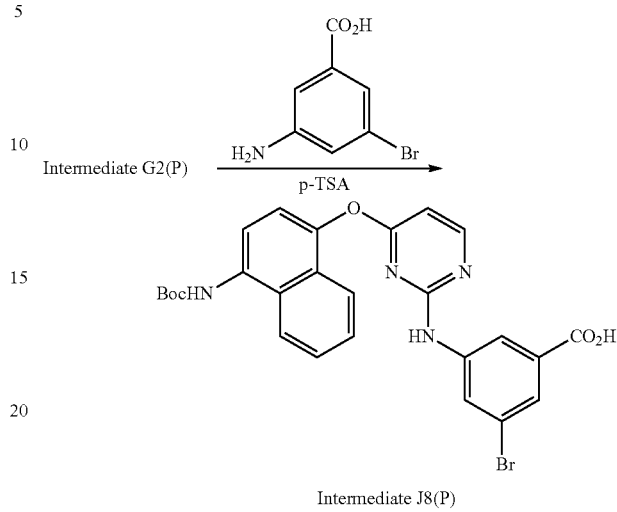

Intermediate J8(P)

To a degassed solution of Intermediate G2(P) (1.5 g, 4.0 mmol) in anhydrous THF (20 mL) was added 3-amino-5-bromobenzoic acid (1.57 g, 7.26 mmol) and p-TSA monohydrate (153 mg, 0.807 mmol) and the reaction mixture heated to 65° C. for 24 hr. The resulting mixture was cooled to RT and was diluted with $NH_3$ in MeOH (0.7 M, 60 mL) and then evaporated in vacuo. The same process was repeated more and the residue so obtained was then triturated with MeOH (60 mL). The solid thus obtained was collected by filtration and dried in vacuo to provide the title compound, Intermediate J8(P), as a pale brown solid (1.33 g, 57%); $R^t$ 4.21 min (Method 3); m/z 552/554 (M+H)$^+$, (ES$^+$).

Intermediate J9(P): 3-((6-((4-(((tert-Butoxycarbonyl) amino)naphthalen-1-yl)oxy) pyrimidin-4-yl)amino)-5-methoxybenzoic acid

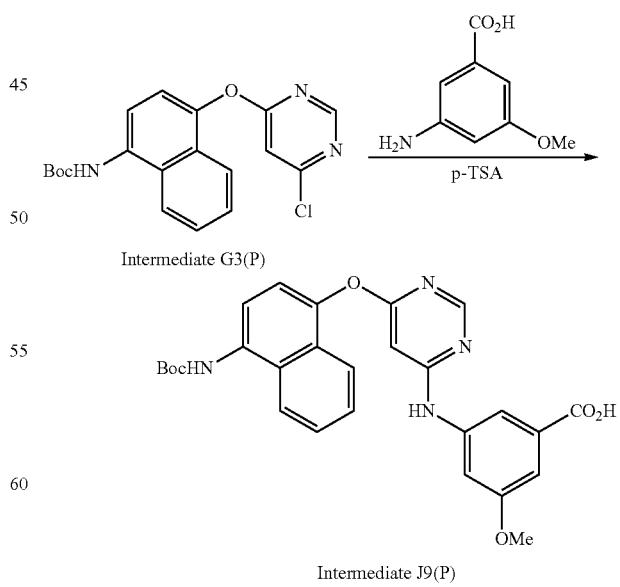

Intermediate J9(P)

To a solution of Intermediate G3(P) (5.00 g, 2.56 mmol) in anhydrous THF (50 mL) was added 3-amino-5-methoxybenzoic acid (4.50 g, 26.9 mmol) and p-TSA monohydrate (512 mg, 2.69 mmol) and the reaction mixture heated to 65° C. for 18 hr, and then at reflux for an additional 4 hr. The resulting mixture was diluted with DMF (20 mL) and was heated to 95° C. for 2 hr and then maintained at RT for 3 days. The mixture was reheated to 95° C. for 24 hr was then cooled and evaporated in vacuo. The residue was dissolved in MeOH and loaded onto SCX resin (25 g). The desired material did not retain on the resin and the loading fraction was collected and evaporated in vacuo. The residue was co-evaporated twice with NH₃ (0.7 M, 200 mL) then dissolved in EtOAc/THF (10:1 v/v, 250 mL) and washed with brine (3×100 mL). The organic phase was evaporated in vacuo and the residue was triturated with MeOH (100 mL) then collected by filtration and washed with further MeOH (3×10 mL) to afford the title compound, Intermediate J9(P), as a brown solid (2.67 g, 34%); R$^t$ 1.58 min (Method 2 basic); m/z 503 (M+H)$^+$, (ES$^+$).

Intermediate J10(P): 3-((4-((4-((tert-Butoxycarbonyl)amino)naphthalen-1-yl)oxy)-pyrimidin-2-yl)amino)-5-ethynylbenzoic acid

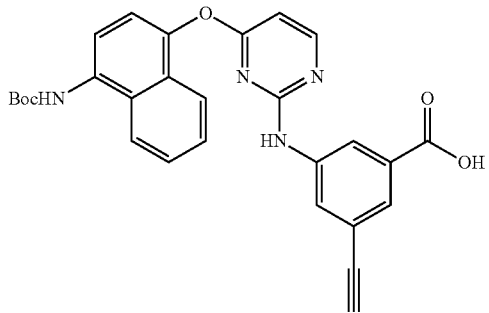 [SMILES: C#Cc1cc(Nc2nccc(Oc3ccc(NC(=O)OC(C)(C)C)c4ccccc34)n2)cc(C(=O)O)c1]

To a partially dissolved suspension of ammonium chloride (0.065 g, 1.219 mmol) in IPA (70 mL) was added methyl 3-ethynyl-5-nitrobenzoate (0.5 g, 2.437 mmol) and a mixture of iron powder (1.36 g, 24.35 mmol) in water (5 mL). The reaction was heated at reflux for 2 h. The reaction was cooled to rt and filtered through celite. The filtrate was concentrated in vacuo giving an orange, waxy solid. The crude product was purified by chromatography on the Companion (40 g column, 0-5% MeOH in DCM) to afford methyl 3-amino-5-ethynylbenzoate (332 mg) as a pale yellow solid.

$^1$H NMR (DMSO-d6) 400 MHz, δ: 7.21 (t, 1H), 7.12 (s, 1H), 6.87 (t, 1H), 5.62 (s, 2H), 4.13 (s, 1H), 3.81 (s, 3H).

LCMS m/z 176 (M+H)$^+$ (ES$^+$)

A suspension of Intermediate G2(P) (1.5 g, 4.03 mmol), the product from the step immediately above (1.41 g, 8.05 mmol) and p-TSA monohydrate (0.15 g, 0.789 mmol) in THF/DMF (60 mL, 1:1) was heated at 60° C. overnight. The reaction was cooled to rt and partitioned between EtOAc (60 mL) and sat. aq. NaHCO₃ (100 mL). The aqueous layer was extracted with EtOAc (2×60 mL). The combined organic extracts were washed with water (2×100 mL), brine (2×50 mL), dried (MgSO₄), filtered and concentrated in vacuo. The crude product was purified by chromatography on the Companion (80 g column, 0-5% MeOH in DCM) to afford the product as an orange solid. The solid was triturated in a mixture of MeOH and hexane giving the product as a white solid at 90% purity. The remaining 10% was identified as the de-boc material. The mixture was suspended in DCM (70 ml) and a small volume of THF added for solubility (5 ml). Triethylamine was added (0.14 ml, 0.8 mmol) followed by di-tert-butyl dicarbonate (90 mg, 0.4 mmol). The reaction was stirred at rt overnight. The reaction mixture was concentrated onto silica and crude product purified by chromatography on the Companion (80 g column, 10-50% EtOAc in hexane) to afford methyl 3-((4-((4-((tert-butoxycarbonyl)amino)naphthalen-1-yl)oxy)pyrimidin-2-yl)amino)-5-ethynylbenzoate (476 mg) as a white solid.

$^1$H NMR (DMSO-d6) 400 MHz, δ: 9.87 (s, 1H), 9.34 (s, 1H), 8.48 (d, 1H), 8.30 (s, 1H), 8.10 (d, 1H), 8.03 (s, 1H), 7.82 (d, 1H), 7.49-7.54 (m, 3H), 7.49 (s, 1H), 7.43 (d, 1H), 6.63 (d, 1H), 4.21 (s, 1H), 3.83 (s, 3H), 1.52 (s, 9H).

To a stirred solution of the product from the step immediately above (0.476 g, 0.932 mmol) in THF (10 mL) was added sodium hydroxide (1.0 M aq.) (10 mL, 10.00 mmol) and the reaction vigorously stirred at rt overnight. The temperature of the reaction was increased to 50° C. and stirring continued for 6 h. The reaction was cooled to rt, diluted with water (40 ml) and the THF removed in vacuo giving a cloudy suspension. The suspension was acidified to pH 2 with 1M HCl and the resulting solid isolated by filtration, washing with more water. The solid was dried under vacuum at 40° C. for 4 h, affording Intermediate J10(P) (436 mg) as a white solid.

$^1$H NMR (DMSO-d6) 400 MHz, δ: 13.09 (s, 1H), 9.84 (s, 1H), 9.33 (s, 1H), 8.48 (d, 1H), 8.28 (s, 1H), 8.10 (d, 1H), 8.01 (s, 1H), 7.82 (d, 1H), 7.54-7.63 (m, 3H), 7.42-7.48 (m, 2H), 6.61 (d, 1H), 4.18 (s, 1H), 1.52 (s, 9H).

Intermediate M1: 3-(tert-Butyl)-1-(4-(dimethylamino)phenyl)-1H-pyrazole-5-carboxylic acid

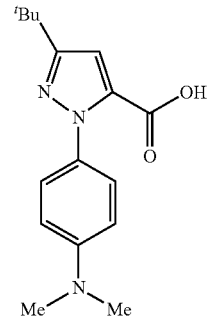 [SMILES: CN(C)c1ccc(-n2nc(C(C)(C)C)cc2C(=O)O)cc1]

Pyridine (350 µL, 4.33 mmol) followed by activated 4A molecular sieves (0.5 g) were added to a stirred mixture of (4-(dimethylamino)phenyl)boronic acid (575 mg, 3.48 mmol), ethyl 3-(tert-butyl)-1H-pyrazole-5-carboxylate (425 mg, 2.166 mmol) and copper (II) acetate (590 mg, 3.25 mmol) in DCM (15 mL) at rt. open to the air. The mixture was stirred for 4 h. A mixture of ether/isohexane (3:1, 300 mL) was added and the solid was filtered off. The filtrate was evaporated under reduced pressure and the residue was purified by chromatography on the Companion (80 g column, 0-60% ether/isohexane) to afford ethyl 3-(tert-butyl)-1-(4-(dimethylamino)phenyl)-1H-pyrazole-5-carboxylate (464 mg) as a colourless oil.

LCMS m/z 316 (M+H)$^+$ (ES$^+$)

1 M sodium hydroxide solution (1.5 mL, 1.500 mmol) was added to a stirred solution of the product from step (i) above (0.46 g, 1.458 mmol) in tetrahydrofuran (3 mL) at rt. The mixture was stirred for 3 h at rt then methanol (1 mL) was added and the mixture was stirred for a further 1 h. The mixture was then heated to 40° C. for 1 h, diluted with water (10 mL) and washed with diethyl ether (2×10 mL). The aqueous phases was treated with 1 M HCl (1.5 mL) and extracted with ethyl acetate (3×10 mL). The combined organic phases were washed with saturated brine (10 mL), dried (MgSO₄) and concentrated to yield Intermediate M1 (395 mg) as an off-white solid.

$^1$H NMR (400 MHz; CDCl₃) δ: 7.28-7.22 (m, 2H), 6.91 (s, 1H), 6.74-6.67 (m, 2H), 2.98 (s, 6H), 1.35 (s, 9H).

LCMS m/z 288 (M+H)$^+$ (ES$^+$); 286 (M−H)$^-$ (ES$^-$)

Compound Examples of the Invention

Example 1

3-((4-((4-(3-(3-(tert-Butyl)-1-(p-tolyl)-1H-pyrazol-5-yl)ureido)naphthalen-1-yl)oxy)pyridin-2-yl)amino)-5-methoxy-N-(2-morpholinoethyl)benzamide

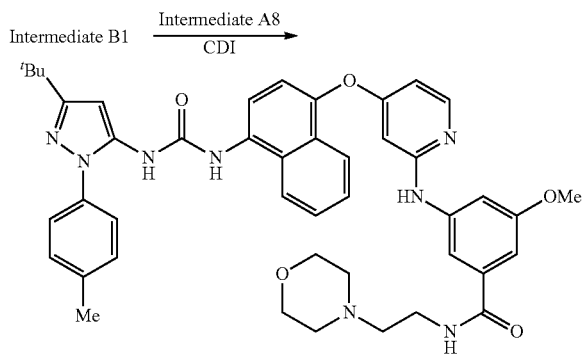

Example 1

To a solution of Intermediate A8 (74 mg, 0.32 mmol) in DCM (1.0 mL) was added CDI (54 mg, 0.34 mmol) and the reaction mixture kept at 40° C. for 2 hr. An aliquot of this solution (310 μL, 0.099 mmol), containing the pre-formed pyrazole CDI adduct, was added to a solution of Intermediate B1 (50 mg, 0.078 mmol) in THF (1.0 mL) at RT and the resulting mixture maintained at this temperature for 18 hr. A second aliquot of the pyrazole CDI adduct (160 μL, 0.05 mmol) was then added and after 3 hr at RT the reaction mixture was partitioned between EtOAc (50 mL) and saturated aq NaHCO$_3$ (50 mL). The organic phase was separated and was washed sequentially with saturated aq NaHCO$_3$ (2×50 mL), water (2×50 mL) and brine (2×50 mL) and then dried and evaporated in vacuo. The residue was purified by preparative HPLC to afford the title compound, Example 1, as a pale purple solid (16 mg, 22%); R$^t$ 2.63 min (Method 3); m/z 767 (M−H)$^-$ (ES$^-$); $^1$H NMR δ: 1.29 (9H, s), 2.37-2.45 (9H, over-lapping m), 3.34 (2H, m), 3.55-3.57 (4H, over-lapping m), 3.73 (3H, s), 6.11 (1H, d), 6.41 (1H, s), 6.56 (1H, dd), 6.85 (1H, m), 7.34-7.40 (3H, over-lapping m), 7.45-7.50 (3H, over-lapping m), 7.56 (1H, m), 7.65 (1H, m), 7.84 (1H, d), 7.97 (1H, d), 8.09-8.12 (2H, over-lapping m), 8.22-8.27 (2H, over-lapping m), 8.84 (1H, br s), 9.07 (1H, br s), 9.19 (1H, br s).

Example 2

3-((4-((4-(3-(3-(tert-Butyl)-1-(p-tolyl)-1H-pyrazol-5-yl)ureido)naphthalen-1-yl)oxy)pyrimidin-2-yl)amino)benzamide

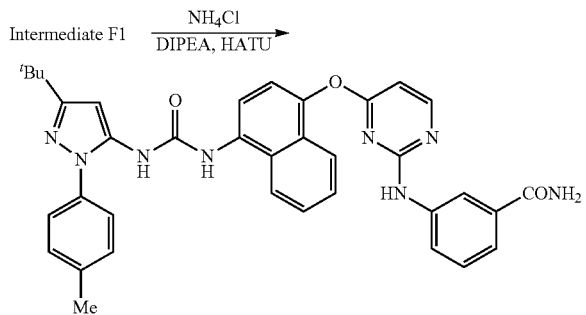

Example 2

To a suspension of Intermediate F1 (50 mg, 0.080 mmol) in THF (1.5 mL) was added DIPEA (28 μL, 0.16 mmol) and HATU (36 mg, 0.096 mmol) and after 10 min at RT the reaction mixture was treated with NH$_4$Cl (4.7 mg, 0.088 mmol). The resulting mixture was maintained at RT for 18 hr and was then partitioned between saturated aq NaHCO$_3$ (3.0 mL) and EtOAc (3.0 mL). The organic phase was separated and was washed with hydrochloric acid (1.0 M, 3.0 mL) and with brine (3.0 mL) and then dried and evaporated in vacuo. The residue was purified by flash column chromatography (SiO$_2$, 4.0 g, MeOH in EtOAc, 0-100%, gradient elution) to afford the title compound, Example 2, as a white solid (8 mg, 16%); R$^t$ 2.30 min (Method 2 acidic); m/z 627 (M+H)$^+$ (ES$^+$); m/z 625 (M−H)$^-$ (ES$^-$); $^1$H NMR δ: 1.29 (9H, s), 2.40 (3H, s), 6.42 (1H, s), 6.55 (1H, d), 6.99 (1H, m), 7.23 (1H, br s), 7.29 (1H, d), 7.36-7.42 (3H, over-lapping m), 7.44-7.50 (3H, over-lapping m), 7.53-7.65 (2H, over-lapping m), 7.75 (1H, br s), 7.81 (1H, d), 7.89-7.94 (2H, over-lapping m), 8.07 (1H, d), 8.40 (1H, d), 8.75 (1H, br s), 9.13 (1H, br s), 9.60 (1H, br s).

Example 3

3-((4-((4-(3-(3-(tert-Butyl)-1-(p-tolyl)-1H-pyrazol-5-yl)ureido)naphthalen-1-yl)oxy)pyrimidin-2-yl)amino)-N-(2-morpholinoethyl)benzamide

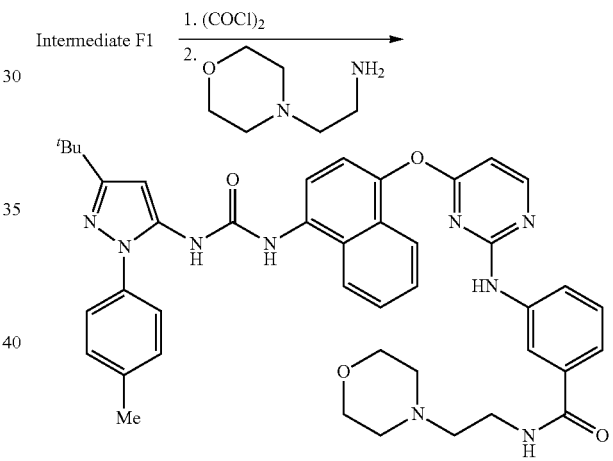

Example 3

To a suspension of Intermediate F1 (680 mg, 1.08 mmol) in DCM (10 mL) at 0° C. was added oxalyl chloride (110 μL, 1.30 mmol) and DMF (1 drop) and the resulting red mixture maintained at 0° C. for 20 min and then warmed to RT. After 1 hr a second aliquot of oxalyl chloride (110 μL, 1.30 mmol) was added and the resulting mixture kept at RT for 2 hr and then evaporated in vacuo to afford a red solid (800 mg). This material was used in the subsequent amide coupling without purification or characterization. To a suspension of a portion of the solid obtained above (60 mg, 0.080 mmol) in DCM (1.5 mL) was added DIPEA (32 μL, 0.19 mmol) and 2-morpholinoethanamine (13 μL, 0.10 mmol) and the reaction mixture maintained at RT for 3 hr. The resulting mixture was washed sequentially with saturated aq. NaHCO$_3$ (5.0 mL), water (5.0 mL) and with brine (5.0 mL) and then purified directly by flash column chromatography (SiO$_2$, 12 g, MeOH in EtOAc, 0-100%, gradient elution) to afford the title compound, Example 3, as a pale yellow solid (35 mg, 50%); R$^t$ 1.82 min (Method 2 acidic); m/z 740 (M+H)$^+$ (ES$^+$); $^1$H NMR δ: 1.29 (9H, s), 2.36-2.45 (9H, over-lapping m), 3.32 (2H, m), 3.54-3.56 (4H, over-lapping m), 6.42 (1H, s), 6.56 (1H, d), 7.01 (1H, m), 7.24 (1H, d), 7.35-7.50 (6H, over-lapping m), 7.53-7.65 (2H, over-lapping m), 7.81 (1H, d), 7.87 (1H, br s), 7.92 (1H, d), 8.07 (1H, d), 8.18 (1H, m), 8.40 (1H, d), 8.75 (1H, br s), 9.13 (1H, br s), 9.62 (1H, br s).

Example 4

4-((4-((4-(3-(3-(tert-Butyl)-1-(p-tolyl)-1H-pyrazol-5-yl)ureido)naphthalen-1-yl)oxy)pyrimidin-2-yl)amino)-N-(2-hydroxyethyl)-3-methoxybenzamide

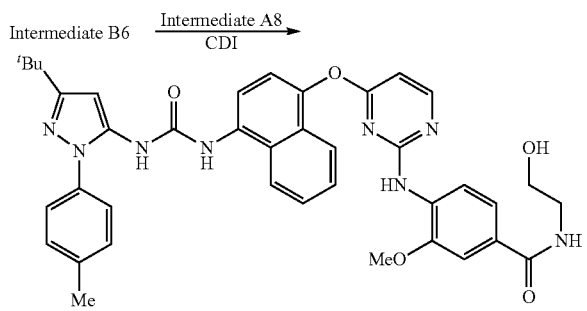

Example 4

To a solution of CDI (55 mg, 0.34 mmol) in DCM (1.0 mL) was added Intermediate A8 (77 mg, 0.34 mmol) and the reaction mixture maintained at RT for 3 hr. An aliquot of this solution (0.80 mL, 0.27 mmol) was added to a solution of Intermediate B6 (50 mg, 0.11 mmol) in THF (1.0 mL) at RT and the mixture kept at this temperature for 18 hr and then quenched by the addition of MeOH (2.0 mL). The volatiles were evaporated in vacuo and the residue was purified by flash column chromatography (SiO$_2$, 12 g [0.7 M NH$_3$ in MeOH] in DCM, 0-10%, gradient elution) to afford the title compound, Example 4, as a pale pink solid (28 mg, 34%); R$^t$ 3.83 min (Method 3); m/z 701 (M+H)$^+$ (ES$^+$); $^1$H NMR δ: 1.29 (9H, s), 2.40 (3H, s), 3.27 (2H, m), 3.47 (2H, m), 3.84 (3H, s), 4.70 (1H, m), 6.45 (1H, s), 6.63 (1H, d), 7.14 (1H, m), 7.38-7.43 (4H, over-lapping m), 7.48 (2H, m), 7.54-7.66 (3H, over-lapping m), 7.82 (1H, m), 7.96-7.98 (2H, over-lapping m), 8.09 (1H, d), 8.25 (1H, m), 8.43 (1H, d), 8.81 (1H, s), 9.17 (1H, s).

Example 5

N-(2-(Dimethylamino)ethyl)-3-((4-((4-(3-(3-isopropyl-1-(p-tolyl)-1H-pyrazol-5-yl)ureido)naphthalen-1-yl)oxy)pyrimidin-2-yl)amino)-5-methoxybenzamide

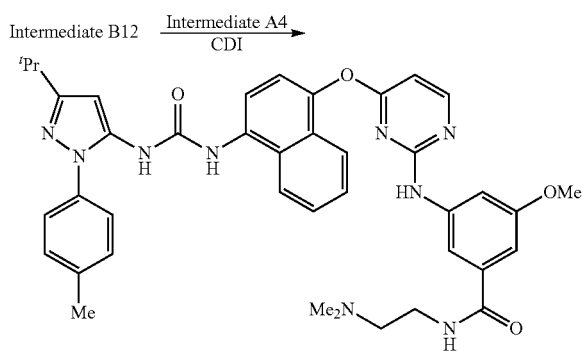

Example 5

To a solution of CDI (380 mg, 2.30 mmol) in DCM (5.0 mL) was added Intermediate A4 (0.50 g, 2.3 mmol) and the reaction mixture kept at RT for 3 hr. An aliquot of the resulting solution (1.0 mL, 0.46 mmol) was added to a solution of Intermediate B12 (50 mg, 0.11 mmol) in THF (2.0 mL) at RT and after 18 hr the reaction mixture was quenched by the addition of MeOH (3.0 mL). The mixture was evaporated in vacuo and the residue was purified by flash column chromatography (SiO$_2$, 12 g [0.7 M NH$_3$ in MeOH] in DCM, 3-5%, gradient elution) to afford the title compound, Example 5, as a pale pink solid (60 mg, 76%); R$^t$ 1.91 min (Method 2, acidic); m/z 714 (M+H)$^+$ (ES$^+$); $^1$H NMR δ: 1.24 (6H, d), 2.16 (6H, s), 2.35 (2H, t), 2.40 (3H, s), 2.88 (1H, m), 3.30 (2H, m), 3.57 (3H, s), 6.37 (1H, s), 6.53 (1H, d), 6.86 (1H, br s), 7.33 (1H, br s), 7.37-7.40 (3H, over-lapping m), 7.47 (2H, d), 7.56-7.63 (3H, over-lapping m), 7.82 (1H, d), 7.93 (1H, d), 8.05 (1H, d), 8.16 (1H, t), 8.41 (1H, d), 8.78 (1H, br s), 9.09 (1H, br s), 9.59 (1H, br s).

Example 6

N-(2-(Dimethylamino)ethyl)-3-((4-((4-(3-(3-isopropyl-1-(4-methoxyphenyl)-1H-pyrazol-5-yl)ureido)naphthalen-1-yl)oxy)pyrimidin-2-yl)amino)-5-methoxy benzamide

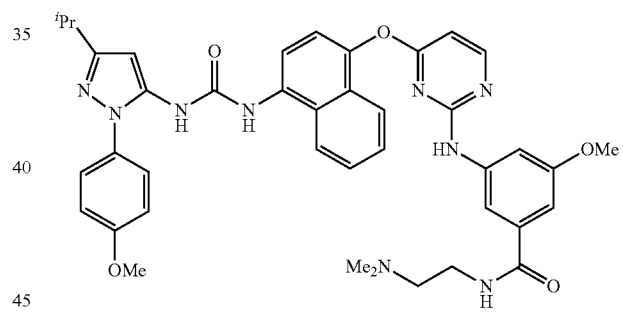

Example 6

To a solution of CDI (43 mg, 0.26 mmol) in DCM (2.0 mL) at RT was added Intermediate A5 (61 mg, 0.26 mmol) and the mixture maintained at this temperature for 18 hr. The resulting solution was added to a solution of Intermediate B12 (50 mg, 0.11 mmol) in THF (2.0 mL) at RT and after 24 hr the reaction mixture was quenched by the addition of MeOH (3.0 mL) The volatiles were evaporated in vacuo and the residue was purified by preparative HPLC to afford a formate salt of the title compound, Example 6, as a white solid (31 mg, 38%); 1.78 min (Method 2 acidic); m/z 367 (M+2H)$^{2+}$ (ES$^+$); $^1$H NMR δ: 1.24 (6H, d), 2.21 (6H, s), 2.44 (2H, t), 2.89 (1H, m), 3.32 (2H, m), 3.56 (3H, s), 3.83 (3H, s), 6.35 (1H, s), 6.53 (1H, d), 6.86 (1H, br s), 7.10 (2H, m), 7.33 (1H, br s), 7.39 (1H, d), 7.48 (2H, m), 7.56-7.62 (3H, over-lapping m), 7.82 (1H, d), 7.92 (1H, d), 8.06 (1H, d), 8.19 (1H, m), 8.41 (1H, d), 8.82 (1H, br s), 9.16 (1H, br s), 9.59 (1H, br s).

Example 7

3-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)-5-(trifluoromethyl)benzamide

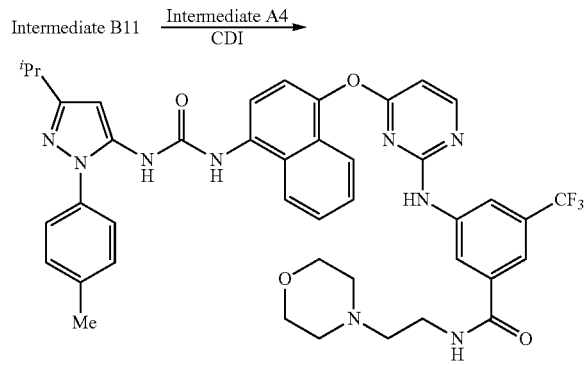

Example 7

To a solution of CDI (380 mg, 2.30 mmol) in DCM (5.0 mL) was added Intermediate A4 (500 mg, 2.32 mmol) and the reaction mixture kept at RT for 3 hr. An aliquot of the resulting solution (0.80 mL, 0.37 mmol) was added to a solution of Intermediate B11 (100 mg, 0.181 mmol) in THF (1.5 mL) at RT and after 24 hr the reaction mixture was quenched by the addition of MeOH (2.0 mL). The volatiles were evaporated in vacuo and the residue was purified by flash column chromatography (SiO$_2$, 12 g, [0.7 M NH$_3$ in MeOH] in DCM, 0-5%, gradient elution) to afford the title compound, Example 7, as a pale pink solid (52 mg, 34%); R$^t$ 3.03 min (Method 3); m/z 794 (M+H)$^+$ (ES$^+$), m/z 792 (M−H)$^−$ (ES$^−$); $^1$H NMR δ: 1.24 (6H, d), 2.44-2.47 (9H, over-lapping m), 2.89 (1H, m), 3.37 (2H, m), 3.55-3.57 (4H, over-lapping m), 6.36 (1H, s), 6.63 (1H, d), 7.36-7.42 (3H, over-lapping m), 7.46 (2H, m), 7.57 (1H, m), 7.60-7.64 (2H, over-lapping m), 7.82 (1H, m), 7.93 (1H, d), 8.06 (1H, m), 8.11 (1H, br s), 8.28 (1H, br s), 8.47 (1H, m), 8.51 (1H, m), 8.78 (1H, s), 9.09 (1H, s), 9.97 (1H, s).

Example 8

3-((4-((4-(3-(3-Isopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide (Route A)

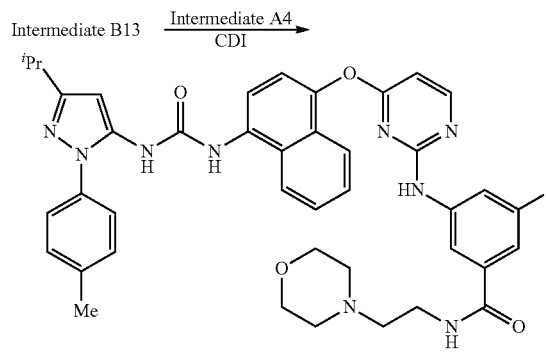

Example 8

To a solution of CDI (12.3 g, 76.0 mmol) in DCM (150 mL) was added Intermediate A4 (15.0 g, 69.0 mmol) portion-wise and the resulting mixture kept at RT for 5 hr. An aliquot of this solution (60 mL, 28 mmol) was added to a solution of Intermediate B13 (13.4 g, 22.0 mmol) in DCM (150 mL) at RT. After 2 hr an second aliquot of the CDI adduct (9.0 mL, 4.1 mmol) was added and the resulting mixture was maintained at RT for 17 hr and was then partitioned between DCM (200 mL) and sat. aq. NaHCO$_3$ (200 mL). The aq phase was separated and was extracted with DCM (2×200 mL) and the combined organic extracts were washed with aq. NaOH (2.0 M, 2×200 mL) and then with brine (2×200 mL). The aq. NaHCO$_3$ and NaOH washings were combined and the suspended solids were isolated by filtration. The aq filtrate was extracted with DCM (2×200 mL) and with 2-Me THF (2×200 mL). All of the organic extracts were combined and then dried and concentrated in vacuo. The residue was combined with the solid isolated from the filtration of the aq washings and this material was purified by flash column chromatography (SiO$_2$, 330 g, [0.7 M NH$_3$ in MeOH] in EtOAc, 5-10%, gradient elution). The crude product so obtained was stirred in IPA (200 mL) for 16 hr and then isolated by filtration to provide the title compound, Example 8, as a pale brown solid (8.83 g, 52%); R$^t$ 2.30 min (Method 2 basic); m/z 756 (M+H)$^+$ (ES$^+$); $^1$H NMR δ: 1.24 (6H, d), 2.38-2.44 (9H, overlapping m), 2.90 (1H, m), 3.31-3.36 (2H, overlapping m), 3.54-3.56 (7H, overlapping m), 6.37 (1H, s), 6.53 (1H, d), 6.85 (1H, m), 7.31 (1H, br. s), 7.36-7.41 (3H, overlapping m), 7.45-7.47 (2H, overlapping m), 7.54-7.64 (3H, overlapping m), 7.82 (1H, m), 7.94 (1H, d), 8.06 (1H, d), 8.19 (1H, m), 8.40 (1H, d), 8.79 (1H, s), 9.10 (1H, s).

(Route B)

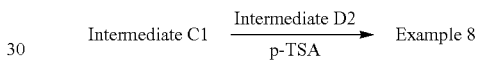

A suspension of Intermediate C1 (150 mg, 0.292 mmol) and Intermediate D2 (163 mg, 0.585 mmol) in DMF (1.5 mL) was added p-TSA.H2O (111 mg, 0.555 mmol) and the reaction mixture heated to 70° C. for 3 hr and then cooled to RT and poured onto sat. aq. NaHCO$_3$ (20 mL). The precipitate so formed was collected by filtration and was washed with water (2×10 mL) and with Et$_2$O (20 mL) and then dried in vacuo at 50° C. for 3 hr. The resulting solid was suspended in MeOH (10 mL) with stirring for 5 hr and then collected by filtration, washed with MeOH (2×5 mL) and with Et$_2$O (2×10 mL) and dried to afford the title compound, Example 8, as a pale pink solid (88 mg, 40%); R$^t$ 1.81 min (Method 4); m/z 378.5 (M+2H)$^{2+}$ (ES$^+$).

Example 9

3-Methoxy-N-(2-morpholinoethyl)-5-((4-((4-(3-(3-(perfluoroethyl)-1-(p-tolyl)-1H-pyrazol-5-yl)ureido)naphthalen-1-yl)oxy)pyrimidin-2-yl)amino)benzamide

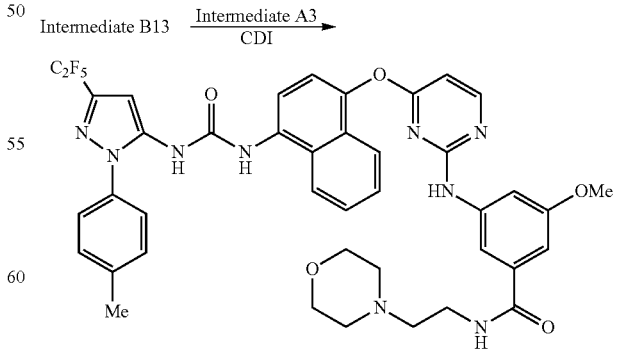

Example 9

To a solution of CDI (56 mg, 0.34 mmol) in DCM (0.6 mL) was added drop-wise a solution of Intermediate A3

(100 mg, 0.34 mmol) in DCM (0.6 mL) and the mixture was maintained at RT for 18 hr. The resulting solution was added to a solution of Intermediate B13 (124 mg, 0.240 mmol) in THF (0.5 mL) and the reaction mixture was kept at RT for 3 hr and was then quenched by the addition of MeOH (2.0 mL) The volatiles were evaporated in vacuo and the residue was purified by preparative HPLC. The formate salt so obtained was partitioned between DCM and saturated aq. NaHCO$_3$. and the organic phase was separated, dried and evaporated in vacuo. The residue was purified by flash column chromatography (SiO$_2$, 12 g, [0.7 M NH$_3$ in MeOH] in DCM, 0.5-6%, gradient elution) to afford the title compound, Example 9, as an off white solid (37 mg, 12%); R$^t$ 3.14 min (Method 3); m/z 832 (M+H)$^+$ (ES$^+$); $^1$H NMR δ: 2.36-2.46 (9H, over-lapping m), 3.33 (2H, m), 3.54-3.57 (7H, over-lapping m), 6.54 (1H, d), 6.85 (1H, s), 6.93 (1H, s), 7.31 (1H, s), 7.42 (1H, d), 7.47 (2H, d), 7.54-7.59 (4H, over-lapping m), 7.63 (1H, dd), 7.83 (1H, d), 7.93 (1H, d), 8.05 (1H, d), 8.17 (1H, t), 8.40 (1H, d), 9.12 (1H, s), 9.23 (1H, s), 9.59 (1H, s).

Example 10

3-((4-((4-(3-(3-Isopropyl-1-(6-methoxypyridin-3-yl)-1H-pyrazol-5-yl)ureido) naphthalen-1-yl)oxy)pyrimidin-2-yl)amino)-5-methoxy-N-(2-morpholinoethyl)benzamide

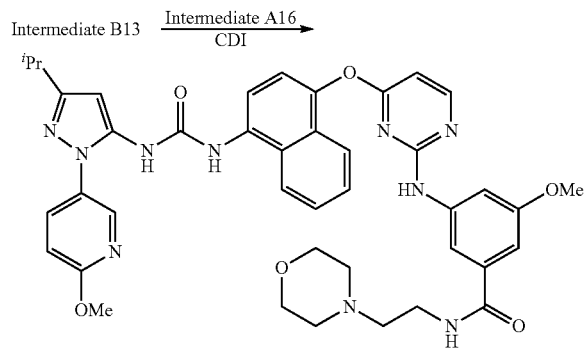

Example 10

To a solution of CDI (59 mg, 0.37 mmol) in DCM (0.4 mL) was added drop-wise a solution of Intermediate A16 (85 mg, 0.34 mmol) in DCM (0.6 mL) and the reaction mixture maintained at RT for 5 hr. The resulting solution was added to a solution of Intermediate B13 (47 mg, 0.092 mmol) in THF (0.3 mL) at RT and the reaction mixture was maintained at RT for 1.5 hr and then quenched by the addition of MeOH (1.5 mL). The volatiles were evaporated in vacuo and the residue was purified by flash column chromatography (SiO$_2$, 12 g, [0.7 M NH$_3$ in MeOH] in DCM, 0-10%, gradient elution). The impure material so obtained was purified by preparative HPLC to afford the title compound, Example 10, as an off white solid (18 mg, 6%); R$^t$ 2.68 min (Method 3); m/z 773 (M+H)$^+$ (ES$^+$); $^1$H NMR δ: 1.24 (6H, d), 2.36-2.45 (6H, over-lapping m), 2.90 (1H, sept), 3.32 (2H, m), 3.53-3.57 (7H, over-lapping m), 3.94 (3H, s), 6.39 (1H, s), 6.54 (1H, d), 6.85 (1H, s), 7.03 (1H, d), 7.32 (1H, s), 7.40 (1H, d), 7.53-7.58 (2H, over-lapping m), 7.62 (1H, dd), 7.82 (1H, d), 7.90-7.93 (2H, over-lapping d), 8.05 (1H, d), 8.21 (1H, t), 8.39-8.41 (2H, over-lapping m), 8.85 (1H, s), 9.08 (1H, s), 9.61 (1H, s).

Example 11

3-((4-((4-(3-(3-Isopropyl-1-(4-methoxyphenyl)-1H-pyrazol-5-yl)ureido) naphthalen-1-yl)oxy)pyrimidin-2-yl)amino)-5-methoxy-N-(2-methoxyethyl)benzamide

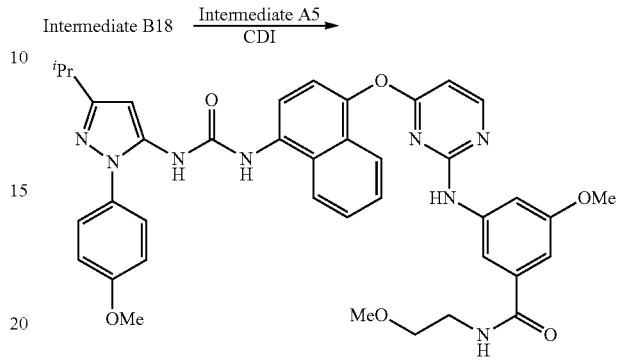

Example 11

To a solution of CDI (88 mg, 0.54 mmol) in DCM (1.0 mL) was added Intermediate A5 (126 mg, 0.540 mmol) and the reaction mixture kept at RT for 18 hr. The resulting solution was added to a solution of Intermediate B18 (50 mg, 0.11 mmol) in THF (1.0 mL) at RT and the mixture was maintained at RT for 5 hr was then quenched by the addition of MeOH (3.0 mL). After evaporation of the volatiles in vacuo the residue was purified by preparative HPLC to afford the formate salt of the title compound, Example 11, as an off white solid (5.0 mg, 6%); R$^t$ 2.22 min (Method 2 acidic); m/z 717 (M+H)$^+$ (ES$^+$); $^1$H NMR δ: 1.24 (6H, d), 2.89 (1H, m), 3.25 (3H, s), 3.38-3.42 (4H, over-lapping m), 3.57 (3H, s), 3.83 (3H, s), 6.34 (1H, s), 6.53 (1H, d), 6.88 (1H, t), 7.10 (2H, m), 7.33 (1H, br s), 7.40 (1H, d), 7.49 (2H, m), 7.55-7.61 (3H, over-lapping m), 7.81 (1H, d), 7.92 (1H, d), 8.07 (1H, d), 8.30 (1H, t), 8.39 (1H, d), 8.47 8.93 (1H, br s), 9.25 (1H, br s), 9.59 (1H, br s).

Example 12

1-(3-Isopropyl-1-(p-tolyl)-1H-pyrazol-5-yl)-3-(4-((2-((3-methoxy-5-(morpholine-4-carbonyl)phenyl)amino)pyrimidin-4-yl)oxy)naphthalen-1-yl)urea

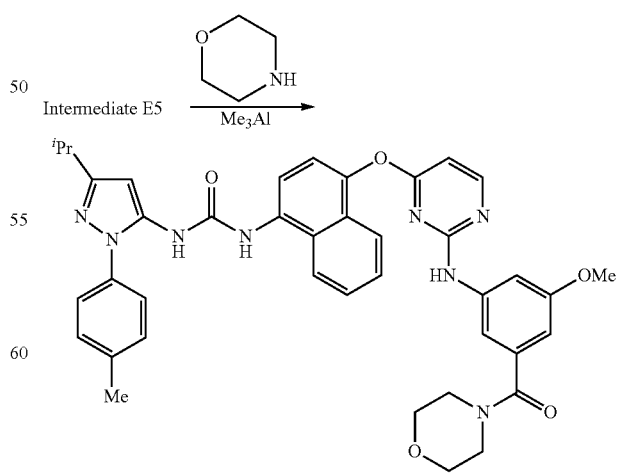

Example 12

To a solution of morpholine (13 μL, 0.15 mmol) in THF (3.0 mL) was added a solution of trimethylaluminium at RT (2M in hexane, 76 μL, 0.15 mmol) and reaction mixture kept at RT for 20 min. The resulting mixture was added to a solution of Intermediate E5, (50 mg, 0.076 mmol), in THF (3.0 mL) and the mixture was maintained at RT for 3 days. A second aliquot of the morpholine-trimethylaluminium adduct was prepared in an identical manner on half the original scale and was added to the reaction mixture. After 18 hr at RT the mixture was heated to 40° C. for 24 hr, then cooled to RT and was diluted with hydrochloric acid (1.0 M, 6.0 mL). The mixture was partitioned between EtOAc (20 mL) and water (20 mL) and the organic phase was separated and then dried and evaporated in vacuo to furnish the title compound, Example 12, as an off white solid (33 mg, 60%); $R^t$ 2.38 min (Method 2, acidic); m/z 713 (M+H)$^+$ (ES$^+$); $^1$H NMR δ: 1.24 (6H, d), 2.40 (3H, s), 2.90 (1H, m), 3.30 (2H, m), 3.55-3.58 (9H, over-lapping m), 6.37 (1H, s), 6.43 (1H, br s), 6.57 (1H, d), 7.16 (1H, br s), 7.25 (1H, br s), 7.36-7.40 (3H, over-lapping m), 7.46 (2H, m), 7.56-7.62 (2H, over-lapping m), 7.81 (1H, d), 7.93 (1H, d), 8.06 (1H, d), 8.42 (1H, d), 8.80 (1H, br s), 9.09 (1H, br s), 9.61 (1H, br s).

Example 13

5-((4-((4-(3-(3-(tert-Butyl)-1-(p-tolyl)-1H-pyrazol-5-yl)ureido)naphthalen-1-yl)oxy)pyrimidin-2-yl) amino)-2-methoxy-N-(2-morpholinoethyl)benzamide

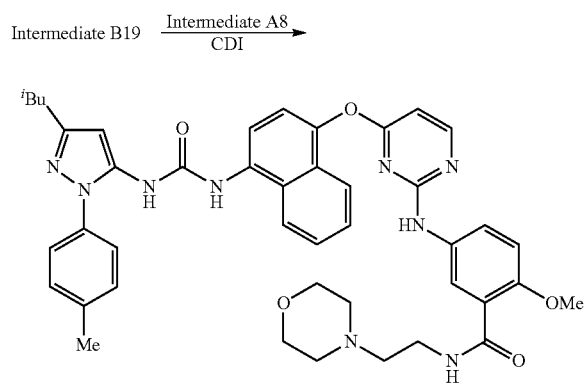

Example 13

To a solution of CDI (44 mg, 0.27 mmol) in DCM (1.0 mL) was added Intermediate A8 (62 mg, 0.27 mmol) and the resulting mixture maintained at RT for 4 days. An aliquot of this solution (0.50 mL, 0.14 mmol) was added to a solution of Intermediate B19 (50 mg, 0.089 mmol) in THF (1.0 mL) at RT and the reaction mixture was kept at RT for 3 days and was then quenched by the addition of MeOH (1.0 mL). The volatiles were evaporated in vacuo and the residue was purified by flash column chromatography (SiO$_2$, 12 g, [0.7 M NH$_3$ in MeOH] in DCM, 0-5%, gradient elution) to afford the title compound, Example 13, as a pale orange solid (41 mg, 57%); $R^t$ 2.98 min (Method 3); m/z 770 (M+H)* (ES$^+$); $^1$H NMR δ: 1.29 (9H, s), 2.40-2.45 (9H, over-lapping m), 3.36 (2H, m), 3.57-3.59 (4H, over-lapping m), 3.80 (3H, s), 6.40 (1H, s), 6.56 (1H, d), 6.79 (1H, m), 7.38-7.43 (4H, over-lapping m), 7.47 (2H, m), 7.53-7.63 (2H, over-lapping m), 7.81 (2H, m), 7.90 (1H, d), 8.06 (1H, d), 8.30 (1H, m), 8.35 (1H, d), 8.78 (1H, s), 9.14 (1H, s), 9.51 (1H, s).

Example 14

3-((6-((4-(3-(3-isopropyl-1-(4-methoxyphenyl)-1H-pyrazol-5-yl)ureido) naphthalen-1-yl)oxy)pyrimidin-4-yl)amino)-5-methoxy-N-(2-morpholinoethyl)benzamide

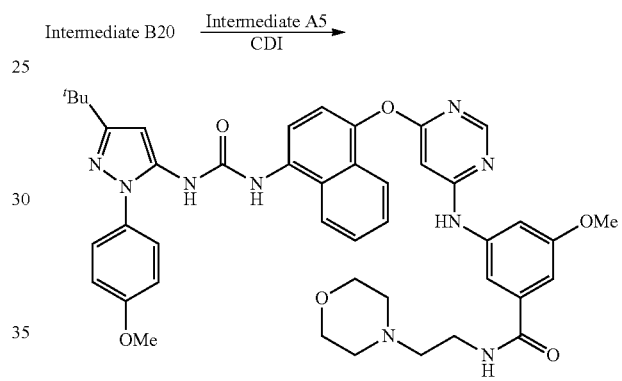

Example 14

To a solution of CDI (44 mg, 0.27 mmol) in DCM (1.0 mL) was added Intermediate A5 (60 mg, 0.26 mmol) and the reaction mixture kept at 40° C. for 4 hr. An aliquot of the resulting solution (0.42 mL, 0.11 mmol) was added to a solution of Intermediate B20 (50 mg, 0.089 mmol) in THF (1.0 mL) at RT and the mixture maintained at RT for 18 hr and then partitioned between EtOAc (50 mL) and saturated aq NaHCO$_3$ (50 mL). The organic phase was separated and was washed sequentially with saturated aq NaHCO$_3$ (2×50 mL), water (2×50 mL) and brine (2×50 mL) and then dried and evaporated in vacuo. The residue was purified by flash column chromatography (SiO$_2$, 12 g, [0.7 M NH$_3$ in MeOH] in DCM, 0-10%, gradient elution) to afford the title compound, Example 14, as a pale orange solid (52 mg, 67%); $R^t$ 1.68 min (Method 4); m/z 772 (M+H)$^+$ (ES$^+$); m/z 770 (M−H)$^−$ (ES$^−$); $^1$H NMR δ: 1.24 (6H, d), 2.38-2.47 (6H, over-lapping m), 2.89 (1H, m), 3.36 (2H, m), 3.55-3.57 (4H, over-lapping m), 3.77 (3H, s), 3.84 (3H, s), 6.16 (1H, s), 6.35 (1H, s), 7.02 (1H, m), 7.12 (2H, m), 7.35 (1H, d), 7.46-7.51 (3H, over-lapping m), 7.53-7.66 (3H, over-lapping m), 7.79 (1H, d), 7.92 (1H, d), 8.05 (1H, d), 8.30-8.35 (2H, over-lapping m), 8.72 (1H, br s), 9.09 (1H, br s), 9.67 (1H, br s).

Examples 15 to 72

TABLE 3

Additional Compound Examples of the Invention

| Structure, Name and Example No. | Analytical Data [Generic Route] |
|---|---|
| 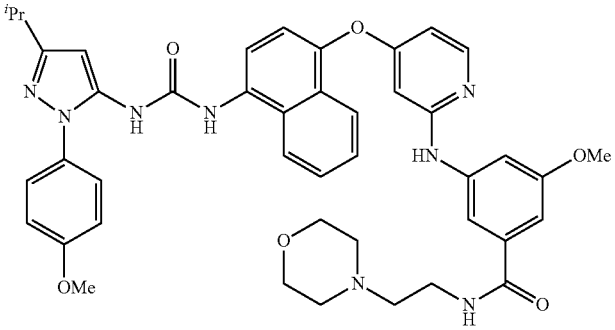 [SMILES: COc1ccc(-n2nc(C(C)C)cc2NC(=O)Nc2ccc(Oc3ccnc(Nc4cc(OC)cc(C(=O)NCCN5CCOCC5)c4)c3)c3ccccc23)cc1]<br>15: 3-((4-((4-(3-(3-isopropyl-1-(4-methoxyphenyl)-1H-pyrazol-5-yl)ureido)naphthalen-1-yl)oxy)pyridin-2-yl)amino)-5-methoxy-N-(2-morpholinoethyl)benzamide. | $R^t$ 2.39 min (Method 3); m/z 771 (M + H)$^+$ (ES$^+$); m/z 769 (M − H)$^−$ (ES); $^1$H NMR δ: 1.24 (6H, d), 2.37-2.45 (6H, over-lapping m), 2.89 (1H, m), 3.25-3.45 (2H, m, partially obscured by H$_2$O peak), 3.55-3.57 (4H, over-lapping m), 3.73 (3H, s), 3.83 (3H, s), 6.10 (1H, d), 6.34 (1H, s), 6.57 (1H, dd), 6.85 (1H, s), 7.09-7.13 (2H, over-lapping m), 7.36 (1H, d), 7.47-7.51 (3H, over-lapping m), 7.54-7.66 (3H, over-lapping m), 7.83 (1H, d), 7.95 (1H, d), 8.10 (2H, d), 8.24 (1H, t), 8.93 (1H, br s), 9.07 (1H, br s), 9.28 (1H, br s). |
| 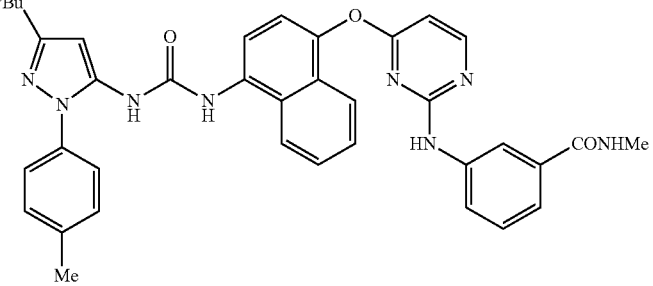<br>16: 3-((4-((4-(3-(3-(tert-butyl)-1-(p-tolyl)-1H-pyrazol-5-yl)ureido)naphthalen-1-yl)oxy)pyrimidin-2-yl)amino)-N-methylbenzamide. | $R^t$ 2.38 min (Method 2, acidic); m/z 641 (M + H)$^+$ (ES$^+$); $^1$H NMR δ: 1.29 (9H, s), 2.40 (3H, s), 2.74 (3H, d), 6.41 (1H, s), 6.56 (1H, d), 7.01 (1H, m), 7.23 (1H, d), 7.35-7.50 (6H, over-lapping m), 7.53-7.65 (2H, over-lapping m), 7.81 (1H, d), 7.87 (1H, br s), 7.92 (1H, d), 8.07 (1H, d), 8.22 (1H, m), 8.40 (1H, d), 8.75 (1H, br s), 9.12 (1H, br s), 9.61 (1H, br s). |
| 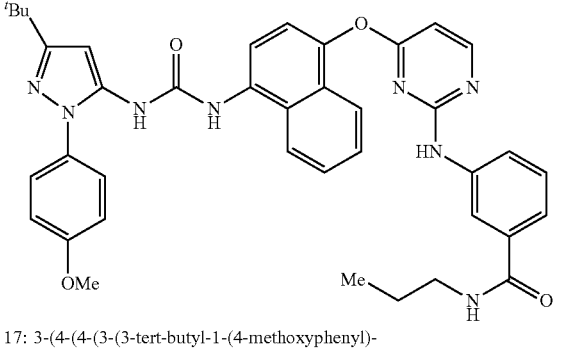<br>17: 3-(4-(4-(3-(3-tert-butyl-1-(4-methoxyphenyl)-1H-pyrazol-5-yl)ureido)naphthalen-1-yloxy)pyrimidin-2-ylamino)-N-propylbenzamide. | $R^t$ 2.46 min (Method 2, acidic); m/z 685 (M + H)$^+$ (ES$^+$); $^1$H NMR δ: 0.86 (3H, t), 1.29 (9H, s), 1.49 (2H, m), 3.17 (2H, m), 3.84 (3H, s), 6.40 (1H, s), 6.55 (1H, d), 7.01 (1H, m), 7.13 (2H, m), 7.25 (1H, d), 7.41 (1H, d), 7.46-7.49 (3H, over-lapping m), 7.56 (1H, m), 7.62 (1H, m), 7.82 (1H, d), 7.87 (1H, br s), 7.93 (1H, d), 8.06 (1H, d), 8.24 (1H, t), 8.40 (1H, d), 8.70 (1H, s), 9.11 (1H, s), 9.60 (1H, s). |
| 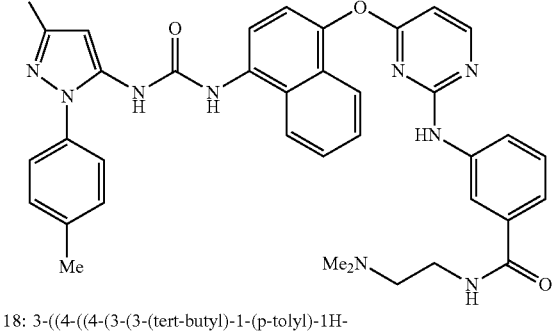<br>18: 3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)benzamide. | $R^t$ 1.84 min (Method 2, acidic); m/z 698 (M + H)$^+$ (ES$^+$); $^1$H NMR δ: 1.29 (9H, s), 2.15 (6H, s), 2.35 (2H, t), 2.39 (3H, s), 3.29 (2H, m), 6.41 (1H, s), 6.55 (1H, d), 7.01 (1H, m), 7.24 (1H, d), 7.37-7.40 (3H, over-lapping m), 7.47-7.48 (3H, over-lapping m), 7.56 (1H, m), 7.62 (1H, m), 7.81 (1H, d), 7.88 (1H, s), 7.91 (1H, d), 8.08 (1H, d), 8.14 (1H, m), 8.40 (1H, d), 8.84 (1H, s), 9.20 (1H, s), 9.61 (1H, s). |

TABLE 3-continued

Additional Compound Examples of the Invention

| Structure, Name and Example No. | Analytical Data [Generic Route] |
|---|---|
| 19: 3-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide. | $R^t$ 1.80 min (Method 2 acidic); m/z 726 (M + H)$^+$ (ES$^+$), 724 (M − H)$^−$ (ES$^−$); $^1$H NMR δ: 1.24 (6H, d), 2.32-2.47 (9H, over-lapping m), 2.89 (1H, m), 3.35 (2H, m), 3.51-3.59 (4H, over-lapping m), 6.37 (1H, s), 6.56 (1H, d), 7.03 (1H, m), 7.24 (1H, d), 7.36-7.42 (3H, over-lapping m), 7.45-7.49 (3H, over-lapping m), 7.56 (1H, m), 7.62 (1H, m), 7.81 (1H, m), 7.88 (1H, br s), 7.92 (1H, d), 8.07 (1H, d), 8.18 (1H, br s), 8.40 (1H, d), 8.78 (1H, s), 9.13 (1H, s), 9.62 (1H, s). |
| 20: 3-((4-((4-(3-(3-isopropyl-1-(4-methoxyphenyl)-1H-pyrazol-5-yl)ureido)naphthalen-1-yl)oxy)pyrimidin-2-yl)amino)-N-(2-morpholinoethyl)benzamide. | $R^t$ 2.71 min (Method 3); m/z 742 (M + H)$^+$ (ES$^+$); $^1$H NMR δ: 1.24 (6H, d), 2.37-2.44 (6H, over-lapping m), 2.89 (1H, m), 3.33 (2H, m), 3.53-3.57 (4H, m), 3.84 (3H, s), 6.36 (1H, s), 6.55 (1H, d), 7.03 (1H, t), 7.13 (2H, d), 7.24 (1H, d), 7.40 (1H, d), 7.45-7.51 (3H, over-lapping m), 7.56 (1H, dd), 7.62 (1H, dd), 7.81 (1H, d), 7.87 (1H, br s), 7.92 (1H, d), 8.06 (1H, d), 8.17 (1H, m), 8.40 (1H, d), 8.71 (1H, s), 9.11 (1H, s), 9.62 (1H, s). |
| 21: 3-((4-((4-(3-(3-(tert-butyl)-1-(4-methoxyphenyl)-1H-pyrazol-5-yl)ureido)naphthalen-1-yl)oxy)pyrimidin-2-yl)amino)-N-(2-morpholinoethyl)benzamide. | $R^t$ 1.81 min (Method 4); m/z 756 (M + H)$^+$ (ES$^+$); m/z 754 (M − H)$^−$ (ES$^−$); $^1$H NMR δ: 1.29 (9H, s), 2.36-2.45 (6H, over-lapping m), 3.32 (2H, m), 3.55 (4H, m), 3.83 (3H, s), 6.39 (1H, s), 6.56 (1H, d), 7.02 (1H, m), 7.11 (2H, m), 7.24 (1H, d), 7.40 (1H, d), 7.44-7.64 (5H, over-lapping m), 7.81 (1H, m), 7.88 (1H, br s), 7.91 (1H, d), 8.08 (1H, d), 8.18 (1H, m), 8.40 (1H, d), 8.89 (1H, s), 9.27 (1H, s), 9.62 (1H, s). [Compound isolated by preparative HPLC and characterised as its formic acid salt.] |
| 22: 3-((4-((4-(3-(3-(3-methyloxetan-3-yl)-1-(p-tolyl)-1H-pyrazol-5-yl)ureido)naphthalen-1-yl)oxy)pyrimidin-2-yl)amino)-N-(2-morpholinoethyl)benzamide. | $R^t$ 2.60 min (Method 3); m/z 754 (M + H)$^+$ (ES$^+$); $^1$H NMR δ: 1.67 (3H, s), 2.37-2.45 (9H, over-lapping m), 3.34 (2H, m), 3.54-3.56 (4H, over-lapping m), 4.48 (2H, d), 4.86 (2H, d), 6.55 (1H, s), 6.56 (1H, d), 7.03 (1H, t), 7.24 (1H, d), 7.39-7.42 (3H, over-lapping m), 7.47 (1H, d), 7.51 (2H, d), 7.56 (1H, dd), 7.62 (1H, dd), 7.81 (1H, d), 7.87 (1H, s), 7.92 (1H, d), 8.06 (1H, d), 8.17 (1H, t), 8.39 (1H, d), 8.84 (1H, s), 9.15 (1H, s), 9.62 (1H, s). |

TABLE 3-continued

Additional Compound Examples of the Invention

| Structure, Name and Example No. | Analytical Data [Generic Route] |
|---|---|
| 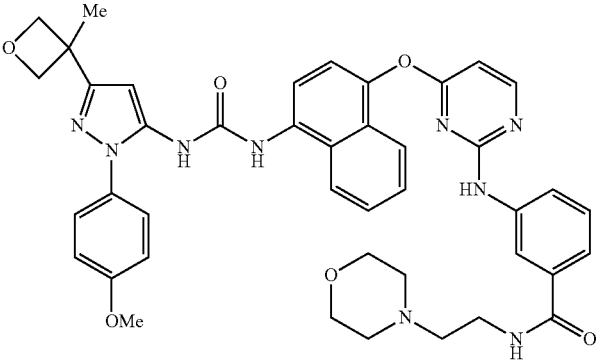 [SMILES: COc1ccc(-n2nc(C3(C)COC3)cc2NC(=O)Nc2ccc(Oc3ccnc(Nc4cccc(C(=O)NCCN5CCOCC5)c4)n3)c3ccccc23)cc1]<br>23: 3-((4-((4-(3-(1-(4-methoxyphenyl)-3-(3-methyl oxetan-3-yl)-1H-pyrazol-5-yl)ureido)naphthalen-1-yl)oxy)pyrimidin-2-yl)amino)-N-(2-morpholinoethyl)benzamide. | $R^r$ 2.52 min (Method 3); m/z 770 (M + H)$^+$ (ES$^+$); $^1$H NMR δ: 1.67 (3H, s), 2.36-2.45 (6H, over-lapping m), 3.33 (2H, m), 3.54-3.56 (4H, over-lapping m), 3.85 (3H, s), 4.47 (2H, d), 4.85 (2H, d), 6.54 (1H, s), 6.55 (1H, d), 7.02 (1H, t), 7.14 (2H, m), 7.24 (1H, d), 7.41 (1H, d), 7.47 (1H, d), 7.51-7.58 (3H, over-lapping m), 7.62 (1H, dd), 7.81 (1H, d), 7.87 (1H, br s), 7.92 (1H, d), 8.06 (1H, d), 8.17 (1H, t), 8.39 (1H, d), 8.79 (1H, s), 9.14 (1H, s), 9.62 (1H, s). |
| 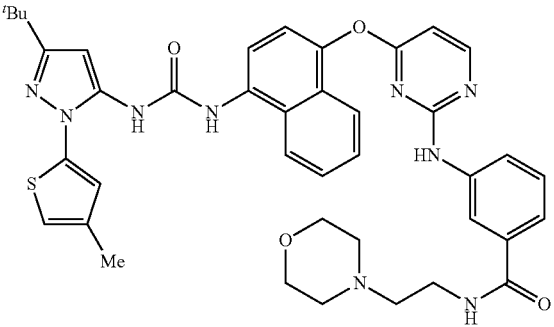 [SMILES: Cc1csc(-n2nc(C(C)(C)C)cc2NC(=O)Nc2ccc(Oc3ccnc(Nc4cccc(C(=O)NCCN5CCOCC5)c4)n3)c3ccccc23)c1]<br>24: 3-((4-((4-(3-(3-(tert-butyl)-1-(4-methylthio phen-2-yl)-1H-pyrazol-5-yl)ureido)naphthalen-1-yl)oxy)pyrimidin-2-yl)amino)-N-(2-morpholinoethyl)benzamide. | $R^r$ 1.98 min (Method 2, acidic); m/z 746 (M + H)$^+$ (ES$^+$); $^1$H NMR δ: 1.27 (9H, s), 2.27 (3H, d), 2.40 (6H, br s), 3.35 (2H, m), 3.56 (4H, br s), 6.41 (1H, s), 6.57 (1H, d), 7.02 (1H, m), 7.09-7.12 (2H, over-lapping m), 7.24 (1H, d), 7.42 (1H, d), 7.47 (1H, br d), 7.58 (1H, m), 7.65 (1H, m), 7.83 (1H, m), 7.88 (1H, br s), 7.92 (1H, d), 8.14 (1H, d), 8.18 (1H, br s), 8.40 (1H, d), 8.85 (1H, s), 9.26 (1H, s), 9.63 (1H, s). |
| 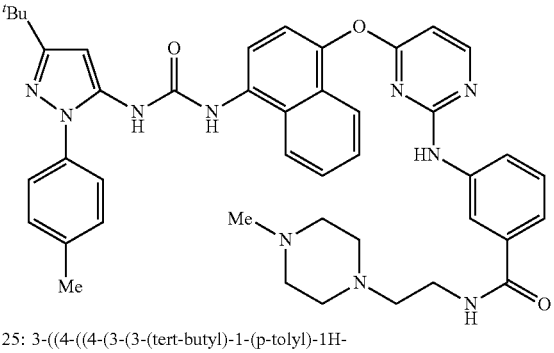<br>25: 3-((4-((4-(3-(3-(tert-butyl)-1-(p-tolyl)-1H-pyrazol-5-yl)ureido)naphthalen-1-yl)oxy)pyrimidin-2-yl)amino)-N-(2-(4-methylpiperazin-1-yl)ethyl)benzamide. | $R^r$ 1.91 min (Method 2, acidic); m/z 753 (M + H)$^+$ (ES$^+$); $^1$H NMR δ: 1.29 (9H, s), 2.12 (3H, s), 2.28-2.43 (12H, over-lapping m), 3.29 (3H, m), 6.41 (1H, s), 6.56 (1H, d), 7.01 (1H, t), 7.23 (1H, d), 7.37-7.40 (3H, over-lapping m), 7.45-7.48 (3H, over-lapping m), 7.56 (1H, m), 7.62 (1H, m), 7.81 (1H, d), 7.87 (1H, s), 7.91 (1H, d), 8.08 (1H, d), 8.15 (1H, m), 8.40 (1H, d), 8.85 (1H, s), 9.21 (1H, s), 9.61 (1H, s). |
| 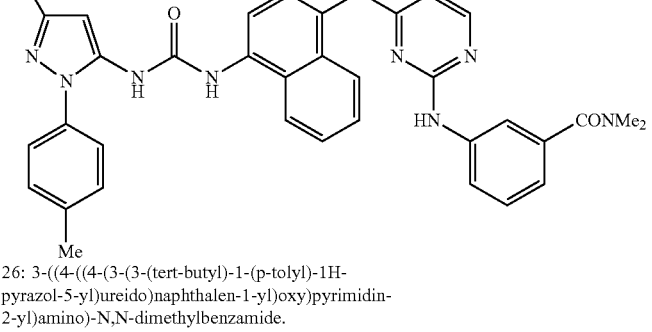<br>26: 3-((4-((4-(3-(3-(tert-butyl)-1-(p-tolyl)-1H-pyrazol-5-yl)ureido)naphthalen-1-yl)oxy)pyrimidin-2-yl)amino)-N,N-dimethylbenzamide. | $R^r$ 2.49 min (Method 2); m/z 655 (M + H)$^+$ (ES$^+$); $^1$H NMR δ: 1.29 (9H, s), 2.40 (3H, s), 2.80 (3H, br s), 2.93 (3H, br s), 6.41 (1H, s), 6.59 (1H, d), 6.80 (1H, d), 7.01 (1H, m), 7.37-7.39 (4H, over-lapping m), 7.46-7.48 (3H, over-lapping m), 7.56 (1H, m), 7.62 (1H, m), 7.81 (1H, d), 7.91 (1H, d), 8.07 (1H, d), 8.41 (1H, d), 8.76 (1H, s), 9.12 (1H, s), 9.64 (1H, s). |

TABLE 3-continued

Additional Compound Examples of the Invention

| Structure, Name and Example No. | Analytical Data [Generic Route] |
|---|---|
| 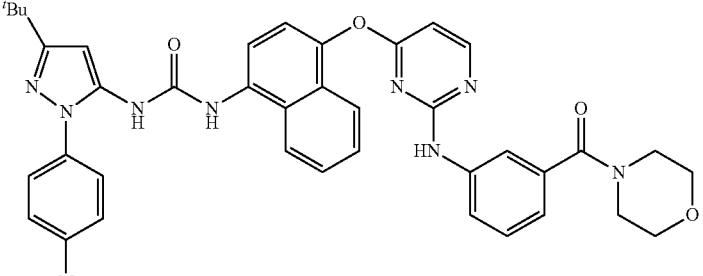<br>27: 1-(3-(tert-butyl)-1-(p-tolyl)-1H-pyrazol-5-yl)-3-(4-((2-((3-(morpholine-4-carbonyl)phenyl)amino)pyrimidin-4-yl)oxy)naphthalen-1-yl)urea. | $R^t$ 2.36 min (Method 2, acidic); m/z 697 (M + H)$^+$ (ES$^+$); $^1$H NMR δ: 1.29 (9H, s), 2.40 (3H, s), 3.56 (8H, br s), 6.41 (1H, s), 6.58 (1H, d), 6.83 (1H, d), 7.03 (1H, m), 7.39-7.40 (4H, over-lapping m), 7.47 (2H, m), 7.51 (1H, m), 7.56 (1H, m), 7.62 (1H, m), 7.81 (1H, d), 7.92 (1H, d), 8.07 (1H, d), 8.41 (1H, d), 8.76 (1H, s), 9.12 (1H, s), 9.65 (1H, s). |
| 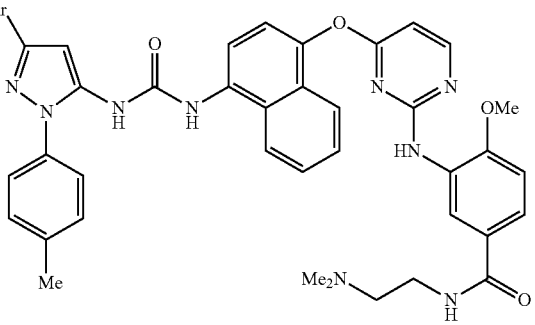<br>28: N-(2-(dimethylamino)ethyl)-3-((4-((4-(3-(3-isopropyl-1-(p-tolyl)-1H-pyrazol-5-yl)ureido)naphthalen-1-yl)oxy)pyrimidin-2-yl)amino)-4-methoxybenzamide. | $R^t$ 2.77 min (Method 3); m/z 714 (M + H)$^+$ (ES$^+$); $^1$H NMR δ: 1.24 (6H, d), 2.18 (6H, s), 2.38-2.41 (5H, over-lapping m), 2.90 (1H, m), 3.33 (2H, m), 3.79 (3H, s), 6.38 (1H, s), 6.42 (1H, d), 7.03 (1H, d), 7.37-7.42 (3H, over-lapping m), 7.47 (2H, m), 7.54-7.66 (3H, over-lapping m), 7.83 (1H, m), 7.91 (1H, d), 8.06 (1H, d), 8.16-8.19 (2H, over-lapping m), 8.28 (1H, m), 8.32 (1H, d), 8.80 (1H, s), 9.10 (1H, s). |
| 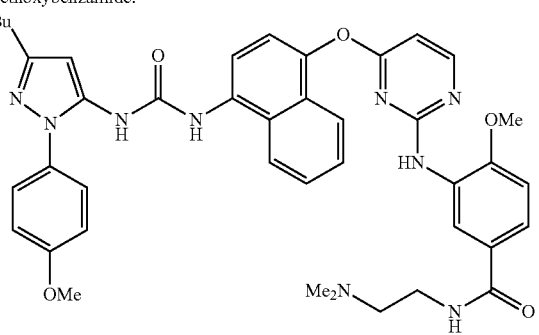<br>29: 3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)-4-methoxybenzamide. | $R^t$ 2.92 min (Method 3); m/z 728 (M + H)$^+$ (ES$^+$); $^1$H NMR δ: 1.29 (9H, s), 2.16 (6H, s), 2.36-2.40 (5H, over-lapping m), 3.31 (2H, m), 3.78 (3H, s), 6.40-6.41 (2H, over-lapping m), 7.02 (1H, d), 7.36-7.41 (3H, over-lapping m), 7.46 (2H, m), 7.53-7.64 (3H, over-lapping m), 7.82 (1H, m), 7.91 (1H, d), 8.05 (1H, d), 8.15-8.18 (2H, over-lapping m), 8.28 (1H, m), 8.31 (1H, d), 8.77 (1H, s), 9.09 (1H, s). |
| 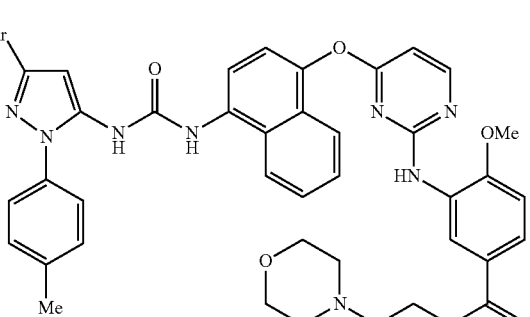<br>30: 3-((4-((4-(3-(3-isopropyl-1-(p-tolyl)-1H-pyrazol-5-yl)ureido)naphthalen-1-yl)oxy)pyrimidin-2-yl)amino)-4-methoxy-N-(2-morpholinoethyl)benzamide. | $R^t$ 1.83 min (Method 4); m/z 756 (M + H)$^+$ (ES$^+$); $^1$H NMR δ: 1.24 (6H, d), 2.40-2.46 (9H, over-lapping m), 2.89 (1H, m), 3.37 (2H, m), 3.53-3.56 (4H, over-lapping m), 3.78 (3H, s), 6.37 (1H, s), 6.42 (1H, d), 7.03 (1H, d), 7.36-7.41 (3H, over-lapping m), 7.46 (2H, m), 7.52-7.64 (3H, over-lapping m), 7.82 (1H, m), 7.90 (1H, d), 8.05 (1H, d), 8.16-8.21 (2H, over-lapping m), 8.26 (1H, m), 8.31 (1H, d), 8.83 (1H, s), 9.12 (1H, s). |

TABLE 3-continued

Additional Compound Examples of the Invention

| Structure, Name and Example No. | Analytical Data [Generic Route] |
|---|---|
| 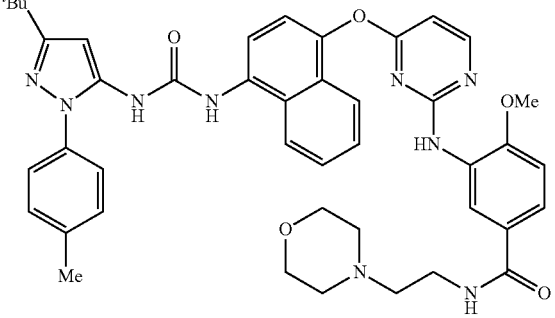<br>31: 3-((4-((4-(3-(3-(tert-butyl)-1-(p-tolyl)-1H-pyrazol-5-yl)ureido)naphthalen-1-yl)oxy)pyrimidin-2-yl)amino)-4-methoxy-N-(2-morpholinoethyl)benzamide. | $R^t$ 2.95 min (Method 3); m/z 770 (M + H)$^+$ (ES$^+$); $^1$H NMR δ: 1.28 (9H, s), 2.40-2.46 (9H, over-lapping m), 3.35 (2H, m), 3.53-3.56 (4H, over-lapping m), 3.78 (3H, s), 6.41-6.42 (2H, over-lapping m), 7.02 (1H, d), 7.36-7.41 (3H, over-lapping m), 7.46 (2H, m), 7.57-7.64 (3H, over-lapping m), 7.82 (1H, m), 7.90 (1H, d), 8.05 (1H, d), 8.15-8.19 (2H, over-lapping m), 8.27 (1H, d), 8.31 (1H, d), 8.81 (1H, s), 9.13 (1H, s). |
| 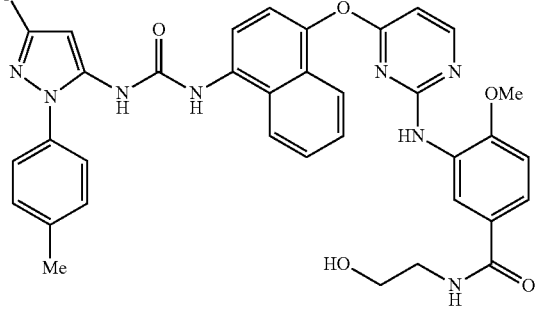<br>32: N-(2-hydroxyethyl)-3-((4-((4-(3-(3-isopropyl-1-(p-tolyl)-1H-pyrazol-5-yl)ureido)naphthalen-1-yl)oxy)pyrimidin-2-yl)amino)-4-methoxybenzamide. | $R^t$ 3.35 min (Method 3); m/z 687 (M + H)$^+$ (ES$^+$); $^1$H NMR δ: 1.24 (6H, d), 2.40 (3H, s), 2.89 (1H, m), 3.30 (2H, m), 3.50 (2H, m), 3.79 (3H, s), 4.69 (1H, m), 6.37 (1H, s), 6.40 (1H, d), 7.02 (1H, d), 7.36-7.41 (3H, over-lapping m), 7.46 (2H, m), 7.56-7.65 (3H, over-lapping m), 7.83 (1H, m), 7.90 (1H, d), 8.05 (1H, d), 8.13 (1H, s), 8.20 (1H, m), 8.28-8.32 (2H, over-lapping m), 8.77 (1H, s), 9.08 (1H, s). |
| 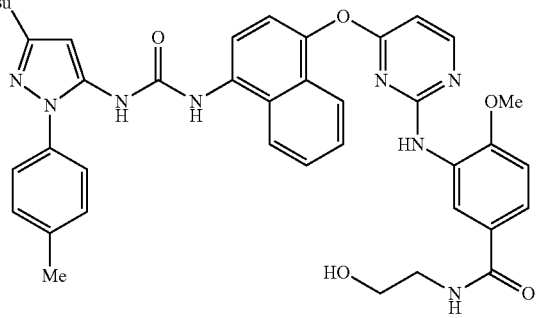<br>33: 3-((4-((4-(3-(3-(tert-butyl)-1-(p-tolyl)-1H-pyrazol-5-yl)ureido)naphthalen-1-yl)oxy)pyrimidin-2-yl)amino)-N-(2-hydroxyethyl)-4-methoxybenzamide. | $R^t$ 3.57 min (Method 3); m/z 701 (M + H)$^+$ (ES$^+$); $^1$H NMR δ: 1.29 (9H, s), 2.40 (3H, s), 3.30 (2H, m), 3.49 (2H, m), 3.79 (3H, s), 4.69 (1H, m), 6.39-6.41 (2H, over-lapping m), 7.02 (1H, d), 7.37-7.41 (3H, over-lapping m), 7.46 (2H, m), 7.56-7.64 (3H, over-lapping m), 7.81 (1H, m), 7.90 (1H, d), 8.05 (1H, d), 8.13 (1H, s), 8.20 (1H, m), 8.29-8.32 (2H, over-lapping m), 8.75 (1H, s), 9.08 (1H, s). |
| 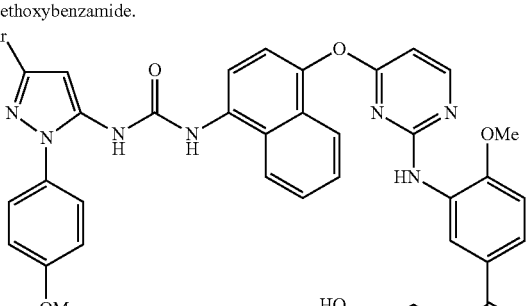<br>34: N-(2-hydroxyethyl)-3-((4-((4-(3-(3-isopropyl-1-(4-methoxyphenyl)-1H-pyrazol-5-yl)ureido)naphthalen-1-yl)oxy)pyrimidin-2-yl)amino)-4-methoxybenzamide. | $R^t$ 3.22 min (Method 3); m/z 703 (M + H)$^+$ (ES$^+$); $^1$H NMR δ: 1.24 (6H, d), 2.88 (1H, m), 3.30 (2H, m), 3.49 (2H, m), 3.79 (3H, s), 3.84 (3H, s), 4.69 (1H, m), 6.35 (1H, s), 6.39 (1H, d), 7.03 (1H, d), 7.12 (2H, m), 7.40 (1H, d), 7.48 (2H, m), 7.56-7.64 (3H, over-lapping m), 7.83 (1H, m), 7.90 (1H, d), 8.04 (1H, d), 8.13 (1H, s), 8.20 (1H, m),<br>8.29-8.32 (2H, over-lapping m), 8.72 (1H, s), 9.07 (1H, s). |

TABLE 3-continued

Additional Compound Examples of the Invention

| Structure, Name and Example No. | Analytical Data [Generic Route] |
|---|---|
| 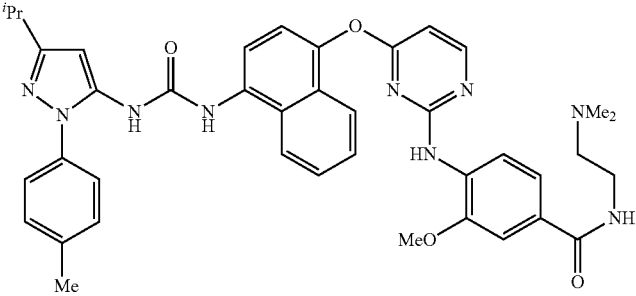 [SMILES: COc1cc(C(=O)NCCN(C)C)ccc1Nc1nccc(Oc2ccc(NC(=O)Nc3cc(C(C)C)nn3-c3ccc(C)cc3)c3ccccc23)n1]<br>35: N-(2-(dimethylamino)ethyl)-4-((4-((4-(3-(3-isopropyl-1-(p-tolyl)-1H-pyrazol-5-yl)ureido)naphthalen-1-yl)oxy)pyrimidin-2-yl)amino)-3-methoxybenzamide. | $R^t$ 2.90 min (Method 3); m/z 714 (M + H)$^+$ (ES$^+$), m/z 712 (M − H)$^-$ (ES$^-$); δ: 1.24 (6H, d), 2.14 (6H, s), 2.33 (2H, m), 2.40 (3H, s), 2.90 (1H, m), 3.28 (2H, m), 3.83 (3H, s), 6.40 (1H, s), 6.64 (1H, d), 7.10 (1H, d), 7.37-7.42 (4H, over-lapping m), 7.48 (2H, m), 7.56 (1H, m), 7.60-7.65 (2H, over-lapping m), 7.81 (1H, m), 7.96-7.98 (2H, over-lapping m), 8.09 (1H, d), 8.14 (1H, m), 8.43 (1H, d), 8.82 (1H, s), 9.16 (1H, s). |
| 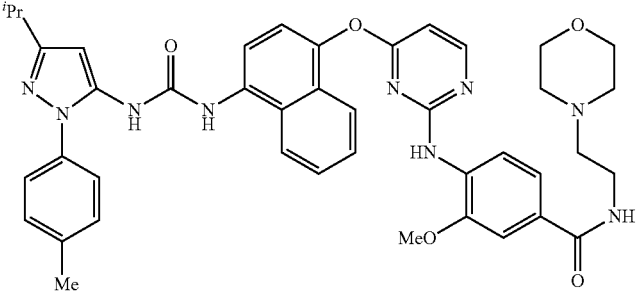 [SMILES: COc1cc(C(=O)NCCN2CCOCC2)ccc1Nc1nccc(Oc2ccc(NC(=O)Nc3cc(C(C)C)nn3-c3ccc(C)cc3)c3ccccc23)n1]<br>36: 4-((4-((4-(3-(3-isopropyl-1-(p-tolyl)-1H-pyrazol-5-yl)ureido)naphthalen-1-yl)oxy)pyrimidin-2-yl)amino)-3-methoxy-N-(2-morpholinoethyl)benzamide. | $R^t$ 2.91 min (Method 3); m/z 756 (M + H)$^+$ (ES$^+$); $^1$H NMR δ: 1.24 (6H, d), 2.36-2.42 (9H, over-lapping m), 2.90 (1H, m), 3.29 (2H, br s), 3.53-3.56 (4H, over-lapping m), 3.83 (3H, s), 6.40 (1H, s), 6.64 (1H, d), 7.10 (1H, m), 7.36-7.43 (4H, over-lapping m), 7.48 (2H, m), 7.54-7.65 (3H, over-lapping m), 7.82 (1H, m), 7.95-7.98 (2H, over-lapping m), 8.09 (1H, d), 8.15 (1H, m), 8.42 (1H, d), 8.81 (1H, s), 9.15 (1H, s). |
| 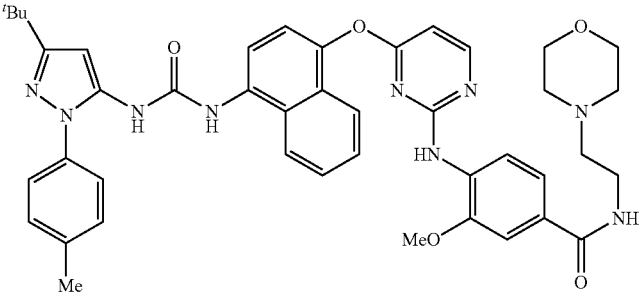<br>37: 4-((4-((4-(3-(3-tert-butyl)-1-(p-tolyl)-1H-pyrazol-5-yl)ureido)naphthalen-1-yl)oxy)pyrimidin-2-yl)amino)-3-methoxy-N-(2-morpholinoethyl)benzamide. | $R^t$ 3.06 min (Method 3); m/z 770 (M + H)$^+$ (ES$^+$); $^1$H NMR δ: 1.29 (9H, s), 2.37-2.42 (9H, over-lapping m), 3.29 (2H, m), 3.53-3.56 (4H, over-lapping m), 3.83 (3H, s), 6.45 (1H, s), 6.65 (1H, d), 7.10 (1H, m), 7.36-7.43 (4H, over-lapping m), 7.48 (2H, m), 7.56-7.63 (3H, over-lapping m), 7.82 (1H, m), 7.96-7.98 (2H, over-lapping m), 8.10 (1H, d), 8.15 (1H, m), 8.42 (1H, d), 8.80 (1H, s), 9.16 (1H, s). |
| 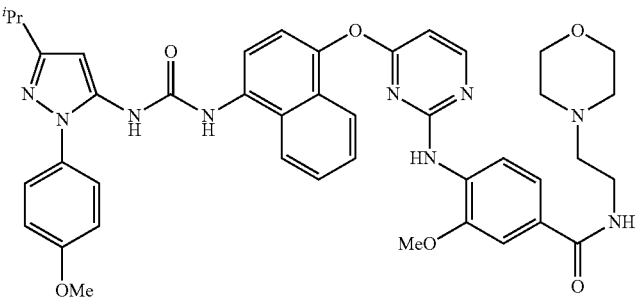 [SMILES: COc1ccc(-n2nc(C(C)C)cc2NC(=O)Nc2ccc(Oc3ccnc(Nc4ccc(C(=O)NCCN5CCOCC5)cc4OC)n3)c3ccccc23)cc1]<br>38: 4-((4-((4-(3-(3-isopropyl-1-(4-methoxyphenyl)-1H-pyrazol-5-ypureido)naphthalen-1-yl)oxy)pyrimidin-2-yl)amino)-3-methoxy-N-(2-morpholinoethyl)benzamide. | $R^t$ 2.83 min (Method 3); m/z 772 (M + H)$^+$ (ES$^+$); $^1$H NMR δ: 1.25 (6H, d), 2.44-2.48 (6H, over-lapping m), 2.90 (1H, m), 3.31 (2H, m), 3.56-3.58 (4H, over-lapping m), 3.83 (3H, s), 3.84 (3H, s), 6.39 (1H, s), 6.66 (1H, d), 7.10-7.15 (3H, over-lapping m), 7.38 (1H, m), 7.43 (1H, d), 7.51 (2H, m), 7.55-7.66 (3H, over-lapping m), 7.82 (1H, d), 7.96-8.00 (2H, over-lapping m), 8.09 (1H, d), 8.20 (1H, m), 8.42 (1H, d), 8.80 (1H, s), 9.18 (1H, s). |

TABLE 3-continued

Additional Compound Examples of the Invention

| Structure, Name and Example No. | Analytical Data [Generic Route] |
|---|---|
| 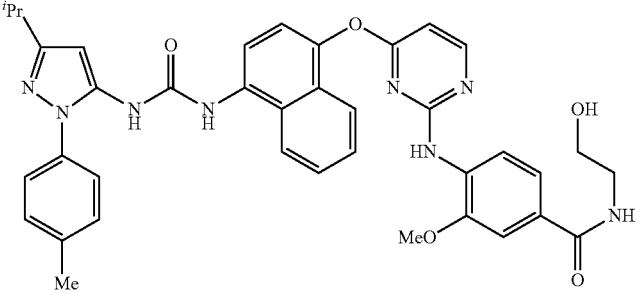 [SMILES: COc1cc(C(=O)NCCO)ccc1Nc1nccc(Oc2ccc(NC(=O)Nc3cc(C(C)C)nn3-c3ccc(C)cc3)c3ccccc23)n1]<br>39: N-(2-hydroxyethyl)-4-((4-((4-(3-(3-isopropyl-1-(p-tolyl)-1H-pyrazol-5-yl)ureido)naphthalen-1-yl)oxy)pyrimidin-2-yl)amino)-3-methoxybenzamide. | $R^t$ 3.61 min (Method 3); m/z 687 (M + H)$^+$ (ES$^+$); $^1$H NMR δ: 1.24 (6H, d), 2.40 (3H, s), 2.90 (1H, m), 3.28 (2H, m), 3.48 (2H, m), 3.84 (3H, s), 4.70 (1H, m), 6.40 (1H, s), 6.63 (1H, d), 7.13 (1H, d), 7.38-7.43 (4H, over-lapping m), 7.48 (2H, m), 7.54-7.65 (3H, over-lapping m), 7.81 (1H, m), 7.95-7.97 (2H, over-lapping m), 8.09 (1H, d), 8.25 (1H, m), 8.42 (1H, d), 8.82 (1H, s), 9.17 (1H, s). |
| 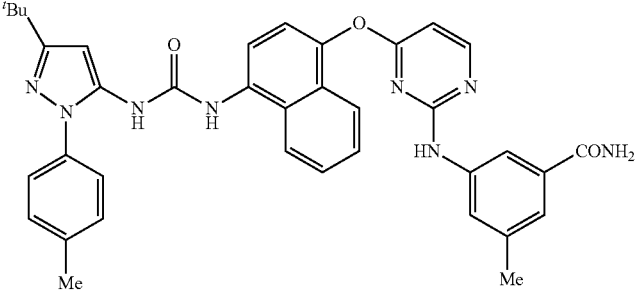 [SMILES: Cc1ccc(-n2nc(C(C)(C)C)cc2NC(=O)Nc2ccc(Oc3ccnc(Nc4cc(C)cc(C(N)=O)c4)n3)c3ccccc23)cc1]<br>40: 3-((4-((4-(3-(3-tert-butyl)-1-(p-tolyl)-1H-pyrazol-5-yl)ureido)naphthalen-1-yl)oxy)pyrimidin-2-yl)amino)-5-methylbenzamide. | $R^t$ 2.46 min (Method 2 acidic); m/z 641 (M + H)$^+$ (ES$^+$); m/z 639 (M – H)$^-$ (ES$^-$); $^1$H NMR δ: 1.37 (9H, s), 2.05 (3H, s), 2.47 (3H, s), 6.48 (1H, s), 6.60 (1H, d), 7.14 (1H, br s), 7.31-7.35 (2H, over-lapping m), 7.38-7.45 (4H, over-lapping m), 7.51-7.59 (3H, over-lapping m), 7.82 (1H, d), 7.89 (1H, d), 7.96 (1H, d), 8.36 (1H, d). |
| 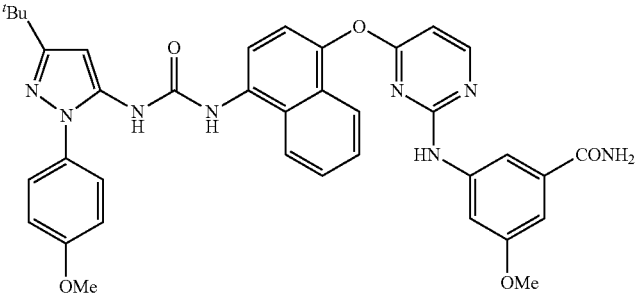 [SMILES: COc1ccc(-n2nc(C(C)(C)C)cc2NC(=O)Nc2ccc(Oc3ccnc(Nc4cc(OC)cc(C(N)=O)c4)n3)c3ccccc23)cc1]<br>41: 3-((4-((4-(3-(3-tert-butyl)-1-(4-methoxyphenyl)-1H-pyrazol-5-yl)ureido)naphthalen-1-yl)oxy)pyrimidin-2-yl)amino)-5-methoxybenzamide. | $R^t$ 2.20 min (Method 2 acidic); m/z 673 (M + H)$^+$ (ES$^+$); $^1$H NMR δ: 1.29 (9H, s), 3.57 (3H, s), 3.83 (3H, s), 6.39 (1H, s), 6.54 (1H, d), 6.92 (1H, m), 7.11 (2H, m), 7.24 (1H, s), 7.31 (1H, s), 7.40 (1H, d), 7.49 (2H, m), 7.53-7.64 (3H, over-lapping m), 7.75 (1H, br s), 7.81 (1H, dd), 7.94 (1H, d), 8.11 (1H, d), 8.41 (1H, d), 8.87 (1H, br s), 9.20 (1H, br s), 9.61 (1H, br s). |
| 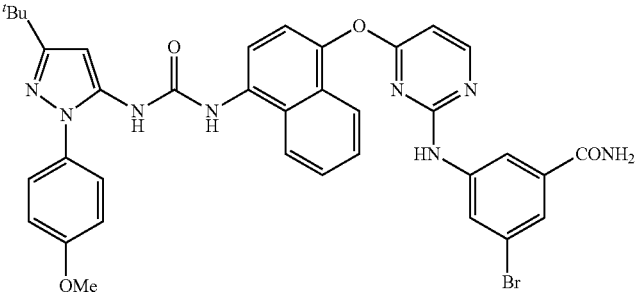 [SMILES: COc1ccc(-n2nc(C(C)(C)C)cc2NC(=O)Nc2ccc(Oc3ccnc(Nc4cc(Br)cc(C(N)=O)c4)n3)c3ccccc23)cc1]<br>42: 3-bromo-5-((4-((4-(3-(3-tert-butyl)-1-(4-methoxyphenyl)-1H-pyrazol-5-yl)ureido)naphthalen-1-yl)oxy)pyrimidin-2-yl)amino)benzamide. | $R^t$ 2.33 min (Method 2 acidic); m/z 721, 723 (M + H)$^+$ (ES$^+$); $^1$H NMR δ: 1.29 (9H, s), 3.83 (3H, s), 6.38 (1H, s), 6.65 (1H, d), 7.10 (2H, m), 7.36-7.42 (2H, over-lapping m), 7.47-7.63 (6H, over-lapping m), 7.79 (1H, d), 7.87-7.92 (2H, over-lapping m), 7.97 (1H, d), 8.17 (1H, d), 8.46 (1H, d), 9.04 (1H, br s), 9.32 (1H, br s), 9.88 (1H, br s). |

TABLE 3-continued

Additional Compound Examples of the Invention

| Structure, Name and Example No. | Analytical Data [Generic Route] |
|---|---|
| 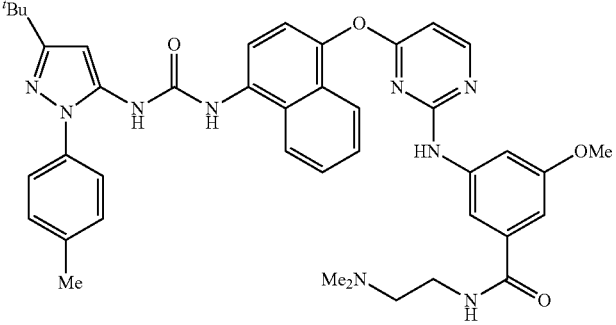 [SMILES: COc1cc(Nc2nccc(Oc3ccc(NC(=O)Nc4cc(C(C)(C)C)nn4-c4ccc(C)cc4)c4ccccc34)n2)cc(C(=O)NCCN(C)C)c1]<br>43: 3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)-5-methoxybenzamide. | $R^t$ 1.92 min (Method 2 acidic); m/z 728 (M + H)$^+$ (ES$^+$); $^1$H NMR δ: 1.29 (9H, s), 2.16 (6H, s), 2.36 (2H, t), 2.40 (3H, s), 3.29 (2H, m), 3.56 (3H, s), 6.41 (1H, s), 6.53 (1H, d), 6.86 (1H, br s), 7.33 (1H, br s), 7.37-7.39 (3H, over-lapping m), 7.45 (2H, d), 7.56-7.62 (3H, over-lapping m), 7.82 (1H, d), 7.94 (1H, d), 8.07 (1H, d), 8.15 (1H, t), 8.41 (1H, d), 8.77 (1H, br s), 9.09 (1H, br s), 9.59 (1H, br s). |
| 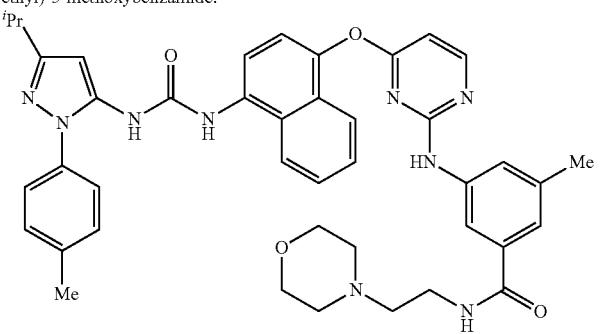<br>44: 3-((4-((4-(3-(3-isopropyl-1-(p-tolyl)-1H-pyrazol-5-yl)ureido)naphthalen-1-yl)oxy)pyrimidin-2-yl)amino)-5-methyl-N-(2-morpholinoethyl)benzamide. | $R^t$ 2.86 min (Method 3); m/z 740 (M + H)$^+$ (ES$^+$), m/z 738 (M − H)$^-$ (ES$^-$); $^1$H NMR δ: 1.24 (6H, d), 1.96 (3H, s), 2.37-2.43 (9H, over-lapping m), 2.89 (1H, m), 3.34 (2H, m), 3.53-3.56 (4H, over-lapping m), 6.37 (1H, s), 6.59 (1H, d), 7.04 (1H, s), 7.30 (1H, s), 7.37-7.42 (3H, over-lapping m), 7.46 (2H, m), 7.54-7.64 (3H, over-lapping m), 7.81 (1H, m), 7.97 (1H, d), 8.06-8.13 (2H, over-lapping m), 8.40 (1H, d), 8.78 (1H, s), 9.10 (1H, s), 9.58 (1H, s). |
| 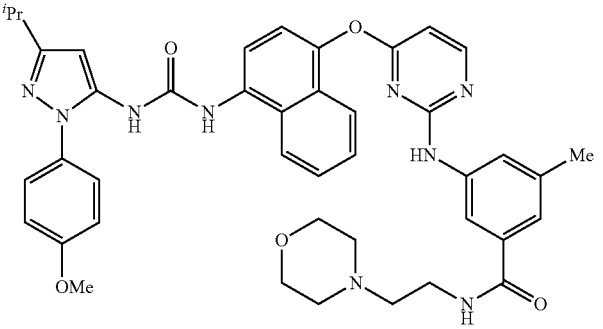 [SMILES: Cc1ccc(-n2nc(C(C)C)cc2NC(=O)Nc2ccc(Oc3ccnc(Nc4cc(C)cc(C(=O)NCCN5CCOCC5)c4)n3)c3ccccc23)cc1]<br>45: 3-((4-((4-(3-(3-isopropyl-1-(4-methoxyphenyl)-1H-pyrazol-5-yl)ureido)naphthalen-1-yl)oxy)pyrimidin-2-yl)amino)-5-methyl-N-(2-morpholinoethyl)benzamide. | $R^t$ 2.78 min (Method 3); m/z 756 (M + H)$^+$ (ES$^+$), m/z 754 (M − H)$^-$ (ES$^-$); $^1$H NMR δ: 1.24 (6H, d), 1.96 (3H, s), 2.36-2.43 (6H, over-lapping m), 2.89 (1H, m), 3.36 (2H, m), 3.53-3.56 (4H, over-lapping m), 3.84 (3H, s), 6.35 (1H, s), 6.58 (1H, d), 7.04 (1H, s), 7.12 (2H, m), 7.30 (1H, br s), 7.41 (1H, d), 7.48 (2H, m), 7.53-7.64 (3H, over-lapping m), 7.81 (1H, d), 7.97 (1H, d), 8.06 (1H, d), 8.11 (1H, m), 8.40 (1H, d), 8.73 (1H, s), 9.09 (1H, s), 9.58 (1H, s). |
| 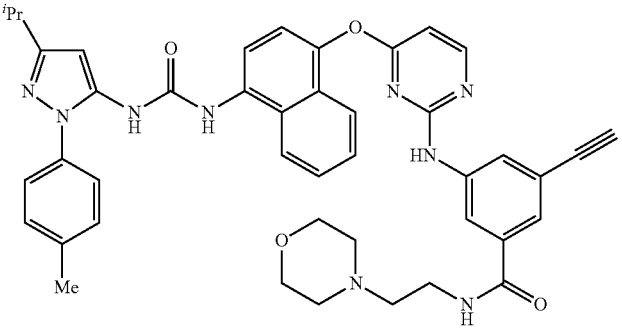 [SMILES: C#Cc1cc(Nc2nccc(Oc3ccc(NC(=O)Nc4cc(C(C)C)nn4-c4ccc(C)cc4)c4ccccc34)n2)cc(C(=O)NCCN2CCOCC2)c1]<br>46: 3-ethynyl-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide. | $R^t$ 1.97 min (Method 2, acidic); m/z 750 (M + H)$^+$ (ES$^+$); $^1$H NMR δ: 1.24 (6H, d), 2.39-2.46 (9H, over-lapping m), 2.90 (1H, m), 3.34 (2H, m), 3.55-3.57 (4H, over-lapping m), 4.11 (1H, s), 6.37 (1H, s), 6.56 (1H, d), 7.37-7.43 (4H, over-lapping m), 7.48 (2H, m), 7.55-7.65 (2H, over-lapping m), 7.81-7.87 (2H, over-lapping m), 7.93 (1H, d), 8.06-8.08 (2H, over-lapping m), 8.35 (1H, m), 8.43 (1H, d), 8.82 (1H, s), 9.12 (1H, s), 9.75 (1H, s). |

TABLE 3-continued

Additional Compound Examples of the Invention

| Structure, Name and Example No. | Analytical Data [Generic Route] |
|---|---|
| 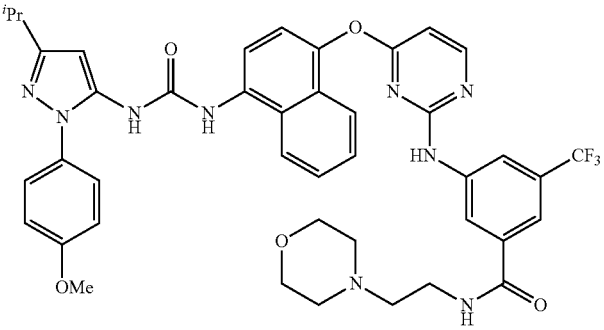 [SMILES: COc1ccc(-n2nc(C(C)C)cc2NC(=O)Nc2ccc(Oc3ccnc(Nc4cc(C(=O)NCCN5CCOCC5)cc(C(F)(F)F)c4)n3)c3ccccc23)cc1]<br>47: 3-((4-((4-(3-(3-isopropyl-1-(4-methoxyphenyl)-1H-pyrazol-5-yl)ureido)naphthalen-1-yl)oxy)pyrimidin-2-yl)amino)-N-(2-morpholinoethyl)-5-(trifluoromethyl)benzamide. | $R^t$ 2.95 min (Method 3); m/z 810 (M + H)$^+$ (ES$^+$), m/z 808 (M − H)$^−$ (ES$^−$); $^1$H NMR δ: 1.24 (6H, d), 2.38-2.46 (6H, over-lapping m), 2.88 (1H, m), 3.37 (2H, m), 3.54-3.56 (4H, over-lapping m), 3.84 (3H, s), 6.35 (1H, s), 6.62 (1H, d), 7.12 (2H, m), 7.41 (1H, d), 7.48 (2H, m), 7.54-7.64 (3H, over-lapping m), 7.81 (1H, m), 7.93 (1H, m), 8.05 (1H, d), 8.11 (1H, br s), 8.28 (1H, br s), 8.47 (1H, d), 8.51 (1H, t), 8.73 (1H, s), 9.07 (1H, s), 9.96 (1H, s). |
| 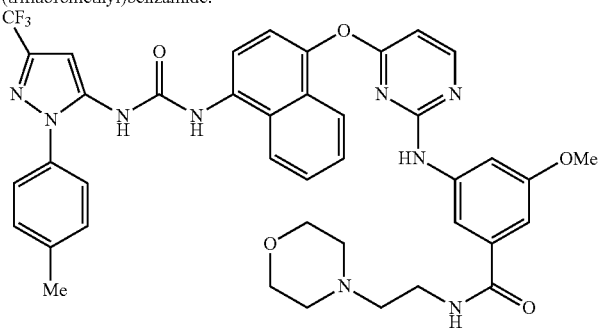<br>48: 3-methoxy-N-(2-morpholinoethyl)-5-((4-((4-(3-(1-(p-tolyl)-3-(trifluoromethyl)-1H-pyrazol-5-yl)ureido)naphthalen-1-yl)oxy)pyrimidin-2-yl)amino)benzamide. | $R^t$ 2.97 min (Method 3); m/z 782 (M + H)$^+$ (ES$^+$); $^1$H NMR δ: 2.36-2.45 (9H, over-lapping m), 3.34 (2H, m), 3.54-3.57 (7H, over-lapping m), 6.54 (1H, d), 6.85 (1H, s), 6.91 (1H, s), 7.31 (1H, s), 7.42 (1H, d), 7.46 (2H, d), 7.54-7.59 (4H, over-lapping m), 7.62 (1H, dd), 7.83 (1H, d), 7.92 (1H, d), 8.04 (1H, d), 8.18 (1H, t), 8.40 (1H, d), 9.13 (1H, s), 9.24 (1H, s), 9.59 (1H, s). |
| 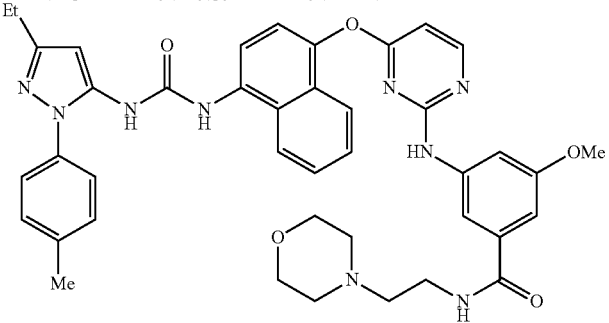 [SMILES: CCc1cc(NC(=O)Nc2ccc(Oc3ccnc(Nc4cc(OC)cc(C(=O)NCCN5CCOCC5)c4)n3)c3ccccc23)n(-c2ccc(C)cc2)n1]<br>49: 3-((4-((4-(3-(3-ethyl-1-(p-tolyl)-1H-pyrazol-5-yl)ureido)naphthalen-1-yl)oxy)pyrimidin-2-yl)amino)-5-methoxy-N-(2-morpholinoethyl)benzamide. | $R^t$ 2.70 min (Method 3); m/z 742 (M + H)$^+$ (ES$^+$); $^1$H NMR δ: 1.21 (3H, t), 2.38-2.45 (9H, over-lapping m), 2.58 (2H, q), 3.33 (2H, m), 3.53-3.58 (7H, over-lapping m), 6.35 (1H, s), 6.53 (1H, d), 6.85 (1H, s), 7.32 (1H, s), 7.37 (2H, d), 7.40 (1H, d), 7.45 (2H, d), 7.54-7.58 (2H, over-lapping m), 7.62 (1H, dd), 7.82 (1H, d), 7.94 (1H, d), 8.06 (1H, d), 8.18 (1H, t), 8.40 (1H, d), 8.78 (1H, s), 9.08 (1H, s), 9.59 (1H, s). |
| 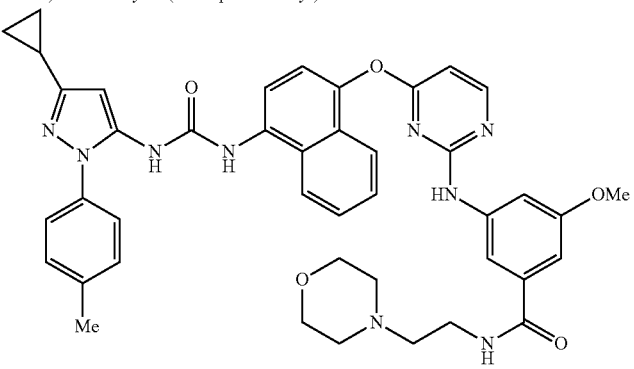<br>50: 3-((4-((4-(3-(3-cyclopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide. | $R^t$ 2.74 min (Method 3); m/z 754 (M + H)$^+$ (ES$^+$); $^1$H NMR δ: 0.69 (2H, m), 0.89 (2H, m), 1.89 (1H, m), 2.38-2.45 (9H, over-lapping m), 3.33 (2H, m), 3.54-3.56 (7H, over-lapping m), 6.21 (1H, s), 6.54 (1H, d), 6.85 (1H, s), 7.32 (1H, s), 7.37 (2H, d), 7.40 (1H, d), 7.44 (2H, d), 7.53-7.58 (2H, over-lapping m), 7.62 (1H, dd), 7.82 (1H, d), 7.92 (1H, d), 8.05 (1H, d), 8.17 (1H, t), 8.40 (1H, d), 8.76 (1H, s), 9.07 (1H, s), 9.59 (1H, s). |

TABLE 3-continued

Additional Compound Examples of the Invention

| Structure, Name and Example No. | Analytical Data [Generic Route] |
|---|---|
| 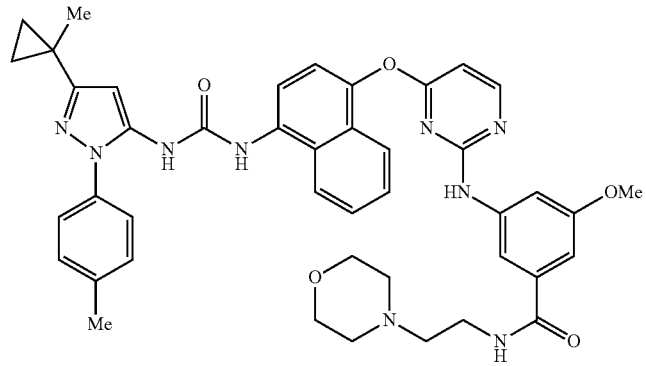 [SMILES: COc1cc(Nc2nccc(Oc3ccc(NC(=O)Nc4cc(C5(C)CC5)nn4-c4ccc(C)cc4)c4ccccc34)n2)cc(C(=O)NCCN2CCOCC2)c1]<br>51: 3-methoxy-5-((4-((4-(3-(3-(1-methylcyclo propyl)-1-(p-tolyl)-1H-pyrazol-5-yl)ureido) naphthalen-1-yl)oxy)pyrimidin-2-yl)amino)-N-(2-morpholinoethyl)benzamide. | $R^t$ 2.89 min (Method 3); m/z 768 (M + H)$^+$ (ES$^+$); $^1$H NMR δ: 0.72 (2H, m), 0.92 (2H, m), 1.41 (3H, s), 2.38-2.45 (9H, overlapping m), 3.33 (2H, m), 3.54-3.56 (7H, over-lapping m), 6.27 (1H, s), 6.54 (1H, d), 6.85 (1H, s), 7.32 (1H, s), 7.37 (2H, d), 7.40 (1H, d), 7.44 (2H, d), 7.54-7.58 (2H, over-lapping m), 7.62 (1H, dd), 7.82 (1H, d), 7.93 (1H, d), 8.05 (1H, d), 8.18 (1H, t), 8.40 (1H, d), 8.76 (1H, s), 9.07 (1H, s), 9.59 (1H, s). |
| 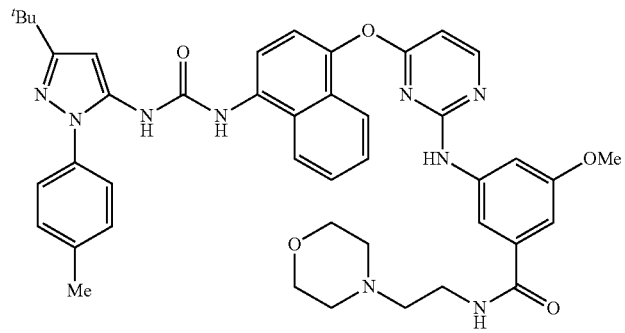 [SMILES: COc1cc(Nc2nccc(Oc3ccc(NC(=O)Nc4cc(C(C)(C)C)nn4-c4ccc(C)cc4)c4ccccc34)n2)cc(C(=O)NCCN2CCOCC2)c1]<br>52: 3-((4-((4-(3-(3-(tert-butyl)-1-(p-tolyl)-1H-pyrazol-5-yl)ureido)naphthalen-1-yl)oxy)pyrimidin-2-yl)amino)-5-methoxy-N-(2-morpholinoethyl)benzamide. | $R^t$ 1.93 min (Method 2 acidic); m/z 770 (M + H)$^+$ (ES$^+$); $^1$H NMR δ: 1.29 (9H, s), 2.37-2.46 (9H, over-lapping m), 3.35 (2H, m), 3.54-3.56 (7H, over-lapping m), 6.41 (1H, s), 6.53 (1H, d), 6.85 (1H, m), 7.31 (1H, m), 7.36-7.41 (3H, over-lapping m), 7.48 (2H, m), 7.54-7.58 (2H, over-lapping m), 7.62 (1H, m), 7.82 (1H, m), 7.94 (1H, d), 8.06 (1H, m), 8.17 (1H, m), 8.40 (1H, d), 8.79 (1H, s), 9.11 (1H, s), 9.59 (1H, s). |
| 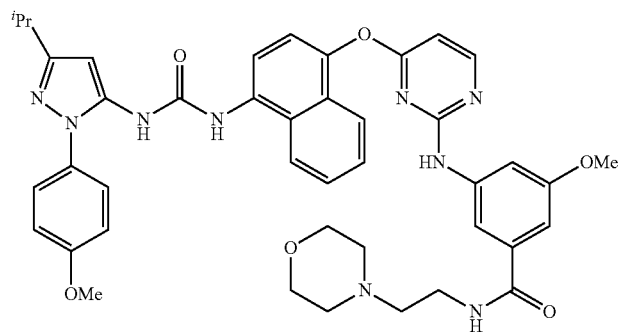<br>53: 3-((4-((4-(3-(3-isopropyl-1-(4-methoxyphenyl)-1H-pyrazol-5-yl)ureido)naphthalen-1-yl)oxy) pyrimidin-2-yl)amino)-5-methoxy-N-(2-morpholinoethyl)benzamide. | $R^t$ 2.22 min (Method 2 basic); m/z 772 (M + H)$^+$ (ES$^+$), 770 (M − H)$^-$ (ES$^-$); $^1$H NMR δ: 1.23 (6H, d), 2.37-2.44 (6H, over-lapping m), 2.88 (1H, m), 3.35 (2H, m), 3.54-3.56 (7H, over-lapping m), 3.83 (3H, s), 6.35 (1H, s), 6.54 (1H, d), 6.85 (1H, m), 7.12 (2H, m), 7.31 (1H, br s), 7.40 (1H, d), 7.48 (2H, m), 7.54-7.58 (2H, overlapping m), 7.62 (1H, m), 7.81 (1H, m), 7.94 (1H, d), 8.06 (1H, d), 8.20 (1H, m), 8.40 (1H, d), 8.77 (1H, s), 9.11 (1H, s), 9.61 (1H, s). |

TABLE 3-continued

Additional Compound Examples of the Invention

| Structure, Name and Example No. | Analytical Data [Generic Route] |
|---|---|
| 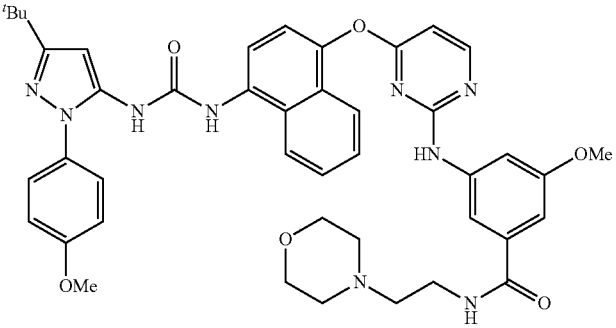<br>54: 3-((4-((4-(3-(3-(tert-butyl)-1-(4-methoxyphenyl)-1H-pyrazol-5-yl)ureido)naphthalen-1-yl)oxy)pyrimidin-2-yl)amino)-5-methoxy-N-(2-morpholinoethyl)benzamide. | $R^t$ 1.88 min (Method 2 acidic); m/z 786 (M + H)$^+$ (ES$^+$); $^1$H NMR δ: 1.28 (9H, s), 2.38-2.44 (6H, over-lapping m), 3.35 (2H, m), 3.54-3.56 (7H, over-lapping m), 3.84 (3H, s), 6.39 (1H, s), 6.53 (1H, d), 6.85 (1H, m), 7.12 (2H, m), 7.32 (1H, m), 7.40 (1H, d), 7.48 (2H, m), 7.54-7.58 (2H, over-lapping m), 7.62 (1H, m), 7.82 (1H, d), 7.94 (1H, d), 8.06 (1H, d), 8.17 (1H, m), 8.40 (1H, d), 8.73 (1H, s), 9.09 (1H, s), 9.59 (1H, s). |
| 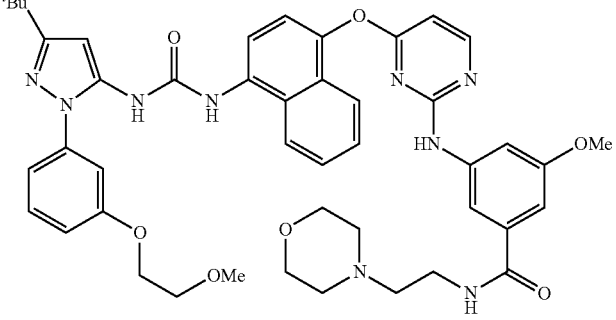<br>55: 3-((4-((4-(3-(3-(tert-butyl)-1-(3-(2-methoxyethoxy)phenyl)-1H-pyrazol-5-yl)ureido)naphthalen-1-yl)oxy)pyrimidin-2-yl)amino)-5-methoxy-N-(2-morpholinoethyl)benzamide. | $R^t$ 2.91 min (Method 3); m/z 830 (M − H)$^+$ (ES$^+$); $^1$H NMR δ: 1.30 (9H, s), 2.37-2.44 (6H, over-lapping m), 3.29 (3H, s), 3.34 (2H, m), 3.53-3.58 (7H, over-lapping m), 3.67 (2H, m), 4.18 (2H, m), 6.43 (1H, s), 6.53 (1H, d), 6.85 (1H, s), 7.00-7.04 (1H, d), 7.17-7.20 (2H, over-lapping m), 7.33 (1H, s), 7.40 (1H, d), 7.46 (1H, m), 7.54-7.64 (3H, over-lapping m), 7.82 (1H, d), 7.92 (1H, d), 8.08 (1H, d), 8.17 (1H, m), 8.40 (1H, d), 8.82 (1H, s), 9.13 (1H, s), 9.59 (1H, s). |
| 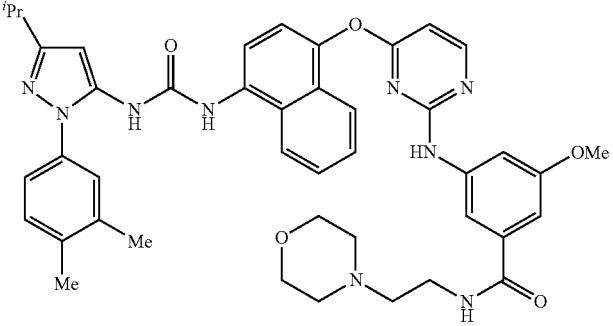 [SMILES: COc1cc(Nc2nccc(Oc3ccc(NC(=O)Nc4cc(C(C)C)nn4-c4ccc(C)c(C)c4)c4ccccc34)n2)cc(C(=O)NCCN2CCOCC2)c1]<br>56: 3-((4-((4-(3-(1-(3,4-dimethylphenyl)-3-isopropyl-1H-pyrazol-5-yl)ureido)naphthalen-1-yl)oxy)pyrimidin-2-yl)amino)-5-methoxy-N-(2-morpholinoethyl)benzamide. | $R^t$ 1.74 min (Method 2, acidic); m/z 770 (M + H)$^+$ (ES$^+$); $^1$H NMR δ: 1.24 (6H, d), 2.30 (3H, s), 2.32 (3H, s), 2.36-2.44 (6H, over-lapping m), 2.89 (1H, sept), 3.32 (2H, m), 3.54-3.57 (7H, over-lapping m), 6.36 (1H, s), 6.53 (1H, d), 6.85 (1H, s), 7.26-7.36 (4H, over-lapping m), 7.40 (1H, d), 7.53-7.58 (2H, over-lapping m), 7.61 (1H, dd), 7.82 (1H, d), 7.94 (1H, d), 8.06 (1H, d), 8.17 (1H, t), 8.40 (1H, d), 8.75 (1H, s), 9.08 (1H, s), 9.59 (1H, s). |
| 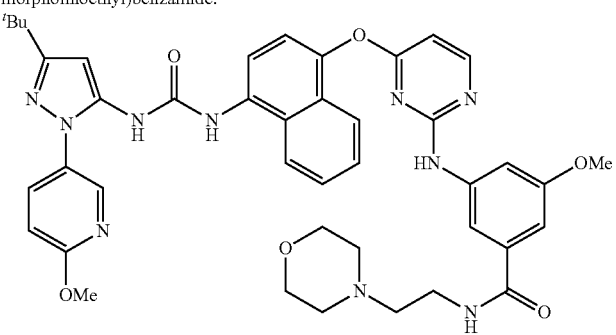<br>57: 3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)-5-methoxy-N-(2-morpholinoethyl)benzamide. | $R^t$ 1.89 min (Method 2 acidic); m/z 787 (M + H)$^+$ (ES$^+$); $^1$H NMR δ: 1.29 (9H, s), 2.38-2.45 (6H, over-lapping m), 3.35 (2H, m), 3.54-3.56 (7H, over-lapping m), 3.94 (3H, s), 6.43 (1H, s), 6.53 (1H, d), 6.85 (1H, m), 7.03 (1H, d), 7.32 (1H, s), 7.40 (1H, d), 7.54-7.58 (2H, over-lapping m), 7.62 (1H, m), 7.82 (1H, d), 7.91 (2H, over-lapping m), 8.04 (1H, d), 8.18 (1H, t), 8.39-8.42 (2H, over-lapping m), 8.81 (1H, s), 9.07 (1H, s), 9.59 (1H, s). |

TABLE 3-continued

Additional Compound Examples of the Invention

| Structure, Name and Example No. | Analytical Data [Generic Route] |
|---|---|
| 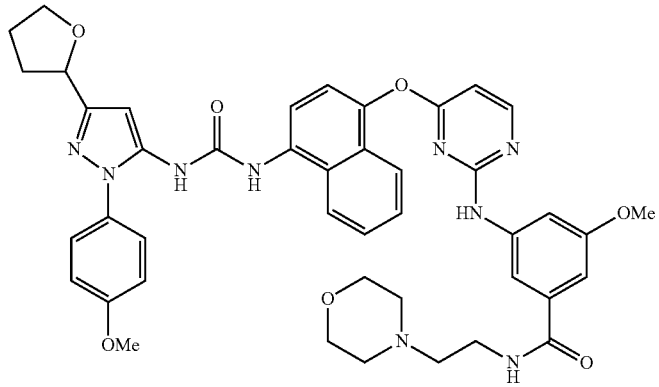 [SMILES: COc1ccc(-n2nc(C3CCCO3)cc2NC(=O)Nc2ccc(Oc3ccnc(Nc4cc(OC)cc(C(=O)NCCN5CCOCC5)c4)n3)c3ccccc23)cc1]<br>58: 3-methoxy-5-((4-((4-(3-(1-(4-methoxyphenyl)-3-(tetrahydrofuran-2-yl)-1H-pyrazol-5-yl)ureido)naphthalen-1-yl)oxy)pyrimidin-2-yl)amino)-N-(2-morpholinoethyl)benzamide. | R$^t$ 2.55 min (Method 3); m/z 800 (M + H)$^+$ (ES$^+$); $^1$H NMR δ: 1.89-2.04 (3H, overlapping m), 2.17 (1H, m), 2.36-2.44 (6H, over-lapping m), 3.32 (2H, m), 3.54-3.57 (7H, over-lapping m), 3.76 (1H, m), 3.84 (3H, s), 3.88 (1H, m), 4.78 (1H, m), 6.44 (1H, s), 6.54 (1H, d), 6.85 (1H, s), 7.13 (2H, d), 7.31 (1H, s), 7.41 (1H, d), 7.49 (2H, d), 7.53-7.58 (2H, over-lapping m), 7.61 (1H, dd), 7.81 (1H, d), 7.93 (1H, d), 8.05 (1H, d), 8.20 (1H, t), 8.40 (1H, d), 8.83 (1H, s), 9.14 (1H, s), 9.61 (1H, s). |
| 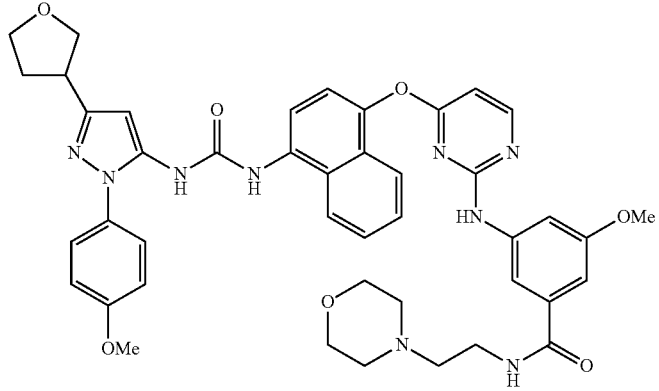 [SMILES: COc1ccc(-n2nc(C3CCOC3)cc2NC(=O)Nc2ccc(Oc3ccnc(Nc4cc(OC)cc(C(=O)NCCN5CCOCC5)c4)n3)c3ccccc23)cc1]<br>59: 3-methoxy-5-((4-((4-(3-(1-(4-methoxyphenyl)-3-(tetrahydrofuran-3-yl)-1H-pyrazol-5-yl)ureido)naphthalen-1-yl)oxy)pyrimidin-2-yl)amino)-N-(2-morpholinoethyl)benzamide. | R$^t$ 2.51 min (Method 3); m/z 800 (M + H)$^+$ (ES$^+$); $^1$H NMR δ: 2.05 (1H, m), 2.26 (1H, m), 2.36-2.45 (6H, over-lapping m), 3.29-3.41 (3H, over-lapping m), 3.53-3.56 (7H, over-lapping m), 3.69 (1H, t), 3.76-3.90 (5H, over-lapping m), 4.02 (1H, t), 6.40 (1H, s), 6.53 (1H, d), 6.85 (1H, s), 7.12 (2H, d), 7.32 (1H, s), 7.40 (1H, d), 7.49 (2H, d), 7.54-7.62 (3H, over-lapping m), 7.82 (1H, d), 7.93 (1H, d), 8.05 (1H, d), 8.18 (1H, t), 8.40 (1H, d), 8.77 (1H, s), 9.09 (1H, s), 9.59 (1H, s). |
| 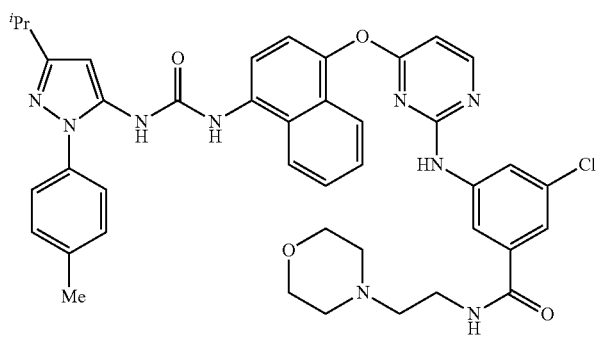 [SMILES: Cc1ccc(-n2nc(C(C)C)cc2NC(=O)Nc2ccc(Oc3ccnc(Nc4cc(Cl)cc(C(=O)NCCN5CCOCC5)c4)n3)c3ccccc23)cc1]<br>60: 3-chloro-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide. | R$^t$ 1.91 min (Method 4); m/z 761 (M + H)$^+$ (ES$^+$), m/z 759 (M − H)$^-$ (ES); $^1$H NMR δ:<br>1.24 (6H, d), 2.36-2.44 (9H, over-lapping m), 2.89 (1H, m), 3.34 (2H, m), 3.53-3.56 (4H, over-lapping m), 6.36 (1H, s), 6.65 (1H, d), 7.27 (1H, m), 7.36-7.42 (3H, over-lapping m), 7.46 (2H, m), 7.55 (1H, m), 7.61 (1H, m), 7.68 (1H, br s), 7.79-7.81 (2H, over-lapping m), 7.97 (1H, d), 8.07 (1H, d), 8.33 (1H, t), 8.45 (1H, d), 8.84 (1H, s), 9.13 (1H, s), 9.87 (1H, s). |

TABLE 3-continued

Additional Compound Examples of the Invention

| Structure, Name and Example No. | Analytical Data [Generic Route] |
|---|---|
| 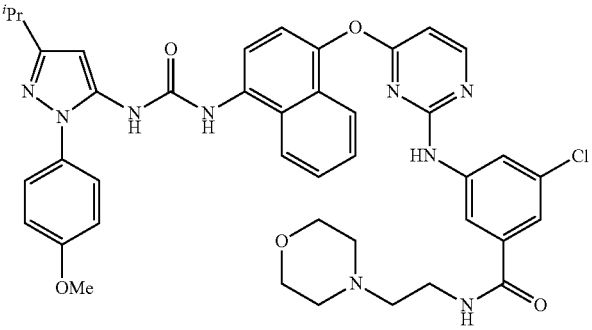 [SMILES: COc1ccc(-n2nc(C(C)C)cc2NC(=O)Nc2ccc(Oc3ccnc(Nc4cc(Cl)cc(C(=O)NCCN5CCOCC5)c4)n3)c3ccccc23)cc1]<br>61: 3-chloro-5-((4-((4-(3-(3-isopropyl-1-(4-methoxy phenyl)-1H-pyrazol-5-yl)ureido)naphthalen-1-yl) oxy)pyrimidin-2-yl)amino)-N-(2-morpholinoethyl)benzamide. | $R^t$ 2.84 min (Method 3); m/z 776, 778 (M + H)$^+$ (ES$^+$), m/z 774, 776 (M − H)$^-$ (ES$^-$); $^1$H NMR δ: 1.24 (6H, d), 2.37-2.44 (6H, over-lapping m), 2.88 (1H, m), 3.37 (2H, m), 3.54-3.56 (4H, over-lapping m), 3.84 (3H, s), 6.35 (1H, s), 6.65 (1H, d), 7.12 (2H, m), 7.27 (1H, s), 7.41 (1H, d), 7.48 (2H, m), 7.56 (1H, m), 7.61 (1H, m), 7.68 (1H, br s), 7.79-7.81 (2H, over-lapping m), 7.98 (1H, d), 8.06 (1H, d), 8.33 (1H, t), 8.45 (1H, d), 8.73 (1H, s), 9.08 (1H, s), 9.87 (1H, s). |
| 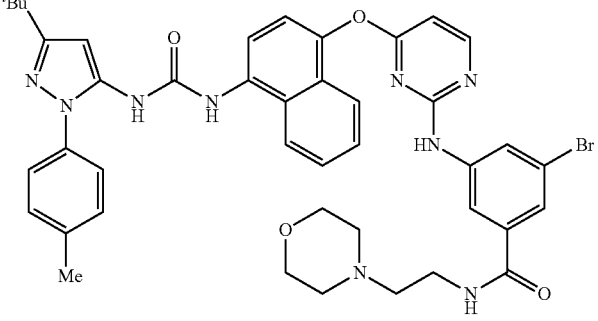<br>62: 3-bromo-5-((4-((4-(3-(3-(tert-butyl)-1-(p-tolyl)-1H-pyrazol-5-yl)ureido)naphthalen-1-yl)oxy) pyrimidin-2-yl)amino)-N-(2-morpholinoethyl)benzamide. | $R^t$ 2.02 min (Method 2 acidic); m/z 818, 820 (M + H)$^+$ (ES$^+$); m/z 816, 818 (M − H)$^-$ (ES$^-$); $^1$H NMR δ: 1.29 (9H, s), 2.37-2.44 (9H, over-lapping m), 3.33 (2H, m), 3.53-3.56 (4H, over-lapping m), 6.40 (1H, s), 6.64 (1H, d), 7.37-7.42 (4H, over-lapping m), 7.46 (2H, m), 7.56 (1H, m), 7.62 (1H, m), 7.80 (1H, m), 7.86 (2H, br s), 7.97 (1H, d), 8.08 (1H, m), 8.34 (1H, m), 8.45 (1H, d), 8.80 (1H, s), 9.12 (1H, s), 9.85 (1H, s).<br>[Compound isolated by preparative HPLC and characterised as its formic acid salt] |
| 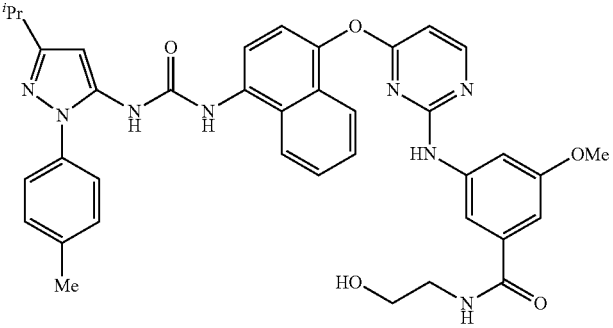 [SMILES: COc1cc(Nc2nccc(Oc3ccc(NC(=O)Nc4cc(C(C)C)nn4-c4ccc(C)cc4)c4ccccc34)n2)cc(C(=O)NCCO)c1]<br>63: N-(2-hydroxyethyl)-3-((4-((4-(3-(3-isopropyl-1-(p-tolyl)-1H-pyrazol-5-yl)ureido)naphthalen-1-yl) oxy)pyrimidin-2-yl)amino)-5-methoxybenzamide. | $R^t$ 2.13 min (Method 2 acidic); m/z 687 (M + H)$^+$ (ES$^+$); $^1$H NMR δ: 1.24 (6H, d), 2.39 (3H, s), 2.90 (1H, m), 3.29 (2H, m), 3.47 (2H, m), 3.57 (3H, s), 4.70 (1H, br s), 6.35 (1H, s), 6.53 (1H, d), 6.89 (1H, m), 7.33-7.38 (4H, over-lapping m), 7.46 (2H, m), 7.56-7.61 (3H, over-lapping m), 7.81 (1H, d), 7.92 (1H, d), 8.08 (1H, d), 8.23 (1H, t), 8.40 (1H, d), 9.00 (1H, br s), 9.28 (1H, br s), 9.58 (1H, br s).<br>[Compound isolated by preparative HPLC and characterised as its formic acid salt.] |
| 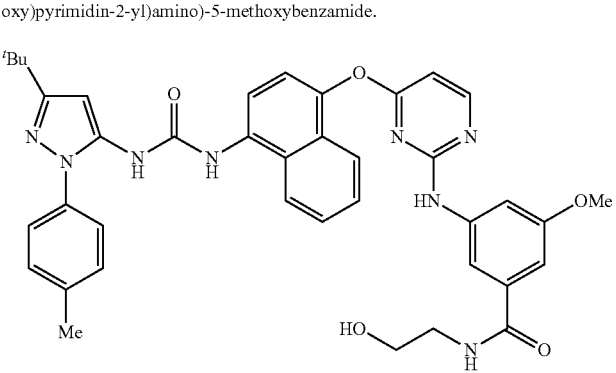<br>64: 3-((4-((4-(3-(3-(tert-butyl)-1-(p-tolyl)-1H-pyrazol-5-yl)ureido)naphthalen-1-yl)oxy) pyrimidin-2-yl)amino)-N-(2-hydroxyethyl)-5-methoxybenzamide. | $R^t$ 2.29 min (Method 2 acidic); m/z 701 (M + H)$^+$ (ES$^+$); $^1$H NMR δ: 1.29 (9H, s), 2.40 (3H, s), 3.29 (2H, m), 3.48 (2H, t), 3.57 (3H, s), 4.69 (1H, br s), 6.40 (1H, s), 6.53 (1H, d), 6.89 (1H, m), 7.33 (1H, br s), 7.36-7.41 (3H, over-lapping m), 7.47 (2H, m), 7.56-7.62 (3H, over-lapping m), 7.82 (1H, d), 7.93 (1H, d), 8.07 (1H, d), 8.22 (1H, t), 8.40 (1H, d), 8.84 (1H, br s), 9.16 (1H, br s), 9.58 (1H, br s).<br>[Compound isolated by preparative HPLC and characterised as its formic acid salt.] |

TABLE 3-continued

Additional Compound Examples of the Invention

| Structure, Name and Example No. | Analytical Data [Generic Route] |
|---|---|
| 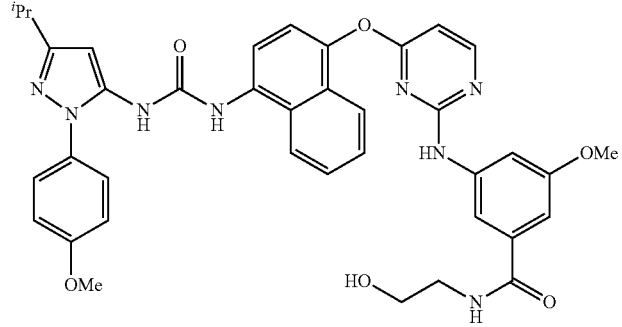 [SMILES: COc1ccc(-n2nc(C(C)C)cc2NC(=O)Nc2ccc(Oc3ccnc(Nc4cc(OC)cc(C(=O)NCCO)c4)n3)c3ccccc23)cc1]<br>65: N-(2-hydroxyethyl)-3-((4-((4-(3-(3-isopropyl-1-(4-methoxyphenyl)-1H-pyrazol-5-yl)ureido)naphthalen-1-yl)oxy)pyrimidin-2-yl)amino)-5-methoxybenzamide. | $R^t$ 2.04 min (Method 2 acidic); m/z 703 (M + H)$^+$ (ES$^+$); $^1$H NMR δ: 1.24 (6H, d), 2.89 (1H, m), 3.29 (2H, m), 3.48 (2H, t), 3.57 (3H, s), 3.83 (3H, s), 4.70 (1H, br s), 6.33 (1H, s), 6.53 (1H, d), 6.90 (1H, m), 7.10 (2H, m), 7.34 (1H, br s), 7.39 (1H, d), 7.49 (2H, m), 7.55-7.60 (3H, over-lapping m), 7.81 (1H, d), 7.91 (1H, d), 8.09 (1H, d), 8.23 (1H, t), 8.40 (1H, d), 9.06 (1H, br s), 9.36 (1H, br s), 9.58 (1H, br s).<br>[Compound isolated by preparative HPLC and characterised as its formic acid salt.] |
| 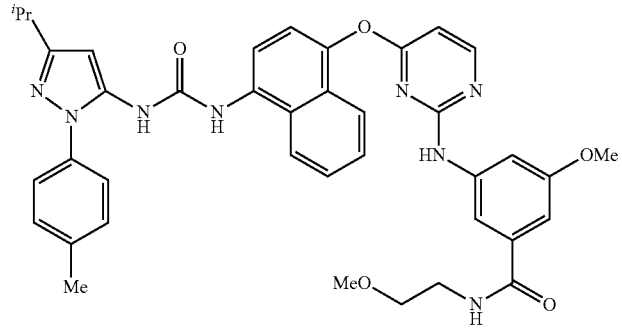 [SMILES: COCCNC(=O)c1cc(Nc2nccc(Oc3ccc(NC(=O)Nc4cc(C(C)C)nn4-c4ccc(C)cc4)c4ccccc34)n2)cc(OC)c1]<br>66: 3-((4-((4-(3-(3-isopropyl-1-(p-tolyl)-1H-pyrazol-5-yl)ureido)naphthalen-1-yl)oxy)pyrimidin-2-yl)amino)-5-methoxy-N-(2-methoxyethyl)benzamide. | $R^t$ 2.32 min (Method 2 acidic); m/z 701 (M + H)$^+$ (ES$^+$); $^1$H NMR δ: 1.25 (6H, d), 2.40 (3H, s), 2.90 (1H, m), 3.26 (3H, s), 3.37-3.43 (4H, over-lapping m), 3.58 (3H, s), 6.36 (1H, s), 6.54 (1H, d), 6.89 (1H, s), 7.36-7.40 (4H, over-lapping m), 7.47 (2H, d), 7.56-7.65 (3H, over-lapping m), 7.82 (1H, d), 7.92 (1H, d), 8.09 (1H, d), 8.32 (1H, t), 8.41 (1H, d), 9.00 (1H, br s), 9.27 (1H, br s), 9.59 (1H, br s).<br>[Compound isolated by preparative HPLC and characterised as its formic acid salt] |
| 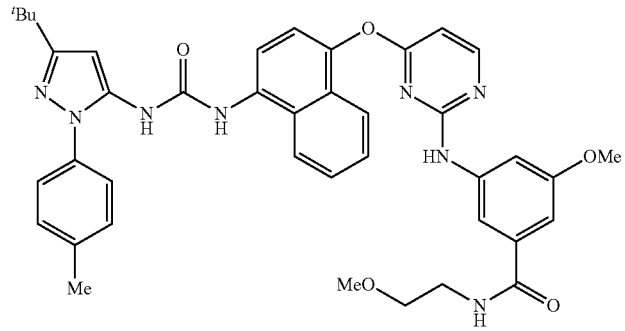 [SMILES: COCCNC(=O)c1cc(Nc2nccc(Oc3ccc(NC(=O)Nc4cc(C(C)(C)C)nn4-c4ccc(C)cc4)c4ccccc34)n2)cc(OC)c1]<br>67: 3-((4-((4-(3-(3-tert-butyl)-1-(p-tolyl)-1H-pyrazol-5-yl)ureido)naphthalen-1-yl)oxy)pyrimidin-2-yl)amino)-5-methoxy-N-(2-methoxyethyl)benzamide. | $R^t$ 2.46 min (Method 2 acidic); m/z 715 (M + H)$^+$ (ES$^+$); $^1$H NMR δ: 1.29 (9H, s), 2.40 (3H, s), 3.25 (3H, s), 3.38-3.42 (4H, over-lapping m), 3.57 (3H, br s), 6.42 (1H, s), 6.54 (1H, d), 6.88 (1H, br t), 7.32 (1H, br s), 7.38-7.40 (3H, over-lapping m), 7.46 (2H, m), 7.54-7.58 (2H, over-lapping m), 7.62 (1H, m), 7.82 (1H, d), 7.95 (1H, d), 8.07 (1H, d), 8.34 (1H, t), 8.41 (1H, d), 8.79 (1H, br s), 9.11 (1H, br s), 9.61 (1H, br s). |

TABLE 3-continued

Additional Compound Examples of the Invention

| Structure, Name and Example No. | Analytical Data [Generic Route] |
|---|---|
| 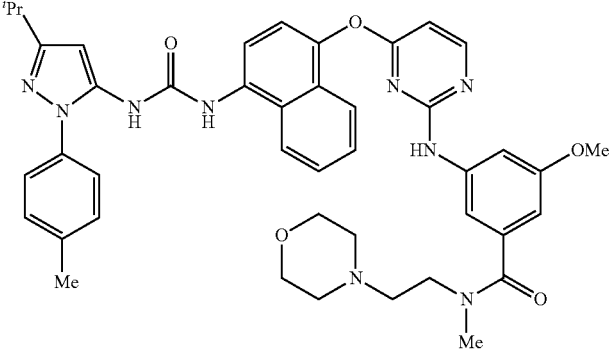 [SMILES: COc1cc(Nc2nccc(Oc3ccc(NC(=O)Nc4cc(C(C)C)nn4-c4ccc(C)cc4)c4ccccc34)n2)cc(C(=O)N(C)CCN2CCOCC2)c1]<br>68: 3-((4-((4-(3-(3-isopropyl-1-(p-tolyl)-1H-pyrazol-5-yl)ureido)naphthalen-1-yl)oxy)pyrimidin-2-yl)amino)-5-methoxy-N-methyl-N-(2-morpholino ethyl)benzamide. | $R^t$ 1.80 min (Method 2 acidic); m/z 770 (M + H)$^+$ (ES$^+$); $^1$H NMR δ: 1.24 (6H, d), 2.13 (2H, br s), 2.35-2.40 (7H, over-lapping m), 2.80-2.91 (4H, over-lapping m), 3.22 (1H, br s), 3.43 (2H, br s), 3.55 (6H, br s), 6.36 (2H, s), 6.56 (1H, d), 7.14-7.20 (2H, over-lapping m), 7.38 (3H, t), 7.46 (2H, d), 7.56-7.62 (2H, over-lapping m), 7.81 (1H, d), 7.92 (1H, d), 7.07 (1H, d), 8.42 (1H, d), 8.83 (1H, s), 9.12 (1H, br s), 9.61 (1H, br s). Compound isolated by preparative HPLC and characterised as its formic acid salt.] |
| 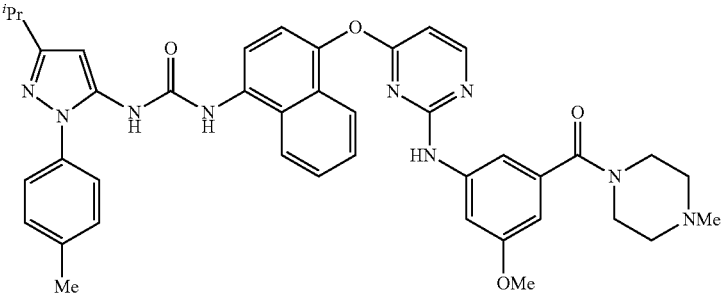 [SMILES: COc1cc(Nc2nccc(Oc3ccc(NC(=O)Nc4cc(C(C)C)nn4-c4ccc(C)cc4)c4ccccc34)n2)cc(C(=O)N2CCN(C)CC2)c1]<br>69: 1-(3-isopropyl-1-(p-tolyl)-1H-pyrazol-5-yl)-3-(4-((2-((3-methoxy-5-(4-methylpiperazine-1-carbonyl)phenyl)amino)pyrimidin-4-yl)oxy)naphthalen-1-yl)urea. | $R^t$ 1.70 min (Method 2 acidic); m/z 726 (M + H)$^+$ (ES$^+$); $^1$H NMR δ: 1.24 (6H, d), 2.31-2.43 (7H, over-lapping m), 2.90 (1H, m), 3.44-3.54 (10H, over-lapping m), 6.36 (1H, s), 6.41 (1H, s), 6.57 (1H, d), 7.16 (1H, br s), 7.25 (1H, br s), 7.37-7.39 (3H, over-lapping m), 7.47 (2H, d), 7.56-7.62 (2H, over-lapping m), 7.80 (1H, d), 7.93 (1H, d), 8.11 (1H, d), 8.42 (1H, d), 8.93 (1H, br s), 9.19 (1H, br s), 9.63 (1H, br s). [Compound isolated by preparative HPLC and characterised as its formic acid salt.] |
| 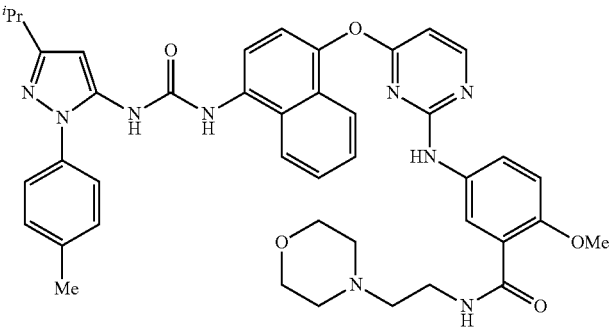 [SMILES: COc1ccc(Nc2nccc(Oc3ccc(NC(=O)Nc4cc(C(C)C)nn4-c4ccc(C)cc4)c4ccccc34)n2)cc1C(=O)NCCN1CCOCC1]<br>70: 5-((4-((4-(3-(3-isopropyl-1-(p-tolyl)-1H-pyrazol-5-yl)ureido)naphthalen-1-yl)oxy)pyrimidin-2-yl)amino)-2-methoxy-N-(2-morpholinoethyl)benzamide. | $R^t$ 2.83 min (Method 3); m/z 756 (M + H)$^+$ (ES$^+$); $^1$H NMR δ: 1.24 (6H, d), 2.40-2.45 (9H, over-lapping m), 2.89 (1H, m), 3.36 (2H, m), 3.57-3.59 (4H, over-lapping m), 3.80 (3H, s), 6.36 (1H, s), 6.55 (1H, d), 6.78 (1H, m), 7.37-7.43 (4H, over-lapping m), 7.47 (2H, m), 7.53-7.63 (2H, over-lapping m), 7.81 (2H, m), 7.90 (1H, d), 8.06 (1H, d), 8.30 (1H, m), 8.35 (1H, d), 8.79 (1H, s), 9.14 (1H, s), 9.50 (1H, s). |
| 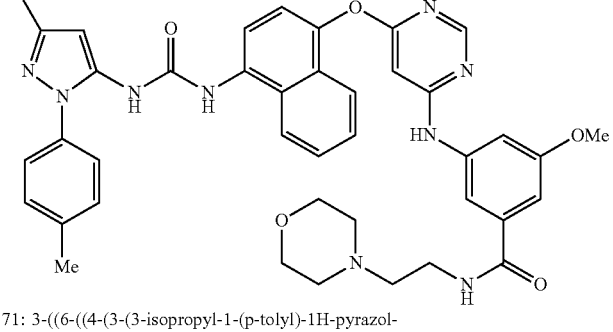<br>71: 3-((6-((4-(3-(3-isopropyl-1-(p-tolyl)-1H-pyrazol-5-yl)ureido)naphthalen-1-yl)oxy)pyrimidin-4-yl)amino)-5-methoxy-N-(2-morpholinoethyl)benzamide. | $R^t$ 1.74 min (Method 4); m/z 756 (M + H)$^+$ (ES$^+$); m/z 754 (M − H)$^-$ (ES$^-$); $^1$H NMR δ: 1.24 (6H, d), 2.38-2.52 (9H, over-lapping m), 2.89 (1H, m), 3.34 (2H, m), 3.55-3.57 (4H, over-lapping m), 3.75 (3H, s), 6.15 (1H, s), 6.37 (1H, s), 7.02 (1H, m), 7.34-7.40 (3H, over-lapping m), 7.44-7.49 (3H, over-lapping m), 7.54-7.61 (3H, over-lapping m), 7.81 (1H, d), 7.92 (1H, d), 8.06 (1H, d), 8.30-8.37 (2H, over-lapping m), 8.77 (1H, br s), 9.10 (1H, br s), 9.67 (1H, br s). |

TABLE 3-continued

Additional Compound Examples of the Invention

| Structure, Name and Example No. | Analytical Data [Generic Route] |
|---|---|
| 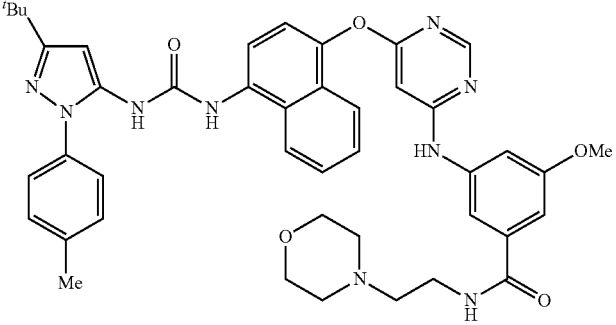<br>72: 3-((6-((4-(3-(3-(tert-butyl)-1-(p-tolyl)-1H-pyrazol-5-yl)ureido)naphthalen-1-yl)oxy)pyrimidin-4-yl)amino)-5-methoxy-N-(2-morpholinoethyl)benzamide. | $R^t$ 1.86 min (Method 4); m/z 770 (M + H)$^+$ (ES$^+$); m/z 768 (M − H)$^-$ (ES$^-$); $^1$H NMR δ:<br>1.29 (9H, s), 2.38-2.53 (9H, over-lapping m), 3.35 (2H, m), 3.55-3.57 (4H, over-lapping m), 3.77 (3H, s), 6.15 (1H, m), 6.41 (1H, s), 7.02 (1H, m), 7.34-7.40 (3H, over-lapping m), 7.44-7.50 (3H, over-lapping m), 7.53-7.66 (3H, over-lapping m), 7.80 (1H, d), 7.92 (1H, d), 8.07 (1H, d), 8.30-8.35 (2H, over-lapping m), 8.79 (1H, br s), 9.14 (1H, br s), 9.67 (1H, br s).<br>[Compound isolated by preparative HPLC and characterised as its formic acid salt.] |

Example 73

3-((4-((4-(3-(3-(tert-Butyl)-1-(6-methoxypyridin-3-yl)-1H-pyrazol-5-yl) ureido)naphthalen-1-yl)oxy) pyrimidin-2-yl)amino)-5-ethynyl-N-(2-morpholino-ethyl)benzamide

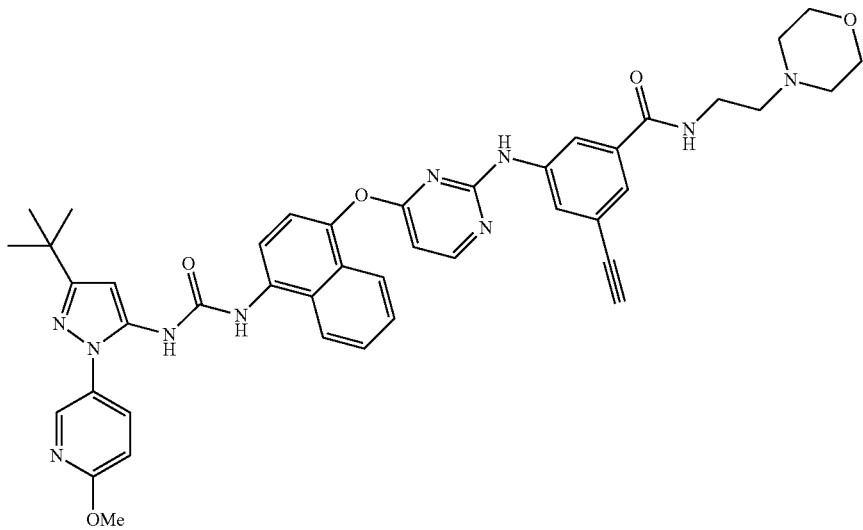 [SMILES: C#Cc1cc(Nc2nccc(Oc3ccc(NC(=O)Nc4cc(C(C)(C)C)nn4-c4ccc(OC)nc4)c4ccccc34)n2)cc(C(=O)NCCN2CCOCC2)c1]

To a stirred solution of Intermediate A11* (150 mg, 0.389 mmol) and Intermediate B21 (198 mg, 0.389 mmol) in iso-propyl acetate (5 mL) was added triethylamine (10 µL, 0.072 mmol). The resulting mixture was heated at 70° C. for 90 min. The reaction was cooled to rt and the solvent removed in vacuo. The crude product was purified by chromatography on silica gel (40 g column, 0-10% MeOH in DCM) to afford a white solid, which was triturated with diethyl ether to afford the title compound (198 mg) as a white solid.

$^1$H NMR (DMSO-d6) 400 MHz, δ: 9.76 (s, 1H), 9.07 (s, 1H), 8.82 (s, 1H), 8.43 (d, 1H), 8.41-8.40 (m, 1H), 8.39-8.34 (br m, 1H), 8.05-8.03 (m, 2H), 7.93-7.90 (m, 2H), 7.87-7.83 (br s, 1H), 7.83-7.80 (m, 1H), 7.64-7.60 (m, 1H), 7.59-7.55 (m, 1H), 7.43-7.41 (m, 2H), 7.04-7.02 (m, 1H), 6.56 (d, 1H), 6.43 (s, 1H), 4.12 (s, 1H), 3.94 (s, 3H), 3.58-3.52 (br m, 4H), 2H under H$_2$O at 3.34 ppm, 2.47-2.34 (m, 6H), 1.29 (s, 9H).

LCMS m/z 781 (M+H)$^+$ (ES$^+$); 779 (M−H)$^-$ (ES$^-$)

Example 74

3-Ethynyl-N-(2-morpholinoethyl)-5-((4-((4-(3-(3-(perfluoroethyl)-1-(p-tolyl)-1H-pyrazol-5-yl)ureido)naphthalen-1-yl)oxy)pyrimidin-2-yl)amino)benzamide

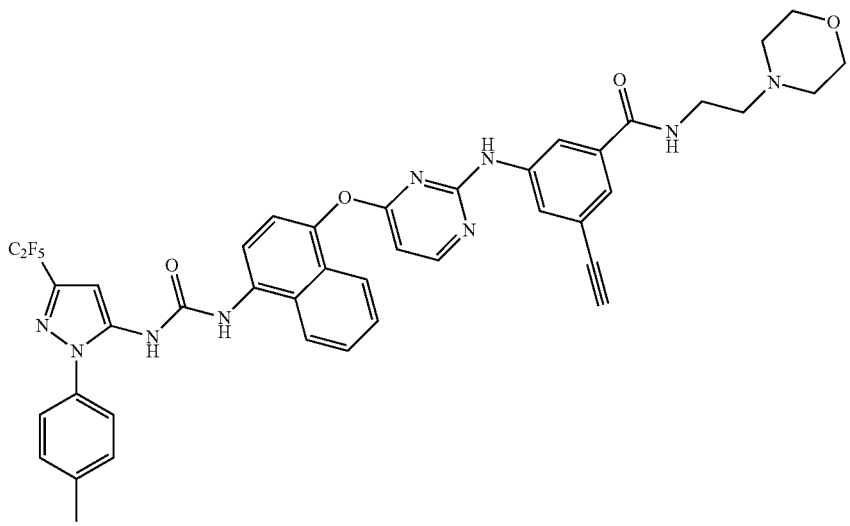

Triethylamine (4.00 µL, 0.029 mmol) was added to a mixture of Intermediate A3* (56.6 mg, 0.138 mmol) and Intermediate B21 (70 mg, 0.138 mmol) in isopropyl acetate (1.6 mL) and the mixture heated at 60° C. for 1 h during which time a thick suspension was formed. The reaction was cooled to rt and diluted with DCM and MeOH (3:1, 15 mL). The solution was concentrated onto silica gel. The crude product was purified by chromatography on the Companion (40 g column, 0-10% MeOH in DCM) to afford the title compound (78 mg) as a white solid.

$^1$H NMR (DMSO-d6) 400 MHz, δ: 9.77 (s, 1H), 9.24 (s, 1H), 9.13 (s, 1H), 8.45 (d, 1H), 8.37 (t, 1H), 8.04-8.06 (m, 2H), 7.94 (d, 1H), 7.82-7.85 (m, 2H), 7.56-7.66 (m, 4H), 7.43-7.49 (m, 4H), 6.94 (s, 1H), 6.58 (d, 1H), 4.13 (s, 1H), 3.55 (t, 4H), 3.32-3.37 (m, 2H), 2.39-2.45 (m, 9H)

LCMS m/z 826 (M+H)$^+$ (ES$^+$)

Example 75

3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(2-morpholinoethyl)benzamide

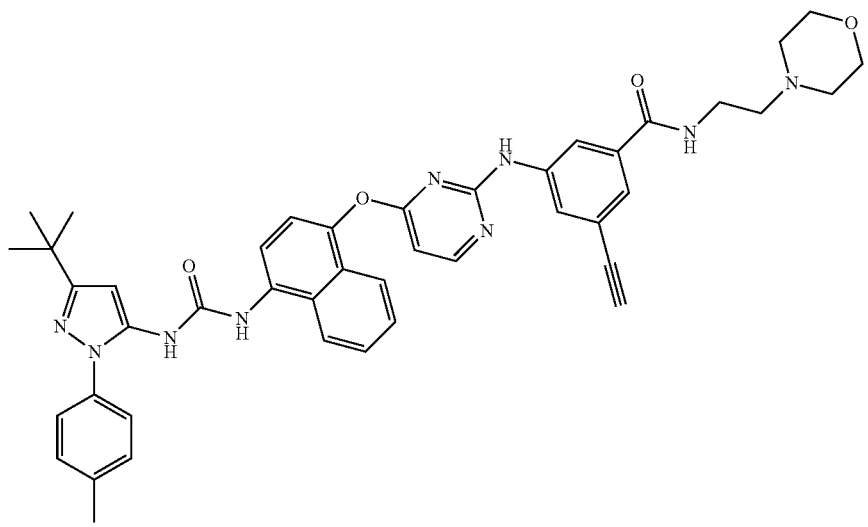 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NCCN2CCOCC2)c1]

To Intermediate A8* (150 mg, 0.429 mmol) stirring in iso-propyl acetate (5 mL) under $N_2$ at rt, was added Intermediate B21 (218 mg, 0.429 mmol) followed by triethylamine (9.27 µL, 0.067 mmol), and the reaction mixture heated to 70° C. for 90 min. Reaction was stopped and the mixture diluted with EtOAc (5 mL) before filtering and washing with further EtOAc (2×20 mL). Precipitate was dried under vacuum affording the title compound (228 mg) as a white solid.

$^1$H NMR (DMSO-d6) 400 MHz, δ 9.76 (s, 1H), 9.10 (s, 1H), 8.78 (s, 1H), 8.44 (d, 1H), 8.42 (br s, 1H), 8.04 (d, 2H), 7.93 (d, 1H), 7.85 (br s, 1H), 7.81 (d, 1H), 7.63 (t, 1H), 7.57 (t, 1H), 7.42 (m, 6H), 6.56 (d, 1H), 6.41 (s, 1H), 4.12 (s, 1H), 3.55 (br s, 4H), 3.33 (m, 2H), 2.40 (m, 9H), 1.29 (s, 9H).

LCMS m/z 764 (M+H)$^+$ (ES$^+$)

Example 76

3-Ethynyl-N-(2-morpholinoethyl)-5-((4-((4-(3-(1-(p-tolyl)-3-(1,1,1-trifluoro-2-methylpropan-2-yl)-1H-pyrazol-5-yl)ureido)naphthalen-1-yl)oxy)pyrimidin-2-yl)amino)-benzamide

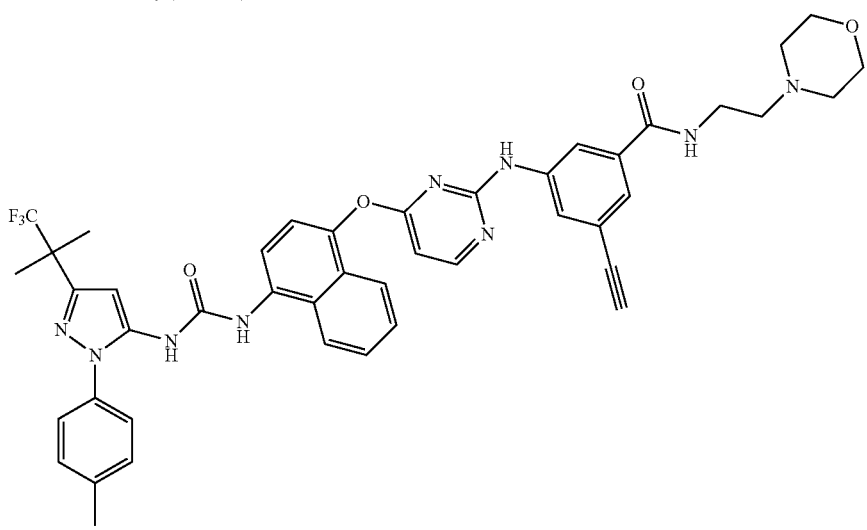

Triethylamine (5 µL, 0.036 mmol) was added to a mixture of Intermediate A19* (70 mg, 0.174 mmol) and Intermediate B21 (100 mg, 0.189 mmol) in isopropyl acetate (2 mL) and the mixture heated at 50° C. for 2 h. The resulting solid was collected by filtration and washed with isopropyl acetate (2 mL) followed by isohexane (2 mL). The filter cake was resuspended in acetonitrile (2 mL) and collected by filtration to afford the title compound (65 mg) as a white solid.

$^1$H NMR (DMSO-d6) 400 MHz, δ: 9.75 (s, 1H), 9.14 (s, 1H), 8.88 (s, 1H), 8.44 (d, 1H), 8.35 (d, 1H), 8.10-8.01 (m, 2H), 7.94 (d, 1H), 7.89-7.79 (m, 2H), 7.68-7.54 (m, 2H), 7.54-7.37 (m, 6H), 6.60 (s, 1H), 6.56 (d, 1H), 4.11 (s, 1H), 3.60-3.51 (m, 4H), 2H under water peak, 2.48-2.31 (m, 6H), 2.42 (s, 3H), 1.53 (s, 6H).

LCMS m/z 818 (M+H)$^+$ (ES$^+$); 816 (M−H)$^−$ (ES$^−$)

Example 77

3-((4-((4-(3-(3-(tert-Butyl)-1-(4-methoxyphenyl)-1H-pyrazol-5-yl)ureido)-naphthalen-1-yl)oxy)pyrimidin-2-yl)amino)-5-ethynyl-N-(2-morpholinoethyl)benzamide

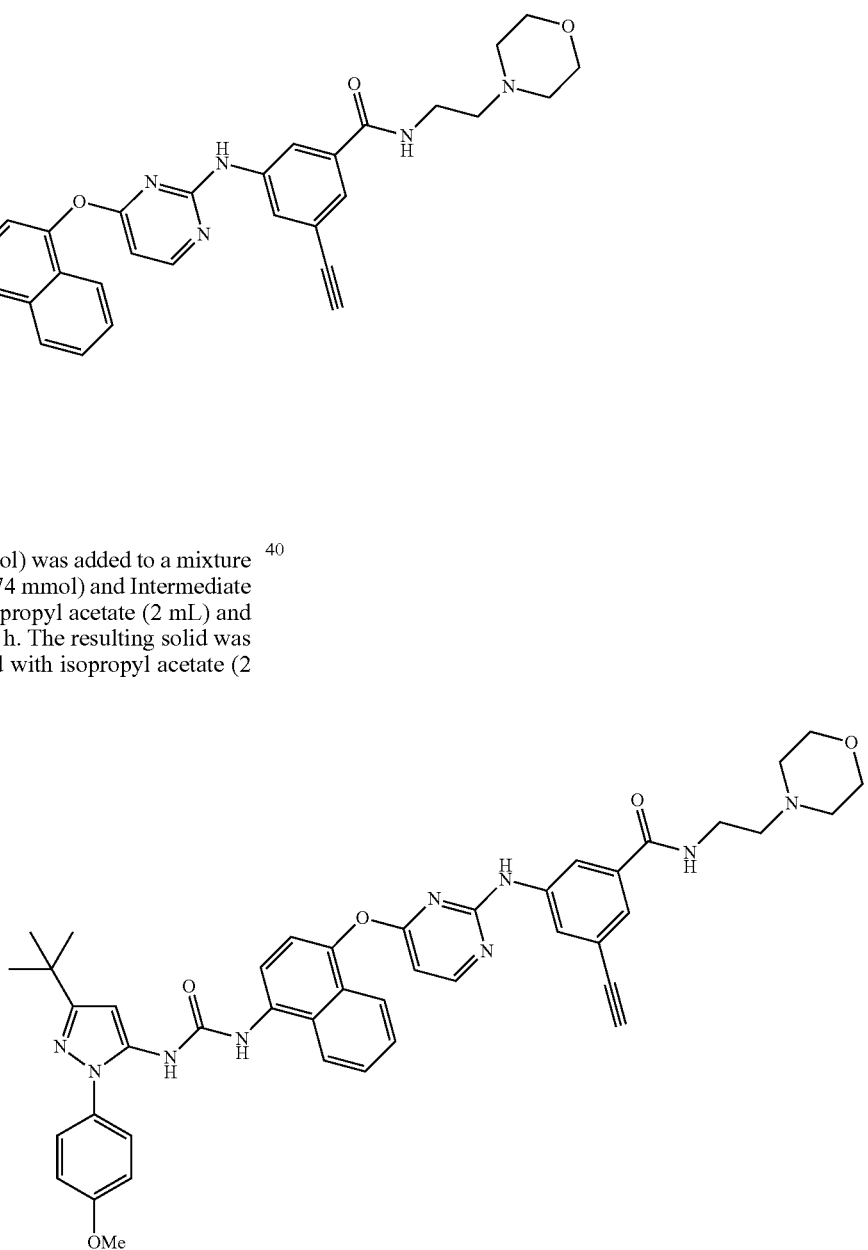

Triethylamine (5 μL, 0.036 mmol) was added to a mixture of Intermediate A9* (70 mg, 0.192 mmol) and Intermediate B21 (111 mg, 0.209 mmol) in isopropyl acetate (2 mL) and the mixture heated at 50° C. for 2 h. The resulting solid was collected by filtration and washed with isopropyl acetate (2 mL) followed by isohexane (2 mL). The filter cake was resuspended in acetonitrile (4 mL) and collected by filtration to afford the title compound (45 mg) as a white solid.

$^1$H NMR (DMSO-d6) 400 MHz, δ: 9.75 (s, 1H), 9.08 (s, 1H), 8.72 (s, 1H), 8.43 (s, 1H), 8.39-8.30 (m, 1H), 8.09-8.01 (m, 2H), 7.94 (d, 1H), 7.88-7.79 (m, 2H), 7.66-7.60 (m, 1H), 7.60-7.54 (m, 1H), 7.52-7.46 (m, 2H), 7.45-7.40 (m, 2H), 7.15-7.10 (m, 2H), 6.55 (d, 1H), 6.40 (s, 1H), 4.11 (s, 1H), 3.84 (s, 3H), 3.60-3.50 (m, 4H), 3.39-3.31 (m, 2H), 2.48-2.32 (m 6H), 1.29 (s, 9H).

LCMS m/z 780 (M+H)$^+$ (ES$^+$); 778 (M−H)$^−$ (ES$^−$)

Example 78

3-((4-((4-(3-(3-(2-Cyanopropan-2-yl)-1-(p-tolyl)-1H-pyrazol-5-yl)ureido)-naphthalen-1-yl)oxy)pyrimidin-2-yl)amino)-5-ethynyl-N-(2-morpholinoethyl)benzamide Intermediate B21 (99 mg, 0.194 mmol) in isopropyl acetate (2 mL) and the mixture heated at 60° C. for 1 h during which time a thick suspension was formed. The suspension was filtered and the solid obtained was dried at 40° C. under vacuum affording the title compound (118 mg) as a white solid.

$^1$H NMR (DMSO-d6) 400 MHz, δ: 9.77 (s, 1H), 9.16 (s, 1H), 8.94 (s, 1H), 8.44 (d, 1H), 8.37 (t, 1H), 8.05-8.07 (m, 2H), 7.95 (d, 1H), 7.82-7.86 (m, 2H), 7.56-7.66 (m, 2H), 7.51 (d, 2H), 7.42-7.45 (m, 4H), 6.63 (s, 1H), 6.57 (d, 1H), 4.12 (s, 1H), 3.56 (t, 4H), 2H under water peak, 2.39-2.45 (m, 6H), 2.43 (s, 3H), 1.71 (s, 6H).

LCMS m/z 388 (M+2H)$^{2+}$ (ES$^+$)

Example 79

3-Ethynyl-5-((4-((4-(3-(3-(2-methoxypropan-2-yl)-1-(p-tolyl)-1H-pyrazol-5-yl)ureido)naphthalen-1-yl)oxy)pyrimidin-2-yl)amino)-N-(2-morpholinoethyl)benzamide

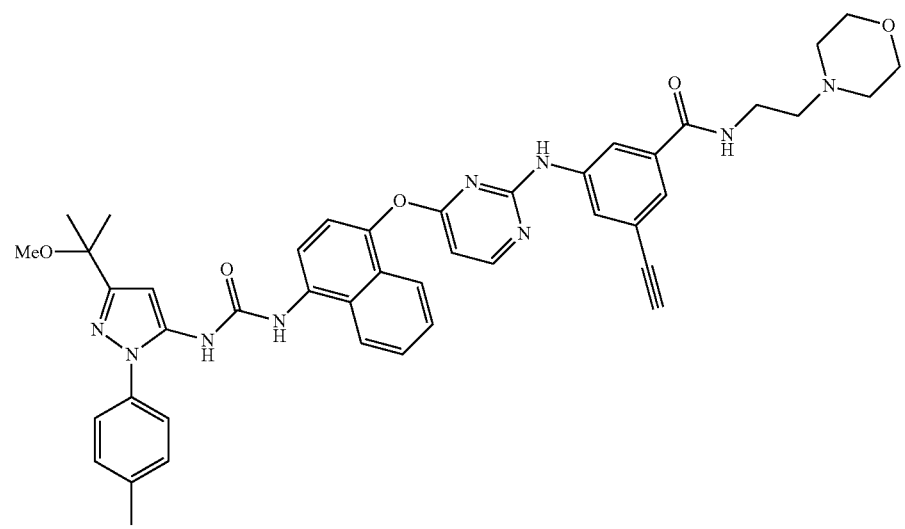 [SMILES: C#Cc1cc(Nc2nccc(Oc3ccc(NC(=O)Nc4cc(C(C)(C)OC)nn4-c4ccc(C)cc4)c4ccccc34)n2)cc(C(=O)NCCN2CCOCC2)c1]

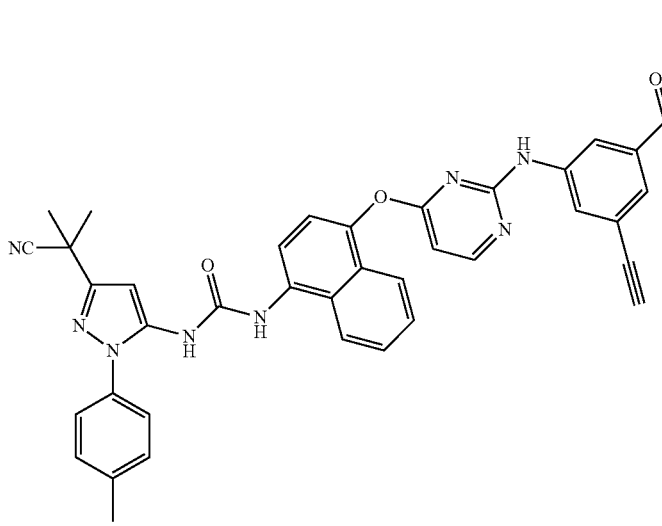

Triethylamine (6.00 μL, 0.043 mmol) was added to a mixture of Intermediate A20* (70 mg, 0.194 mmol) and Triethylamine (6.00 μL, 0.043 mmol) was added to a mixture of Intermediate A22* (70 mg, 0.192 mmol) and Intermediate B21 (97 mg, 0.192 mmol) in isopropyl acetate (2 mL) and the mixture heated at 60° C. for 1 h during which time a thick suspension was formed. The mixture was filtered and the resulting solid dried at 40° C. under vacuum overnight. The material was triturated in a mixture of Et$_2$O and EtOAc (2:1) with sonication and the suspended solid re-isolated by filtration, washing with EtOAc. The material was dried at 40° C. under vacuum affording the title compound (38 mg) as pale grey solid.

$^1$H NMR (DMSO-d6) 400 MHz, δ: 9.77 (s, 1H), 9.12 (s, 1H), 8.85 (s, 1H), 8.44 (d, 1H), 8.37 (t, 1H), 8.06-8.08 (m, 2H), 7.94 (d, 1H), 7.86 (s, 1H), 7.82 (d, 1H), 7.56-7.65 (m, 2H), 7.49 (d, 2H), 7.40-7.45 (m, 4H), 6.57 (d, 1H), 6.48 (s, 1H), 4.13 (s, 1H), 3.56 (t, 4H), 2H under water peak, 3.05 (s, 3H), 2.40-2.45 (m, 6H), 2.42 (s, 3H), 1.48 (s, 6H).

LCMS m/z 391 (M+2H)$^{2+}$ (ES+)

Example 80

3-((4-((4-(3-(3-(tert-Butyl)-1-(4-(dimethylamino) phenyl)-1H-pyrazol-5-yl)ureido)naphthalen-1-yl) oxy)pyrimidin-2-yl)amino)-5-ethynyl-N-(2-morpholinoethyl)-benzamide DPPA (107 μL, 0.496 mmol) was added to a stirred solution of Intermediate M1 (95 mg, 0.331 mmol) and triethylamine (92 μL, 0.661 mmol) in DMF (3 mL) at 0° C. The mixture was allowed to warm to rt and stir for 45 min. Intermediate B21 (177 mg, 0.347 mmol) was added and the mixture was heated to 100° C. for 2 h. The mixture was diluted with water (10 mL) and extracted with ethyl acetate (3×10 mL). The combined organic phases were washed with saturated brine (10 mL), dried (MgSO$_4$) and concentrated under reduced pressure. The crude product was purified by chromatography on the Companion (40 g column, 0-10% MeOH/DCM) to afford a pale brown gum. The gum was stirred in acetonitrile for 18 h and the precipitate was collected by filtration to yield the title compound (88 mg) as a white solid.

$^1$H NMR (DMSO-d6) 400 MHz, δ: 9.76 (s, 1H), 9.13 (s, 1H), 8.68 (s, 1H), 8.44 (d, 1H), 8.41-8.31 (m, 1H), 8.11-8.03 (m, 2H), 7.97 (d, 1H), 7.86 (s, 1H), 7.82 (d, 1H), 7.66-7.60 (m, 1H), 7.60-7.54 (m, 1H), 7.45-7.39 (m, 2H), 7.38-7.31 (m, 2H), 6.91-6.83 (m, 2H), 6.46 (d, 1H), 6.38 (s, 1H), 4.12 (s, 1H), 3.60-3.50 (m, 4H), 2H under water peak, 3.02-2.93 (m, 6H), 2.48-2.30 (s, 6H), 1.28 (s, 9H).

LCMS m/z 793 (M+H)$^+$ (ES$^+$); 791 (M–H)$^-$ (ES$^-$)
LCMS m/z 813 (M+H)$^+$ (ES$^+$)

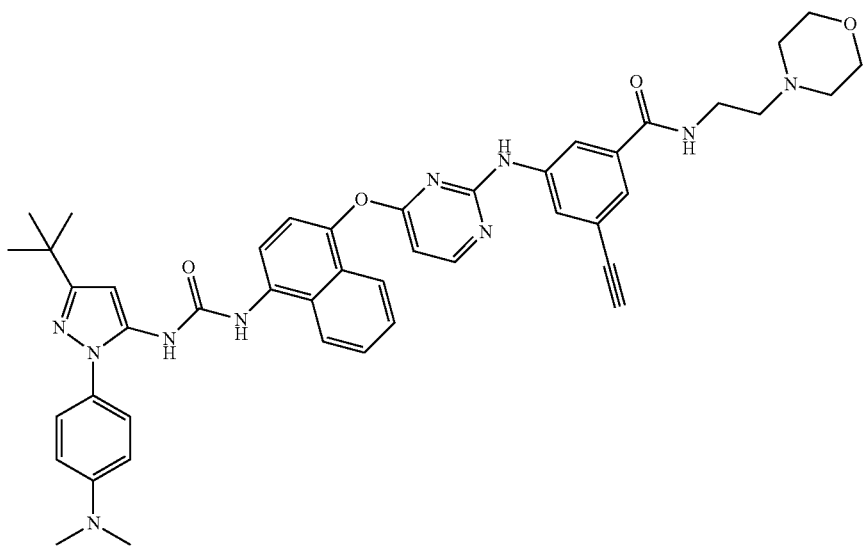 [SMILES: C#Cc1cc(Nc2nccc(Oc3ccc(NC(=O)Nc4cc(C(C)(C)C)nn4-c4ccc(N(C)C)cc4)c4ccccc34)n2)cc(C(=O)NCCN2CCOCC2)c1]

Example 81

(S)-3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(1-morpholinopropan-2-yl)benzamide

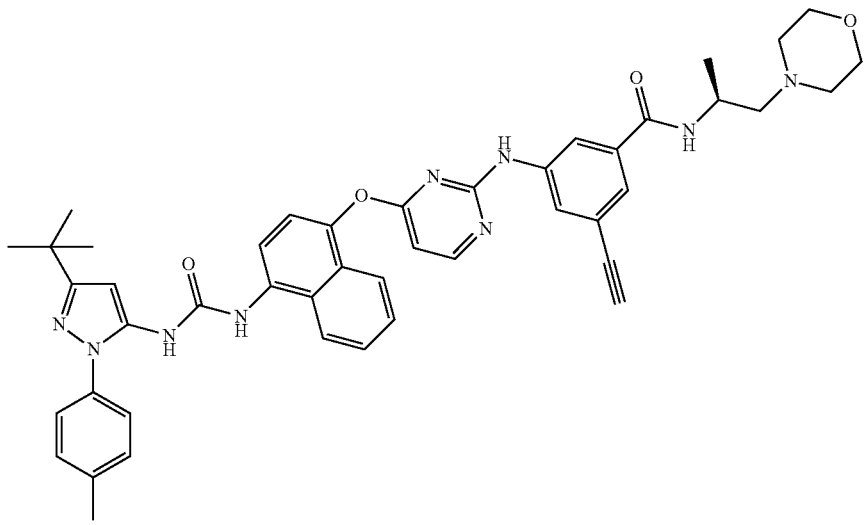 [SMILES: C#Cc1cc(Nc2nccc(Oc3ccc(NC(=O)Nc4cc(C(C)(C)C)nn4-c4ccc(C)cc4)c4ccccc34)n2)cc(C(=O)N[C@@H](C)CN2CCOCC2)c1]

Triethylamine (5.00 µl, 0.036 mmol) was added to a mixture of Intermediate A8* (60 mg, 0.172 mmol) and Intermediate B22 (100 mg, 0.191 mmol) in isopropyl acetate (3 mL) and the mixture heated at 60° C. for 1 h during which time a gel-like solid was formed. The reaction was cooled to rt and diluted with EtOAc. The suspended solid was collected by filtration, washing with further EtOAc. The recovered solid was dried at 40° C. under vacuum overnight affording the title compound (87 mg) as a beige solid.

$^1$H NMR (DMSO-d6) 400 MHz, δ: 9.74 (s, 1H), 9.08 (s, 1H), 8.76 (s, 1H), 8.44 (d, 1H), 8.13 (d, 1H), 8.05-8.08 (m, 2H), 7.94 (d, 1H), 7.88 (s, 1H), 7.83 (d, 1H), 7.56-7.65 (m, 2H), 7.37-7.48 (m, 6H), 6.55 (d, 1H), 6.41 (s, 1H), 4.13-4.20 (m, 1H), 4.11 (s, 1H), 3.53 (t, 4H), 2.34-2.44 (m, 8H), 2.26 (dd, 1H), 1.30 (s, 9H), 1.12 (d, 3H).

LCMS m/z 778 (M+H)$^+$ (ES$^+$)

Example 82

3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(2-methyl-1-morpholinopropan-2-yl)-benzamide

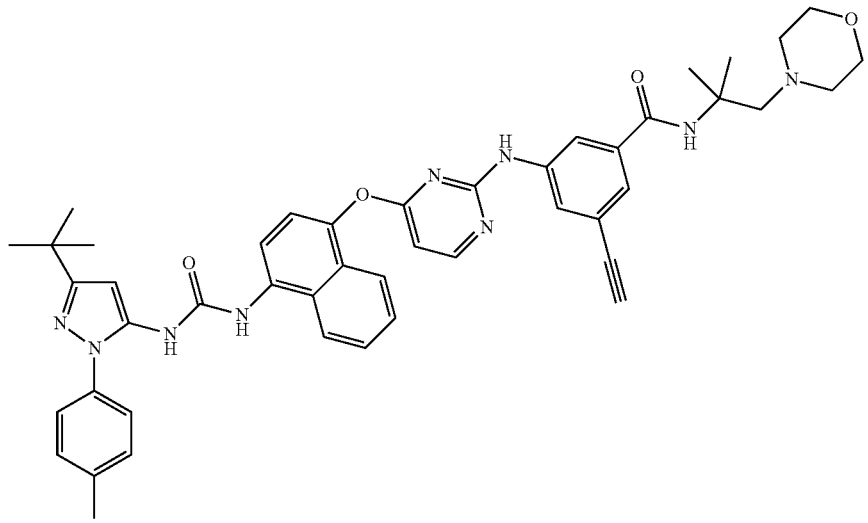 [SMILES: C#Cc1cc(Nc2nccc(Oc3ccc(NC(=O)Nc4cc(C(C)(C)C)nn4-c4ccc(C)cc4)c4ccccc34)n2)cc(C(=O)NC(C)(C)CN2CCOCC2)c1]

Triethylamine (10.0 µL, 0.072 mmol) was added to a mixture of Intermediate A8* (118 mg, 0.339 mmol) and Intermediate B23 (200 mg, 0.373 mmol) in isopropyl acetate (4 mL) and the mixture heated at 60° C. for 1 h during which time a gel-like solid was formed. The reaction mixture was cooled to rt and diluted with EtOAc. The solid was collected by filtration washing with EtOAc. The solid obtained was further dried at 40° C. under vacuum to afford the title compound (201 mg) as a white solid.

$^1$H NMR (DMSO-d6) 400 MHz, δ: 9.72 (s, 1H), 9.09 (s, 1H), 8.76 (s, 1H), 8.44 (d, 1H), 8.07 (d, 1H), 7.93-7.97 (m, 2H), 7.87 (s, 1H), 7.83 (d, 1H), 7.56-7.66 (m, 3H), 7.37-7.46 (m, 6H), 6.55 (d, 1H), 6.41 (s, 1H), 4.09 (s, 1H), 3.53 (t, 4H), 2.61 (s, 2H), 2.47 (t, 4H), 2.41 (s, 3H), 1.31 (s, 6H), 1.30 (s, 9H).

LCMS m/z 793 (M+H)$^+$ (ES$^+$)

Example 83

(R)-3-((4-((4-(3-(3-(tert-Butyl)-1-(p-tolyl)-1H-pyrazol-5-yl)ureido)naphthalen-1-yl)oxy)pyrimidin-2-yl)amino)-5-ethynyl-N-(1-morpholinopropan-2-yl)benzamide

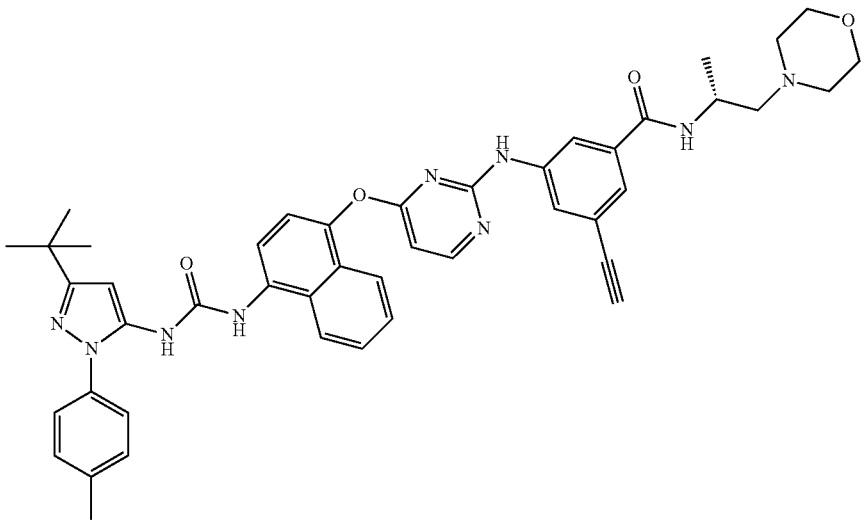 [SMILES: C#Cc1cc(Nc2nccc(Oc3ccc(NC(=O)Nc4cc(C(C)(C)C)nn4-c4ccc(C)cc4)c4ccccc34)n2)cc(C(=O)N[C@H](C)CN2CCOCC2)c1]

Triethylamine (6.00 µL, 0.043 mmol) was added to a mixture of Intermediate A8* (72.9 mg, 0.209 mmol) and Intermediate B24 (120 mg, 0.230 mmol) in isopropyl acetate (4 mL) and the mixture heated at 60° C. for 1 h during which time a gel-like solid was formed. The reaction was cooled to rt and diluted with EtOAc. The suspended solid was collected by filtration, washing with further EtOAc. The recovered solid was dried at 40° C. under vacuum overnight to afford the title compound (111 mg) as a pale beige solid.

$^1$H NMR (DMSO-d6) 400 MHz, δ: 9.74 (s, 1H), 9.08 (s, 1H), 8.76 (s, 1H), 8.44 (d, 1H), 8.13 (d, 1H), 8.05-8.08 (m, 2H), 7.94 (d, 1H), 7.88 (s, 1H), 7.83 (d, 1H), 7.56-7.65 (m, 2H), 7.37-7.48 (m, 6H), 6.55 (d, 1H), 6.41 (s, 1H), 4.13-4.20 (m, 1H), 4.11 (s, 1H), 3.53 (t, 4H), 2.34-2.44 (m, 8H), 2.26 (dd, 1H), 1.30 (s, 9H), 1.12 (d, 3H).

LCMS m/z 390 (M+2H)$^{2+}$ (ES$^+$)

Example 84

3-((4-((4-(3-(3-(tert-Butyl)-1-(4-methoxyphenyl)-1H-pyrazol-5-yl)ureido)-naphthalen-1-yl)oxy)pyrimidin-2-yl)amino)-5-ethynyl-N-(2-methoxyethyl)benzamide

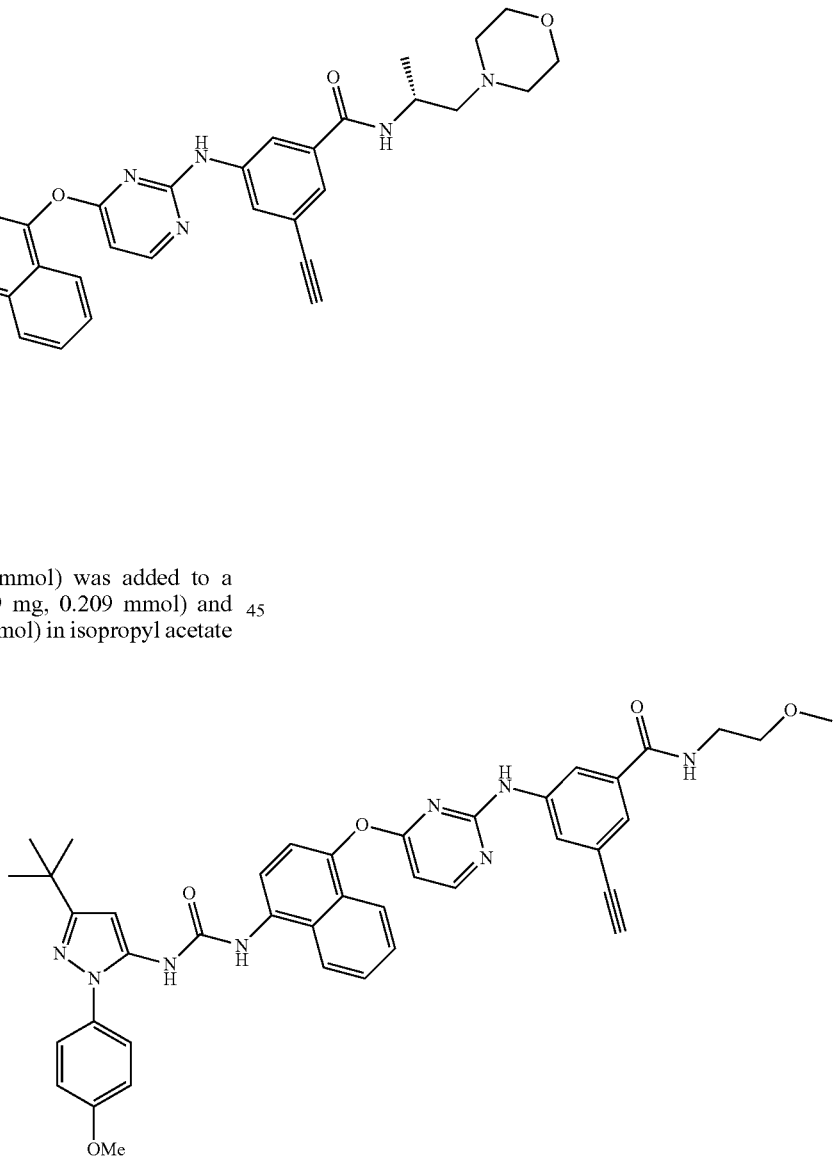

To a stirred solution of Intermediate C3 (152 mg, 0.274 mmol) and Intermediate D4 (95 mg, 0.411 mmol) in DMF (4 mL) was added p-TSA monohydrate (26 mg, 0.137 mmol). The resulting solution was heated at 60° C. overnight. The reaction was cooled to it and partitioned between EtOAc (30 mL) and sat aq. NaHCO₃ (30 mL). The aqueous phase was back extracted with EtOAc (30 mL). The combined organic extracts were washed with water (2×50 mL), brine (50 mL), dried (MgSO₄), filtered and concentrated in vacuo to afford an orange solid (236 mg). The crude product was purified by chromatography on silica gel (40 g column, 0-10% MeOH in DCM) to afford pink solid, which was triturated with Et₂O to afford the title compound (79 mg) as a white solid.

¹H NMR (DMSO-d6) 400 MHz, δ: 9.75 (s, 1H), 9.07 (s, 1H), 8.72 (s, 1H), 8.47 (t, 1H), 8.43 (d, 1H), 8.06-8.04 (m, 2H), 7.93 (d, 1H), 7.86 (br s, 1H), 7.81 (d, 1H), 7.64-7.54 (m, 2H), 7.50-7.46 (m, 2H), 7.44-7.41 (m, 2H), 7.14-7.10 (m, 2H), 6.55 (d, 1H), 6.39 (s, 1H), 4.11 (s, 1H), 3.84 (s, 3H), 3.45-3.35 (m, 4H), 3.25 (s, 3H), 1.28 (s, 9H).

LCMS m/z 725 (M+H)⁺ (ES⁺); 723 (M−H)⁻ (ES⁻)

night. The reaction was cooled to it and partitioned between EtOAc (30 mL) and sat aq. NaHCO₃ (30 mL). The aqueous phase was back extracted with EtOAc (30 mL). The combined organic extracts were washed with water (2×50 mL), brine (50 mL), dried (MgSO₄), filtered and concentrated in vacuo to afford an orange solid (221 mg). The crude product was purified by chromatography on silica gel (40 g column, 0-10% MeOH in DCM) to afford a pale pink solid (96 mg), which was triturated with Et₂O and then MeCN to afford the title compound (50 mg) as a pale pink solid.

¹H NMR (DMSO-d6) 400 MHz, δ: 9.75 (s, 1H), 9.08 (s, 1H), 8.72 (s, 1H), 8.43 (d, 1H), 8.21 (d, 1H), 8.06-8.04 (m, 2H), 7.94 (d, 1H), 7.88 (br s, 1H), 7.83-7.81 (m, 1H), 7.64-7.55 (m, 2H), 7.50-7.46 (m, 3H), 7.42 (d, 1H), 7.14-7.10 (m, 2H), 6.54 (d, 1H), 6.39 (s, 1H), 4.18-4.11 (m, 2H), 3.84 (s, 3H), 3.39-3.35 (m, 1H), 3.26-3.23 (m, 4H), 1.28 (s, 9H), 1.10 (d, 3H).

LCMS m/z 739 (M+H)⁺ (ES⁺); 737 (M−H)⁻ (ES⁻)

Example 85

(S)-3-((4-((4-(3-(3-(tert-Butyl)-1-(4-methoxyphenyl)-1H-pyrazol-5-yl)ureido)-naphthalen-1-yl)oxy)pyrimidin-2-yl)amino)-5-ethynyl-N-(1-methoxypropan-2-yl)-benzamide Example 86

3-Methoxy-5-((4-((4-(3-(1-(4-methoxyphenyl)-3-(prop-1-en-2-yl)-1H-pyrazol-5-yl)ureido)naphthalen-1-yl)oxy)pyrimidin-2-yl)amino)-N-(2-morpholinoethyl)-benzamide

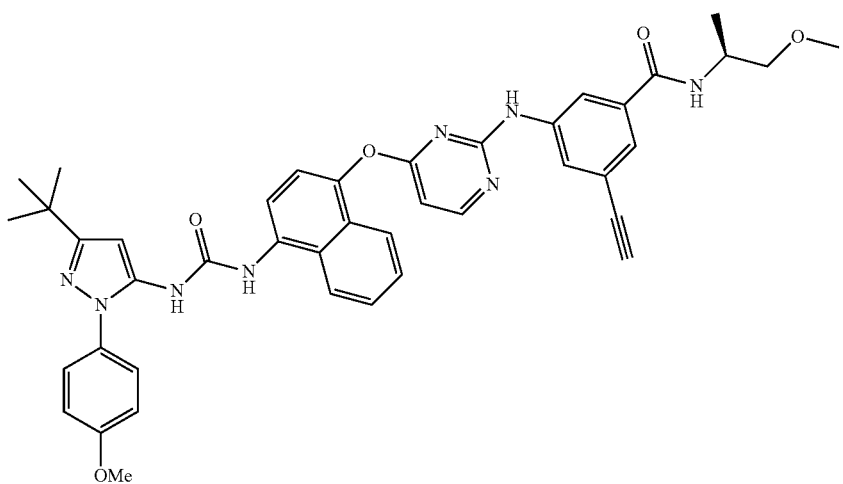 [SMILES: C#Cc1cc(Nc2nccc(Oc3ccc(NC(=O)Nc4cc(C(C)(C)C)nn4-c4ccc(OC)cc4)c4ccccc34)n2)cc(C(=O)N[C@@H](C)COC)c1]

To a stirred solution of Intermediate C3 (150 mg, 0.271 mmol) and Intermediate D6 (103 mg, 0.406 mmol) in DMF (4 mL) was added p-TSA monohydrate (26 mg, 0.137 mmol). The resulting solution was heated at 60° C. over-

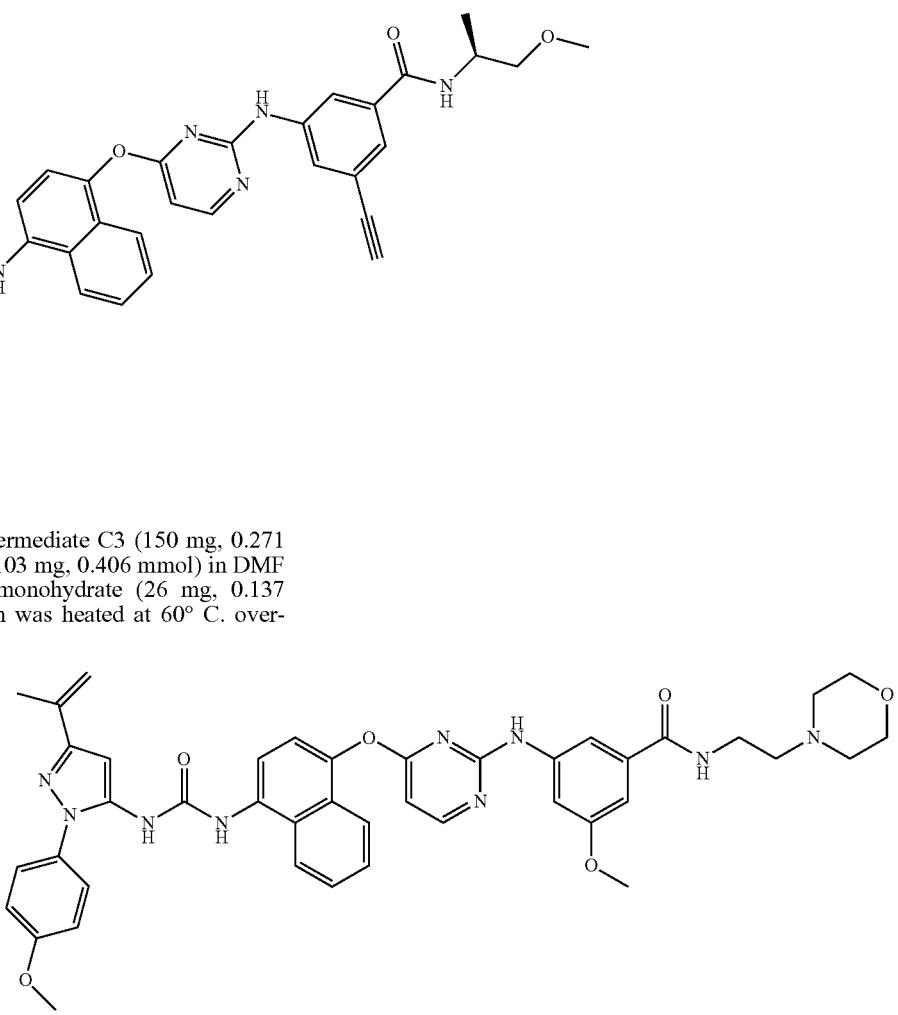

The title compound can be prepared using methods analogous to those described above (for example by reaction of Intermediate A21 with phenyl chloroformate, followed by reaction of the resulting phenyl carbamate with Intermediate B13).

¹H NMR (400 MHz, DMSO-d6) δ 9.59 (s, 1H), 9.11 (s, 1H), 8.78 (s, 1H), 8.40 (d, 1H), 8.18 (br t, 1H), 8.05 (d, 1H), 7.94 (d, 1H0, 7.82 (d, 1H), 7.64-7.50 (m, 5H), 7.41 (d, 1H), 7.32 (s, 1H), 7.14 (d, 2H), 6.85 (s, 1H), 6.70 (s, 1H), 6.54 (d, 1H), 5.52 (s, 1H), 5.10 (s, 1H), 3.85 (s, 3H), 3.58-3.52 (m, 7H), 3.37-3.34 (m, 2H), 2.44-2.36 (m, 6H), 2.06 (s, 3H).

LCMS m/z 768 (M−H)⁻ (ES⁻)

Example 87

3-((4-(2,3-Dichloro-4-(3-(3-isopropyl-1-(p-tolyl)-1H-pyrazol-5-yl)ureido)-phenoxy)pyrimidin-2-yl)amino)-5-ethynyl-N-(2-morpholinoethyl)benzamide Intermediate C4 (150 mg, 0.282 mmol) was dissolved in DMF (1.5 mL) and added to Intermediate D1 (100 mg, 0.367 mmol) and p-TSA monohydrate (80 mg, 0.423 mmol). Stirred at 70° C. (block temperature) for 4 h then poured into sat. aq. NaHCO₃ solution (20 mL) and the product extracted with EtOAc (2×20 mL). Organics bulked and washed with 20% w/w brine solution (20 mL), dried (MgSO₄), filtered and evaporated to a brown solid. The crude product was purified by chromatography on the Companion (40 g column, 2% MeOH:DCM to 8%) then triturated with 3×MeCN (3 ml) to afford the title compound (93 mg).

¹H NMR (400 MHz, DMSO-d6) δ 9.87 (s, 1H), 9.20 (s, 1H), 8.80 (s, 1H), 8.45 (d, 1H), 8.37 (s, 1H), 8.14 (d, 1H), 7.98 (s, 1H), 7.84 (s, 1H), 7.52-7.26 (m, 6H), 6.63 (d, 1H), 6.35 (s, 1H), 4.05 (s, 1H), 3.59-3.52 (m, 4H), 2.97-2.82 (m, 1H), 2.47-2.33 (m, 9H), 1.23 (d, 6H). 2H obscured by water peak 3.32 ppm LCMS m/z 768/770 (M+H)+ (ES+)

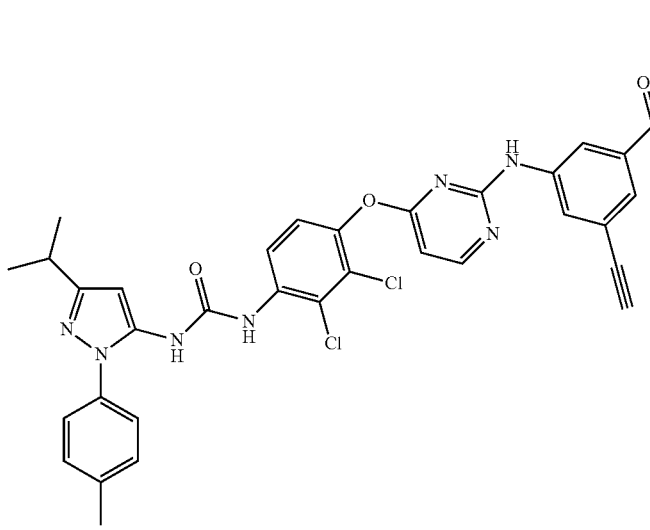

Example 88

3-((4-(2,3-Difluoro-4-(3-(3-isopropyl-1-(p-tolyl)-1H-pyrazol-5-yl)ureido)-phenoxy)pyrimidin-2-yl)amino)-5-ethynyl-N-(2-morpholinoethyl)benzamide

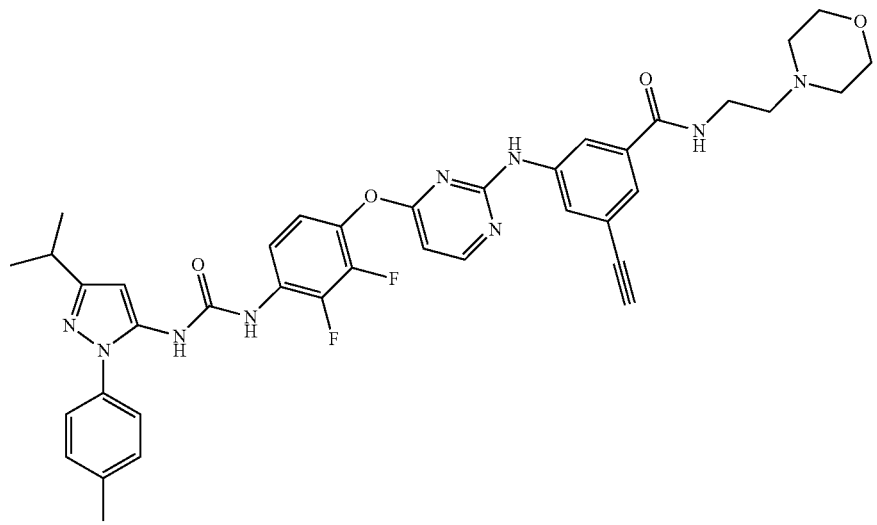 [SMILES: C#Cc1cc(Nc2nccc(Oc3ccc(NC(=O)Nc4cc(C(C)C)nn4-c4ccc(C)cc4)c(F)c3F)n2)cc(C(=O)NCCN2CCOCC2)c1]

To a stirred solution of Intermediate C5 (151 mg, 0.303 mmol) in THF/DMF (4 mL, 1:1) was added p-TSA monohydrate (86 mg, 0.454 mmol) followed by Intermediate D1 (124 mg, 0.454 mmol). The resulting mixture was heated at 60° C. overnight, cooled to rt and partitioned between EtOAc (30 mL) and sat. aq. NaHCO$_3$ solution (20 mL). The aqueous layer was extracted with EtOAc (2×30 mL). The combined organic extracts were washed with water (3×40 mL), brine (50 mL), dried (MgSO$_4$), filtered and concentrated in vacuo to afford a cream solid. The crude product was purified by chromatography on silica gel (80 g column, 0-10% MeOH in DCM) then purified by preparative HPLC (Waters, Acidic (0.1% Formic acid), Waters X-Select Prep-C18, 5 μm, 19×50 mm column, 25-50% MeCN in Water) to afford the title compound 0.2 Formic Acid (65 mg) as a white solid.

$^1$H NMR (DMSO-d6) 400 MHz, δ: 9.88 (s, 1H) 9.14 (s, 1H) 8.88 (s, 1H) 8.46 (d, 1H) 8.34 (t, 1H) 7.97-7.92 (br m, 2H) 7.84 (s, 1H) 7.43-7.40 (m, 3H) 7.37-7.35 (m, 2H) 7.23-7.18 (m, 1H) 6.65 (d, 1H) 6.35 (s, 1H) 4.01 (s, 1H) 3.56-3.53 (m, 4H), 2H under water peak at 3.32 ppm, 2.92-2.85 (m, 1H) 2.43 (t, 2H) 2.41-2.35 (br m, 7H) 1.23 (d, 6H).

LCMS m/z 736 (M+H)+ (ES+); 734 (M−H)− (ES−)

Example 89

3-((4-(2,3-Dichloro-4-(3-(3-isopropyl-1-(p-tolyl)-1H-pyrazol-5-yl)ureido)-phenoxy)pyrimidin-2-yl)amino)-5-ethynylbenzamide

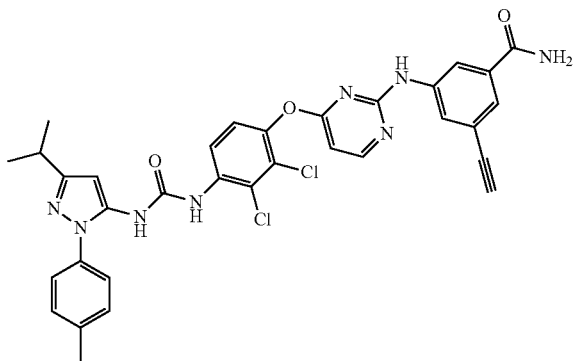 [SMILES: C#Cc1cc(Nc2nccc(Oc3ccc(NC(=O)Nc4cc(C(C)C)nn4-c4ccc(C)cc4)c(Cl)c3Cl)n2)cc(C(N)=O)c1]

Intermediate C4 (150 mg, 0.282 mmol) was dissolved in DMF (2 mL) and added to Intermediate D7 (90 mg, 0.564 mmol) and p-TSA monohydrate (26.8 mg, 0.141 mmol). Stirred at 70° C. (block temperature) for 4 h then poured into sat. aq. NaHCO$_3$ solution (20 mL) and the product extracted with EtOAc (2×20 mL). Organics bulked and washed with 20% w/w brine solution (20 mL), dried (MgSO$_4$), filtered and evaporated to a yellow solid. Preabsorbed onto silica and purified by chromatography on silica gel (40 g column, 4% MeOH:DCM to 8%) then triturated with MeCN (4×3 mL) to afford the title compound (40 mg) as a colourless solid.

$^1$H NMR (400 MHz, DMSO-d6) δ 9.83 (s, 1H), 9.17 (s, 1H), 8.78 (s, 1H), 8.46 (d, 1H), 8.01 (s, 1H), 7.92 (s, 1H), 7.87 (s, 1H), 7.49 (t, 2H), 7.46-7.40 (m, 3H), 7.39-7.33 (m, 3H), 6.62 (d, 1H), 6.35 (s, 1H), 4.01 (s, 1H), 2.90 (hept, 1H), 2.39 (s, 3H), 1.24 (d, 6H).

LCMS m/z 655/657(M+H)+ (ES+)

Example 90

3-((4-(2,3-Dichloro-4-(3-(3-isopropyl-1-(p-tolyl)-1H-pyrazol-5-yl)ureido)-phenoxy)pyrimidin-2-yl)amino)-N-(2-(dimethylamino)ethyl)-5-ethynylbenzamide

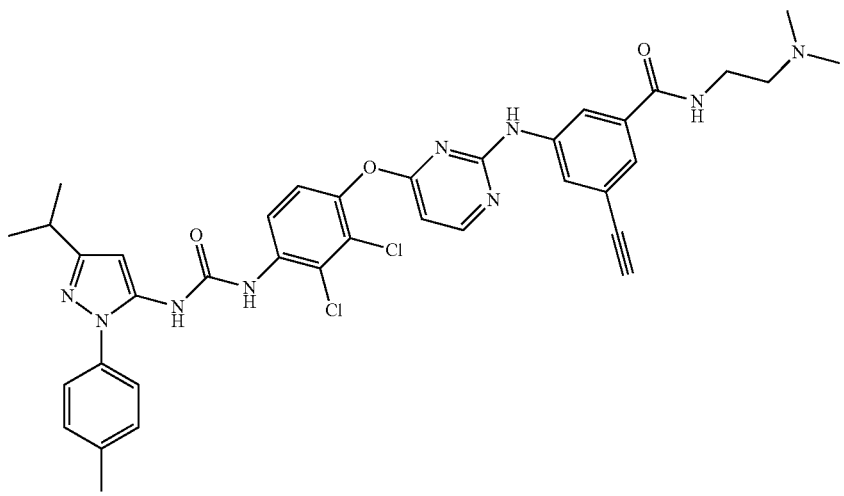 [SMILES: C#Cc1cc(Nc2nccc(Oc3ccc(NC(=O)Nc4cc(C(C)C)nn4-c4ccc(C)cc4)c(Cl)c3Cl)n2)cc(C(=O)NCCN(C)C)c1]

Intermediate C4 (150 mg, 0.282 mmol) was dissolved in DMF (2 mL) and added to Intermediate D8 (130 mg, 0.564 mmol) and p-TSA monohydrate (80 mg, 0.423 mmol). Stirred at 70° C. (block temperature) for 4 h then poured into sat. NaHCO₃ solution (20 mL) and the product extracted with EtOAc (2×20 mL). Organics bulked and washed with 20% w/w brine solution (20 mL), dried (MgSO₄), filtered and evaporated to a colourless solid. Triturated with MeCN (3×2 mL) to afford the title compound (90 mg).

¹H NMR (400 MHz, DMSO-d6) δ 9.84 (s, 1H), 9.18 (s, 1H), 8.78 (s, 1H), 8.45 (d, 1H), 8.34 (t, 1H), 8.13 (d, 1H), 7.97 (s, 1H), 7.85 (s, 1H), 7.46-7.39 (m, 4H), 7.38-7.33 (m, 2H), 6.62 (d, 1H), 6.35 (s, 1H), 4.02 (s, 1H), 3.37-3.26 (m, 2H), 2.89 (hept, 1H), 2.43-2.33 (m, 5H), 2.17 (s, 6H), 1.24 (d, 6H).

LCMS m/z 726/728 (M+H)+ (ES+)

Example 91

3-((6-(4-(3-(3-(tert-Butyl)-1-(4-methoxyphenyl)-1H-pyrazol-5-yl)ureido)-2,3-dimethylphenoxy)pyrimidin-4-yl)amino)-5-methoxy-N-(2-morpholinoethyl)benzamide

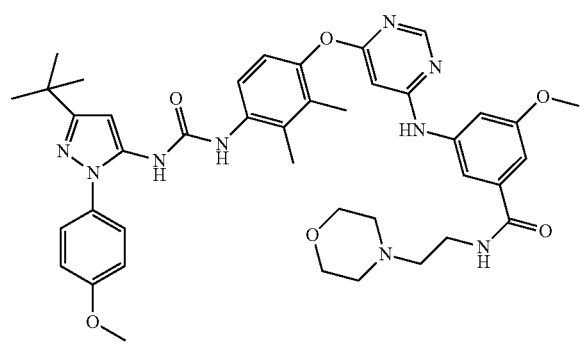 [SMILES: COc1ccc(-n2nc(C(C)(C)C)cc2NC(=O)Nc2ccc(Oc3cc(Nc4cc(OC)cc(C(=O)NCCN5CCOCC5)c4)ncn3)c(C)c2C)cc1]

The title compound can be prepared using methods analogous to those described above.

¹H NMR (400 MHz, DMSO-d6) δ 9.70 (s, 1H), 8.60 (s, 1H), 8.38-8.35 (m, 2H), 8.18 (s, 1H), 7.56-7.43 (m, 5H), 7.10 (d, 2H), 7.02 (s, 1H), 6.94 (d, 1H), 6.33 (s, 1H), 6.04 (s, 1H), 3.83 (s, 3H), 3.79 (s, 3H), 3.57 (t, 4H), 2.47-2.38 (m, 6H), 2.12 (s, 3H), 2.02 (s, 3H), 1.27 (s, 9H). 2H under water peak at 3.35

LCMS m/z 382.6 (M+2H)²⁺ (ES⁺)

Biological Testing: Experimental Methods

Enzyme Binding Assays (Kinomescan)

The kinase enzyme binding activities of compounds disclosed herein were determined using a proprietary assay which measures active site-directed competition binding to an immobilized ligand (Fabian, M. A. et al., Nature Biotechnol., 2005, 23:329-336). These assays were conducted by DiscoverX (formerly Ambit; San Diego, Calif.). The percentage inhibition produced by incubation with a test compound is calculated relative to the non-inhibited control.

Enzyme Inhibition Assays

The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition

The following two assay variants are used for determination of p38 MAPKα inhibition.

Method 1

The inhibitory activities of test compounds against the p38 MAPKα isoform (MAPK14: Invitrogen), are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38a inactive target MAPKAP-K2 (Invitrogen, 600 ng/mL) and FRET peptide (8 μm; a phosphorylation target for MAPKAP-K2) is then added and the kinase reaction is initiated by adding ATP (40 μm, 2.5 μL). The mixture is incubated for 1 hr at RT. Development reagent (protease, 5 μL) is added for 1 hr prior to detection in a fluorescence microplate reader (Varioskan® Flash, Thermo-Fisher Scientific).

Method 2

This method follows the same steps as Method 1 above, but utilises a higher concentration of the p38 MAPKα protein (2.5 μL of 200 ng/mL protein instead of 2.5 μL of 80 ng/mL protein) for mixing with the test compound.

p38 MAPKγ Enzyme Inhibition

The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL at either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) is then added to the enzymes/compound mixtures and incubated for 1 hr. Development reagent (protease, 5 μL) is added for 1 hr prior to detection in a fluorescence microplate reader (Varioskan® Flash, Thermo Scientific).

c-Src and Syk Enzyme Inhibition

The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 4 μg/mL, 0.4 μg/mL, 0.04 μg/mL, or 0.004 μg/mL, 2.5 μL each) for 2 hr at RT. The FRET peptides (8 μM, 2.5 μL), and appropriate ATP solutions (2.5 μL, 800 μM for c-Src, and 60 μM ATP for Syk) are then added to the enzymes/compound mixtures and incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition

The following two assay variants are used for determination of GSK 3α inhibition.

Method 1

The inhibitory activities of compounds of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2

This method follows the same steps as Method 1 above, but utilises a shorter period of mixing of the test compound (105 minutes instead of 2 hours) with the GSK3-α protein.

Cellular Assays (a) LPS-Induced TNFα/IL-8 Release in d-U937 Cells

U937 cells, a human monocytic cell line, are differentiated into macrophage-type cells by incubation with PMA (100 ng/mL) for 48 to 72 hr. Cells are pre-incubated with final concentrations of test compound for 2 hr and are then stimulated with LPS (0.1 µg/mL; from *E. Coli*: O111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 µg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/ml LPS (*Escherichia Coli* O111:B4 from Sigma Aldrich) for 24 hours under normal tissue culture conditions (37° C., 5% $CO_2$). The supernatant is harvested for determination of and TNFα concentrations by sandwich ELISA (Duo-set, R&D systems) and read on the fluorescence microplate reader (Varioskan® Flash, ThermoFisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD38 monoclonal antibodies (0.3 ug/ml eBioscience and 3 ug/ml BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hrs) and pre-treated with compounds at the desired concentration for 2 hours before addition of 5 ng/ml of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages the cells are incubated with 5 ng/ml of GM-CSF (Peprotech) for 7 days under normal tissue culture conditions. Compounds are then added to the cells at the desired concentration for a 2 hour pre-treatment before stimulation with 10 ng/ml LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 µg/mL Poly I:C, ±2% Oligofectamine, 25 µL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS (100 µL) and then endogenous peroxidase is quenched by the addition of washing buffer (100 µL, 0.05% Tween in PBS: PBS-Tween) containing 0.1% sodium azide and 1% hydrogen peroxide. Cells are washed with wash-buffer (3×200 µL). and after blocking the wells with 5% milk in PBS-Tween (100 µL) for 1 hr, the cells are incubated with anti-human ICAM-1 antibody (50 µL; Cell Signalling Technology, Danvers, Mass.) in 1% BSA PBS overnight at 4° C.

The cells are washed with PBS-Tween (3×200 µL) and incubated with the secondary antibody (100 µL; HRP-conjugated anti-rabbit IgG, Dako Ltd., Glostrup, Denmark). The cells are then incubated with of substrate (50 µL) for 2-20 min, followed by the addition of stop solution (50 µL, 1N $H_2SO_4$). The ICAM-1 signal is detected by reading the absorbance at 450 nm against a reference wavelength of 655 nm using a spectrophotometer. The cells are then washed with PBS-Tween (3×200 µL) and total cell numbers in each well are determined by reading absorbance at 595 nm after Crystal Violet staining (50 µL of a 2% solution in PBS) and elution by 1% SDS solution (100 µL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) T cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2 \times 10^5$ cells per well in 100 µL RPMI/10% FBS on 96 well flat bottomed plate (Corning Costar). 25 µL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 hours before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 µL of substrate solution. The reaction is stopped by addition of 50 µL of 1 M $H_2SO_4$, and read for absorbance at 450 nm on a plate reader (Varioskan® Flash, ThermoFisher Scientific). The $IC_{50}$ is determined from the dose response curve.

(h) Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-113 and TNFα levels by R&D ELISA. Percentage inhibition of cytokine release by the test compounds is calculated relative to the cytokine release determined for the DMSO control (100%).

(i) Cell Mitosis Assay

PBMCs from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (Sigma-Aldrich, Poole, UK) for 48 hr, followed by a 20 hr exposure to varying concentrations of test compounds. At 2 hr before collection, PBMCs are treated with demecolcine (0.1 µg/mL; Invitrogen, Paisley, UK) to arrest cells in metaphase. To observe mitotic cells, PBMCs are permeabilised and fixed by adding Intraprep (50 µL; Beckman Coulter, France), and stained with anti-phosphohistone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research,* 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(j) Assessment of HRV16 Induced CPE in MRC5 Cells

MRC-5 cells are infected with HRV16 at an MOI of 1 in DMEM containing 5% FCS and 1.5 mM magnesium chloride, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 µL, 2% formaldehyde, 10% methanol and 0.175% Methylene Blue) for 2 hr at RT. After washing, 1% SDS in distilled water (100 µL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(k) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at an MOI of 0.001 in the LHC8 Media: RPMI-1640 (50:50) containing 15 mM magnesium chloride and incubated for 1 hr at 37° C. for adsorption. The cells are then washed with PBS (3×200 µL), fresh media (200 µL) is added and incubation continued for 4 days. Where appropriate, cells are pre-incubated with the compound or DMSO for 2 hr, and then added again after washout of the virus.

The cells are fixed with 4% formaldehyde in PBS solution (50 µL) for 20 min, washed with WB (3×200 µL), (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No. ab43812, Abcam) in 5% BSA in PBS-tween. After washing, cells are incubated with an HRP-conjugated secondary antibody solution (50 µL) in 5% BSA in PBS-Tween (lot 00053170, Cat. No. P0447, Dako) and then TMB substrate added (50 µL; substrate reagent pack, lot 269472, Cat. No. DY999, R&D Systems, Inc.). This reaction is stopped by the addition of 2N $H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-555}$ readings are corrected to the cell number by dividing the $OD_{450-555}$ by the $OD_{595}$ readings. The percentage inhibition for each well is calculated and the $IC_{50}$ value is calculated from the concentration-response curve generated from the serial dilutions of compound.

(l) The Effect of Test Compounds on Cell Viability: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(m) Accumulation of 13 Catenin in d-U937 Cells

U937 cells, a human monocytic cell line, are differentiated into macrophage-type cells by incubation with PMA; (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 µL, 0.1% sodium azide, 1% $H_2O_2$ in PBS with 0.05% Tween-20) for 20 min. The cells are washed with washing buffer (200 µL; PBS containing 0.05% Tween-20) and incubated with blocking solution (200 µL; 5% milk in PBS) for 1 hr, re-washed with washing buffer (200 µL) and then incubated overnight with anti-β-catenin antibody solution (50 µL) in 1% BSA/PBS (BD, Oxford, UK).

After washing with washing buffer (3×200 µL; PBS containing 0.05% Tween-20), cells are incubated with an HRP-conjugated secondary antibody solution (100 µL) in 1% BSA/PBS (Dako, Cambridge, UK) and the resultant signal is determined colourimetrically (OD: 450 nm with a reference wavelength of 655 nm) using TMB substrate (50 µL; R&D Systems, Abingdon, UK). This reaction is stopped by addition of 1N $H_2SO_4$ solution (50 µL). Cells are then washed with washing buffer and 2% crystal violet solution (50 µL) is applied for 30 min. After washing with washing buffer (3×200 µL), 1% SDS (100 µL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising of the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide) (1 µg/mL) which is defined as unity. A signal less than 0.15 (15%) of that observed for the standard control is designated as "-ve".

(n) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2×10^5$ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(o) Inhibition of Cytokine Release from Myofibroblasts Isolated from IBD Patients Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3×10^5$ cells per well are starved in serum-free medium for 24 h at 37° C., 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

(p) Human Neutrophil Degranulation

Neutrophils are isolated from human peripheral blood as follows: Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 µg/mL) and 1 mM $CaCl_2$) to achieve $5×10^6$ cells/mL.

$5×10^4$ cells are added to each well of a V-bottom 96 well plate and incubated (30 mins, 37° C.) with the appropriate concentration of test compound (0.3-1000 ng/mL) or vehicle (DMSO, 0.5% final conc). Degranulation is stimulated by addition of fMLP (final conc 1 µM) which after a further incubation (30 mins, 37° C.) the cells are removed by centrifugation (5 mins, 1500 rpm) and the supernatants transferred to a flat bottom 96 well plate. An equal volume of tetramethylbenzidine (TMB) is added and after 10 mins the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(q) Cell Cytotoxicity Assay $5×10^4$ TK6 cells (lymphoblastic T cell line) are added to the appropriate number of wells of a 96 well plate in 195 µL of media (RPMI supplemented with 10% foetal bovine serum). 5 µL of DMSO control (final concentration 0.5% v/v) or test compound (final concentration either 5 or 1 µg/mL) is added to the wells and incubated at 37° C., 5% $CO_2$. After 24 hours, the plate is centrifuged at 1300 rpm for 3 minutes and the supernatant discarded. Cells are then resuspended in 7.5 µg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (A) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min). After a further 8 hr the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are shown as mean±S.E.M. (standard error of the mean). The percentage inhibition of neutrophil accumulation is calculated for each treatment relative to vehicle treatment.

(B) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with DSS. On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

(C) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1, 5 or 50 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 μL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

(D) Adoptive Transfer in Mice

On Study day 0, female Balb/C mice are terminated and spleens obtained for CD45RB$^{high}$ cell isolation (Using SCID IBD cell Separation protocol). Approximately $4 \times 10^5$ cells/mL CD45RB$^{high}$ cells are then injected IP (100 μL/mouse) into female SCID animals. On study day 14, mice are weighed and randomized into treatment groups based on body weight. On Day 21, compounds are administered BID, via oral gavage, in a peanut oil vehicle at the dose levels outlined below and a dose volume of 5 mL/kg. Treatment continues until study day 42, at which point the animals are necropsied 4 hours after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

Summary of In Vitro and In Vivo Screening Results

Studies conducted by LeadHunter Discover Services (DiscoveRx Corporation, Fremont, Calif.) using the KINO-MEscan™ technology determined that compound of Example 77 did not have any effect on the binding of the kinases B-Raf and B-Raf (V600e) to their standard ligands.

The in vitro profile of the compound examples of the present invention, as determined using the protocols described above, are presented below (Tables 4a-c). Comparison is made with a structurally related Reference Compound which is: N-(4-(4-(3-(3-tert-butyl-1-p-tolyl-1H-pyrazol-5-yl)ureido)naphthalen-1-yloxy)pyridin-2-yl)-2-methoxyacetamide, that has been described previously as a potent anti-inflammatory agent with anti-viral activity (Ito, K. et al., WO 2010/112936, PCT/GB2010/050575, 7 Oct. 2010 and Ito, K. et al., WO 2010/067130, PCT/GB2009/051702, 17 Jun. 2010). The compounds of the present invention demonstrate a very similar inhibitory profile to the Reference Compound in the range of kinase enzyme assays with the marked exception of the inhibition they possess against the enzyme GSK3α, which is very much weaker than that displayed by the Reference Compound (Table 4a).

TABLE 4a1

The p38 MAPK (Method 1), c-Src, Syk and GSK3α (Method 1) Enzyme Profiles of Compound Examples

| Test Compound Example No. | IC$_{50}$ Values for Enzyme Inhibition (nM) | | | |
|---|---|---|---|---|
| | p38 MAPKα | c-Src | Syk | GSK3α |
| Reference Compound | 12 | 5 | 42 | 45 |
| 1 | 40 | 5 | 10 | 2860 |
| 2 | 27 | 5 | 250 | 1260 |
| 3 | 7 | 1 | 11 | 286 |
| 4 | 26 | 49 | 124 | >14300 |
| 5 | 1 | 2 | 7 | 1470 |
| 6 | 1 | 2 | 5 | 634 |
| 7 | 34 | 13 | 50 | >12600 |
| 8 | 2 | <1 | 3 | 7950 |
| 9 | 49 | 2 | 41 | 8030 |
| 10 | 6 | 2 | 4 | >12900 |
| 11 | 25 | 8 | 75 | >14000 |
| 12 | 6 | 5 | 16 | 509 |
| 13 | 24 | 2 | 16 | 672 |
| 14 | <1 | 4 | >1300 | 355 |
| 15 | 7 | 4 | 16 | 3180 |
| 16 | 34 | 9 | 1390 | 1400 |
| 17 | 54 | 3 | 35 | 309 |
| 18 | 12 | 7 | >1440 | 295 |
| 19 | 2 | 2 | 4 | 1240 |
| 20 | 5 | 2 | 15 | 317 |
| 21 | 10 | 5 | 14 | 356 |
| 22 | <1 | <1 | 292 | 930 |
| 23 | <1 | <1 | 203 | 2990 |
| 24 | 11 | 1 | 14 | 207 |
| 25 | 13 | 4 | >1330 | 285 |
| 26 | 12 | 6 | 14 | 390 |
| 27 | 17 | 4 | 39 | 311 |
| 28 | <1 | <1 | 54 | >14000 |
| 29 | <1 | <1 | 147 | 3210 |
| 30 | 3 | 1 | 103 | >13200 |
| 31 | 8 | 3 | 51 | 9630 |
| 32 | 1 | <2 | 152 | >14600 |
| 33 | 4 | 3 | 98 | >14300 |
| 34 | <1 | 2 | 85 | >14200 |
| 35 | <1 | <1 | 30 | >14000 |
| 36 | 13 | 8 | 169 | >13200 |
| 37 | 44 | 27 | 149 | >13000 |
| 38 | 12 | 9 | 54 | >13000 |
| 39 | 7 | 8 | 130 | >14600 |
| 40 | 52 | 3 | 9 | 1340 |
| 41 | 50 | 10 | 15 | 1200 |
| 42 | 167 | 20 | 67 | >1390 |

TABLE 4a1-continued

The p38 MAPK (Method 1), c-Src, Syk and GSK3α (Method 1) Enzyme Profiles of Compound Examples

| Test Compound Example No. | IC$_{50}$ Values for Enzyme Inhibition (nM) | | | |
|---|---|---|---|---|
| | p38 MAPKα | c-Src | Syk | GSK3α |
| 43 | 4 | 2 | 7 | 197 |
| 44 | <1 | 9 | 17 | 3950 |
| 45 | 4 | 4 | >1320 | 1630 |
| 47 | 10 | 5 | 12 | 2850 |
| 48 | 18 | 5 | 78 | >12800 |
| 49 | 2 | 1 | 57 | >13500 |
| 50 | 2 | <1 | 32 | >13300 |
| 51 | 15 | <1 | 649 | >13000 |
| 52 | 13 | 3 | 6 | 247 |
| 53 | 2 | <1 | 3 | >13000 |
| 54 | 12 | 2 | 5 | 217 |
| 55 | 9 | 3 | 4 | 281 |
| 56 | <1 | 5 | 12 | >13000 |
| 57 | 5 | <1 | 5 | 283 |
| 58 | <1 | <1 | 296 | 8470 |
| 59 | 2 | <1 | 12 | 1190 |
| 60 | 16 | 13 | 60 | >13200 |
| 61 | 20 | 9 | 32 | 6940 |
| 62 | 22 | 7 | 13 | 995 |
| 63 | 45 | 37 | 865 | 13000 |
| 64 | 8 | 2 | 13 | 122 |
| 65 | 23 | 8 | 61 | >14200 |
| 66 | 24 | 6 | 234 | >14300 |
| 67 | 24 | 4 | 40 | 452 |
| 68 | <1 | <1 | 2 | 111 |
| 69 | 2 | 1 | 8 | 282 |
| 70 | 5 | 2 | 22 | 525 |
| 71 | 2 | <1 | 547 | 5770 |
| 72 | <1 | 4 | 202 | >13000 |
| 86 | 10 | 8 | 20 | >12989 |
| 91 | 9.6 | <1.3 | 131 | 3516 |

TABLE 4a2

The p38 MAPK (Method 2), c-Src, Syk and GSK3α (Method 2) Enzyme Profiles of Compound Examples

| Test Compound Example No. | IC$_{50}$ Values for Enzyme Inhibition (nM) | | | |
|---|---|---|---|---|
| | p38 MAPKα | c-Src | Syk | GSK3α |
| 1 | 50 | 27 | 66 | 6969 |
| 7 | 116 | 27 | 34 | 12064 |
| 8 | 44 | 41 | 224 | 13230 |
| 9 | 174 | 21 | 43 | 6513 |
| 11 | 104 | 15 | 126 | 9947 |
| 36 | NT | NT | NT | 13230 |
| 46 | 41 | 14 | 22 | 11322 |
| 49 | NT | NT | NT | 13480 |
| 50 | NT | NT | NT | 13265 |
| 53 | 37 | 8 | NT | 7264 |
| 73 | 47 | NT | NT | 402 |
| 74 | 1211 | NT | NT | 12110 |
| 75 | 49 | 11 | 28 | 1374 |
| 76 | 233 | 45 | 34 | 1777 |
| 77 | 22 | 12 | 18 | 5946 |
| 78 | NT | 8 | 23 | 2815 |
| 79 | NT | NT | NT | 756 |
| 80 | 437 | 19 | 25 | 12612 |
| 81 | 138 | 21 | 61 | 10356 |
| 82 | NT | NT | NT | 12151 |
| 83 | 261 | 26 | 59 | 11675 |
| 84 | 105 | 15 | 33 | 13797 |
| 85 | 158 | 33 | 92 | 7950 |
| 87 | 408 | 22 | 27 | 5837 |
| 88 | NT | NT | NT | 172 |
| 89 | NT | NT | NT | 15255 |
| 90 | NT | NT | NT | 154 |

The data in Table 4a2 were obtained from assays that were conducted:

according to the same procedures as used to obtain the data in Table 4a1 (except for the p38 MAPK and GSK3α inhibition data, which were each obtained by the Method 2 assay variants, instead of the Method 1 assay variants used to obtain the data of Table 4a1); and in a different laboratory.

The kinase binding profiles of compound Example (8) and of the Reference Compound versus B-RAF p38 MAPK, HCK, cSrc, Syk, and GSK3α were investigated at 500 nM. Compound Example 8 displayed a similar phenotype to the Reference Compound, in that profound inhibition of binding versus p38 MAPK, HCK, cSrc and Syk kinases was demonstrated. However, a notable difference was that compound Example (8) showed much less inhibition of binding to B-Raf and GSK3α than did the Reference Compound (Table 4b).

TABLE 4b

Comparison of the Enzyme Binding Profile of Compound Example (8) with the Reference Compound.

| Test Compound Example No. | % Inhibition of kinase binding at 500 nM | | | | | | |
|---|---|---|---|---|---|---|---|
| | p38 MAPKα | p38 MAPKγ | HCK | cSrc | Syk | B-Raf | GSK3α |
| Reference compound | 100 | 100 | 100 | 100 | 95 | 70 | 84 |
| 8 | 95 | 82 | 99 | 100 | 99 | 29 | 19 |

The compounds of the present invention demonstrate a similar profile to the Reference Compound in cellular assays that reveal anti-inflammatory properties against endotoxin mediated release of both TNFα and IL-8, as well as versus the RNA virus mimic: polyIC induced ICAM-1 expression (Table 4c).

TABLE 4c1

Inhibition of LPS induced TNFα and IL-8 Release (assay (a) above) and PolyIC induced ICAM-1 Expression for Compound Examples

| Test Compound Example No. | LPS Induced Release of Cytokine in d-U937 Cells (nM) | | Poly IC induced ICAM1 in BEAS2B (nM) |
|---|---|---|---|
| | TNFα REC$_{50}$ | IL-8 IC$_{50}$ | IC$_{50}$ |
| Ref. Compound | 0.13 | 1.3 | 2.1 |
| 1 | 0.7 | 1.8 | 3.4 |
| 2 | 0.8 | 4.5 | 1.0 |
| 3 | 0.6 | 1.6 | 0.7 |
| 4 | 0.7 | 6.6 | 4.6 |
| 5 | 0.2 | 1.3 | 0.2 |
| 6 | 0.2 | 1.9 | 1.2 |
| 7 | 0.2 | 1.5 | 1.5 |
| 8 | 0.8 | 0.3 | 1.1 |
| 9 | 0.9 | 1.4 | 6.9 |
| 10 | 1.3 | 1.8 | 7.3 |
| 11 | 0.2 | 1.3 | 1.2 |
| 12 | 0.5 | 1.0 | 2.5 |
| 13 | 0.4 | 0.3 | 1.7 |
| 14 | 1.2 | 5.0 | 3.0 |
| 15 | 0.4 | 1.6 | 26.2 |
| 16 | 1.3 | 1.7 | 1.9 |
| 17 | 1.5 | 1.8 | 2.6 |
| 18 | 1.5 | 1.8 | 2.3 |
| 19 | 0.3 | 0.2 | 2.1 |
| 20 | 1.4 | 2.0 | 2.0 |
| 21 | 1.3 | 1.9 | 0.8 |
| 22 | 4.5 | 1.3 | 4.1 |
| 23 | 5.2 | 2.3 | 27.7 |
| 24 | 1.4 | 0.3 | 1.0 |
| 25 | 0.6 | 1.5 | 1.9 |
| 26 | 0.5 | 2.3 | 11.1 |
| 27 | 1.4 | 4.1 | 11.6 |
| 28 | 2.2 | 32.4 | 140 |
| 29 | 3.8 | 13.7 | 15.1 |
| 30 | 2.1 | 9.0 | 117 |
| 31 | 2.8 | 7.1 | 12.0 |
| 32 | 3.1 | 17.1 | 86.7 |
| 33 | 1.5 | 4.2 | 143 |
| 34 | 14.2 | 73.5 | 79.9 |
| 35 | 27.8 | 3.2 | 140 |
| 36 | 4.7 | 46.0 | 82.3 |
| 37 | 3.7 | 24.1 | 19.6 |
| 38 | 20.2 | 60.6 | 35.7 |
| 39 | 3.6 | 15.7 | 146 |
| 40 | 0.2 | 2.2 | 0.7 |
| 41 | 0.4 | 0.4 | 2.0 |
| 42 | 1.5 | 2.0 | 2.3 |
| 43 | 0.2 | 0.6 | 0.4 |
| 44 | 0.2 | 0.3 | 1.9 |
| 45 | 1.6 | 0.7 | 135 |
| 46 | NT | NT | NT |
| 47 | 0.8 | 1.4 | 3.6 |
| 48 | 3.5 | 20.6 | 32.3 |
| 49 | 9.2 | 17.2 | 33.0 |
| 50 | 5.2 | 8.0 | 16.6 |
| 51 | 1.0 | 0.6 | 3.6 |
| 52 | 0.3 | 1.5 | 5.0 |
| 53 | 0.3 | 1.1 | 4.0 |
| 54 | 0.2 | 0.8 | 2.0 |
| 55 | 3.3 | 2.1 | 5.8 |
| 56 | 1.4 | 1.7 | 85.4 |
| 57 | 0.6 | 1.5 | 1.9 |
| 58 | 11.7 | 46.3 | 2.1 |
| 59 | 2.0 | 6.8 | 39.7 |
| 60 | 1.1 | 3.9 | 132 |
| 61 | 1.1 | 2.0 | 129 |
| 62 | 1.4 | 1.8 | 1.0 |
| 63 | 0.7 | 1.4 | 10.1 |
| 64 | 0.4 | 0.8 | 1.0 |
| 65 | 1.7 | 0.6 | 8.3 |
| 66 | 1.6 | 3.4 | 2.2 |
| 67 | 0.1 | 1.0 | 140 |
| 68 | 0.2 | 0.5 | 3.9 |
| 69 | 0.2 | 0.3 | 7.5 |
| 70 | 0.6 | 1.5 | 8.9 |
| 71 | 2.7 | 1.9 | 7.3 |
| 72 | 1.2 | 2.1 | 2.6 |
| 86 | — | 1.5 | — |

The biological profiles of the compounds of the present invention are similar to those exhibited by the Reference Compound in cellular systems measuring their effects on respiratory virus replication as determined for HRV induced expression of CPE (Table 4d).

TABLE 4c2

Inhibition of cytokine release in stimulated cells (assays (a), (b), (c) and (d) above)

| Test Compound Example No. | IC$_{50}$ Values for Inhibition of Cytokine Release (nM) | | | | | |
|---|---|---|---|---|---|---|
| | dU937 cells | | PBMCs | | | HT29 cells |
| | IL-8 | TNFα | IL-8 | IL-2 | IFNγ | IL-8 |
| 1 | 2.8 | 2.1 | 2.4 | 84.3 | 3.0 | 10.2 |
| 7 | NT | 2.7 | 2.4 | 260.0 | NT | NT |
| 8 | 1.4 | 1.1 | 1.8 | 35.3 | NT | 4.1 |
| 9 | NT | NT | 2.3 | 131.8 | 7.3 | NT |
| 11 | NT | 0.3 | 3.0 | 27.5 | NT | NT |
| 36 | NT | NT | 30.4 | NT | NT | NT |
| 46 | 2.4 | 1.1 | 1.1 | 59.5 | 2.7 | 5.4 |
| 49 | NT | NT | 19.0 | NT | NT | NT |
| 50 | NT | NT | 7.3 | NT | NT | NT |
| 53 | NT | 0.7 | 3.1 | 44.1 | NT | NT |
| 73 | NT | NT | 0.5 | NT | NT | NT |
| 74 | NT | NT | 4.1 | NT | NT | NT |
| 75 | 0.3 | 0.4 | 1.0 | 76.9 | 3.0 | 1.3 |
| 76 | NT | NT | 2.1 | 187.5 | 1.8 | 3.0 |
| 77 | 0.9 | 0.4 | 1.1 | 42.8 | 0.8 | 2.0 |
| 78 | NT | NT | 0.9 | 27.3 | 2.4 | NT |
| 79 | NT | NT | 1.1 | NT | NT | NT |
| 80 | 0.5 | 0.3 | 1.5 | 2.3 | 1.8 | 6.2 |
| 81 | 1.5 | 1.4 | 3.2 | 112.0 | 1.8 | 7.4 |
| 82 | NT | NT | 7.1 | 37.4 | 3.9 | NT |
| 83 | NT | NT | 3.8 | 124.1 | 1.8 | 5.3 |
| 84 | NT | NT | 1.6 | 16.0 | 2.2 | NT |
| 85 | NT | NT | 2.8 | 27.3 | 3.1 | NT |
| 87 | NT | NT | 9.4 | NT | NT | NT |
| 88 | NT | NT | 13.1 | NT | NT | NT |
| 89 | NT | NT | 14.6 | NT | NT | NT |
| 90 | NT | NT | 7.8 | NT | NT | NT |

The data in Table 4c2 stemming from assay (a) were obtained from assays that were conducted:

according to the same procedures as used to obtain the assay (a) data in Table 4c1; but in a different laboratory.

TABLE 4d

The Effects of Compound Examples on Viral Propagation: HRV-16 induced expression of CPE.

| Test Compound Example No. | HRV induced CPE in MRC5 Cells $IC_{50}$ Values (nM) |
|---|---|
| Ref. Compound | 4.7 |
| 1 | 2.9 |
| 8 | 5.4 |
| 9 | 1.7 |
| 23 | 22.3 |
| 30 | 0.43 |
| 40 | 2.9 |
| 42 | 2.2 |
| 50 | 6.8 |
| 51 | 1.9 |
| 53 | 2.0 |

However, advantageously, the compounds of the present invention in general show markedly less activity in assays systems that measure their impact on cell viability and cell division (mitosis) indicating that they are likely to possess an improved side effect profile and a superior therapeutic index over the Reference Compound (Table 4e).

TABLE 4e

Effect of Compound Examples on Cellular Viability and Cell Division

| Test Compound Example No. | Cell viability at time point in d-U937 cells[1] 4 h | 24 h | % Inhibition of mitosis in PBMC cells at 5 µg/mL |
|---|---|---|---|
| Ref. Compd. | −ve | +ve | 87.8 |
| 1 | −ve | −ve | 39.3 |
| 2 | −ve | −ve | 46.5 |
| 3 | −ve | −ve | NT |
| 4 | −ve | −ve | NT |
| 5 | −ve | −ve | 28.3 |
| 6 | −ve | −ve | NT |
| 7 | −ve | −ve | 20.6 |
| 8 | −ve | −ve | 15.3 |
| 9 | −ve | −ve | 20.7 |
| 10 | −ve | −ve | NT |
| 11 | −ve | −ve | 50.7 |
| 12 | −ve | −ve | 27.8 |
| 13 | −ve | −ve | NT |
| 14 | −ve | +ve | NT |
| 15 | −ve | −ve | NT |
| 16 | −ve | −ve | NT |
| 17 | −ve | −ve | NT |
| 18 | −ve | −ve | NT |
| 19 | −ve | −ve | 25.3 |
| 20 | −ve | −ve | NT |
| 21 | −ve | −ve | NT |
| 22 | −ve | −ve | NT |
| 23 | −ve | −ve | 35.6 |
| 24 | −ve | −ve | NT |
| 25 | −ve | −ve | NT |
| 26 | −ve | −ve | NT |
| 27 | −ve | −ve | NT |
| 28 | −ve | −ve | NT |
| 29 | −ve | −ve | NT |
| 30 | −ve | −ve | NT |
| 31 | −ve | −ve | NT |
| 32 | −ve | −ve | NT |
| 33 | −ve | −ve | NT |
| 34 | +ve | −ve | NT |
| 35 | −ve | −ve | NT |
| 36 | −ve | −ve | NT |
| 37 | −ve | −ve | NT |
| 38 | −ve | −ve | NT |
| 39 | −ve | −ve | NT |
| 40 | −ve | −ve | NT |
| 41 | −ve | −ve | NT |
| 42 | −ve | −ve | 12.9 |
| 43 | −ve | −ve | NT |
| 44 | −ve | −ve | 37.2 |
| 45 | −ve | −ve | NT |
| 46 | −ve | −ve | −6.7 |
| 47 | −ve | −ve | NT |
| 48 | −ve | −ve | NT |
| 49 | −ve | −ve | NT |
| 50 | −ve | −ve | NT |
| 51 | −ve | −ve | 20.0 |
| 52 | −ve | −ve | NT |
| 53 | −ve | −ve | 39.4 |
| 54 | −ve | −ve | NT |
| 55 | −ve | −ve | NT |
| 56 | −ve | −ve | NT |
| 57 | −ve | −ve | NT |
| 58 | −ve | −ve | NT |
| 59 | −ve | −ve | NT |
| 60 | −ve | −ve | NT |
| 61 | −ve | −ve | NT |
| 62 | −ve | +ve | NT |
| 63 | −ve | −ve | NT |
| 64 | −ve | −ve | NT |
| 65 | −ve | −ve | 36.7 |
| 66 | −ve | −ve | NT |
| 67 | −ve | −ve | NT |
| 68 | −ve | −ve | NT |
| 69 | −ve | −ve | NT |
| 70 | −ve | −ve | NT |
| 71 | −ve | −ve | NT |
| 72 | −ve | −ve | NT |
| 75 | NT | NT | 2.8 |
| 76 | NT | NT | 23.0 |
| 77 | NT | NT | −0.3 |
| 78 | NT | NT | 2.1 |
| 80 | NT | NT | 10.4 |
| 81 | NT | NT | −2.6 |
| 82 | NT | NT | −6.3 |
| 83 | NT | NT | 20.9 |
| 84 | NT | NT | 0.5 |
| 85 | NT | NT | 6.6 |
| 86 | −ve | −ve | NT |

[1] Cell Viability Screen (MTT Assay): −ve and +ve indicate that the value is below and above respectively, the no significant effect threshold, defined as 30% inhibition at 1 µg/mL at the time point indicated.

Compound Example (8), compound Example (9) and compound Example (86) of the invention were selected for additional profiling in vivo. The potential of these compounds to increase cellular concentrations of β-catenin was assessed and was found to be negative, that is, their inductive effect at a test concentration of 10 µg/mL was less than 15% of the effect produced by the Reference Compound at 1 µg/mL. Results from assay (m) above for further compounds of the examples are provided in Table 4f below.

TABLE 4f

Effect of Compound Examples on β-catenin induction (where NT means not tested)

| Test compound | % β-catenin induction Concentration of test compound | | |
|---|---|---|---|
| | 1 µg/mL | 5 µg/mL | 10 µg/mL |
| Reference compound | 208 | NT | NT |
| 1 | −7 | −6 | NT |
| 11 | −1 | 1 | 1 |
| 73 | 17 | −7 | 7 |
| 75 | −14 | −10 | NT |
| 76 | −3 | −1 | NT |
| 77 | 1 | 0 | −8 |
| 78 | 9 | 0 | NT |
| 80 | 14 | 8 | NT |
| 81 | 3 | −3 | NT |
| 82 | 0 | 9 | NT |
| 83 | −3 | −6 | NT |
| 84 | 3 | 3 | 5 |
| 85 | 7 | 3 | 6 |

Treatment of mice with the test substances was found to produce profound inhibitory effects on LPS-induced neutrophil accumulation in the lungs. As the compounds were administered only once, 8 hr before the endotoxin challenge, these experiments reveal that the drug substances had a long duration of action in this inflammatory model (Table 5a).

TABLE 5a

The Effects of Treatment with Selected Compound Examples on LPS-Induced Airways Neutrophilia in Mice.

| Test Compound Example No. | Neutrophil numbers ($\times 10^5$/mL, +/−SEM) in BAL for drug substances dosed 8 hr pre-LPS challenge (% Inhibition)[1] | |
|---|---|---|
| | Vehicle Control | Test Substance at 0.2 mg/mL |
| Ref. Compd. | 14.0 ± 2.3 | 5.6 ± 0.86 (60) |
| 8 | 14.1 ± 2.3 | 6.1 ± 1.2 (57) |
| 9 | 16.4 ± 2.3 | 8.0 ± 1.6 (51) |

N = 8 animals per group, mean +/− SEM

In addition, treatment of mice with compound Example (8) was found to produce a dose-dependent inhibition on neutrophil accumulation in BALF following endotoxin stimulation and also the inhibitory effects were seen even when treatment occurred 12 hr before exposure to endotoxin (Table 5b).

TABLE 5b

The Effects of Treatment with Compound Example (8) on LPS-Induced Airways Neutrophilia in Mice.

| Compound (8) (mg/mL) | Neutrophil numbers in BAL ($\times 10^5$/mL) at pre-dose time indicated (% inhibition) | | |
|---|---|---|---|
| | 2 hr | 12 hr | 18 h |
| Vehicle | 16.1 ± 2.4 | — | — |
| 0.05 | 9.6 ± 2.0 (40) | — | — |
| 0.2 | 6.6 ± 1.4 (59) | 9.1 ± 1.7 (43) | 14.6 ± 2.5 (9) |
| 1.0 | 3.7 ± 0.61 (77) | — | — |

N = 8 per group, mean +/− SEM

The result of treatment with compound Example (8) on macrophage and neutrophil accumulation in BALF in the mouse cigarette smoke model was investigated (Table 5). The cigarette smoke model used for this study is reported to be a corticosteroid refractory system, (Medicherla S. et al., *J. Pharmacol. Exp. Ther.*, 2008, 324(3):921-9.) and it was confirmed that fluticasone propionate did not inhibit either neutrophil or macrophage accumulation into airways at 1.75 µg/mouse (35 µL, bid, i.n.), the same dose that produced >80% inhibition of LPS-induced neutrophil accumulation.

TABLE 5

The Effects of Treatment with Compound Example (8) on Tobacco smoke-induced Airways Neutrophilia in Mice.

| Treatment with Compound (8) (µg/mL) | Cell numbers in BAL $\times 10^4$/mL (% inhibition) | |
|---|---|---|
| | Macrophage | Neutrophil |
| Vehicle + Air | 3.3 ± 0.27 | 1.8 ± 0.10 |
| Vehicle + Tobacco | 18.4 ± 0.18 | 18.2 ± 0.49 |
| 1.6 | 14.0 ± 0.50 (29) | 13.6 ± 0.51 (28) |
| 8 | 10.9 ± 0.42 (50) | 10.2 ± 0.33 (49) |
| 40 | 8.3 ± 0.38 (67) | 8.2 ± 0.58 (61) |
| 200 | 5.9 ± 0.31 (83) | 5.6 ± 0.39 (77) |

The data for cell numbers are shown as the mean ± SEM, N = 6

As illustrated in Tables 6a and 6b below, the compounds of Example 46 and 77 were also screened in human biopsy assay (h) and in vivo assay (C) above, as conducted over 2 days. Histopathology analysis revealed that the compounds of Examples 46 and 77 both displayed significant activity in the in vivo model of colonic inflammation. In particular, those compounds, when dosed orally at 5 mg/kg, demonstrated marked improvements in ulcer grade and epithelial repair compared to the vehicle control. In addition, the compounds of Examples 46 and 77 produced marked reduction in inflammatory cell infiltrate in the reticular and lamina propria zones. The compounds of Examples 46 and 77 also demonstrated marked anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Addition of Examples 46 and 77 to biopsies in vitro markedly reduced IL-1b, IL-6 and IL-8 release.

TABLE 6a

Summary of results from studies on TNBS-induced colitis in mice.

| Experiment no. | Treatment group | TNBS | | |
|---|---|---|---|---|
| | | n | Ulcer grade | LP inflammation |
| 1 | Non-diseased | 6 | 0.2 ± 0.2 | 0.3 ± 0.2 |
| 1 | TNBS + Vehicle | 12 | 4.0 ± 0.5 | 3.9 ± 0.3 |

TABLE 6a-continued

Summary of results from studies on TNBS-induced colitis in mice.

| Experiment no. | Treatment group | n | TNBS Ulcer grade | LP inflammation |
|---|---|---|---|---|
| 1 | TNBS + Budesonide (2.5 mg/kg) | 11 | 2.9 ± 0.6 | 2.5 ± 0.4 |
| 1 | TNBS + Example 46 (1 mg/kg) | 12 | 3.4 ± 0.6 | 3.1 ± 0.6 |
| 1 | TNBS + Example 46 (5 mg/kg) | 12 | 2.4 ± 0.6 | 2.0 ± 0.5 |
| 2 | Non-diseased | 6 | 0.0 ± 0.0 | 0.3 ± 0.2 |
| 2 | TNBS + Vehicle | 24 | 3.6 ± 0.3 | 3.9 ± 0.3 |
| 2 | TNBS + Example 77 (1 mg/kg) | 12 | 3.1 ± 0.5 | 2.4 ± 0.3 |
| 2 | TNBS + Example 77 (5 mg/kg) | 11 | 2.4 ± 0.5 | 2.1 ± 0.3 |

TABLE 6b

Summary of results from assays using intestinal mucosa biopsies from the inflamed regions of the colon of various patients suffering from ulcerative colitis (a form of IBD).

| Treatment group | Cytokine release from biopsies of UC patients | | | | | |
|---|---|---|---|---|---|---|
| | n | IL-1b release | n | IL-6 release | n | IL-8 release |
| DMSO control | | 100% | | 100% | | 100% |
| Example 46 (1 µg/mL) | 3 | 35 ± 14 | 8 | 44 ± 38 | 8 | 49 ± 35 |
| Example 77 (1 µg/mL) | 5 | 26 ± 16 | 5 | 67 ± 128 | 5 | 36 ± 117 |

As illustrated in Table 7 below, the compound of Example 77 was also screened in the in vivo (adoptive transfer) assay (D) above. Analysis of the ratio of colon weight:length and relative inhibition of cytokine release revealed that the compound of Example 77 also displayed significant activity in this further in vivo model of colonic inflammation.

TABLE 7

Summary of results from adoptive transfer mouse model.

| | Example 77 (5 mg/kg) |
|---|---|
| % Inhibition of colon weight:length | 51%* |
| % inhibition of IL-8 release | 68% |
| % inhibition of overall histopathology score | NT |

*P < 0.05 ANOVA to vehicle
NT: Not tested

Summary of Additional Studies
Determination of Pharmacokinetic Parameters
(I) Studies in Mice Studies were conducted by Sai Life Sciences (Hinjewadi, Pune, India) to investigate the pharmacokinetics and total colon tissue distribution of the compound of Example 77 in male C57BL/6 mice following a single oral administration.

A group of twenty one male mice were dosed with a suspension formulation (in peanut oil) of the compound of Example 77, at a dose of 5 mg/kg. Blood samples (approximately 60 µL) were collected from retro orbital plexus such that the samples were obtained at 1, 2, 4, 6, 8, 12 and 24 hr. The blood samples were collected from a set of three mice at each time point in labelled micro centrifuge tube containing $K_2$EDTA as anticoagulant. Plasma samples were separated by centrifugation at 4000 rpm for 10 min of whole blood and stored below −70° C. until bioanalysis. After collection of blood sample, animals were humanely euthanized by carbon dioxide asphyxiation to collect total colon tissues. The colons were flushed with cold phosphate buffer saline (pH 7.4) to remove contents. The total colon tissues were homogenized with cold phosphate buffer saline (pH 7.4) of twice the weight of colon tissue and stored below −70° C. Total volume was three times the total colon tissue weights. All samples were processed for analysis by protein precipitation using acetonitrile and analyzed with developed LC-MS/MS method (LLOQ: 2.02 ng/mL in plasma and 1.01 ng/mL in colon tissue). Pharmacokinetic parameters were calculated using the non-compartmental analysis tool of Phoenix WinNonlin® software (version 6.3).

(ii) Studies in Rats

A study was conducted by Sai Life Sciences (Hinjewadi, Pune, India) to investigate the pharmacokinetics, as well as plasma and total colon tissue distribution of the compound of Example 77 in male Wistar rats following a single intravenous or oral administration.

30 male Wistar rats were divided into two groups: Group I (p.o.: 5 mg/kg; 27 rats) and Group II (i.v.: 0.25 mg/kg; 3 rats). Animals in Group I were administered orally with an aqueous suspension formulation (having 2% HPMC and 0.5% Tween 80) of the compound of Example 77, at a dose of 5 mg/kg. Animals in Group II were administered intravenously with a solution formulation (in 5% v/v DMSO, 7.5% w/v Solutol HS 15 and 87.5% saline (0.9% w/v NaCl)) of the compound of Example 77 at a dose of 0.25 mg/kg. From each rat, blood samples (approximately 120 µL) were collected from retro orbital plexus such that samples were obtained at pre-dose, 0.05, 0.13, 0.25, 0.5, 1, 2, 4, 8, and 24 hr (i.v.) and pre-dose, 0.5, 1, 2, 4, 6, 8, 12 and 24 hr (p.o.). Immediately after collection, plasma was harvested from blood by centrifugation and stored at −70° C. until analysis. Following collection of blood sample, the animals (Group I) were humanely euthanized by carbon dioxide asphyxiation. The total colon was isolated, flushed with cold phosphate buffer saline (pH 7.4) to remove contents and weighed. The total colon tissues homogenized with ice-cold phosphate buffered saline, pH 7.4. Buffer volume to be used for homogenization was twice the weight of tissue. All the samples were stored below −70° C. until bioanalysis. Total colon tissue homogenate volume was three times. Plasma and total colon tissue samples were quantified by LC-MS/MS method (LLOQ in plasma and total colon tissue=0.5 ng/mL)

(ii) Studies in Beagle Dogs

A study was conducted by Sai Life Sciences (Hinjewadi, Pune, India) to investigate the plasma pharmacokinetics of the compound of Example 77 in male beagle dogs following a single intravenous or oral administration.

A group of three male beagle dogs were administered orally with an aqueous suspension formulation (having 2% HPMC and 0.5% Tween 80) of the compound of Example 77, at a dose of 1 mg/kg. In addition, a group of three male beagle dogs were administered intravenously with a solution formulation (in 5% v/v DMSO, 7.5% w/v Solutol HS 15 and 87.5% saline (0.9% w/v NaCl)) of the compound of Example 77, at a dose of 0.05 mg/kg. Blood samples (approximately 1.5 mL) were collected from jugular vein such that the samples were obtained at pre-dose, 0.25, 0.5, 1, 2, 4, 6, 8, and 24 hr (p.o.) and pre-dose, 0.08, 0.25, 0.5, 1, 2, 4, 8, 12, 24 and 32 hr (i.v.) post dose. The blood samples were collected from a set of three dogs at each time point in labelled micro centrifuge tube containing $K_2EDTA$ as anticoagulant. Plasma samples were separated by centrifugation at 2500 g for 10 min of whole blood and stored below −70° C. until bioanalysis. All samples were processed for analysis by protein precipitation using acetonitrile and analyzed with LC-MS/MS method (LLOQ=0.50 ng/mL). Pharmacokinetic parameters were calculated using the non-compartmental analysis tool of Phoenix WinNonlin® (Version 6.3).

As illustrated in Table 8a below, oral administration of the compound of Example 77 resulted in much higher colon tissue exposure than plasma exposure, particularly in the dog studies (where no plasma exposure at all was observed).

TABLE 8a

Pharmacokinetic parameters determined from studies involving oral administration of the compound of Example 77.

| Bio matrix | Mouse | | Rat | | Dog |
| --- | --- | --- | --- | --- | --- |
| | Dose & route | | | | |
| | 5 mg/kg p.o. | | 5 mg/kg p.o. | | 1 mg/kg p.o. |
| | Plasma | Total colon | Plasma | Total colon | Plasma |
| $T_{max}$ (h) | 1 | 4 | 6 | 4 | — |
| $C_{max}$ (ng/mL) | 3.5 | 1,071 | 2.5 | 2,504 | — |
| $AUC_{LAST}$ (h · ng/mL) | 22 | 7,475 | 17.5 | 20,492 | — |
| $AUC_{INF}$ (h · ng/mL) | 29 | 9,276 | 17.5 | 20,720 | — |
| $F_{po}$ (%) | — | — | 0.1 | — | 0 |

TABLE 8b

Pharmacokinetic parameters determined from studies involving intravenous administration of the compound of Example 77.

| | Rat | Dog |
| --- | --- | --- |
| | Dose | |
| | 0.25 mg/kg | 0.05 mg/kg |
| $C_0$ (ng/mL) | 4,026 | 282.7 |
| $AUC_{LAST}$ (h · ng/mL) | 1,179 | 33.6 |
| $AUC_{INF}$ (h · ng/mL) | 1,187 | 37.0 |
| $T_{1/2}$ (h) | 0.8 | 2.5 |
| CL (mL/min/kg) | 3.5 | 25.4 |
| $V_d$ (L/kg) | 0.1 | 1.8 |

Determination of ADME Parameters

Assessment of certain in vitro ADME (absorption, distribution, metabolism, and excretion) parameters for the compounds of Examples 77 and 80 was conducted by BioFocus (Saffron Walden, UK).

(I) Metabolic Stability

Hepatic Microsomal Stability

Microsomal stability assays were performed with incubations of test compounds at 0.1 μM (n=2, final DMSO concentration 0.25%), and carried out using pooled human, dog and rat hepatic microsomes from Xenotech (Lots 1210153, 0810143 and 1110042, respectively) at 0.25 mg protein/mL in the presence of co-factor, NADPH. The incubations were performed at 37° C. with 100 μL aliquots taken from the incubation, at 0, 2, 5, 10 and 20 minutes and reactions terminated by addition of 100 μL of acetonitrile containing carbamazepine as analytical internal standard. Samples were centrifuged and the supernatant fractions analysed by LC-MS/MS.

The instrument responses (peak heights) were referenced to the zero time-point samples (as 100%) in order to determine the percentage of compound remaining.

Ln plots of the % remaining, for each compound, were used to determine the half-life for the microsomal incubations. Half-life values were calculated from the relationship $T_{1/2}(\text{min}) = -0.693/\lambda$ where λ was the slope of the Ln concentration vs time curve.

The in vitro intrinsic clearance, $CI_{int}$ (mL/min/kg), was calculated and scaled to hepatic extraction ratios using the following scaling parameters and formulae.

Parameters

| | Value | | |
| --- | --- | --- | --- |
| Parameter | Human | Dog | Rat |
| Microsomal protein concentration in incubation (mg/mL) | 0.25 | 0.25 | 0.25 |
| microsomes/g liver (mg) | 52 | 78 | 45 |
| liver weight/kg body weight (g) | 25 | 32 | 50 |
| hepatic blood flow (mL/min/kg) | 21 | 31 | 60 |

Formulae $CI_{int}$(tissue clearance) mL/min/kg=[0.693/$t^{1/2}$(min)]× [1/microsomal protein concentration mg/mL]× [mg microsomes/g liver]×[g liver/kg body weight]

$CI_{int}$(hepatic clearance) mL/min/kg=hepatic blood flow×$CI_{int}$/(hepatic blood flow+$CI_{int}$)

Hepatic extraction ratio (Eh)=$CI_{int}$(hepatic clearance) mL/min/kg/hepatic blood flow (mL/min/kg)

Cryopreserved Hepatocyte Stability

Hepatocyte stability assays were performed with incubations of test compounds (0.1 μm initial concentration, n=2) carried out with pooled human, dog and rat cryopreserved hepatocytes from Celsius (Lot numbers RRW, KLI and WAP, respectively) at a cell density of 0.5 million cells/mL. The incubations were performed at 37° C. with 100 μL samples taken from the incubation, at 0, 10, 20, 45 and 90 minutes, and reactions terminated by addition of 100 μL of acetonitrile containing carbamazepine as analytical internal standard. Samples were centrifuged and the supernatant fractions analysed by LC-MS/MS.

The instrument responses (peak heights) were referenced to the zero time-point samples (as 100%) in order to determine the percentage of compound remaining.

Ln plots of the % remaining, for each compound, were used to determine the half-life for the hepatocyte incubations. Half-life values were calculated from the relationship $T_{1/2}(\text{min}) = -0.693/\lambda$ where λ was the slope of the Ln concentration vs time curve.

Standard compounds testosterone, midazolam and 4-methylumbelliferone are included in the assay design. These compounds give an indication of the metabolic capacity of the cryopreserved preparations for both Phase I and Phase II reactions.

In vitro intrinsic clearance ($CI_{int}$), as µL/min/million cells was calculated by applying the following formula to the half-life values:

$CI_{int} = 0.693/T\frac{1}{2}(min) \times$ incubation volume (µL)/million cells The half-life values were also scaled to hepatic extraction ratios using the scaling factors and formulae below.
Parameters

| Parameter | Value | | |
|---|---|---|---|
| | Human | Dog | Rat |
| Hepatocyte concentration in incubation (million cells/mL) | 0.5 | 0.5 | 0.5 |
| Hepatocellularity (million cells/g liver) | 120 | 240 | 120 |
| liver weight/kg body weight (g) | 25 | 32 | 50 |
| hepatic blood flow (mL/min/kg) | 21 | 31 | 60 |

$CI_{int}$(Tissue Clearance) mL/min/kg=[0.693/ $t\frac{1}{2}$(min)]×[1/hepatocyte concentration (million cells/mL)]×[million cells/g liver]×[g liver/kg body weight]

$CI_{int}$(Hepatic clearance) mL/min/kg=hepatic blood flow×$CI_{int}$/(hepatic blood flow+$CI_{int}$)

Hepatic extraction ratio (Eh)=$CI_{int}$(Hepatic clearance) mL/min/kg/hepatic blood flow (mL/min/kg)

The results catalogued in Tables 9a and 9b indicate that the compounds of Examples 77 and 80 exhibit high hepatic clearance, a feature resulting in lower systemic exposures in an in vivo setting.

TABLE 9a

Summary of hepatic microsome stability tests for the compounds of Examples 77 and 80 (results reported are the arithmetic mean of two experiments).

| | Mean intrinsic clearance (µL/ min/mg protein) | | Mean hepatic extraction ratio (Eh) | |
|---|---|---|---|---|
| Source of hepatic microsomes | Ex. 77 | Ex. 80 | Ex. 77 | Ex. 80 |
| Human | 308 | 216 | 0.94 | 0.93 |
| Dog | 189 | 146 | 0.94 | 0.91 |
| Rat | 120 | 91 | 0.82 | 0.77 |

TABLE 9b

Summary of hepatocyte stability tests for the compounds of Examples 77 and 80 (results reported are the arithmetic mean of two experiments).

| | Mean intrinsic clearance (µL/ min/million cells) | | Mean hepatic extraction ratio (Eh) | |
|---|---|---|---|---|
| Source of hepatocytes | Ex. 77 | Ex. 80 | Ex. 77 | Ex. 80 |
| Human | 16 | <11 | 0.69 | <0.61 |
| Dog | 26 | 11 | 0.87 | 0.73 |
| Rat | 12 | <8 | 0.55 | <0.44 |

(ii) Time-Dependent Inhibition of Cytochromes

CYP450 time-dependent inhibition (TDI) assays were performed with test compound at six test concentrations, 0.062 µM to 15 µM (n=2). The test compounds was pre-incubated for 30 minutes with pooled human hepatic microsomes in 0.1 M Tris buffer, pH 7.4, at 37° C. in the presence of cofactor NADPH. A parallel series of incubations (n=2) were prepared with no pre-incubation. Probe substrates were then added (with additional cofactor) and further incubated for the times specified. Concentrations of probe substrates used in the incubations have been optimised to maintain first order reaction conditions.

Reactions were terminated with acetonitrile containing analytical internal standard (carbamazepine), samples then centrifuged to remove microsomal protein and analysed using optimised LC/MS-MS conditions. The MS data were normalised to internal standard and compared to the appropriate solvent controls to determine the amount of metabolite formed from the probe substrate relative to the "uninhibited" controls. The results are quoted as % inhibition. These values were then plotted using the sigmoidal dose response equation (shown below) and $IC_{50}$'s calculated.

$Y$=bottom+((top−bottom)/1+10^((Log $IC_{50}$−$X$)*Hill slope))

X=Log concentration

Y=response $IC_{50}$ is quoted in µm, i.e. the point at which the inhibition is 50% of the control value.

Positive and negative time-dependent inhibitors were included to demonstrate the potential for specific and potent interactions under the conditions used. Variation in probe turnover between plate wells means that inhibition values recorded below 10-15% may not be significant.

A summary of the specific conditions are shown in the table below.

| Cytochrome P450 isoform | Microsome conc. (mg/mL) | Probe substrate | | Incubation time (min) |
|---|---|---|---|---|
| | | Identity | Conc. (µM) | Metabolite | |
| 3A4 | 0.25 | Midazolam | 7 | 1'-OH-midazolam | 15 |
| 2C9 | 0.25 | Diclofenac | 15 | 1'-OH-diclofenac | 15 |

TABLE 10

Summary of CYP inhibition studies for the compound of Example 77 (results reported are the arithmetic mean of two experiments).

| Cytochrome P450 isoform | 0 min preincubation | | 30 min preincubation | |
|---|---|---|---|---|
| | 15 μM % Inh | IC$_{50}$ (μM) | 15 μM % Inh | IC$_{50}$ (μM) |
| CYP3A4 | 15 | >15 | 35 | >15 |
| CYP2C9 | −4 | >15 | 1 | >15 | hERG Inhibition Studies

The compounds of Examples 75, 77, 80 and 81 were tested for inhibition of the human ether a go-go (hERG) channel using IonWorks™ patch clamp electrophysiology at Essen Bioscience (Welwyn Garden City, England). Eight-point concentration curves were generated using serial 3-fold dilutions from the maximum final assay concentration (3 μM). Electrophysiological recordings were made from a Chinese Hamster Lung cell line stably expressing the full length hERG channel. Single cell ionic currents were measured in the perforated patch clamp configuration (100 μg/mL) amphotericin) at room temperature (21-23° C.) using an IonWorks Quattro instrument. The internal solution contained (mM): 140 KCl, 1 MgCl$_2$, 1 EGTA, 20 HEPES and was buffered to pH 7.3. The external solution contained (mM):138 NaCl, 2.7 KCl, 0.9 CaCl$_2$, 0.5 MgCl$_2$, 8 Na$_2$HPO$_4$, 1.5 KH$_2$PO$_4$, also buffered to pH 7.3. Cells were clamped at a holding potential of −70 mV for 30 s and then stepped to +40 mV for 1 s. This was followed by a hyperpolarising step of 1 s to −30 mV to evoke the hERG tail current. This sequence was repeated 5 times at a frequency of 0.25 Hz. Currents were measured from the tail step at the 5th pulse, and referenced to the holding current. Compounds were then incubated for 6-7 minutes prior to a second measurement of the hERG signal using an identical pulse train. Eight-point concentration curves were generated using serial 3-fold dilutions from the maximum final assay concentration (3 μM).

These studies determined that the compounds of Examples 75, 77, 80 and 81 all have IC$_{50}$ values for the hERG channel of greater than 3 μM.

Diversity Profile

Studies were conducted by Cerep (Celle-Lévescault, France) to investigate the binding of the compound of Example 77 to a diverse selection of receptors and to investigate either the inhibition or activation of a selection of enzymes (the "Diversity Profile" comprising a total of 71 receptors and 26 enzymes).

When studied at a concentration of 300 nM the compound of Example 77 did not significantly bind to any of the receptors or inhibit/activate the enzymes tested (i.e. it inhibited the control specific binding in the receptor binding assays or enzyme assays by less than 25%, as assessed using a suitable radioligand for each receptor or a suitable reference substrate for each enzyme).

Mutagenicity Assessment (Bacterial Reverse Mutation Screen)

Studies were conducted by Sequani (Ledbury, Herefordshire, UK) to assess the compound of Example 77 in vitro for its ability to induce mutations in two histidine dependent auxotrophic mutants of Salmonella typhimurium, strains TA98 and TA100.

The mutation screen was conducted using the plate incorporation method and was performed in both the presence and absence of S-9 mix (a liver post-mitochondrial fraction derived from the livers of Aroclor 1254 treated rats). The bacteria were exposed to the compound of Example 77 dissolved in dimethylsulphoxide, which solvent was also used as the negative control. The dose levels used were 0.32, 1.6, 8, 40, 200, 1000 or 5000 μg/plate.

The compound of Example 77 showed no dose-related or statistically significant increases in revertant colonies in either Salmonella typhimurium strain in the presence or absence of S-9 mix. This indicates the absence of any mutagenic effects for the compound of Example 77 in the Salmonella typhimurium strains studied.

The biological profiles of the compound examples of the present invention, revealed above, indicate that the compounds of formula (I) possess anti-inflammatory properties similar to those of the Reference Compound, disclosed earlier. In addition the pharmacological effects are sustained in vivo for at least 12 hr that suggests they will show a long duration of action in therapeutic use. Advantageously the compounds of formula (I) have a narrower spectrum of kinase inhibitory activity than the Reference Compound, that is typical of many prior art molecules designed for this purpose and show reduced potential for adverse effects on cellular viability and on cell division. The pharmacological profiles exhibited by the compounds of formula (I) are thereby consistent with potent anti-inflammatory agents that are associated with a decreased risk of inducing toxicity in clinical use.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. A compound of formula (I):

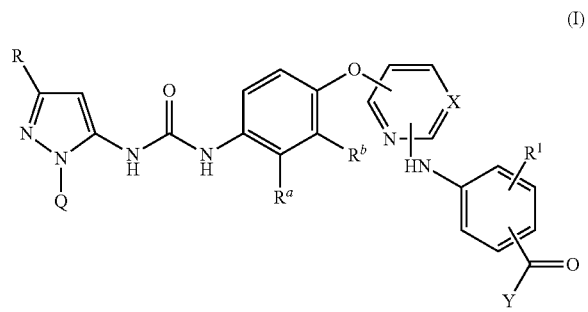

(I)

wherein:
Q represents thienyl, phenyl or pyridinyl, either of which may optionally bear 1 to 3 substituents independently selected from the group consisting of hydroxyl, halogen, C$_{1-6}$ alkyl, C$_{1-6}$ alkoxy, C$_{1-6}$ haloalkoxy, C$_{1-6}$ hydroxyalkyl, NH$_2$, N(H)—C$_{1-6}$ alkyl, N(C$_{1-6}$ alkyl)$_2$, C$_{1-6}$ alkylene-5-10 membered heterocycle and C$_{0-3}$ alkylene-O—O$_{0-6}$ alkylene-5-10 membered heterocycle;

X represents CH or N,

Y represents NR²R³, or a 4-10 heterocycle optionally linked through a heteroatom, wherein said heterocycle bears 0 or 1 substituents selected from the group consisting of halo, OH, $C_{1-6}$ alkyl, $C_{1-4}$ haloalkyl, $C_{0-3}$ alkylene-O—$O_{0-6}$ alkyl, $C_{0-3}$ alkylene-O—$C_{1-3}$ haloalkyl, $C_{0-6}$ alkylene aryl, $C_{0-3}$ alkylene-O—$O_{0-3}$ alkylene aryl, $C_{0-6}$ alkylene heteroaryl, $C_{0-3}$ alkylene-O—$O_{0-3}$ alkylene heteroaryl, $C(O)C_{1-6}$ alkyl, $SO_2NR^4R^5$, $C_{0-3}$ alkylene-NR⁴R⁵, $C_{0-3}$ alkylene-NR⁴SO₂R⁵ and $C_{0-3}$ alkylene-NR⁴C(O)R⁵;

R is $C_{1-6}$ alkyl, $C_{2-6}$ alkenyl, $C_{1-6}$ hydroxyalkyl, $C_{1-6}$ haloalkyl, $C_{1-6}$ alkyl substituted by $C_{1-3}$ alkoxy or cyano, $C_{0-2}$ alkylene-$C_{3-8}$ cycloalkyl optionally substituted with $C_{1-3}$ alkyl, or a 4-5 membered heterocycle optionally substituted with $C_{1-3}$ alkyl;

$R^a$ and $R^b$, together with the C-atoms to which they are attached, form a fused phenyl ring that is optionally substituted by one or more substituents selected from the group consisting of $C_{1-3}$ alkyl, $C_{1-3}$ haloalkyl, cyano and halo, or one of $R^a$ and $R^b$ represents H, halo, cyano, $C_{1-3}$ alkyl or $C_{1-3}$ haloalkyl and the other independently represents halo, cyano, $C_{1-3}$ alkyl or $C_{1-3}$ haloalkyl;

R¹ is selected from the group consisting of hydrogen, OH, halogen, CN, $C_{1-6}$ alkyl, $C_{2-6}$ alkenyl, $C_{2-6}$ alkynyl, $C_{1-6}$ haloalkyl, $C_{0-3}$ alkylene-$C_{3-6}$ cycloalkyl, $C_{0-3}$ alkylene-O—$C_{1-3}$ alkylene-$C_{3-6}$ cycloalkyl, $C_{1-6}$ alkoxy, $C_{1-6}$ haloalkoxy, $C_{1-6}$ hydroxyalkyl, $C_{0-3}$ alkylene-$SO_2C_{1-3}$alkyl, $C_{0-3}$ alkylene-$SO_2NR^4R^5$, and $C_{0-3}$ alkylene-NR⁶R⁷ and $C_{0-3}$ alkylene-NCOR⁶R⁷;

R² and R³ are each independently selected from the group consisting of H, $C_{1-8}$ alkyl, $C_{0-6}$ alkylene aryl, $C_{0-6}$ alkylene heteroaryl, and $C_{0-6}$ alkylene-4-10 membered heterocycle, wherein independently each alkyl or alkylene group optionally bears 1 oxo substituent, and optionally one carbon atom in the alkyl chain may each be replaced by a heteroatom selected from O, N or $S(O)_p$, such that when said alkyl or alkylene comprises an amine said amino group is a tertiary amine, wherein each 4-10 membered heterocycle is optionally substituted by 1 or 2 groups independently selected from the group consisting of halo, OH, $C_{1-6}$ alkyl, $C_{1-4}$ haloalkyl, $C_{0-3}$ alkylene-O—$C_{0-6}$ alkyl, $C_{0-3}$ alkylene-O—$C_{1-3}$ haloalkyl, $C_{0-6}$ alkylene aryl, $C_{0-3}$ alkylene-O—$O_{0-3}$ alkylene aryl, $C_{0-6}$ alkyleneheteroaryl, $C_{0-3}$ alkylene-O—$C_{0-3}$ alkylene heteroaryl, $C(O)C_{1-6}$ alkyl, $SO_2NR^8R^9$, and $C_{0-3}$ alkylene-NR⁸R⁹, $C_{0-3}$ alkylene-NR⁸SO₂R⁹ and $C_{0-3}$ alkylene-NR⁸C(O)R⁹;

R⁴ is H or $C_{1-4}$ alkyl;

R⁵ is H or $C_{1-4}$ alkyl,

R⁶ is H or $C_{1-4}$ alkyl, $C(O)C_{1-3}$alkyl and $SO_2C_{1-3}$ alkyl;

R⁷ is H or $C_{1-4}$ alkyl, $C(O)C_{1-3}$alkyl and $SO_2C_{1-3}$ alkyl;

R⁸ is H or $C_{1-4}$ alkyl, and

R⁹ is H or $C_{1-4}$ alkyl, p is 0, 1 or 2 or a pharmaceutically acceptable salt thereof, including all stereoisomers and tautomers thereof.

2. A compound according to claim 1 of formula (Ia2)

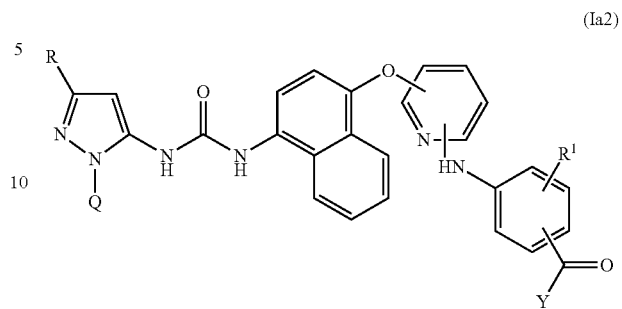

(Ia2)

wherein R, R¹, Q and Y are as defined in claim 1.

3. A compound according to claim 1 of formula (Ib2)

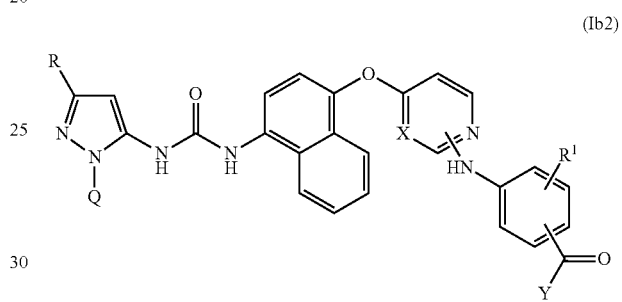

(Ib2)

wherein R, R¹, Q, X and Y are as defined in claim 1.

4. A compound according to claim 1 of formula (Ic):

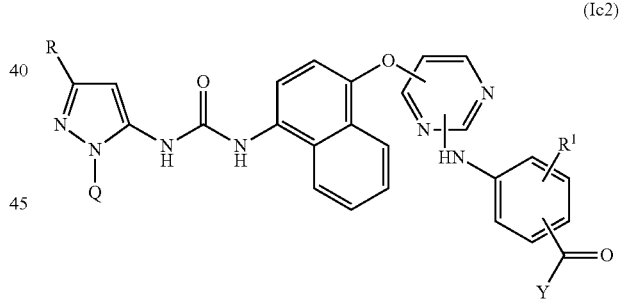

(Ic2)

wherein R, R¹, Q and Y are as defined in claim 1.

5. A compound according to claim 1 of formula (Id2):

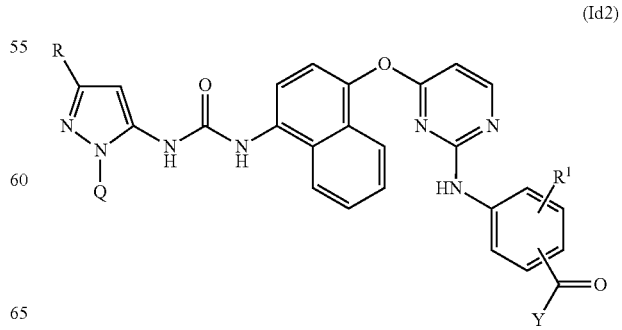

(Id2)

wherein R, R¹, Q and Y are as defined in claim 1.

6. A compound according to claim 1 of formula (Ie2):

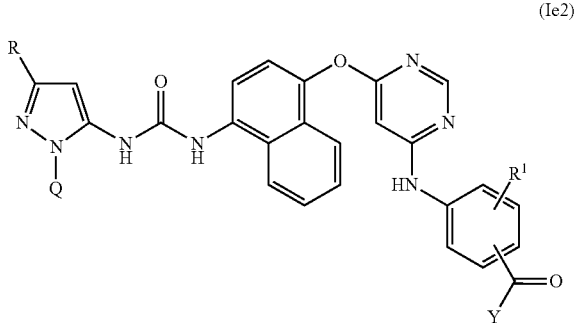

(Ie2)

wherein R, R¹, Q and Y are as defined in claim 1.

7. A compound according to claim 1 of formula (If2):

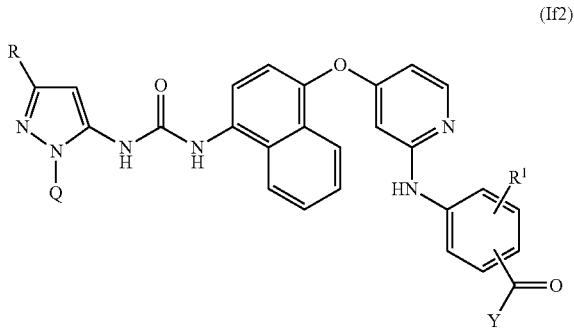

(If2)

wherein R, R¹, Q and Y are as defined in claim 1.

8. A compound according to claim 1 of formula (Ig2):

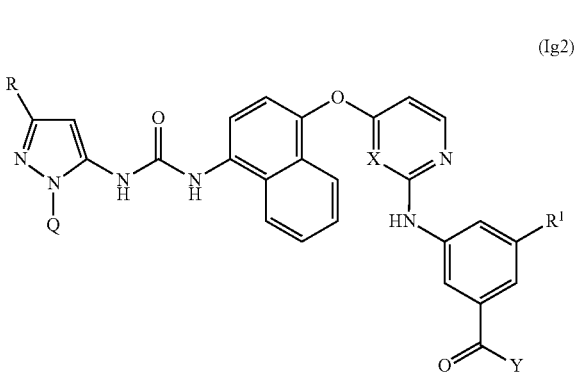

(Ig2)

wherein R, R¹, X, Q and Y are as defined in claim 1.

9. A compound or salt according to claim 1, wherein R represents:
$C_{1-6}$ n-alkyl,
$C_{4-6}$ branched alkyl,
$C_{2-6}$ alkenyl,
$C_{1-6}$ hydroxyalkyl,
$C_{1-6}$ haloalkyl,
$C_{1-6}$ alkyl substituted by $C_{1-3}$ alkoxy or cyano,
$C_{0-2}$ alkylene-$C_{3-8}$ cycloalkyl optionally substituted with $C_{1-3}$ alkyl, or
a 4-5 membered heterocycle optionally substituted with $C_{1-3}$ alkyl.

10. A compound according to claim 1 selected from the group consisting of:
3-((4-((4-(3-(3-(tert-butyl)-1-(p-tolyl)-1H-pyrazol-5-yl)ureido)naphthalen-1-yl)oxy)pyridin-2-yl)amino)-5-methoxy-N-(2-morpholinoethyl)benzamide;
3-((4-((4-(3-(3-(tert-butyl)-1-(p-tolyl)-1H-pyrazol-5-yl)ureido)naphthalen-1-yl)oxy)pyrimidin-2-yl)amino)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-morpholinoethyl)benzamide;
4-((4-((4-(3-(3-(tert-butyl)-1-(p-tolyl)-1H-pyrazol-5-yl)ureido)naphthalen-1-yl)oxy)pyrimidin-2-yl)amino)-N-(2-hydroxyethyl)-3-methoxybenzamide;
N-(2-(dimethylamino)ethyl)-3-((4-((4-(3-(3-isopropyl-1-(p-tolyl)-1H-pyrazol-5-yl)ureido)naphthalen-1-yl)oxy)pyrimidin-2-yl)amino)-5-methoxybenzamide;
N-(2-(dimethylamino)ethyl)-3-((4-((4-(3-(3-isopropyl-1-(4-methoxyphenyl)-1H-pyrazol-5-yl)ureido)naphthalen-1-yl)oxy)pyrimidin-2-yl)amino)-5-methoxybenzamide;
3-((4-((4-(3-(3-isopropyl-1-(p-tolyl)-1H-pyrazol-5-yl)ureido)naphthalen-1-yl)oxy) pyrimidin-2-yl)amino)-N-(2-morpholinoethyl)-5-(trifluoromethyl)benzamide;
3-((4-((4-(3-(3-isopropyl-1-(p-tolyl)-1H-pyrazol-5-yl)ureido)naphthalen-1-yl)oxy) pyrimidin-2-yl)amino)-5-methoxy-N-(2-morpholinoethyl)benzamide;
3-methoxy-N-(2-morpholinoethyl)-5-((4-((4-(3-(3-(perfluoroethyl)-1-(p-tolyl)-1H-pyrazol-5-yl)ureido)naphthalen-1-yl)oxy)pyrimidin-2-yl)amino)benzamide;
3-((4-((4-(3-(3-isopropyl-1-(6-methoxypyridin-3-yl)-1H-pyrazol-5-yl)ureido)naphthalen-1-yl)oxy)pyrimidin-2-yl)amino)-5-methoxy-N-(2-morpholinoethyl)benzamide;
3-((4-((4-(3-(3-isopropyl-1-(4-methoxyphenyl)-1H-pyrazol-5-yl)ureido)naphthalen-1-yl)oxy)pyrimidin-2-yl)amino)-5-methoxy-N-(2-methoxyethyl)benzamide;
1-(3-isopropyl-1-(p-tolyl)-1H-pyrazol-5-yl)-3-(4-((2-((3-methoxy-5-(morpholine-4-carbonyl)phenyl)amino)pyrimidin-4-yl)oxy)naphthalen-1-yl)urea;
5-((4-((4-(3-(3-(tert-butyl)-1-(p-tolyl)-1H-pyrazol-5-yl)ureido)naphthalen-1-yl)oxy)pyrimidin-2-yl)amino)-2-methoxy-N-(2-morpholinoethyl)benzamide;
3-((6-((4-(3-(3-isopropyl-1-(4-methoxyphenyl)-1H-pyrazol-5-yl)ureido)naphthalen-1-yl)oxy)pyrimidin-4-yl)amino)-5-methoxy-N-(2-morpholinoethyl)benzamide;
3-((4-((4-(3-(3-isopropyl-1-(4-methoxyphenyl)-1H-pyrazol-5-yl)ureido)naphthalen-1-yl)oxy)pyridin-2-yl)amino)-5-methoxy-N-(2-morpholinoethyl)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-methylbenzamide;
3-(4-(4-(3-(3-tert-butyl-1-(4-methoxyphenyl)-1H-pyrazol-5-yl)ureido)naphthalen-1-yloxy)pyrimidin-2-ylamino)-N-propylbenzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)benzamide;
3-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide;
3-((4-((4-(3-(3-isopropyl-1-(4-methoxyphenyl)-1H-pyrazol-5-yl)ureido)naphthalen-1-yl)oxy)pyrimidin-2-yl)amino)-N-(2-morpholinoethyl)benzamide;
3-((4-((4-(3-(3-(tert-butyl)-1-(4-methoxyphenyl)-1H-pyrazol-5-yl)ureido)naphthalen-1-yl)oxy)pyrimidin-2-yl)amino)-N-(2-morpholinoethyl)benzamide;
3-((4-((4-(3-(3-(3-methyloxetan-3-yl)-1-(p-tolyl)-1H-pyrazol-5-yl)ureido)naphthalen-1-yl)oxy)pyrimidin-2-yl)amino)-N-(2-morpholinoethyl)benzamide;
3-((4-((4-(3-(1-(4-methoxyphenyl)-3-(3-methyloxetan-3-yl)-1H-pyrazol-5-yl)ureido)naphthalen-1-yl)oxy)pyrimidin-2-yl)amino)-N-(2-morpholinoethyl)benzamide;

3-((4-((4-(3-(3-(tert-butyl)-1-(4-methylthiophen-2-yl)-1H-pyrazol-5-yl)ureido)naphthalen-1-yl)oxy)pyrimidin-2-yl)amino)-N-(2-morpholinoethyl)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-(4-methylpiperazin-1-yl)ethyl)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-N,N-dimethylbenzamide;
1-(3-(tert-butyl)-1-(p-tolyl)-1H-pyrazol-5-yl)-3-(4-((2-((3-(morpholine-4-carbonyl)phenyl)amino)pyrimidin-4-yl)oxy)naphthalen-1-yl)urea;
N-(2-(dimethylamino)ethyl)-3-((4-((4-(3-(3-isopropyl-1-(p-tolyl)-1H-pyrazol-5-yl)ureido)naphthalen-1-yl)oxy)pyrimidin-2-yl)amino)-4-methoxybenzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)-4-methoxybenzamide;
3-((4-((4-(3-(3-isopropyl-1-(p-tolyl)-1H-pyrazol-5-yl)ureido)naphthalen-1-yl)oxy)pyrimidin-2-yl)amino)-4-methoxy-N-(2-morpholinoethyl)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-4-methoxy-N-(2-morpholinoethyl)benzamide;
N-(2-hydroxyethyl)-3-((4-((4-(3-(3-isopropyl-1-(p-tolyl)-1H-pyrazol-5-yl)ureido)naphthalen-1-yl)oxy)pyrimidin-2-yl)amino)-4-methoxybenzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-hydroxyethyl)-4-methoxybenzamide;
N-(2-hydroxyethyl)-3-((4-((4-(3-(3-isopropyl-1-(4-methoxyphenyl)-1H-pyrazol-5-yl)ureido)naphthalen-1-yl)oxy)pyrimidin-2-yl)amino)-4-methoxybenzamide;
N-(2-(dimethylamino)ethyl)-4-((4-((4-(3-(3-isopropyl-1-(p-tolyl)-1H-pyrazol-5-yl)ureido)naphthalen-1-yl)oxy)pyrimidin-2-yl)amino)-3-methoxybenzamide;
4-((4-((4-(3-(3-isopropyl-1-(p-tolyl)-1H-pyrazol-5-yl)ureido)naphthalen-1-yl)oxy)pyrimidin-2-yl)amino)-3-methoxy-N-(2-morpholinoethyl)benzamide;
4-((4-((4-(3-(3-(tert-butyl)-1-(p-tolyl)-1H-pyrazol-5-yl)ureido)naphthalen-1-yl)oxy)pyrimidin-2-yl)amino)-3-methoxy-N-(2-morpholinoethyl)benzamide;
4-((4-((4-(3-(3-isopropyl-1-(4-methoxyphenyl)-1H-pyrazol-5-yl)ureido)naphthalen-1-yl)oxy)pyrimidin-2-yl)amino)-3-methoxy-N-(2-morpholinoethyl)benzamide;
N-(2-hydroxyethyl)-4-((4-((4-(3-(3-isopropyl-1-(p-tolyl)-1H-pyrazol-5-yl)ureido)naphthalen-1-yl)oxy)pyrimidin-2-yl)amino)-3-methoxybenzamide;
3-((4-((4-((3-(3-(tert-butyl)-1-(p-tolyl)-1H-pyrazol-5-yl)ureido)naphthalen-1-yl)oxy)pyrimidin-2-yl)amino)-5-methylbenzamide;
3-((4-((4-(3-(3-(tert-butyl)-1-(4-methoxyphenyl)-1H-pyrazol-5-yl)ureido)naphthalen-1-yl)oxy)pyrimidin-2-yl)amino)-5-methoxybenzamide;
3-bromo-5-((4-((4-(3-(3-(tert-butyl)-1-(4-methoxyphenyl)-1H-pyrazol-5-yl)ureido)naphthalen-1-yl)oxy)pyrimidin-2-yl)amino)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-(dimethylamino)ethyl)-5-methoxybenzamide;
3-((4-((4-(3-(3-isopropyl-1-(p-tolyl)-1H-pyrazol-5-yl)ureido)naphthalen-1-yl)oxy)pyrimidin-2-yl)amino)-5-methyl-N-(2-morpholinoethyl)benzamide;
3-((4-((4-(3-(3-isopropyl-1-(4-methoxyphenyl)-1H-pyrazol-5-yl)ureido)naphthalen-1-yl)oxy)pyrimidin-2-yl)amino)-5-methyl-N-(2-morpholinoethyl)benzamide;
3-((4-((4-(3-(3-isopropyl-1-(4-methoxyphenyl)-1H-pyrazol-5-yl)ureido)naphthalen-1-yl)oxy)pyrimidin-2-yl)amino)-N-(2-morpholinoethyl)-5-(trifluoromethyl)benzamide;
3-methoxy-N-(2-morpholinoethyl)-5-((4-((4-(3-(1-(p-tolyl)-3-(trifluoromethyl)-1H-pyrazol-5-yl)ureido)naphthalen-1-yl)oxy)pyrimidin-2-yl)amino)benzamide;
3-((4-((4-(3-(3-ethyl-1-(p-tolyl)-1H-pyrazol-5-yl)ureido)naphthalen-1-yl)oxy)pyrimidin-2-yl)amino)-5-methoxy-N-(2-morpholinoethyl)benzamide;
3-((4-((4-(3-(3-cyclopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide;
3-methoxy-5-((4-((4-(3-(3-(1-methylcyclopropyl)-1-(p-tolyl)-1H-pyrazol-5-yl)ureido)naphthalen-1-yl)oxy)pyrimidin-2-yl)amino)-N-(2-morpholinoethyl)benzamide;
3-((4-((4-(3-(3-(tert-butyl)-1-(p-tolyl)-1H-pyrazol-5-yl)ureido)naphthalen-1-yl)oxy)pyrimidin-2-yl)amino)-5-methoxy-N-(2-morpholinoethyl)benzamide;
3-((4-((4-(3-(3-isopropyl-1-(4-methoxyphenyl)-1H-pyrazol-5-yl)ureido)naphthalen-1-yl)oxy)pyrimidin-2-yl)amino)-5-methoxy-N-(2-morpholinoethyl)benzamide;
3-((4-((4-(3-(3-(tert-butyl)-1-(4-methoxyphenyl)-1H-pyrazol-5-yl)ureido)naphthalen-1-yl)oxy)pyrimidin-2-yl)amino)-5-methoxy-N-(2-morpholinoethyl)benzamide;
3-((4-((4-(3-(3-(tert-butyl)-1-(3-(2-methoxyethoxy)phenyl)-1H-pyrazol-5-yl)ureido)naphthalen-1-yl)oxy)pyrimidin-2-yl)amino)-5-methoxy-N-(2-morpholinoethyl)benzamide;
3-((4-((4-(3-(1-(3,4-dimethylphenyl)-3-isopropyl-1H-pyrazol-5-yl)ureido)naphthalen-1-yl)oxy)pyrimidin-2-yl)amino)-5-methoxy-N-(2-morpholinoethyl)benzamide;
3-((4-((4-((3-(3-(tert-butyl)-1-(6-methoxypyridin-3-yl)-1H-pyrazol-5-yl)ureido)naphthalen-1-yl)oxy)pyrimidin-2-yl)amino)-5-methoxy-N-(2-morpholinoethyl)benzamide;
3-methoxy-5-((4-((4-(3-(1-(4-methoxyphenyl)-3-(tetrahydrofuran-2-yl)-1H-pyrazol-5-yl)ureido)naphthalen-1-yl)oxy)pyrimidin-2-yl)amino)-N-(2-morpholinoethyl)benzamide;
3-methoxy-5-((4-((4-(3-(1-(4-methoxyphenyl)-3-(tetrahydrofuran-3-yl)-1H-pyrazol-5-yl)ureido)naphthalen-1-yl)oxy)pyrimidin-2-yl)amino)-N-(2-morpholinoethyl)benzamide;
3-chloro-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide;
3-chloro-5-((4-((4-(3-(3-isopropyl-1-(4-methoxyphenyl)-1H-pyrazol-5-yl)ureido)naphthalen-1-yl)oxy)pyrimidin-2-yl)amino)-N-(2-morpholinoethyl)benzamide;
3-bromo-5-((4-((4-(3-(3-(tert-butyl)-1-(p-tolyl)-1H-pyrazol-5-yl)ureido)naphthalen-1-yl)oxy)pyrimidin-2-yl)amino)-N-(2-morpholinoethyl)benzamide;
N-(2-hydroxyethyl)-3-((4-((4-(3-(3-isopropyl-1-(p-tolyl)-1H-pyrazol-5-yl)ureido)naphthalen-1-yl)oxy)pyrimidin-2-yl)amino)-5-methoxybenzamide;
3-((4-((4-(3-(3-(tert-butyl)-1-(p-tolyl)-1H-pyrazol-5-yl)ureido)naphthalen-1-yl)oxy)pyrimidin-2-yl)amino)-N-(2-hydroxyethyl)-5-methoxybenzamide;
N-(2-hydroxyethyl)-3-((4-((4-(3-(3-isopropyl-1-(4-methoxyphenyl)-1H-pyrazol-5-yl)ureido)naphthalen-1-yl)oxy)pyrimidin-2-yl)amino)-5-methoxybenzamide;

3-((4-((4-(3-(3-isopropyl-1-(p-tolyl)-1H-pyrazol-5-yl)ureido)naphthalen-1-yl)oxy)pyrimidin-2-yl)amino)-5-methoxy-N-(2-methoxyethyl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-methoxy-N-(2-methoxyethyl)benzamide;

3-((4-((4-(3-(3-isopropyl-1-(p-tolyl)-1H-pyrazol-5-yl)ureido)naphthalen-1-yl)oxy)pyrimidin-2-yl)amino)-5-methoxy-N-methyl-N-(2-morpholinoethyl)benzamide;

1-(3-isopropyl-1-(p-tolyl)-1H-pyrazol-5-yl)-3-(4-((2-((3-methoxy-5-(4-methylpiperazine-1-carbonyl)phenyl)amino)pyrimidin-4-yl)oxy)naphthalen-1-yl)urea;

5-((4-((4-(3-(3-isopropyl-1-(p-tolyl)-1H-pyrazol-5-yl)ureido)naphthalen-1-yl)oxy)pyrimidin-2-yl)amino)-2-methoxy-N-(2-morpholinoethyl)benzamide;

3-((6-((4-(3-(3-isopropyl-1-(p-tolyl)-1H-pyrazol-5-yl)ureido)naphthalen-1-yl)oxy)pyrimidin-4-yl)amino)-5-methoxy-N-(2-morpholinoethyl)benzamide;

3-((6-((4-((3-(3-(tert-butyl)-1-(p-tolyl)-1H-pyrazol-5-yl)ureido)naphthalen-1-yl)oxy)pyrimidin-4-yl)amino)-5-methoxy-N-(2-morpholinoethyl)benzamide;

3-ethynyl-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide;

3-((4-((4-(3-(3-(tert-butyl)-1-(6-methoxypyridin-3-yl)-1H-pyrazol-5-yl)ureido)naphthalen-1-yl)oxy)pyrimidin-2-yl)amino)-5-ethynyl-N-(2-morpholinoethyl)benzamide;

3-ethynyl-N-(2-morpholinoethyl)-5-((4-((4-(3-(3-(perfluoroethyl)-1-(p-tolyl)-1H-pyrazol-5-yl)ureido)naphthalen-1-yl)oxy)pyrimidin-2-yl)amino)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-morpholinoethyl)benzamide;

3-ethynyl-N-(2-morpholinoethyl)-5-((4-((4-(3-(1-(p-tolyl)-3-(1,1,1-trifluoro-2-methylpropan-2-yl)-1H-pyrazol-5-yl)ureido)naphthalen-1-yl)oxy)pyrimidin-2-yl)amino)benzamide;

3-((4-((4-(3-(3-(tert-butyl)-1-(4-methoxyphenyl)-1H-pyrazol-5-yl)ureido)naphthalen-1-yl)oxy)pyrimidin-2-yl)amino)-5-ethynyl-N-(2-morpholinoethyl)benzamide;

3-((4-((4-(3-(3-(2-cyanopropan-2-yl)-1-(p-tolyl)-1H-pyrazol-5-yl)ureido)naphthalen-1-yl)oxy)pyrimidin-2-yl)amino)-5-ethynyl-N-(2-morpholinoethyl)benzamide;

3-ethynyl-5-((4-((4-(3-(3-(2-methoxypropan-2-yl)-1-(p-tolyl)-1H-pyrazol-5-yl)ureido)-naphthalen-1-yl)oxy)pyrimidin-2-yl)amino)-N-(2-morpholinoethyl)benzamide;

3-((4-((4-(3-(3-(tert-butyl)-1-(4-(dimethylamino)phenyl)-1H-pyrazol-5-yl)ureido)naphthalen-1-yl)oxy)pyrimidin-2-yl)amino)-5-ethynyl-N-(2-morpholinoethyl)benzamide;

(S)-3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(1-morpholinopropan-2-yl)benzamide;

3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(2-methyl-1-morpholinopropan-2-yl)benzamide;

(R)-3-((4-((4-(3-(3-(tert-butyl)-1-(p-tolyl)-1H-pyrazol-5-yl)ureido)naphthalen-1-yl)oxy)pyrimidin-2-yl)amino)-5-ethynyl-N-(1-morpholinopropan-2-yl)benzamide;

3-((4-((4-(3-(3-(tert-butyl)-1-(4-methoxyphenyl)-1H-pyrazol-5-yl)ureido)-naphthalen-1-yl)oxy)pyrimidin-2-yl)amino)-5-ethynyl-N-(2-methoxyethyl)benzamide;

(S)-3-((4-((4-(3-(3-(tert-butyl)-1-(4-methoxyphenyl)-1H-pyrazol-5-yl)ureido)-naphthalen-1-yl)oxy)pyrimidin-2-yl)amino)-5-ethynyl-N-(1-methoxypropan-2-yl)benzamide;

3-methoxy-5-((4-((4-(3-(1-(4-methoxyphenyl)-3-(prop-1-en-2-yl)-1H-pyrazol-5-yl)ureido)naphthalen-1-yl)oxy)pyrimidin-2-yl)amino)-N-(2-morpholinoethyl)benzamide;

3-((4-(2,3-Dichloro-4-(3-(3-isopropyl-1-(p-tolyl)-1H-pyrazol-5-yl)ureido)phenoxy)-pyrimidin-2-yl)amino)-5-ethynyl-N-(2-morpholinoethyl)benzamide;

3-((4-(2,3-Difluoro-4-(3-(3-isopropyl-1-(p-tolyl)-1H-pyrazol-5-yl)ureido)phenoxy)-pyrimidin-2-yl)amino)-5-ethynyl-N-(2-morpholinoethyl)benzamide;

3-((4-(2,3-Dichloro-4-(3-(3-isopropyl-1-(p-tolyl)-1H-pyrazol-5-yl)ureido)phenoxy)-pyrimidin-2-yl)amino)-5-ethynylbenzamide;

3-((4-(2,3-Dichloro-4-(3-(3-isopropyl-1-(p-tolyl)-1H-pyrazol-5-yl)ureido)phenoxy)-pyrimidin-2-yl)amino)-N-(2-(dimethylamino)ethyl)-5-ethynylbenzamide; and 3-((6-(4-(3-(3-(tert-butyl)-1-(4-methoxyphenyl)-1H-pyrazol-5-yl)ureido)-2,3-dimethylphenoxy)pyrimidin-4-yl)amino)-5-methoxy-N-(2-morpholinoethyl)benzamide, or a pharmaceutically acceptable salt thereof.

11. A compound according to claim 1, wherein the compound is not 3-((4-((4-(3-(3-Isopropyl-1-(p-tolyl)-1H-pyrazol-5-yl)ureido)naphthalen-1-yl)oxy)pyrimidin-2-yl)amino)-5-methoxy-N-(2-morpholinoethyl)benzamide.

12. A compound according to claim 1 that is 3-((4-((4-(3-(3-(tert-butyl)-1-(4-methoxyphenyl)-1H-pyrazol-5-yl)ureido)naphthalen-1-yl)oxy)pyrimidin-2-yl)amino)-5-ethynyl-N-(2-morpholinoethyl)benzamide, or a pharmaceutically acceptable salt thereof.

13. A pharmaceutical composition comprising a compound according to claim 1, in combination with one or more pharmaceutically acceptable diluents or carriers.

14. A combination product comprising:
(A) a compound according to claim 1; and
(B) another substance, which substance is a therapeutic agent,
wherein each of components (A) and (B) are formulated in admixture with a pharmaceutically-acceptable adjuvant, diluent or carrier.

15. A method for the therapeutic treatment of a disease in a subject in need thereof comprising administering to said subject a compound according to claim 1, wherein the disease is selected from the group consisting of COPD, chronic bronchitis, emphysema, asthma, pediatric asthma, cystic fibrosis, sarcoidosis, idiopathic pulmonary fibrosis, allergic rhinitis, rhinitis, sinusitis, allergic conjunctivitis, conjunctivitis, keratoconjunctivitis sicca (dry eye), glaucoma, diabetic retinopathy, macular edema, diabetic macular edema, central retinal vein occlusion (CRVO), dry and/or wet age related macular degeneration (AMD), post-operative cataract inflammation, uveitis, posterior uveitis, anterior uveitis, pan uveitis, corneal graft and limbal cell transplant rejection, gluten sensitive enteropathy (coeliac disease), eosinophilic esophagitis, intestinal graft versus host disease, Crohn's disease, ulcerative colitis, rheumatoid arthritis and osteoarthritis.

16. The method according to claim 15, wherein the disease is selected from the group consisting of COPD, asthma, keratoconjunctivitis sicca (dry eye), uveitis, posterior uveitis, anterior uveitis, pan uveitis, Crohn's disease and ulcerative colitis.

17. A method of treatment of inflammation in a subject in need thereof, comprising administering to said subject a compound according to claim 1 in combination with an anti-viral therapy, wherein the inflammation is a component in a disease selected from the group consisting of COPD and asthma and wherein said subject is suffering from a viral exacerbation of said disease.

18. The method of claim 17, wherein said administering is by intravitreal injection of a solution or suspension of the compound.

* * * * *

UNITED STATES PATENT AND TRADEMARK OFFICE
CERTIFICATE OF CORRECTION

PATENT NO. : 9,701,670 B2
APPLICATION NO. : 14/422158
DATED : July 11, 2017
INVENTOR(S) : Cariou et al.

It is certified that error appears in the above-identified patent and that said Letters Patent is hereby corrected as shown below:

On the Title Page

In References Cited, under Other Publications:

Item (56), Page 3, Column 1, Line 28, change "Diease:" to --Disease:--.

In the Specification

At Column 10, Line 50, after "(I)" insert --.--.

At Column 14, Line 30, change "heterocyle" to --heterocycle--.

At Column 15, Line 56, after "(Ie2)," insert --(If1),--.

At Column 16, Line 35, change "heterocyle" to --heterocycle--.

At Column 17, Line 41-51 (structure), change " 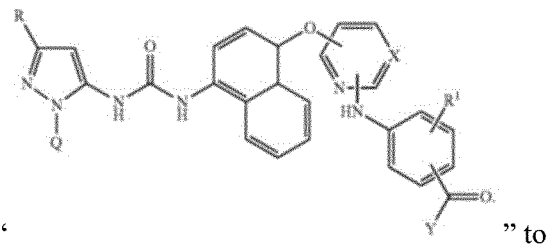 " to 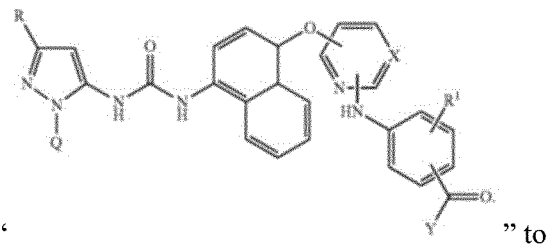 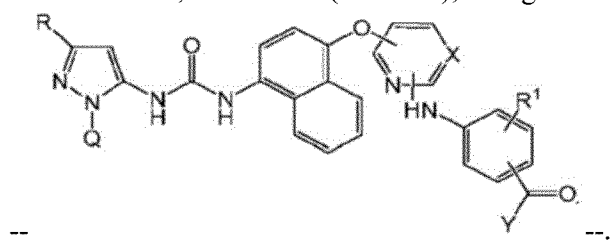 --.

Signed and Sealed this
Third Day of December, 2019

Andrei Iancu
*Director of the United States Patent and Trademark Office*

CERTIFICATE OF CORRECTION (continued)
U.S. Pat. No. 9,701,670 B2

At Column 19, Line 23, change "ureido) naphthalen" to --ureido)naphthalen--.

At Column 19, Line 26, change "yl) ureido)" to --yl)ureido)--.

At Column 19, Line 36 (approx.), change "yl) ureido)" to --yl)ureido)--.

At Column 19, Line 42, change "oxy) pyrimidin" to --oxy)pyrimidin--.

At Column 19, Line 51, change "oxy) pyrimidin" to --oxy)pyrimidin--.

At Column 19, Line 60, change "yloxy) pyrimidin" to --yloxy)pyrimidin--.

At Column 20, Line 2, change "oxy) pyrimidin" to --oxy)pyrimidin--.

At Column 20, Line 5, change "oxy) pyrimidin" to --oxy)pyrimidin--.

At Column 20, Line 8, change "oxy) pyrimidin" to --oxy)pyrimidin--.

At Column 20, Line 24, change "amino) pyrimidin" to --amino)pyrimidin--.

At Column 20, Line 27, change "ureido) naphthalen" to --ureido)naphthalen--.

At Column 20, Line 45, change "ureido) naphthalen" to --ureido)naphthalen--.

At Column 20, Line 48, change "ureido) naphthalen" to --ureido)naphthalen--.

At Column 20, Line 57, change "oxy) pyrimidin" to --oxy)pyrimidin--.

At Column 20, Line 66, change "oxy) pyrimidin" to --oxy)pyrimidin--.

At Column 21, Line 11, change "oxy) pyrimidin" to --oxy)pyrimidin--.

At Column 21, Line 14, change "oxy) pyrimidin" to --oxy)pyrimidin--.

At Column 21, Line 32, change "oxy) pyrimidin" to --oxy)pyrimidin--.

At Column 21, Line 35, change "oxy) pyrimidin" to --oxy)pyrimidin--.

At Column 21, Line 37, change "methoxyethoxyl)" to --methoxyethoxy)--.

At Column 21, Line 41 (approx.), change "oxy) pyrimidin" to --oxy)pyrimidin--.

At Column 21, Line 47, change "ureido) naphthalen" to --ureido)naphthalen--.

At Column 21, Line 51, change "ureido) naphthalen" to --ureido)naphthalen--.

At Column 21, Line 55, change "oxy) pyrimidin" to --oxy)pyrimidin--.

At Column 21, Line 60, change "oxy) pyrimidin" to --oxy)pyrimidin--.

At Column 22, Line 2, change "ureido) naphthalen" to --ureido)naphthalen--.

At Column 22, Line 14, change "urea," to --urea;--.

At Column 22, Line 25 (approx.), change "oxy) pyrimidin" to --oxy)pyrimidin--.

At Column 27, Line 18, change "toleune," to --toluene,--.

At Column 27, Line 65, change "R$^1$" to --R$^f$--.

At Column 28, Line 24-25, change "triphenyphosphine," to --triphenylphosphine,--.

At Column 34, Line 55-61, change " 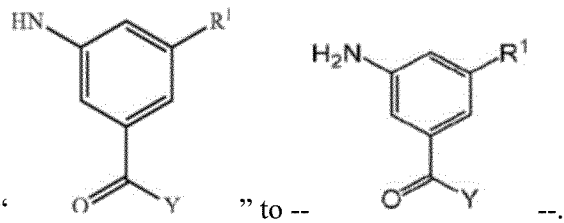 " to -- --.

At Column 40, Line 6, change "polyosyl" to --polyoxyl--.

At Column 40, Line 23, change "Pemulen®," to --Pemulen(R),--.

At Column 40, Line 35, change "benzalkoniurn" to --benzalkonium--.

At Column 41, Line 25, change "bisalazide);" to --balsalazide);--.

At Column 44, Line 59, change "MeOH The" to --MeOH. The--.

At Column 45, Line 21, change "mLmin$^{-1}$;" to --mL min$^{-1}$;--.

At Column 46, Line 13 (approx.), change "mLmin$^{-1}$;" to --mL min$^{-1}$;--.

At Column 53, Line 33, after "3H)" insert --.--.

At Column 56, Line 28-29, change "methoxyethoxyl)" to --methoxyethoxy)--.

At Column 56, Line 51 (approx.), change "methoxyethoxyl)" to --methoxyethoxy)--.

At Column 60, Line 28, delete "LCMS m/z 361 (M+H)$^+$ (ES$^+$); 359 (M-H)$^-$ (ES$^-$)" and insert the same on Column 60, Line 29, as a new paragraph.

CERTIFICATE OF CORRECTION (continued)
U.S. Pat. No. 9,701,670 B2

At Column 61, Line 45 (approx.), after "g)" insert --.--.

At Column 64, Line 9, change "amino) pyrimidin" to --amino)pyrimidin--.

At Column 70, Line 21 (approx.), change "Fe" to --$R^t$--.

At Column 75, Line 44 (approx.), change "B15" to --B19--.

At Column 75, Line 58 (approx.), change "amino) pyrimidin" to --amino)pyrimidin--.

At Column 76, Line 32 (approx.), change "mL)." to --mL)--.

At Column 76, Line 35-36, change "amino) pyrimidin" to --amino)pyrimidin--.

At Column 85, Line 34, after "3H)" insert --.--.

At Column 86, Line 21, change "ethynyl benzamide" to --ethynylbenzamide--.

At Column 86, Line 64, change "b" to --δ--.

At Column 87, Line 50, change "ureido) naphthalen" to --ureido)naphthalen--.

At Column 88, Line 34, change "ureido) naphthalen" to --ureido)naphthalen--.

At Column 89, Line 11, change "yl) ureido)" to --yl)ureido)--.

At Column 90, Line 33 (approx.), change "ureido) naphthalen" to --ureido)naphthalen--.

At Column 91, Line 5, change "($ES^+$);" to --($ES^+$).--.

At Column 92, Line 10-11, change "ureido) naphthalen" to --ureido)naphthalen--.

At Column 93, Line 36, after "($ES^-$)" insert --.--.

At Column 94, Line 56, change "it" to --rt--.

At Column 94, Line 66, change "(s, 2H)" to --(s, 2H).--.

At Column 94, Line 66-67, delete "LCMS m/z 290/2/4 (M+H)+ ES+)" and insert the same on Column 94, Line 67, as a new paragraph.

At Column 96, Line 2, change "oxy) pyrimidin" to --oxy)pyrimidin--.

At Column 97, Line 17, change "oxy) pyrimidin" to --oxy)pyrimidin--.

CERTIFICATE OF CORRECTION (continued)
U.S. Pat. No. 9,701,670 B2

At Column 100, Line 11, change "oxy) pyrimidin" to --oxy)pyrimidin--.

At Column 102, Line 11, change "3((4-" to --3-((4--.

At Column 104, Line 1, change "5((4-" to --5-((4--.

At Column 112, Line 23 (approx.), change "br.s)," to --br s),--.

At Column 112, Line 34 (approx.), change "H2O" to --$H_2O$--.

At Column 114, Line 4 (approx.), change "ureido) naphthalen" to --ureido)naphthalen--.

At Column 116, Line 16 (approx.), change "ureido) naphthalen" to --ureido)naphthalen--.

At Column 127-128 (Structure No. 38) (Table 3-continued), Line 2 (approx.), change "ypureido" to --yl)ureido)--.

At Column 133-134 (Structure No. 47) (Table 3-continued), Line 4 (approx.) (Table 3), "ypureido" to --yl)ureido)--.

At Column 147, Line 64 (approx.), change "iso-propyl" to --isopropyl--.

At Column 150, Line 35, after "9H)" insert --.--.

At Column 151, Line 2, change "iso-propyl" to --isopropyl--.

At Column 162, Line 1, change "it" to --rt--.

At Column 164, Line 15 (approx.), after "ppm" insert --.--.

At Column 167, Line 49, after "3.35" insert --.--.

At Column 169, Line 21, change "O111" to --0111--.

At Column 169, Line 40, change "O111" to --0111--.

At Column 171, Line 26, change "IL-113" to --IL-1β--.

At Column 172, Line 34, change "$OD_{450-555}$" to --$OD_{450-655}$--.

At Column 172, Line 35, change "$OD_{450-555}$" to --$OD_{450-655}$--.

At Column 172, Line 56, change "13" to --β--.

At Column 174, Line 15-29, delete "Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis-Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 μg/mL) and 1 mM $CaCl_2$) to achieve $5×10^6$ cells/mL."
and insert the same on Column 174, Line 16 as a new paragraph.

At Column 186, Line 58, after "ng/mL)" insert --.--.

In the Claims

At Column 193, Claim number 1, Line 6 (approx.), change "O—$O_{0-6}$" to --O—$C_{0-6}$--.

At Column 193, Claim number 1, Line 7 (approx.), change "O—$O_{0-3}$" to --O—$C_{0-3}$--.

At Column 193, Claim number 1, Line 9 (approx.), change "O—$O_{0-3}$" to --O—$C_{0-3}$--.

At Column 196, Claim number 10, Line 18, change "oxy) pyrimidin" to --oxy)pyrimidin--.

At Column 196, Claim number 10, Line 21, change "oxy) pyrimidin" to --oxy)pyrimidin--.